(12) United States Patent
Friedman et al.

(10) Patent No.: US 7,812,137 B2
(45) Date of Patent: Oct. 12, 2010

(54) DB, THE RECEPTOR FOR LEPTIN, NUCLEIC ACIDS ENCODING THE RECEPTOR, AND USES THEREOF

(75) Inventors: Jeffrey M. Friedman, New York, NY (US); Gwo-Hwa Lee, New York, NY (US); Ricardo Proenca, Astoria, NY (US); Ella Ioffe, New York, NY (US)

(73) Assignee: The Rockefeller University, New York, NY (US)

( * ) Notice: Subject to any disclaimer, the term of this patent is extended or adjusted under 35 U.S.C. 154(b) by 190 days.

(21) Appl. No.: 11/585,709

(22) Filed: Oct. 24, 2006

(65) Prior Publication Data

US 2007/0048836 A1    Mar. 1, 2007

Related U.S. Application Data

(60) Division of application No. 08/783,734, filed on Jan. 16, 1997, now Pat. No. 7,148,004, which is a continuation-in-part of application No. 08/599,974, filed on Feb. 14, 1996, which is a continuation-in-part of application No. 08/586,594, filed on Jan. 16, 1996.

(51) Int. Cl.
  C08H 1/00    (2006.01)
  C07K 14/00   (2006.01)
  A61K 38/24   (2006.01)

(52) U.S. Cl. .................. 530/402; 530/350; 530/399

(58) Field of Classification Search .................. None
See application file for complete search history.

(56) References Cited

U.S. PATENT DOCUMENTS

| | | | | |
|---|---|---|---|---|
| 4,179,337 A | * | 12/1979 | Davis et al. | ................. 435/181 |
| 5,359,046 A | | 10/1994 | Capon et al. | |
| 5,643,748 A | | 7/1997 | Snodgrass et al. | .......... 435/69.1 |
| 6,506,877 B1 | * | 1/2003 | Tartaglia et al. | ............. 530/350 |

FOREIGN PATENT DOCUMENTS

| | | |
|---|---|---|
| WO | WO 90/14092 | 11/1990 |
| WO | WO 91/06666 | 5/1991 |
| WO | WO 91/09955 | 7/1991 |
| WO | 9712037 | 9/1996 |
| WO | 9635787 | 11/1996 |
| WO | 9725424 | 1/1997 |
| WO | 9731015 | 2/1997 |
| WO | 9712037 | 4/1997 |
| WO | 9740380 | 4/1997 |
| WO | 9741217 A1 | 4/1997 |
| WO | 9741263 | 4/1997 |
| WO | 9742340 | 5/1997 |
| WO | 9719952 | 6/1997 |
| WO | 9725425 | 7/1997 |
| WO | 9726523 | 7/1997 |

OTHER PUBLICATIONS

Turton et al., Nature, 379:69 (1996).
Campfield et al., Science, 269:546 (1995).
Considine et al., J. Clin. Invest., 95:2986 (1995).
Halaas et al., Science, 269:543 (1995).
Hamilton et al., Nature Med., 1:953 (1995).
Lonnqvist et al., Nature Med., 1:950 (1995).
Maffei et al., Nature Med., 1:1155 (1995).
Modl et al., Dytogenetics Cell Genetics, 67:232 (1995).
Pellymounter et al., Science, 269:540, (1995).
Stephens et al., Nature, 377:530 (1995).
Tartaglia et al. (1995) Cell 83:1263-71.
Church et al, Nature Genetics, 6:98 (1994).
Kishimoto et al. (1994) Cell 76:253-62.
Milatovich et al., Somatic Cell Mol. Gen., 20:75 (1994).
Zhang et al., Nature, 372:425 (1994).
Bahary et al., Mammalian Genome, 4:511-515 (1993).
Davis et al. (1993) Science 259:1736-9.
Davis et al. (1993) Science 260:1805-7.
Sanchez et al., J. Exp. Med., 178:1049 (1993).
Morgan et al., Nucl. Acids Res., 20:5173 (1992).
Friedman et al., Genomics, 11:1054-1062 (1991).
Fukunaga, et al., EMBO, 10:2855 (1991).
Moll et al., Am. J. Hum. Genet., 49:1243-1255 (1991).
Murakami et al., Proc. Natl. Acad. Sci. USA, 88:11349 (1991).
Truett et al., Proc. Natl. Acad. Sci. USA, 88:7806-7809 (1991).
Bahary et al. (1990) Proc. Natl. Acad. Sci. USA 87:8642-6.
Riley et al., Nucl. Acids Res., 18:2887 (1990).
Bray et al., Am. J. Clin. Nutr., 50:891-902 (1989).
Leiter, Endocrinology, 124:912-922 (1989).
Burkhardt et al. (1994) Mol. Cell. Biol., 14:1095-103.
Coleman et al., Diabetologia, 14:141-148 (1978).
Coleman, Diabetologia, 9:294-298 (1973).
Bennett et al., Current Biology, 6(9): 1170-80, 1996.
Chen et al., Cell, 84: 491-95, 1996.
Cioffi et al., Nature Medicine, 2(5) : 585-89, 1996.
Chua et al., Science, 271: 994-6, 1996.
Iida et al.. Biochem Biophs Res Comm, 224: 597-604, 1996.
Wang et al., "Rapid analysis of gene expression (RAGE) facilitates universal expression profiling," Nuc. Acids. Res, vol. 27, p. 4609-4618 (1999).

(Continued)

Primary Examiner—Gary B. Nickol
Assistant Examiner—Shulamith H Shafer
(74) Attorney, Agent, or Firm—Steptoe & Johnson LLP

(57) ABSTRACT

The present invention relates to identification of a receptor for a satiety factor, which is involved in body weight homeostasis. Mutations in this receptor are associated with obese phenotypes. In particular, the present invention relates to identification and characterization of the receptor for leptin, including a naturally occurring soluble form of the receptor that is expected to modulate leptin activity, in particular to agonize leptin activity. The invention further relates to the nucleic acids encoding the receptor, and to methods for using the receptor, e.g., to identify leptin analogs, therapeutically, such as in gene therapy or in soluble form as an agonist or antagonist of leptin activity, or diagnostically.

6 Claims, 12 Drawing Sheets

OTHER PUBLICATIONS

Kaufman et al., "Trangenic analysis of a 100-kb Human beta-Globin Cluster-Containing DNA Fragment Propagated as a Bacterial Artificial Chromosome," *Blood*, vol. 94, p. 3178-3784 (1999).

Wigley et al., "Site-specific transgene insertion: an approach," *Reprod. Fertil. Dev.*, vol. 6, p. 585-588 (1994).

Campbell et al., "Totipotency or Multipotentiality of Cultured Cells: Applications and Progress," *Theriogenology*, vol. 47(1), p. 63-72 (1997).

Phillips, "The challenge of gene therapy and DNA delivery," *Journal of Pharmacy and Pharmacology*, vol. 53, p. 1169-1174 (2001).

* cited by examiner

SEQUENCE LISTING

<160> NUMBER OF SEQ ID NOS: 126

<210> SEQ ID NO 1
<211> LENGTH: 2529
<212> TYPE: DNA
<213> ORGANISM: Mus musculus

<400> SEQUENCE: 1
gggctcaggt cggcgtcgta ccagccgctg aagcggttct ccaggttcca ggcgctctcg      60
ccatgccgga tcagcaccag cttgtagctc gtgccgaatt cggcacgagg ttgctttggg     120
aatgagcaag gtcaaaactg ctctgcactc acagacaaca ctgaagggaa gacactggct     180
tcagtagtga aggcttcagt ttttcgccag ctaggtgtaa actgggacat agagtgctgg     240
atgaaagggg acttgacatt attcatctgt catatggagc cattacctaa gaaccccttc     300
aagaattatg actctaaggt ccatcttttta tatgatctgc ctgaagtcat agatgattcg     360

-continued

```
cctctgcccc cactgaaaga cagcttttcag actgtccaat gcaactgcag tcttcgggga    420
tgtgaatgtc atgtgccggt acccagagcc aaactcaact acgctcttct gatgtatttg    480
gaaatcacat ctgccggtgt gagttttcag tcacctctga tgtcactgca gcccatgctt    540
gttgtgaaac ccgatccacc cttaggtttg catatggaag tcacagatga tggtaattta    600
aagatttctt gggacagcca aacaatggca ccatttccgc ttcaatatca ggtgaaatat    660
ttagagaatt ctacaattgt aagagaggct gctgaaattg tctcagctac atctctgctg    720
gtagacagtg tgcttcctgg atcttcatat gaggtccagg tgaggagcaa gagactggat    780
ggttcaggag tctggagtga ctggagttca cctcaagtct ttaccacaca agatgttgtg    840
tattttccac ccaaaattct gactagtgtt ggatcgaatg cttcttttca ttgcatctac    900
aaaaacgaaa accagattat ctcctcaaaa cagatagttt ggtggaggaa tctagctgag    960
aaaatccctg agatacagta cagcattgtg agtgaccgag ttagcaaagt taccttctcc   1020
aacctgaaag ccaccagacc tcagggaaag tttacctatg acgcagtgta ctgctgcaat   1080
gagcaggcgt gccatcaccg ctatgctgaa ttatacgtga tcgatgtcaa tatcaatata   1140
tcatgtgaaa ctgacgggta cttaactaaa atgacttgca gatggtcacc cagcacaatc   1200
caatcactag tgggaagcac tgtgcagctg aggtatcaca ggcgcagcct gtattgtcct   1260
gatagtccat ctattcatcc tacgtctgag cccaaaaact gcgtcttaca gagagacggc   1320
ttttatgaat gtgttttcca gccaatcttt ctattatctg gctatacaat gtggatcagg   1380
atcaaccatt ctttaggttc acttgactcg ccaccaacgt gtgtccttcc tgactccgta   1440
gtaaaaccac tacctccatc taacgtaaaa gcagagatta ctgtaaacac tggattattg   1500
aaagtatctt gggaaaagcc agtctttccg gagaataacc ttcaattcca gattcgatat   1560
ggcttaagtg gaaaagaaat acaatggaag acacatgagg tattcgatgc aaagtcaaag   1620
tctgccagcc tgctggtgtc agacctctgt gcagtctatg tggtccaggt tcgctgccgg   1680
cggttggatg gactaggata ttggagtaat tggagcagtc cagcctatac gcttgtcatg   1740
gatgtaaaag ttcctatgag agggcctgaa ttttggagaa aaatggatgg ggacgttact   1800
aaaaaggaga gaaatgtcac cttgctttgg aagcccctga cgaaaaatga ctcactgtgt   1860
agtgtgagga ggtacgtggt gaagcatcgt actgccccaca atgggacgtg gtcagaagat   1920
gtgggaaatc ggaccaatct cactttcctg tggacagaac cagcgcacac tgttacagtt   1980
ctggctgtca attccctcgg cgcttccctt gtgaatttta accttaccct ctcatggccc   2040
atgagtaaag tgagtgctgt ggagtcactc agtgcttatc ccctgagcag cagctgtgtc   2100
atcctttcct ggacactgtc acctgatgat tatagtctgt tatatctggt tattgaatgg   2160
aagatcctta tgaagatga tggaatgaag tggcttagaa ttccctcgaa tgttaaaaag   2220
ttttatatcc acgataattt tattcccatc gagaaatatc agtttagtct ttacccagta   2280
tttatggaag gagttggaaa accaaagata attaatggtt tcaccaaaga tgctatcgac   2340
aagcagcaga atgacgcagg gctgtatgtc attgtaccca taattatttc ctcttgtgtc   2400
ctactgctcg gaacactgtt aatttcacac cagagaatga aaaagttgtt ttgggacgat   2460
gttccaaacc ccaagaattg ttcctgggca caaggactga atttccaaaa gagaacggac   2520
actctttga                                                           2529
```

<210> SEQ ID NO 2
<211> LENGTH: 842
<212> TYPE: PRT
<213> ORGANISM: Mus musculus

```
<220> FEATURE:
<221> NAME/KEY: MISC_FEATURE
<222> LOCATION: (29)..(29)
<223> OTHER INFORMATION: X can be any amino acid

<400> SEQUENCE: 2

Gly Leu Arg Ser Ala Ser Tyr Gln Pro Leu Lys Arg Phe Ser Arg Phe
1               5                   10                  15

Gln Ala Leu Ser Pro Cys Arg Ile Ser Thr Ser Leu Xaa Leu Val Pro
            20                  25                  30

Asn Ser Ala Arg Gly Cys Phe Gly Asn Glu Gln Gly Gln Asn Cys Ser
        35                  40                  45

Ala Leu Thr Asp Asn Thr Glu Gly Lys Thr Leu Ala Ser Val Val Lys
    50                  55                  60

Ala Ser Val Phe Arg Gln Leu Gly Val Asn Trp Asp Ile Glu Cys Trp
65                  70                  75                  80

Met Lys Gly Asp Leu Thr Leu Phe Ile Cys His Met Glu Pro Leu Pro
                85                  90                  95

Lys Asn Pro Phe Lys Asn Tyr Asp Ser Lys Val His Leu Leu Tyr Asp
            100                 105                 110

Leu Pro Glu Val Ile Asp Asp Ser Pro Leu Pro Leu Lys Asp Ser
        115                 120                 125

Phe Gln Thr Val Gln Cys Asn Cys Ser Leu Arg Gly Cys Glu Cys His
    130                 135                 140

Val Pro Val Pro Arg Ala Lys Leu Asn Tyr Ala Leu Leu Met Tyr Leu
145                 150                 155                 160

Glu Ile Thr Ser Ala Gly Val Ser Phe Gln Ser Pro Leu Met Ser Leu
                165                 170                 175

Gln Pro Met Leu Val Val Lys Pro Asp Pro Pro Leu Gly Leu His Met
            180                 185                 190

Glu Val Thr Asp Asp Gly Asn Leu Lys Ile Ser Trp Asp Ser Gln Thr
        195                 200                 205

Met Ala Pro Phe Pro Leu Gln Tyr Gln Val Lys Tyr Leu Glu Asn Ser
    210                 215                 220

Thr Ile Val Arg Glu Ala Ala Glu Ile Val Ser Ala Thr Ser Leu Leu
225                 230                 235                 240

Val Asp Ser Val Leu Pro Gly Ser Ser Tyr Glu Val Gln Val Arg Ser
                245                 250                 255

Lys Arg Leu Asp Gly Ser Gly Val Trp Ser Asp Trp Ser Ser Pro Gln
            260                 265                 270

Val Phe Thr Thr Gln Asp Val Val Tyr Phe Pro Pro Lys Ile Leu Thr
        275                 280                 285

Ser Val Gly Ser Asn Ala Ser Phe His Cys Ile Tyr Lys Asn Glu Asn
    290                 295                 300

Gln Ile Ile Ser Ser Lys Gln Ile Val Trp Trp Arg Asn Leu Ala Glu
305                 310                 315                 320

Lys Ile Pro Glu Ile Gln Tyr Ser Ile Val Ser Asp Arg Val Ser Lys
                325                 330                 335

Val Thr Phe Ser Asn Leu Lys Ala Thr Arg Pro Arg Gly Lys Phe Thr
            340                 345                 350

Tyr Asp Ala Val Tyr Cys Cys Asn Glu Gln Ala Cys His His Arg Tyr
        355                 360                 365

Ala Glu Leu Tyr Val Ile Asp Val Asn Ile Asn Ile Ser Cys Glu Thr
    370                 375                 380
```

-continued

```
Asp Gly Tyr Leu Thr Lys Met Thr Cys Arg Trp Ser Pro Ser Thr Ile
385                 390                 395                 400

Gln Ser Leu Val Gly Ser Thr Val Gln Leu Arg Tyr His Arg Ser
            405                 410                 415

Leu Tyr Cys Pro Asp Ser Pro Ser Ile His Pro Thr Ser Glu Pro Lys
            420                 425                 430

Asn Cys Val Leu Gln Arg Asp Gly Phe Tyr Glu Cys Val Phe Gln Pro
            435                 440                 445

Ile Phe Leu Leu Ser Gly Tyr Thr Met Trp Ile Arg Ile Asn His Ser
        450                 455                 460

Leu Gly Ser Leu Asp Ser Pro Pro Thr Cys Val Leu Pro Asp Ser Val
465                 470                 475                 480

Val Lys Pro Leu Pro Pro Ser Asn Val Lys Ala Glu Ile Thr Val Asn
            485                 490                 495

Thr Gly Leu Leu Lys Val Ser Trp Glu Lys Pro Val Phe Pro Glu Asn
            500                 505                 510

Asn Leu Gln Phe Gln Ile Arg Tyr Gly Leu Ser Gly Lys Glu Ile Gln
            515                 520                 525

Trp Lys Thr His Glu Val Phe Asp Ala Lys Ser Lys Ser Ala Ser Leu
        530                 535                 540

Leu Val Ser Asp Leu Cys Ala Val Tyr Val Val Gln Val Arg Cys Arg
545                 550                 555                 560

Arg Leu Asp Gly Leu Gly Tyr Trp Ser Asn Trp Ser Ser Pro Ala Tyr
            565                 570                 575

Thr Leu Val Met Asp Val Lys Val Pro Met Arg Gly Pro Glu Phe Trp
            580                 585                 590

Arg Lys Met Asp Gly Asp Val Thr Lys Lys Glu Arg Asn Val Thr Leu
            595                 600                 605

Leu Trp Lys Pro Leu Thr Lys Asn Asp Ser Leu Cys Ser Val Arg Arg
        610                 615                 620

Tyr Val Val Lys His Arg Thr Ala His Asn Gly Thr Trp Ser Glu Asp
625                 630                 635                 640

Val Gly Asn Arg Thr Asn Leu Thr Phe Leu Trp Thr Glu Pro Ala His
            645                 650                 655

Thr Val Thr Val Leu Ala Val Asn Ser Leu Gly Ala Ser Leu Val Asn
            660                 665                 670

Phe Asn Leu Thr Phe Ser Trp Pro Met Ser Lys Val Ser Ala Val Glu
        675                 680                 685

Ser Leu Ser Ala Tyr Pro Leu Ser Ser Ser Cys Val Ile Leu Ser Trp
        690                 695                 700

Thr Leu Ser Pro Asp Asp Tyr Ser Leu Leu Tyr Leu Val Ile Glu Trp
705                 710                 715                 720

Lys Ile Leu Asn Glu Asp Asp Gly Met Lys Trp Leu Arg Ile Pro Ser
            725                 730                 735

Asn Val Lys Lys Phe Tyr Ile His Asp Asn Phe Ile Pro Ile Glu Lys
            740                 745                 750

Tyr Gln Phe Ser Leu Tyr Pro Val Phe Met Glu Gly Val Gly Lys Pro
        755                 760                 765

Lys Ile Ile Asn Gly Phe Thr Lys Asp Ala Ile Asp Lys Gln Gln Asn
        770                 775                 780

Asp Ala Gly Leu Tyr Val Ile Val Pro Ile Ile Ile Ser Ser Cys Val
785                 790                 795                 800

Leu Leu Leu Gly Thr Leu Leu Ile Ser His Gln Arg Met Lys Lys Leu
```

```
                  805                 810                 815
Phe Trp Asp Asp Val Pro Asn Pro Lys Asn Cys Ser Trp Ala Gln Gly
        820                 825                 830

Leu Asn Phe Gln Lys Arg Thr Asp Thr Leu
        835                 840

<210> SEQ ID NO 3
<211> LENGTH: 2848
<212> TYPE: DNA
<213> ORGANISM: Mus musculus
<220> FEATURE:
<221> NAME/KEY: misc_feature
<222> LOCATION: (44)..(44)
<223> OTHER INFORMATION: N can be A, C, T or G
<220> FEATURE:
<221> NAME/KEY: misc_feature
<222> LOCATION: (67)..(67)
<223> OTHER INFORMATION: N can be A, C, T or G
<220> FEATURE:
<221> NAME/KEY: misc_feature
<222> LOCATION: (234)..(234)
<223> OTHER INFORMATION: N can be A, C, T or G
<220> FEATURE:
<221> NAME/KEY: misc_feature
<222> LOCATION: (483)..(483)
<223> OTHER INFORMATION: N can be A, C, T or G
<220> FEATURE:
<221> NAME/KEY: misc_feature
<222> LOCATION: (527)..(527)
<223> OTHER INFORMATION: N can be A, C, T or G
<220> FEATURE:
<221> NAME/KEY: misc_feature
<222> LOCATION: (564)..(564)
<223> OTHER INFORMATION: N can be A, C, T or G
<220> FEATURE:
<221> NAME/KEY: misc_feature
<222> LOCATION: (1237)..(1237)
<223> OTHER INFORMATION: N can be A, C, T or G
<220> FEATURE:
<221> NAME/KEY: misc_feature
<222> LOCATION: (1335)..(1335)
<223> OTHER INFORMATION: N can be A, C, T or G
<220> FEATURE:
<221> NAME/KEY: misc_feature
<222> LOCATION: (2038)..(2038)
<223> OTHER INFORMATION: N can be A, C, T or G
<220> FEATURE:
<221> NAME/KEY: misc_feature
<222> LOCATION: (2179)..(2179)
<223> OTHER INFORMATION: N can be A, C, T or G
<220> FEATURE:
<221> NAME/KEY: misc_feature
<222> LOCATION: (2182)..(2182)
<223> OTHER INFORMATION: N can be A, C, T or G
<220> FEATURE:
<221> NAME/KEY: misc_feature
<222> LOCATION: (2183)..(2183)
<223> OTHER INFORMATION: N can be A, C, T or G
<220> FEATURE:
<221> NAME/KEY: misc_feature
<222> LOCATION: (2219)..(2219)
<223> OTHER INFORMATION: N can be A, C, T or G
<220> FEATURE:
<221> NAME/KEY: misc_feature
<222> LOCATION: (2576)..(2576)
<223> OTHER INFORMATION: N can be A, C, T or G
<220> FEATURE:
<221> NAME/KEY: misc_feature
<222> LOCATION: (2610)..(2610)
<223> OTHER INFORMATION: N can be A, C, T or G

<400> SEQUENCE: 3
ctcattgaga gtgccaacgg gaaggcttaa ttaacctttg gaantgagtc cgaagagtct      60
ggaagtntgt aagatggaag atactataca agatacttca gagctgtaca ttcttccagg    120
```

```
gatgtaggct agcagttatt tcattagtat atgtctattt tagaatggga agaattagga    180
agatgaatgg agcctgtgtc tttcactact ctcccaggag gttccagaat agcnaaagtg    240
tcagccagaa ttcttgaagt catagactgg agttagagat gaacataagc tcatgttaag    300
cctgggttac ttcttatcat ccttaatttt gaaagctaag agggcctaac catcaagaac    360
gtcctggagg aaagaatgtt tttaacgcca ttattcagtc aaagaaatta agacttgaga    420
gaaatgctca tttcttctct catgatggct ccttacacct tacttctacc gtacgatcca    480
tgnggcccta cccacgcagg atacatgcat ctatatgaga gtgtctnccc cttctaactc    540
agagactctt gttctagtct gtgntataaa attcagcttg tggaagcttt ctgaggggtt    600
ggcagcattc aattttacct gcaataggta aaggtaatct tttgggaagt gaagagtgtt    660
attagacatt tcagaaagaa caaacaggat tggggctgct atgtgttcta cacaggaatc    720
ttccataaca cagaataatt tatgtagata gagacaagat ggaaatgccc agggccccaa    780
aatagccgct gttatttgtt aaccttcaag gttttctgtt tgtttatctg tttcttgcgc    840
aggatcatct tccaagcaca tcctggggga acagtggcag agtcactcga gttcatgaaa    900
ctatggtgac atctgagctt ccttggttct tcacagaaca taagcagttc ctttgcttgc    960
ttgttagatg agaaaacttc cttgtcagtc tgtctctacg actagaatgg aaagccttac   1020
tacttcctat gtattcttaa tatttcaaat gtcctaatta tgtttggctt ctctgtcttt   1080
aagggattta gtctctggat ttgaagaaat aaataaataa ataaaggaaa actaattttc   1140
tcgtgccgga tgactgctag ctgagctcag gcctactgca ttctacattt cgactctctc   1200
cctcttcccc agtgctttag cactggactg ggcagtncct ggcctggtct aactcctgtt   1260
tcctggtggg aatgtataat aagaactcca tgagttctgg tataaacact gtggtctgtg   1320
tgctaattaa atctngtgtt tcctacagcc cctgacgaaa atgactcac tgtgtagtgt    1380
gaggaggtac gtggtgaagc atcgtactgc ccacaatggg acgtggtcag aagatgtggg   1440
aaatcggacc aatctcactt tcctgtggac agaaccagcg cacactgtta cagttctggc   1500
tgtcaattcc ctcggcgctt cccttgtgaa ttttaacctt accttctcat ggcccatgag   1560
taaagtgagt gctgtggagt cactcagtgc ttatcccctg agcagcagct gtgtcatcct   1620
ttcctggaca ctgtcacctg atgattatag tctgttatat ctggttattg aatggaagat   1680
ccttaatgaa gatgatggaa tgaagtggct tagaattccc tcgaatgtta aaaagttttta  1740
tatccacgat aattttattc ccatcgagaa atatcagttt agtctttacc cagtatttat   1800
ggaaggagtt ggaaaaccaa agataattaa tggtttcacc aaagatgcta tcgacaagca   1860
gcagaatgac gcagggctgt atgtcattgt acccataatt atttcctctt gtgtcctact   1920
gctcggaaca ctgttaattt cacaccagag aatgaaaaag ttgttttggg acgatgttcc   1980
aaacccccaag aattgttcct gggcacaagg actgaatttc caaaagcctg aaacattnga  2040
gcatcttttt accaagcatg cagaatcagt gatatttggt cctcttcttc tggagcctga   2100
acccatttca gaagaaatca gtgtcgatac agcttggaaa aataaagatg agatggtccc   2160
agcagctatg gtctccctnc tnnggaccac accagaccct gaaagcagtt ctatttgtnt   2220
tagtgaccag tgtaacagtg ctaacttctc tgggtctcag agcacccagg taacctgtga   2280
ggatgagtgt cagagacaac cctcagttaa atatgcaact ctggtcagca acgataaact   2340
agtggaaact gatgaagagc aagggtttat ccatagtcct gtcagcaact gcatctccag   2400
taatcattcc ccactgaggc agtctttctc tagcagctcc tgggagacag aggcccagac   2460
```

```
atttttcctt ttatcagacc agcaacccac catgatttca ccacaacttt cattctcggg    2520
gttggatgag cttttggaac tggagggaag ttttcctgaa gaaaatcaca gggagnagtc    2580
tgtctgttat ctaggagtca cctccgtccn cagaagagag agtggtgtgc ttttgactgg    2640
tgaggcagga atcctgtgca cattcccagc ccagtgtctg ttcagtgaca tcaggatcct    2700
ccaggagaga tgctcacact ttgtagaaaa taatttgagt ttagggacct ctggtgagaa    2760
ctttggtcct aacatgcccc aattccaaac ctgttccacg cacagtcaca agataatgga    2820
gaataagatg tgtgacttaa ctgtgtaa                                       2848
```

<210> SEQ ID NO 4
<211> LENGTH: 582
<212> TYPE: PRT
<213> ORGANISM: Mus musculus
<220> FEATURE:
<221> NAME/KEY: MISC_FEATURE
<222> LOCATION: (79)..(79)
<223> OTHER INFORMATION: X can be any amino acid

<400> SEQUENCE: 4

```
Leu Arg Asp Leu Val Ser Gly Phe Glu Glu Ile Asn Lys Ile Lys Glu
1               5                   10                  15

Asn Phe Ser Arg Ala Gly Leu Leu Ala Glu Leu Arg Pro Thr Ala Phe
            20                  25                  30

Tyr Ile Ser Thr Leu Ser Leu Phe Pro Ser Ala Leu Ala Leu Asp Trp
        35                  40                  45

Ala Val Pro Gly Leu Val Leu Leu Phe Pro Gly Gly Asn Val Glu Leu
    50                  55                  60

His Glu Phe Trp Tyr Lys His Cys Gly Leu Cys Ala Asn Ile Xaa Cys
65                  70                  75                  80

Phe Leu Gln Pro Leu Thr Lys Asn Asp Ser Leu Cys Ser Val Arg Arg
                85                  90                  95

Tyr Val Val Lys His Arg Thr Ala His Asn Gly Thr Trp Ser Glu Asp
            100                 105                 110

Val Gly Asn Arg Thr Asn Leu Thr Phe Leu Trp Thr Glu Pro Ala His
        115                 120                 125

Thr Val Thr Val Leu Ala Val Asn Ser Leu Gly Ala Ser Leu Val Asn
    130                 135                 140

Phe Asn Leu Thr Phe Ser Trp Pro Met Ser Lys Val Ser Ala Val Glu
145                 150                 155                 160

Ser Leu Ser Ala Tyr Pro Leu Ser Ser Cys Val Ile Leu Ser Trp
                165                 170                 175

Thr Leu Ser Pro Asp Asp Tyr Ser Leu Leu Tyr Leu Val Ile Glu Trp
            180                 185                 190

Lys Ile Leu Asn Glu Asp Asp Gly Met Lys Trp Leu Arg Ile Pro Ser
        195                 200                 205

Asn Val Lys Lys Phe Tyr Ile His Asp Asn Phe Ile Pro Ile Glu Lys
    210                 215                 220

Tyr Gln Phe Ser Leu Tyr Pro Val Phe Met Glu Gly Val Gly Lys Pro
225                 230                 235                 240

Lys Ile Ile Asn Gly Phe Thr Lys Asp Ala Ile Asp Lys Gln Gln Asn
                245                 250                 255

Asp Ala Gly Leu Tyr Val Ile Val Pro Ile Ile Ile Ser Ser Cys Val
            260                 265                 270

Leu Leu Leu Gly Thr Leu Leu Ile Ser His Gln Arg Met Lys Lys Leu
        275                 280                 285
```

Phe Trp Asp Asp Val Pro Asn Pro Lys Asn Cys Ser Trp Ala Gln Gly
    290                 295                 300

Leu Asn Phe Gln Lys Pro Glu Thr Phe Glu Gln Leu Phe Thr Lys His
305                 310                 315                 320

Ala Glu Ser Val Ile Phe Gly Pro Leu Leu Leu Glu Pro Glu Pro Ile
                325                 330                 335

Ser Glu Glu Ile Ser Val Asp Thr Ala Trp Lys Asn Lys Asp Glu Met
            340                 345                 350

Val Pro Ala Ala Met Val Ser Leu Leu Leu Thr Thr Pro Asp Pro Glu
        355                 360                 365

Ser Ser Ser Ile Cys Ile Ser Asp Gln Cys Asn Ser Ala Asn Phe Ser
    370                 375                 380

Gly Ser Gln Ser Thr Gln Val Thr Cys Glu Asp Cys Gln Arg Gln
385                 390                 395                 400

Pro Ser Val Lys Tyr Ala Thr Leu Val Ser Asn Asp Lys Leu Val Glu
                405                 410                 415

Thr Asp Glu Glu Gln Gly Phe Ile His Ser Pro Val Ser Asn Cys Ile
            420                 425                 430

Ser Ser Asn His Ser Pro Leu Arg Gln Ser Phe Ser Ser Ser Ser Trp
        435                 440                 445

Glu Thr Glu Ala Gln Thr Phe Phe Leu Leu Ser Asp Gln Gln Pro Thr
    450                 455                 460

Met Ile Ser Pro Gln Leu Ser Phe Ser Gly Leu Asp Glu Leu Leu Glu
465                 470                 475                 480

Leu Glu Gly Ser Phe Pro Glu Glu Asn His Arg Glu Lys Ser Val Cys
                485                 490                 495

Tyr Leu Gly Val Thr Ser Val Asn Arg Arg Glu Ser Gly Val Leu Leu
            500                 505                 510

Thr Gly Glu Ala Gly Ile Leu Cys Thr Phe Pro Ala Gln Cys Leu Phe
        515                 520                 525

Ser Asp Ile Arg Ile Leu Gln Glu Arg Cys Ser His Phe Val Glu Asn
    530                 535                 540

Asn Leu Ser Leu Gly Thr Ser Gly Glu Asn Phe Val Pro Tyr Met Pro
545                 550                 555                 560

Gln Phe Gln Thr Cys Ser Thr His Ser His Lys Ile Met Glu Asn Lys
                565                 570                 575

Met Cys Asp Leu Thr Val
            580

<210> SEQ ID NO 5
<211> LENGTH: 961
<212> TYPE: DNA
<213> ORGANISM: Mus musculus
<220> FEATURE:
<221> NAME/KEY: misc_feature
<222> LOCATION: (160)..(160)
<223> OTHER INFORMATION: N can be A, C, T or G
<220> FEATURE:
<221> NAME/KEY: misc_feature
<222> LOCATION: (258)..(258)
<223> OTHER INFORMATION: N can be A, C, T or G

<400> SEQUENCE: 5
tttaagggat ttagtctctg gatttgaaga aataaataaa taaataaagg aaaactaatt    60
ttctcgtgcc ggatgactgc tagctgagct caggcctact gcattctaca tttcgactct   120
ctccctcttc cccagtgctt tagcactgga ctgggcagtn cctggcctgg tctaactcct   180

```
gtttcctggt gggaatgtat aataagaact ccatgagttc tggtataaac actgtggtct      240
gtgtgctaat taaatctngt gtttcctaca gcccctgacg aaaaatgact cactgtgtag      300
tgtgaggagg tacgtggtga agcatcgtac tgcccacaat gggacgtggt cagaagatgt      360
gggaaatcgg accaatctca ctttcctgtg acagaacca gcgcacactg ttacagttct       420
ggctgtcaat tccctcggcg cttcccttgt gaattttaac cttaccttct catgcccat       480 gagtaaagtg agtgctgtgg agtcactcag tgcttatccc ctgagcagca gctgtgtcat      540
cctttcctgg acactgtcac ctgatgatta gtctgttta tatctggtta ttgaatggaa       600
gatccttaat gaagatgatg gaatgaagtg gcttagaatt ccctcgaatg ttaaaaagtt      660
ttatatccac gataatttta ttcccatcga gaaatatcag tttagtcttt acccagtatt      720
tatggaagga gttggaaaac caaagataat taatggtttc accaaagatg ctatcgacaa      780
gcagcagaat gacgcagggc tgtatgtcat tgtacccata attatttcct cttgtgtcct      840
actgctcgga acactgttaa tttcacacca gagaatgaaa aagttgtttt gggacgatgt      900
tccaaacccc aagaattgtt cctgggcaca aggactgaat ttccaaaagg tcactgttta      960
a                                                                      961
```

<210> SEQ ID NO 6
<211> LENGTH: 319
<212> TYPE: PRT
<213> ORGANISM: Mus musculus
<220> FEATURE:
<221> NAME/KEY: MISC_FEATURE
<222> LOCATION: (14)..(14)
<223> OTHER INFORMATION: X can be any amino acid
<220> FEATURE:
<221> NAME/KEY: MISC_FEATURE
<222> LOCATION: (19)..(19)
<223> OTHER INFORMATION: X can be any amino acid
<220> FEATURE:
<221> NAME/KEY: MISC_FEATURE
<222> LOCATION: (25)..(25)
<223> OTHER INFORMATION: X can be any amino acid
<220> FEATURE:
<221> NAME/KEY: MISC_FEATURE
<222> LOCATION: (58)..(58)
<223> OTHER INFORMATION: X can be any amino acid
<220> FEATURE:
<221> NAME/KEY: MISC_FEATURE
<222> LOCATION: (67)..(67)
<223> OTHER INFORMATION: X can be any amino acid
<220> FEATURE:
<221> NAME/KEY: MISC_FEATURE
<222> LOCATION: (68)..(68)
<223> OTHER INFORMATION: X can be any amino acid
<220> FEATURE:
<221> NAME/KEY: MISC_FEATURE
<222> LOCATION: (84)..(84)
<223> OTHER INFORMATION: X can be any amino acid
<220> FEATURE:
<221> NAME/KEY: MISC_FEATURE
<222> LOCATION: (86)..(86)
<223> OTHER INFORMATION: X can be any amino acid

<400> SEQUENCE: 6

```
Leu Arg Asp Leu Val Ser Gly Phe Glu Glu Ile Asn Lys Xaa Ile Lys
1               5                   10                  15

Glu Asn Xaa Phe Ser Arg Ala Gly Xaa Leu Leu Ala Glu Leu Arg Pro
            20                  25                  30

Thr Ala Phe Tyr Ile Ser Thr Leu Ser Leu Phe Pro Ser Ala Leu Ala
        35                  40                  45

Leu Asp Trp Ala Val Pro Gly Leu Val Xaa Leu Leu Phe Pro Gly Gly
```

```
                50                  55                  60
Asn Val Xaa Xaa Glu Leu His Glu Phe Trp Tyr Lys His Cys Gly Leu
 65                  70                  75                  80

Cys Ala Asn Xaa Ile Xaa Cys Phe Leu Gln Pro Leu Thr Lys Asn Asp
                 85                  90                  95

Ser Leu Cys Ser Val Arg Arg Tyr Val Val Lys His Arg Thr Ala His
            100                 105                 110

Asn Gly Thr Trp Ser Glu Asp Val Gly Asn Arg Thr Asn Leu Thr Phe
        115                 120                 125

Leu Trp Thr Glu Pro Ala His Thr Val Thr Val Leu Ala Val Asn Ser
130                 135                 140

Leu Gly Ala Ser Leu Val Asn Phe Asn Leu Thr Phe Ser Trp Pro Met
145                 150                 155                 160

Ser Lys Val Ser Ala Val Glu Ser Leu Ser Ala Tyr Pro Leu Ser Ser
                165                 170                 175

Ser Cys Val Ile Leu Ser Trp Thr Leu Ser Pro Asp Asp Tyr Ser Leu
            180                 185                 190

Leu Tyr Leu Val Ile Glu Trp Lys Ile Leu Asn Glu Asp Asp Gly Met
        195                 200                 205

Lys Trp Leu Arg Ile Pro Ser Asn Val Lys Lys Phe Tyr Ile His Asp
210                 215                 220

Asn Phe Ile Pro Ile Glu Lys Tyr Gln Phe Ser Leu Tyr Pro Val Phe
225                 230                 235                 240

Met Glu Gly Val Gly Lys Pro Lys Ile Ile Asn Gly Phe Thr Lys Asp
                245                 250                 255

Ala Ile Asp Lys Gln Gln Asn Asp Ala Gly Leu Tyr Val Ile Val Pro
            260                 265                 270

Ile Ile Ile Ser Ser Cys Val Leu Leu Leu Gly Thr Leu Leu Ile Ser
        275                 280                 285

His Gln Arg Met Lys Lys Leu Phe Trp Asp Asp Val Pro Asn Pro Lys
290                 295                 300

Asn Cys Ser Trp Ala Gln Gly Leu Asn Phe Gln Lys Val Thr Val
305                 310                 315

<210> SEQ ID NO 7
<211> LENGTH: 2703
<212> TYPE: DNA
<213> ORGANISM: Mus musculus

<400> SEQUENCE: 7
atgatgtgtc agaaattcta tgtggttttg ttacactggg aatttcttta tgtgatagct      60
gcacttaacc tggcatatcc aatctctccc tggaaattta gttgttttg tggaccaccg      120 aacacaaccg atgactcctt tctctcacct gctggagccc caaacaatgc ctcggctttg     180
aaggggcttt ctgaagcaat tgttgaagct aaatttaatt caagtggtat ctacgttcct     240
gagttatcca aaacagtctt ccactgttgc tttgggaatg agcaaggtca aaactgctct     300
gcactcacag acaacactga agggaagaca ctggcttcag tagtgaaggc ttcagttttt     360
cgccagctag gtgtaaactg ggacatagag tgctggatga aggggacttt gacattattc     420
atctgtcata tggagccatt acctaagaac cccttcaaga attatgactc taaggtccat     480 ctttttatatg atctgcctga agtcatagat gattcgcctc tgcccccact gaaagacagc     540
tttcagactg tccaatgcaa ctgcagtctt cggggatgtg aatgtcatgt gccggtaccc     600
agagccaaac tcaactacgc tcttctgatg tatttggaaa tcacatctgc cggtgtgagt     660
```

-continued

```
tttcagtcac ctctgatgtc actgcagccc atgcttgttg tgaaacccga tccacccttc      720
ggtttgcata tggaagtcac agatgatggt aatttaaaga tttcttggga cagccaaaca      780
atggcaccat ttccgcttca atatcaggtg aaatatttag agaattctac aattgtaaga      840
gaggctgctg aaattgtctc agctacatct ctgctggtag acagtgtgct tcctggatct      900
tcatatgagg tccaggtgag gagcaagaga ctggatggtt caggagtctg gagtgactgg      960
agttcacctc aagtctttac cacacaagat gttgtgtatt ttccacccaa aattctgact     1020
agtgttggat cgaatgcttc ttttcattgc atctacaaaa acgaaaacca gattatctcc     1080
tcaaaacaga tagtttggtg gaggaatcta gctgagaaaa tccctgagat acagtacagc     1140
attgtgagtg accgagttag caaagttacc ttctccaacc tgaaagccac cagacctcga     1200
gggaagttta cctatgacgc agtgtactgc tgcaatgagc aggcgtgcca tcaccgctat     1260
gctgaattat acgtgatcga tgtcaatatc aatatatcat gtgaaactga cgggtactta     1320
actaaaatga cttgcagatg gtcacccagc acaatccaat cactagtggg aagcactgtg     1380
cagctgaggt atcacaggcg cagcctgtat tgtcctgata gtccatctat tcatcctacg     1440
tctgagccca aaaactgcgt cttacagaga gacggctttt atgaatgtgt tttccagcca     1500
atctttctat tatctggcta tacaatgtgg atcaggatca accattcttt aggttcactt     1560
gactcgccac caacgtgtgt ccttcctgac tccgtagtaa aaccactacc tccatctaac     1620
gtaaaagcag agattactgt aaacactgga ttattgaaag tatcttggga aaagccagtc     1680
tttccggaga ataaccttca attccagatt cgatatggct taagtggaaa agaaatacaa     1740
tggaagacac atgaggtatt cgatgcaaag tcaaagtctg ccagcctgct ggtgtcagac     1800
ctctgtgcag tctatgtggt ccaggttcgc tgccggcggt tggatggact aggatattgg     1860
agtaattgga gcagtccagc ctatacgctt gtcatggatg taaaagttcc tatgagaggg     1920
cctgaattt ggagaaaaat ggatggggac gttactaaaa aggagagaaa tgtcaccttg      1980
ctttggaagc ccctgacgaa aaatgactca ctgtgtagtg tgaggaggta cgtggtgaag     2040
catcgtactg cccacaatgg gacgtggtca gaagatgtgg gaaatcggac caatctcact     2100
ttcctgtgga cagaaccagc gcacactgtt acagttctgg ctgtcaattc cctcggcgct     2160
tcccttgtga atttaacct taccttctca tggcccatga gtaaagtgag tgctgtggag      2220
tcactcagtg cttatcccct gagcagcagc tgtgtcatcc tttcctggac actgtcacct     2280
gatgattata gtctgttata tctggttatt gaatggaaga tccttaatga agatgatgga     2340
atgaagtggc ttagaattcc ctcgaatgtt aaaaagtttt atatccacga taatttatt      2400
cccatcgaga aatatcagtt tagtctttac ccagtattta tggaaggagt tggaaaacca     2460
aagataatta atggtttcac caaagatgct atcgacaagc agcagaatga cgcagggctg     2520
tatgtcattg tacccataat tatttcctct tgtgtcctac tgctcggaac actgttaatt     2580
tcacaccaga gaatgaaaaa gttgttttgg gacgatgttc caaaccccaa gaattgttcc     2640
tgggcacaag gactgaattt ccaaaaggat atatctttac atgaagtttt tatttcaga      2700
tag                                                                   2703
```

<210> SEQ ID NO 8
<211> LENGTH: 900
<212> TYPE: PRT
<213> ORGANISM: Mus musculus

<400> SEQUENCE: 8

-continued

```
Met Met Cys Gln Lys Phe Tyr Val Val Leu Leu His Trp Glu Phe Leu
1               5                   10                  15

Tyr Val Ile Ala Ala Leu Asn Leu Ala Tyr Pro Ile Ser Pro Trp Lys
                20                  25                  30

Phe Lys Leu Phe Cys Gly Pro Pro Asn Thr Thr Asp Asp Ser Phe Leu
            35                  40                  45

Ser Pro Ala Gly Ala Pro Asn Asn Ala Ser Ala Leu Lys Gly Ala Ser
50                      55                      60

Glu Ala Ile Val Glu Ala Lys Phe Asn Ser Ser Gly Ile Tyr Val Pro
65                      70                      75                  80

Glu Leu Ser Lys Thr Val Phe His Cys Cys Phe Gly Asn Glu Gln Gly
                85                  90                  95

Gln Asn Cys Ser Ala Leu Thr Asp Asn Thr Glu Gly Lys Thr Leu Ala
            100                 105                 110

Ser Val Val Lys Ala Ser Val Phe Arg Gln Leu Gly Val Asn Trp Asp
            115                 120                 125

Ile Glu Cys Trp Met Lys Gly Asp Leu Thr Leu Phe Ile Cys His Met
            130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Asp Ser Pro Leu Pro Pro
                165                 170                 175

Leu Lys Asp Ser Phe Gln Thr Val Gln Cys Asn Cys Ser Leu Arg Gly
            180                 185                 190

Cys Glu Cys His Val Pro Val Pro Arg Ala Lys Leu Asn Tyr Ala Leu
            195                 200                 205

Leu Met Tyr Leu Glu Ile Thr Ser Ala Gly Val Ser Phe Gln Ser Pro
210                 215                 220

Leu Met Ser Leu Gln Pro Met Leu Val Val Lys Pro Asp Pro Pro Leu
225                 230                 235                 240

Gly Leu His Met Glu Val Thr Asp Asp Gly Asn Leu Lys Ile Ser Trp
                245                 250                 255

Asp Ser Gln Thr Met Ala Pro Phe Pro Leu Gln Tyr Gln Val Lys Tyr
            260                 265                 270

Leu Glu Asn Ser Thr Ile Val Arg Glu Ala Ala Glu Ile Val Ser Ala
            275                 280                 285

Thr Ser Leu Leu Val Asp Ser Val Leu Pro Gly Ser Ser Tyr Glu Val
            290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro
                325                 330                 335

Lys Ile Leu Thr Ser Val Gly Ser Asn Ala Ser Phe His Cys Ile Tyr
            340                 345                 350

Lys Asn Glu Asn Gln Ile Ile Ser Ser Lys Gln Ile Val Trp Trp Arg
            355                 360                 365

Asn Leu Ala Glu Lys Ile Pro Glu Ile Gln Tyr Ser Ile Val Ser Asp
            370                 375                 380

Arg Val Ser Lys Val Thr Phe Ser Asn Leu Lys Ala Thr Arg Pro Arg
385                 390                 395                 400

Gly Lys Phe Thr Tyr Asp Ala Val Tyr Cys Cys Asn Glu Gln Ala Cys
            405                 410                 415

His His Arg Tyr Ala Glu Leu Tyr Val Ile Asp Val Asn Ile Asn Ile
```

-continued

```
                420             425             430
Ser Cys Glu Thr Asp Gly Tyr Leu Thr Lys Met Thr Cys Arg Trp Ser
            435                 440                 445

Pro Ser Thr Ile Gln Ser Leu Val Gly Ser Thr Val Gln Leu Arg Tyr
        450                 455                 460

His Arg Arg Ser Leu Tyr Cys Pro Asp Ser Pro Ser Ile His Pro Thr
465                 470                 475                 480

Ser Glu Pro Lys Asn Cys Val Leu Gln Arg Asp Gly Phe Tyr Glu Cys
                485                 490                 495

Val Phe Gln Pro Ile Phe Leu Leu Ser Gly Tyr Thr Met Trp Ile Arg
            500                 505                 510

Ile Asn His Ser Leu Gly Ser Leu Asp Ser Pro Thr Cys Val Leu
            515                 520                 525

Pro Asp Ser Val Val Lys Pro Leu Pro Pro Ser Asn Val Lys Ala Glu
        530                 535                 540

Ile Thr Val Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Ser Gly
                565                 570                 575

Lys Glu Ile Gln Trp Lys Thr His Glu Val Phe Asp Ala Lys Ser Lys
            580                 585                 590

Ser Ala Ser Leu Leu Val Ser Asp Leu Cys Ala Val Tyr Val Val Gln
        595                 600                 605

Val Arg Cys Arg Arg Leu Asp Gly Leu Gly Tyr Trp Ser Asn Trp Ser
610                 615                 620

Ser Pro Ala Tyr Thr Leu Val Met Asp Val Lys Val Pro Met Arg Gly
625                 630                 635                 640

Pro Glu Phe Trp Arg Lys Met Asp Gly Asp Val Thr Lys Lys Glu Arg
                645                 650                 655

Asn Val Thr Leu Leu Trp Lys Pro Leu Thr Lys Asn Asp Ser Leu Cys
            660                 665                 670

Ser Val Arg Arg Tyr Val Val Lys His Arg Thr Ala His Asn Gly Thr
        675                 680                 685

Trp Ser Glu Asp Val Gly Asn Arg Thr Asn Leu Thr Phe Leu Trp Thr
690                 695                 700

Glu Pro Ala His Thr Val Thr Val Leu Ala Val Asn Ser Leu Gly Ala
705                 710                 715                 720

Ser Leu Val Asn Phe Asn Leu Thr Phe Ser Trp Pro Met Ser Lys Val
                725                 730                 735

Ser Ala Val Glu Ser Leu Ser Ala Tyr Pro Leu Ser Ser Ser Cys Val
            740                 745                 750

Ile Leu Ser Trp Thr Leu Ser Pro Asp Asp Tyr Ser Leu Leu Tyr Leu
        755                 760                 765

Val Ile Glu Trp Lys Ile Leu Asn Glu Asp Asp Gly Met Lys Trp Leu
770                 775                 780

Arg Ile Pro Ser Asn Val Lys Lys Phe Tyr Ile His Asp Asn Phe Ile
785                 790                 795                 800

Pro Ile Glu Lys Tyr Gln Phe Ser Leu Tyr Pro Val Phe Met Glu Gly
                805                 810                 815

Val Gly Lys Pro Lys Ile Ile Asn Gly Phe Thr Lys Asp Ala Ile Asp
            820                 825                 830

Lys Gln Gln Asn Asp Ala Gly Leu Tyr Val Ile Val Pro Ile Ile Ile
        835                 840                 845
```

```
Ser Ser Cys Val Leu Leu Gly Thr Leu Leu Ile Ser His Gln Arg
    850                 855                 860
Met Lys Lys Leu Phe Trp Asp Asp Val Pro Asn Pro Lys Asn Cys Ser
865                 870                 875                 880
Trp Ala Gln Gly Leu Asn Phe Gln Lys Asp Ile Ser Leu His Glu Val
                885                 890                 895
Phe Ile Phe Arg
            900

<210> SEQ ID NO 9
<211> LENGTH: 2461
<212> TYPE: DNA
<213> ORGANISM: Mus musculus

<400> SEQUENCE: 9
```

| | | | | | |
|---|---|---|---|---|---|
| gaggaatcgt | tctgcaaatc | caggtgtaca | cctctgaaga | aagatgatgt | gtcagaaatt | 60 |
| ctatgtggtt | ttgttacact | gggaatttct | ttatgtgata | gctgcactta | acctggcata | 120 |
| tccaatctct | ccctggaaat | ttaagttgtt | ttgtggacca | ccgaacacaa | ccgatgactc | 180 |
| ctttctctca | cctgctggag | ccccaaacaa | tgcctcggct | ttgaagggg | cttctgaagc | 240 |
| aattgttgaa | gctaaattta | attcaagtgg | tatctacgtt | cctgagttat | ccaaaacagt | 300 |
| cttccactgt | tgctttggga | tgagcaagg | tcaaaactgc | tctgcactca | cagacaacac | 360 |
| tgaagggaag | acactggctt | cagtagtgaa | ggcttcagtt | tttcgccagc | taggtgtaaa | 420 |
| ctgggacata | gagtgctgga | tgaaggggga | cttgacatta | ttcatctgtc | atatggagcc | 480 |
| attacctaag | aaccccttca | gaattatga | ctctaaggtc | catcttttat | atgatctgcc | 540 |
| tgaagtcata | gatgattcgc | tctgccccc | actgaaagac | agctttcaga | ctgtccaatg | 600 |
| caactgcagt | cttcggggat | gtgaatgtca | tgtgccggta | cccagagcca | aactcaacta | 660 |
| cgctcttctg | atgtatttgg | aaatcacatc | tgccggtgtg | agttttcagt | cacctctgat | 720 |
| gtcactgcag | cccatgcttg | ttgtgaaacc | cgatccaccc | ttaggtttgc | atatggaagt | 780 |
| cacagatgat | ggtaatttaa | agatttcttg | ggacagccaa | acaatggcac | catttccgct | 840 |
| tcaatatcag | gtgaaatatt | tagagaattc | tacaattgta | agagaggctg | ctgaaattgt | 900 |
| ctcagctaca | tctctgctgg | tagacagtgt | gcttcctgga | tcttcatatg | aggtccaggt | 960 |
| gaggagcaag | agactggatg | gttcaggagt | ctggagtgac | tggagttcac | ctcaagtctt | 1020 |
| taccacacaa | gatgttgtgt | attttccacc | caaaattctg | actagtgttg | gatcgaatgc | 1080 |
| ttcttttcat | tgcatctaca | aaaacgaaaa | ccagattatc | tcctcaaaac | agatagtttg | 1140 |
| gtggaggaat | ctagctgaga | aaatccctga | gatacagtac | agcattgtga | gtgaccgagt | 1200 |
| tagcaaagtt | accttctcca | acctgaaagc | caccagacct | cgagggaagt | ttacctatga | 1260 |
| cgcagtgtac | tgctgcaatg | agcaggcgtg | ccatcaccgc | tatgctgaat | atacgtgat | 1320 |
| cgatgtcaat | atcaatatat | catgtgaaac | tgacgggtac | ttaactaaaa | tgacttgcag | 1380 |
| atggtcaccc | agcacaatcc | aatcactagt | gggaagcact | gtgcagctga | ggtatcacag | 1440 |
| gcgcagcctg | tattgtcctg | atagtccatc | tattcatcct | acgtctgagc | ccaaaaactg | 1500 |
| cgtcttacag | agagacggct | tttatgaatg | tgttttccag | ccaatctttc | tattatctgg | 1560 |
| ctatacaatg | tggatcagga | tcaaccattc | tttaggttca | cttgactcgc | caccaacgtg | 1620 |
| tgtccttcct | gactccgtag | taaaaccact | acctccatct | aacgtaaaag | cagagattac | 1680 |
| tgtaaacact | ggattattga | agtatcttg | ggaaaagcca | gtctttccgg | agaataacct | 1740 |

-continued

```
tcaattccag attcgatatg gcttaagtgg aaaagaaata caatggaaga cacatgaggt    1800
attcgatgca aagtcaaagt ctgccagcct gctggtgtca gacctctgtg cagtctatgt    1860
ggtccaggtt cgctgccggc ggttggatgg actaggatat tggagtaatt ggagcagtcc    1920
agcctatacg cttgtcatgg atgtaaaagt tcctatgaga gggcctgaat tttggagaaa    1980
aatggatggg gacgttacta aaaggagag aaatgtcacc ttgctttgga agcccctgac     2040
gaaaaatgac tcactgtgta gtgtgaggag gtacgtggtg aagcatcgta ctgcccacaa    2100
tgggacgtgg tcagaagatg tgggaaatcg gaccaatctc actttcctgt ggacagaacc    2160
agcgcacact gttacagttc tggctgtcaa ttccctcggc gcttcccttg tgaattttaa    2220
ccttaccttc tcatggccca tgagtaaagt gagtgctgtg gagtcactca gtgcttatcc    2280
cctgagcagc agctgtgtca tcctttcctg gacactgtca cctgatgatt atagtctgtt    2340
atatctggtt attgaatgga agatccttaa tgaagatgat ggaatgaagt ggcttagaat    2400
tccctcgaat gttaaaaagt tttatatcca cggtatgtgt actgtacttt tcatggatta    2460
g                                                                   2461
```

<210> SEQ ID NO 10
<211> LENGTH: 805
<212> TYPE: PRT
<213> ORGANISM: Mus musculus

<400> SEQUENCE: 10

```
Met Met Cys Gln Lys Phe Tyr Val Val Leu Leu His Trp Glu Phe Leu
  1               5                  10                  15

Tyr Val Ile Ala Ala Leu Asn Leu Ala Tyr Pro Ile Ser Pro Trp Lys
                 20                  25                  30

Phe Lys Leu Phe Cys Gly Pro Pro Asn Thr Thr Asp Asp Ser Phe Leu
             35                  40                  45

Ser Pro Ala Gly Ala Pro Asn Asn Ala Ser Ala Leu Lys Gly Ala Ser
         50                  55                  60

Glu Ala Ile Val Glu Ala Lys Phe Asn Ser Ser Gly Ile Tyr Val Pro
 65                  70                  75                  80

Glu Leu Ser Lys Thr Val Phe His Cys Cys Phe Gly Asn Glu Gln Gly
                 85                  90                  95

Gln Asn Cys Ser Ala Leu Thr Asp Asn Thr Glu Gly Lys Thr Leu Ala
            100                 105                 110

Ser Val Val Lys Ala Ser Val Phe Arg Gln Leu Gly Val Asn Trp Asp
            115                 120                 125

Ile Glu Cys Trp Met Lys Gly Asp Leu Thr Leu Phe Ile Cys His Met
        130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Ser Pro Leu Pro Pro
                165                 170                 175

Leu Lys Asp Ser Phe Gln Thr Val Gln Cys Asn Cys Ser Leu Arg Gly
            180                 185                 190

Cys Glu Cys His Val Pro Val Pro Arg Ala Lys Leu Asn Tyr Ala Leu
        195                 200                 205

Leu Met Tyr Leu Glu Ile Thr Ser Ala Gly Val Ser Phe Gln Ser Pro
    210                 215                 220

Leu Met Ser Leu Gln Pro Met Leu Val Val Lys Pro Asp Pro Pro Leu
225                 230                 235                 240
```

```
Gly Leu His Met Glu Val Thr Asp Asp Gly Asn Leu Lys Ile Ser Trp
                245                 250                 255

Asp Ser Gln Thr Met Ala Pro Phe Pro Leu Gln Tyr Gln Val Lys Tyr
            260                 265                 270

Leu Glu Asn Ser Thr Ile Val Arg Glu Ala Ala Glu Ile Val Ser Ala
        275                 280                 285

Thr Ser Leu Leu Val Asp Ser Val Leu Pro Gly Ser Ser Tyr Glu Val
290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro
                325                 330                 335

Lys Ile Leu Thr Ser Val Gly Ser Asn Ala Ser Phe His Cys Ile Tyr
            340                 345                 350

Lys Asn Glu Asn Gln Ile Ile Ser Ser Lys Gln Ile Val Trp Trp Arg
        355                 360                 365

Asn Leu Ala Glu Lys Ile Pro Glu Ile Gln Tyr Ser Ile Val Ser Asp
370                 375                 380

Arg Val Ser Lys Val Thr Phe Ser Asn Leu Lys Ala Thr Arg Pro Arg
385                 390                 395                 400

Gly Lys Phe Thr Tyr Asp Ala Val Tyr Cys Cys Asn Glu Gln Ala Cys
                405                 410                 415

His His Arg Tyr Ala Glu Leu Tyr Val Ile Asp Val Asn Ile Asn Ile
            420                 425                 430

Ser Cys Glu Thr Asp Gly Tyr Leu Thr Lys Met Thr Cys Arg Trp Ser
        435                 440                 445

Pro Ser Thr Ile Gln Ser Leu Val Gly Ser Thr Val Gln Leu Arg Tyr
450                 455                 460

His Arg Arg Ser Leu Tyr Cys Pro Asp Ser Pro Ser Ile His Pro Thr
465                 470                 475                 480

Ser Glu Pro Lys Asn Cys Val Leu Gln Arg Asp Gly Phe Tyr Glu Cys
                485                 490                 495

Val Phe Gln Pro Ile Phe Leu Leu Ser Gly Tyr Thr Met Trp Ile Arg
            500                 505                 510

Ile Asn His Ser Leu Gly Ser Leu Asp Ser Pro Pro Thr Cys Val Leu
        515                 520                 525

Pro Asp Ser Val Val Lys Pro Leu Pro Pro Ser Asn Val Lys Ala Glu
530                 535                 540

Ile Thr Val Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Ser Gly
                565                 570                 575

Lys Glu Ile Gln Trp Lys Thr His Glu Val Phe Asp Ala Lys Ser Lys
            580                 585                 590

Ser Ala Ser Leu Leu Val Ser Asp Leu Cys Ala Val Tyr Val Val Gln
        595                 600                 605

Val Arg Cys Arg Arg Leu Asp Gly Leu Gly Tyr Trp Ser Asn Trp Ser
610                 615                 620

Ser Pro Ala Tyr Thr Leu Val Met Asp Val Lys Val Pro Met Arg Gly
625                 630                 635                 640

Pro Glu Phe Trp Arg Lys Met Asp Gly Asp Val Thr Lys Lys Glu Arg
                645                 650                 655

Asn Val Thr Leu Leu Trp Lys Pro Leu Thr Lys Asn Asp Ser Leu Cys
```

-continued

```
                660                 665                 670
Ser Val Arg Arg Tyr Val Val Lys His Arg Thr Ala His Asn Gly Thr
        675                 680                 685

Trp Ser Glu Asp Val Gly Asn Arg Thr Asn Leu Thr Phe Leu Trp Thr
        690                 695                 700

Glu Pro Ala His Thr Val Thr Val Leu Ala Val Asn Ser Leu Gly Ala
705                 710                 715                 720

Ser Leu Val Asn Phe Asn Leu Thr Phe Ser Trp Pro Met Ser Lys Val
                725                 730                 735

Ser Ala Val Glu Ser Leu Ser Ala Tyr Pro Leu Ser Ser Ser Cys Val
            740                 745                 750

Ile Leu Ser Trp Thr Leu Ser Pro Asp Asp Tyr Ser Leu Leu Tyr Leu
            755                 760                 765

Val Ile Glu Trp Lys Ile Leu Asn Glu Asp Asp Gly Met Lys Trp Leu
        770                 775                 780

Arg Ile Pro Ser Asn Val Lys Lys Phe Tyr Ile His Gly Met Cys Thr
785                 790                 795                 800

Val Leu Phe Met Asp
                805

<210> SEQ ID NO 11
<211> LENGTH: 9
<212> TYPE: PRT
<213> ORGANISM: Mus musculus

<400> SEQUENCE: 11

Asn Phe Gln Lys Arg Thr Asp Thr Leu
1               5

<210> SEQ ID NO 12
<211> LENGTH: 277
<212> TYPE: PRT
<213> ORGANISM: Mus musculus

<400> SEQUENCE: 12

Asn Phe Gln Lys Pro Glu Thr Phe Glu His Leu Phe Thr Lys His Ala
1               5                   10                  15

Glu Ser Val Ile Phe Gly Pro Leu Leu Leu Glu Pro Glu Pro Ile Ser
            20                  25                  30

Glu Glu Ile Ser Val Asp Thr Ala Trp Lys Asn Lys Asp Glu Met Val
        35                  40                  45

Pro Ala Ala Met Val Ser Leu Leu Thr Thr Pro Asp Pro Glu Ser
    50                  55                  60

Ser Ser Ile Cys Ile Ser Asp Gln Cys Asn Ser Ala Asn Phe Ser Gly
65                  70                  75                  80

Ser Gln Ser Thr Gln Val Thr Cys Glu Asp Glu Cys Gln Arg Gln Pro
                85                  90                  95

Ser Val Lys Tyr Ala Thr Leu Val Ser Asn Asp Lys Leu Val Glu Thr
            100                 105                 110

Asp Glu Glu Gln Gly Phe Ile His Ser Pro Val Ser Asn Cys Ile Ser
        115                 120                 125

Ser Asn His Ser Pro Leu Arg Gln Ser Phe Ser Ser Ser Trp Glu
    130                 135                 140

Thr Glu Ala Gln Thr Phe Phe Leu Leu Ser Asp Gln Gln Pro Thr Met
145                 150                 155                 160

Ile Ser Pro Gln Leu Ser Phe Ser Gly Leu Asp Glu Leu Leu Glu Leu
```

-continued

```
                165                 170                 175
Glu Gly Ser Phe Pro Glu Asn His Arg Glu Lys Ser Val Cys Tyr
            180                 185                 190
Leu Gly Val Thr Ser Val Asn Arg Arg Glu Ser Gly Val Leu Leu Thr
            195                 200                 205
Gly Glu Ala Gly Ile Leu Cys Thr Phe Pro Ala Gln Cys Leu Phe Ser
        210                 215                 220
Asp Ile Arg Ile Leu Gln Arg Cys Ser His Phe Val Glu Asn Asn
225                 230                 235                 240
Leu Ser Leu Gly Thr Ser Gly Glu Asn Phe Val Pro Tyr Met Pro Gln
                245                 250                 255
Phe Gln Thr Cys Ser Thr His Ser His Lys Ile Met Glu Asn Lys Met
            260                 265                 270
Cys Asp Leu Thr Val
        275

<210> SEQ ID NO 13
<211> LENGTH: 7
<212> TYPE: PRT
<213> ORGANISM: Mus musculus

<400> SEQUENCE: 13

Asn Phe Gln Lys Val Thr Val
1               5

<210> SEQ ID NO 14
<211> LENGTH: 15
<212> TYPE: PRT
<213> ORGANISM: Mus musculus

<400> SEQUENCE: 14

Asn Phe Gln Lys Asp Ile Ser Leu His Glu Val Phe Ile Phe Arg
1               5                   10                  15

<210> SEQ ID NO 15
<211> LENGTH: 13
<212> TYPE: PRT
<213> ORGANISM: Mus musculus

<400> SEQUENCE: 15

Phe Tyr Ile His Gly Met Cys Thr Val Leu Phe Met Asp
1               5                   10

<210> SEQ ID NO 16
<211> LENGTH: 8
<212> TYPE: PRT
<213> ORGANISM: Mus musculus

<400> SEQUENCE: 16

Pro Gln Lys Arg Thr Asp Thr Leu
1               5

<210> SEQ ID NO 17
<211> LENGTH: 6
<212> TYPE: PRT
<213> ORGANISM: Mus musculus

<400> SEQUENCE: 17

Pro Gln Lys Pro Glu Thr
1               5
```

-continued

```
<210> SEQ ID NO 18
<211> LENGTH: 12
<212> TYPE: DNA
<213> ORGANISM: Mus musculus

<400> SEQUENCE: 18
gatggaggga aa                                                              12

<210> SEQ ID NO 19
<211> LENGTH: 12
<212> TYPE: DNA
<213> ORGANISM: Mus musculus

<400> SEQUENCE: 19
gatggaggta aa                                                              12

<210> SEQ ID NO 20
<211> LENGTH: 20
<212> TYPE: DNA
<213> ORGANISM: Mus musculus

<400> SEQUENCE: 20
atcttgggtt ctctgaagaa                                                      20

<210> SEQ ID NO 21
<211> LENGTH: 21
<212> TYPE: DNA
<213> ORGANISM: Mus musculus

<400> SEQUENCE: 21
gagattgtca gtcacagcct c                                                    21

<210> SEQ ID NO 22
<211> LENGTH: 23
<212> TYPE: DNA
<213> ORGANISM: Mus musculus

<400> SEQUENCE: 22
atctgaattg gaatcaaata cac                                                  23

<210> SEQ ID NO 23
<211> LENGTH: 22
<212> TYPE: DNA
<213> ORGANISM: Mus musculus

<400> SEQUENCE: 23
aaatctgtta tccttctgaa ac                                                   22

<210> SEQ ID NO 24
<211> LENGTH: 23
<212> TYPE: DNA
<213> ORGANISM: Mus musculus

<400> SEQUENCE: 24
acactgttaa tttcacacca gag                                                  23

<210> SEQ ID NO 25
<211> LENGTH: 24
<212> TYPE: DNA
<213> ORGANISM: Mus musculus

<400> SEQUENCE: 25
agtcattcaa accattagtt tagg                                                 24
```

```
<210> SEQ ID NO 26
<211> LENGTH: 21
<212> TYPE: DNA
<213> ORGANISM: Mus musculus

<400> SEQUENCE: 26
tggataaacc cttgctcttc a                                              21

<210> SEQ ID NO 27
<211> LENGTH: 22
<212> TYPE: DNA
<213> ORGANISM: Mus musculus

<400> SEQUENCE: 27
tgaacacaac aacataaagc cc                                             22

<210> SEQ ID NO 28
<211> LENGTH: 18
<212> TYPE: DNA
<213> ORGANISM: Mus musculus

<400> SEQUENCE: 28
aggctccctc agggccac                                                  18

<210> SEQ ID NO 29
<211> LENGTH: 25
<212> TYPE: DNA
<213> ORGANISM: Mus musculus

<400> SEQUENCE: 29
gtgactgaat gaagatgtaa tatac                                          25

<210> SEQ ID NO 30
<211> LENGTH: 23
<212> TYPE: DNA
<213> ORGANISM: Mus musculus

<400> SEQUENCE: 30
tgttatatct ggttattgaa tgg                                            23

<210> SEQ ID NO 31
<211> LENGTH: 27
<212> TYPE: DNA
<213> ORGANISM: Mus musculus

<400> SEQUENCE: 31
cattaaatga tttattatca gaattgc                                        27

<210> SEQ ID NO 32
<211> LENGTH: 14
<212> TYPE: PRT
<213> ORGANISM: Mus musculus

<400> SEQUENCE: 32

Glu Pro Leu Pro Lys Asn Pro Phe Lys Asn Tyr Asp Ser Lys
1               5                   10

<210> SEQ ID NO 33
<211> LENGTH: 20
<212> TYPE: PRT
<213> ORGANISM: Mus musculus

<400> SEQUENCE: 33
```

His Arg Arg Ser Leu Tyr Cys Pro Asp Ser Pro Ser Ile His Pro Thr
1               5                   10                  15

Ser Glu Pro Lys
            20

<210> SEQ ID NO 34
<211> LENGTH: 19
<212> TYPE: PRT
<213> ORGANISM: Mus musculus

<400> SEQUENCE: 34

Gln Arg Met Lys Lys Leu Phe Trp Asp Asp Val Pro Asn Pro Lys Asn
1               5                   10                  15

Cys Ser Trp

<210> SEQ ID NO 35
<211> LENGTH: 166
<212> TYPE: DNA
<213> ORGANISM: Mus musculus
<220> FEATURE:
<221> NAME/KEY: misc_feature
<222> LOCATION: (5)..(5)
<223> OTHER INFORMATION: N can be A, C, T or G

<400> SEQUENCE: 35
agggnaagcg ccgagggaat tgacagccag aactgtaaca gtgtgcgctg gttctgtcca        60
caggaaagtg agattggtcc gatttcccac atcttctgac cacgtcccat tgtgggcagt       120
acgatgcttc accacgtacc tcctcacact acacagtgag tcattt                      166

<210> SEQ ID NO 36
<211> LENGTH: 320
<212> TYPE: DNA
<213> ORGANISM: Mus musculus

<400> SEQUENCE: 36
ggtgaagcat cgtactgccc acaatgggac gtggtcagaa gatgtgggaa atcggaccaa        60
tctcactttc ctgtggacag aaccagcgca cactgttaca gttctggctg tcaattccct       120
cggcgcttcc cttgtgaatt ttaaccttac cttctcatgg cccatgagta aagtgagtgc       180
tgtggagtca ctcagtgctt atcccctgag cagcagctgt gtcatccttt cctggacact       240
gtcacctgat gattatagtc tgttatatct ggttattgaa tggaagatcc ttaatgaaga       300
tgatggaatg aagtggctta                                                   320

<210> SEQ ID NO 37
<211> LENGTH: 158
<212> TYPE: DNA
<213> ORGANISM: Mus musculus

<400> SEQUENCE: 37
gattactgga gatgcagttg ctgacaggac tatggataaa cccttgctct tcatcagttt        60
ccactagttt atcgttgctg accagagttg catatttaac tgagggttgt ctctgacact       120
catcctcaca ggttacctgg gtgctctgag acccagag                               158

<210> SEQ ID NO 38
<211> LENGTH: 192
<212> TYPE: DNA
<213> ORGANISM: Mus musculus

<400> SEQUENCE: 38
agagagatcc ctgaccctag ttagatctgt tttcaggctc tgtgttcatt tgatgttcag    60
aagtcagcaa ggttctcata tgtcctgagt tagtaagatg tctcagggtt ccccccatcag   120 ctaacaacca ctttgacatg agaaggcaga aagttaaaga acactacttg gtgttttact   180
taaagatacg ag                                                        192

<210> SEQ ID NO 39
<211> LENGTH: 168
<212> TYPE: DNA
<213> ORGANISM: Mus musculus
<220> FEATURE:
<221> NAME/KEY: misc_feature
<222> LOCATION: (55)..(55)
<223> OTHER INFORMATION: N can be A, C, T or G
<220> FEATURE:
<221> NAME/KEY: misc_feature
<222> LOCATION: (62)..(62)
<223> OTHER INFORMATION: N can be A, C, T or G
<220> FEATURE:
<221> NAME/KEY: misc_feature
<222> LOCATION: (72)..(72)
<223> OTHER INFORMATION: N can be A, C, T or G
<220> FEATURE:
<221> NAME/KEY: misc_feature
<222> LOCATION: (143)..(143)
<223> OTHER INFORMATION: N can be A, C, T or G

<400> SEQUENCE: 39
agactgacaa ggaagttttc tcatctaaca agcaagcaaa ggaactgctt atgtnctgtg    60
angaaccaag gnagctcaga tgtcaccata gtcatcatga actcgagtga ctctgccact   120 gttccccag gatgtgcttg gangataatc ctgcgcaaga aacagata                 168

<210> SEQ ID NO 40
<211> LENGTH: 259
<212> TYPE: DNA
<213> ORGANISM: Mus musculus
<220> FEATURE:
<221> NAME/KEY: misc_feature
<222> LOCATION: (83)..(83)
<223> OTHER INFORMATION: N can be A, C, T or G
<220> FEATURE:
<221> NAME/KEY: misc_feature
<222> LOCATION: (101)..(101)
<223> OTHER INFORMATION: N can be A, C, T or G
<220> FEATURE:
<221> NAME/KEY: misc_feature
<222> LOCATION: (181)..(181)
<223> OTHER INFORMATION: N can be A, C, T or G

<400> SEQUENCE: 40
agaattatga ctctaaggtc catctttat atgatctgcc tgaagtcata gatgattcgc    60
ctctgccccc actgaaagac agnttcaga ctgtccaatg naactgcagt cttcggggat   120
gtgaatgtca tgtgccagta cccagagcca aactcaacta cgctcttctg atgtatttgg   180
naatcacatc tgccggtgtg agttttcagt cacctctgat gtcactgcag cccatgcttg   240
ttgtgaaacc cgatccacc                                                259

<210> SEQ ID NO 41
<211> LENGTH: 250
<212> TYPE: DNA
<213> ORGANISM: Mus musculus
<220> FEATURE:
<221> NAME/KEY: misc_feature
<222> LOCATION: (193)..(193)
<223> OTHER INFORMATION: N can be A, C, T or G

<400> SEQUENCE: 41

```
cttcaacaat tggttcagaa gccccttca aagccgaggc attgtttggg gctccagcag      60
gtgagagaaa ggagtcatcg gttgtgttcg gtggtccaca aaacaactta aatttccagg    120
gagagattgg atatgccagg ttaagtgcag ctatcacata aagaaattcc cagtgtaaca    180
aaaccacata gantttctaa cacatcatct ttcttcagag gtgtacacct ggatttgcag    240
aacgattcct                                                           250

<210> SEQ ID NO 42
<211> LENGTH: 18
<212> TYPE: DNA
<213> ORGANISM: Mus musculus

<400> SEQUENCE: 42
ccgagggaat tgacagcc                                                   18

<210> SEQ ID NO 43
<211> LENGTH: 22
<212> TYPE: DNA
<213> ORGANISM: Mus musculus

<400> SEQUENCE: 43
ctcactgtgt agtgtgagga gg                                              22

<210> SEQ ID NO 44
<211> LENGTH: 19
<212> TYPE: DNA
<213> ORGANISM: Mus musculus

<400> SEQUENCE: 44
tcctgtggac agaaccagc                                                  19

<210> SEQ ID NO 45
<211> LENGTH: 19
<212> TYPE: DNA
<213> ORGANISM: Mus musculus

<400> SEQUENCE: 45
tgacacagct gctgctcag                                                  19

<210> SEQ ID NO 46
<211> LENGTH: 20
<212> TYPE: DNA
<213> ORGANISM: Mus musculus

<400> SEQUENCE: 46
ggtctcagag cacccaggta                                                 20

<210> SEQ ID NO 47
<211> LENGTH: 22
<212> TYPE: DNA
<213> ORGANISM: Mus musculus

<400> SEQUENCE: 47
agagagatcc ctgaccctag tt                                              22

<210> SEQ ID NO 48
<211> LENGTH: 26
<212> TYPE: DNA
<213> ORGANISM: Mus musculus

<400> SEQUENCE: 48
```

-continued

```
aactttctgc cttccttctc atgtca                                         26

<210> SEQ ID NO 49
<211> LENGTH: 22
<212> TYPE: DNA
<213> ORGANISM: Mus musculus

<400> SEQUENCE: 49
tttctcatct aacaagcaag ca                                             22

<210> SEQ ID NO 50
<211> LENGTH: 20
<212> TYPE: DNA
<213> ORGANISM: Mus musculus

<400> SEQUENCE: 50
atctgtttct tgcgcaggat                                                20

<210> SEQ ID NO 51
<211> LENGTH: 18
<212> TYPE: DNA
<213> ORGANISM: Mus musculus

<400> SEQUENCE: 51
cattgtttgg ggctccag                                                  18

<210> SEQ ID NO 52
<211> LENGTH: 20
<212> TYPE: DNA
<213> ORGANISM: Mus musculus

<400> SEQUENCE: 52
aatcgttctg caaatccagg                                                20

<210> SEQ ID NO 53
<211> LENGTH: 21
<212> TYPE: DNA
<213> ORGANISM: Mus musculus

<400> SEQUENCE: 53
tgaagtcata gatgattcgc c                                              21

<210> SEQ ID NO 54
<211> LENGTH: 20
<212> TYPE: DNA
<213> ORGANISM: Mus musculus

<400> SEQUENCE: 54
gttcgtaccc gacgtcactg                                                20

<210> SEQ ID NO 55
<211> LENGTH: 21
<212> TYPE: DNA
<213> ORGANISM: Artificial sequence
<220> FEATURE:
<223> OTHER INFORMATION: oligonucleotide primer

<400> SEQUENCE: 55
ccttgtgccc aggaacaatt c                                              21

<210> SEQ ID NO 56
<211> LENGTH: 25
<212> TYPE: DNA
<213> ORGANISM: Artificial sequence
```

```
<220> FEATURE:
<223> OTHER INFORMATION: oligonucleotide primer

<400> SEQUENCE: 56
gagaataacc ttcaattcca gattc                                         25

<210> SEQ ID NO 57
<211> LENGTH: 28
<212> TYPE: DNA
<213> ORGANISM: Artificial sequence
<220> FEATURE:
<223> OTHER INFORMATION: oligonucleotide primer

<400> SEQUENCE: 57
cccaagctta aggccctctc ataggaac                                      28

<210> SEQ ID NO 58
<211> LENGTH: 26
<212> TYPE: DNA
<213> ORGANISM: Artificial sequence
<220> FEATURE:
<223> OTHER INFORMATION: oligonucleotide primer

<400> SEQUENCE: 58
gacctctctg cagtctatgt ggtcca                                        26

<210> SEQ ID NO 59
<211> LENGTH: 24
<212> TYPE: DNA
<213> ORGANISM: Artificial sequence
<220> FEATURE:
<223> OTHER INFORMATION: oligonucleotide primer

<400> SEQUENCE: 59
gaaaggtttc agtcacgctt gaag                                          24

<210> SEQ ID NO 60
<211> LENGTH: 30
<212> TYPE: DNA
<213> ORGANISM: Artificial sequence
<220> FEATURE:
<223> OTHER INFORMATION: oligonucleotide primer

<400> SEQUENCE: 60
taacctggcg gatccgatct ctccctggaa                                    30

<210> SEQ ID NO 61
<211> LENGTH: 30
<212> TYPE: DNA
<213> ORGANISM: Artificial sequence
<220> FEATURE:
<223> OTHER INFORMATION: oligonucleotide primer

<400> SEQUENCE: 61
attatcagaa taagctttct acagtgtcat                                    30

<210> SEQ ID NO 62
<211> LENGTH: 25
<212> TYPE: DNA
<213> ORGANISM: Artificial sequence
<220> FEATURE:
<223> OTHER INFORMATION: oligonucleotide primer

<400> SEQUENCE: 62
cgcggatcct atgctgaatt atacg                                         25
```

<210> SEQ ID NO 63
<211> LENGTH: 28
<212> TYPE: DNA
<213> ORGANISM: Artificial sequence
<220> FEATURE:
<223> OTHER INFORMATION: oligonucleotide primer

<400> SEQUENCE: 63
cccaagctta aggccctctc ataggaac                                28

<210> SEQ ID NO 64
<211> LENGTH: 24
<212> TYPE: DNA
<213> ORGANISM: Artificial sequence
<220> FEATURE:
<223> OTHER INFORMATION: oligonucleotide primer

<400> SEQUENCE: 64
atcaggagaa tacaggctgc gcct                                    24

<210> SEQ ID NO 65
<211> LENGTH: 24
<212> TYPE: DNA
<213> ORGANISM: Artificial sequence
<220> FEATURE:
<223> OTHER INFORMATION: oligonucleotide primer

<400> SEQUENCE: 65
ctgtattctc ctgatagtcc atct                                    24

<210> SEQ ID NO 66
<211> LENGTH: 26
<212> TYPE: DNA
<213> ORGANISM: Artificial sequence
<220> FEATURE:
<223> OTHER INFORMATION: oligonucleotide primer

<400> SEQUENCE: 66
gactgcagag aggtctgaca ccagca                                  26

<210> SEQ ID NO 67
<211> LENGTH: 24
<212> TYPE: DNA
<213> ORGANISM: Artificial sequence
<220> FEATURE:
<223> OTHER INFORMATION: oligonucleotide primer

<400> SEQUENCE: 67
aaggacagac gttggtggcg agtc                                    24

<210> SEQ ID NO 68
<211> LENGTH: 24
<212> TYPE: DNA
<213> ORGANISM: Artificial sequence
<220> FEATURE:
<223> OTHER INFORMATION: oligonucleotide primer

<400> SEQUENCE: 68
ccaacgtctg tccttcctga ctcc                                    24

<210> SEQ ID NO 69
<211> LENGTH: 45
<212> TYPE: DNA
<213> ORGANISM: Artificial sequence
<220> FEATURE:
<223> OTHER INFORMATION: oligonucleotide primer

```
<400> SEQUENCE: 69
ggagcgaacc tggaccacat agactgcaga gaggtctgac accag          45

<210> SEQ ID NO 70
<211> LENGTH: 45
<212> TYPE: DNA
<213> ORGANISM: Artificial sequence
<220> FEATURE:
<223> OTHER INFORMATION: oligonucleotide primer

<400> SEQUENCE: 70
tctgcagtct atgtggtcca ggttcgctcc cggcggttgg atgga           45

<210> SEQ ID NO 71
<211> LENGTH: 30
<212> TYPE: DNA
<213> ORGANISM: Artificial sequence
<220> FEATURE:
<223> OTHER INFORMATION: oligonucleotide primer

<400> SEQUENCE: 71
ctaggatcct cagtttttcg ccagctaggt                            30

<210> SEQ ID NO 72
<211> LENGTH: 34
<212> TYPE: DNA
<213> ORGANISM: Artificial sequence
<220> FEATURE:
<223> OTHER INFORMATION: oligonucleotide primer

<400> SEQUENCE: 72
gttttggatc cgctaggtgt aaactgggac atag                       34

<210> SEQ ID NO 73
<211> LENGTH: 35
<212> TYPE: DNA
<213> ORGANISM: Artificial sequence
<220> FEATURE:
<223> OTHER INFORMATION: oligonucleotide primer

<400> SEQUENCE: 73
ggtggggatc ctcaaacatc ttgtgtggta aagac                      35

<210> SEQ ID NO 74
<211> LENGTH: 40
<212> TYPE: DNA
<213> ORGANISM: Artificial sequence
<220> FEATURE:
<223> OTHER INFORMATION: oligonucleotide primer

<400> SEQUENCE: 74
ttcagatccc cgaagactgg agttgcattg gacagtctga                 40

<210> SEQ ID NO 75
<211> LENGTH: 40
<212> TYPE: DNA
<213> ORGANISM: Artificial sequence
<220> FEATURE:
<223> OTHER INFORMATION: oligonucleotide primer

<400> SEQUENCE: 75
aactccagtc ttcggggatc tgaatgtcat gtgccggtac                 40

<210> SEQ ID NO 76
```

```
<211> LENGTH: 33
<212> TYPE: DNA
<213> ORGANISM: Artificial sequence
<220> FEATURE:
<223> OTHER INFORMATION: oligonucleotide primer

<400> SEQUENCE: 76
cagtaagctt caaacatctt gtgtggtaaa gac                               33

<210> SEQ ID NO 77
<211> LENGTH: 6
<212> TYPE: PRT
<213> ORGANISM: Mus musculus

<400> SEQUENCE: 77

Asp Arg Trp Gly Ser Tyr
1               5

<210> SEQ ID NO 78
<211> LENGTH: 6
<212> TYPE: PRT
<213> ORGANISM: Mus musculus

<400> SEQUENCE: 78

Asp Arg Trp Gly Ser Ser
1               5

<210> SEQ ID NO 79
<211> LENGTH: 6
<212> TYPE: PRT
<213> ORGANISM: Mus musculus

<400> SEQUENCE: 79

Asp Arg Trp Gly Ser Leu
1               5

<210> SEQ ID NO 80
<211> LENGTH: 33
<212> TYPE: DNA
<213> ORGANISM: Mus musculus

<400> SEQUENCE: 80
tgtcacctaa tgattatagt ctgttatatc tgg                               33

<210> SEQ ID NO 81
<211> LENGTH: 33
<212> TYPE: DNA
<213> ORGANISM: Mus musculus

<400> SEQUENCE: 81
tgtcacctaa tgattaaagt ctgttatatc tgg                               33

<210> SEQ ID NO 82
<211> LENGTH: 32
<212> TYPE: DNA
<213> ORGANISM: Mus musculus

<400> SEQUENCE: 82
ttggagcagt ccagcctata cgcttgtcat gg                                32

<210> SEQ ID NO 83
<211> LENGTH: 32
<212> TYPE: DNA
<213> ORGANISM: Mus musculus
```

-continued

<400> SEQUENCE: 83
ttggagtaat tggagcagtc atggatgtaa aa    32

<210> SEQ ID NO 84
<211> LENGTH: 894
<212> TYPE: PRT
<213> ORGANISM: Mus musculus

<400> SEQUENCE: 84

```
Met Met Cys Gln Lys Phe Tyr Val Val Leu His Trp Glu Phe Leu
1               5                   10                  15

Tyr Val Ile Ala Ala Leu Asn Leu Ala Tyr Pro Ile Ser Pro Trp Lys
            20                  25                  30

Phe Lys Leu Phe Cys Gly Pro Pro Asn Thr Thr Asp Asp Ser Phe Leu
        35                  40                  45

Ser Pro Ala Gly Ala Pro Asn Asn Ala Ser Ala Leu Lys Gly Ala Ser
    50                  55                  60

Glu Ala Ile Val Glu Ala Lys Phe Asn Ser Ser Gly Ile Tyr Val Pro
65                  70                  75                  80

Glu Leu Ser Lys Thr Val Phe His Cys Cys Phe Gly Asn Glu Gln Gly
                85                  90                  95

Gln Asn Cys Ser Ala Leu Thr Asp Asn Thr Glu Gly Lys Thr Leu Ala
            100                 105                 110

Ser Val Val Lys Ala Ser Val Phe Arg Gln Leu Gly Val Asn Trp Asp
        115                 120                 125

Ile Glu Cys Trp Met Lys Gly Asp Leu Thr Leu Phe Ile Cys His Met
130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Ser Pro Leu Pro Pro
                165                 170                 175

Leu Lys Asp Ser Phe Gln Thr Val Gln Cys Asn Cys Ser Leu Arg Gly
            180                 185                 190

Cys Glu Cys His Val Pro Val Pro Arg Ala Lys Leu Asn Tyr Ala Leu
        195                 200                 205

Leu Met Tyr Leu Glu Ile Thr Ser Ala Gly Val Ser Phe Gln Ser Pro
    210                 215                 220

Leu Met Ser Leu Gln Pro Met Leu Val Val Lys Pro Asp Pro Pro Leu
225                 230                 235                 240

Gly Leu His Met Glu Val Thr Asp Asp Gly Asn Leu Lys Ile Ser Trp
                245                 250                 255

Asp Ser Gln Thr Met Ala Pro Phe Pro Leu Gln Tyr Gln Val Lys Tyr
            260                 265                 270

Leu Glu Asn Ser Thr Ile Val Arg Glu Ala Ala Glu Ile Val Ser Ala
        275                 280                 285

Thr Ser Leu Leu Val Asp Ser Val Leu Pro Gly Ser Ser Tyr Glu Val
    290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro
                325                 330                 335

Lys Ile Leu Thr Ser Val Gly Ser Asn Ala Ser Phe His Cys Ile Tyr
            340                 345                 350

Lys Asn Glu Asn Gln Ile Ile Ser Ser Lys Gln Ile Val Trp Trp Arg
```

-continued

```
            355                 360                 365
Asn Leu Ala Glu Lys Ile Pro Glu Ile Gln Tyr Ser Ile Val Ser Asp
    370                 375                 380
Arg Val Ser Lys Val Thr Phe Ser Asn Leu Lys Ala Thr Arg Pro Arg
385                 390                 395                 400
Gly Lys Phe Thr Tyr Asp Ala Val Tyr Cys Cys Asn Glu Gln Ala Cys
                405                 410                 415
His His Arg Tyr Ala Glu Leu Tyr Val Ile Asp Val Asn Ile Asn Ile
                420                 425                 430
Ser Cys Glu Thr Asp Gly Tyr Leu Thr Lys Met Thr Cys Arg Trp Ser
            435                 440                 445
Pro Ser Thr Ile Gln Ser Leu Val Gly Ser Thr Val Gln Leu Arg Tyr
    450                 455                 460
His Arg Arg Ser Leu Tyr Cys Pro Asp Ser Pro Ser Ile His Pro Thr
465                 470                 475                 480
Ser Glu Pro Lys Asn Cys Val Leu Gln Arg Asp Gly Phe Tyr Glu Cys
                485                 490                 495
Val Phe Gln Pro Ile Phe Leu Leu Ser Gly Tyr Thr Met Trp Ile Arg
                500                 505                 510
Ile Asn His Ser Leu Gly Ser Leu Asp Ser Pro Pro Thr Cys Val Leu
            515                 520                 525
Pro Asp Ser Val Val Lys Pro Leu Pro Pro Ser Asn Val Lys Ala Glu
    530                 535                 540
Ile Thr Val Asn Thr Gly Leu Leu Lys Val Ser Trp Glu Lys Pro Val
545                 550                 555                 560
Phe Pro Glu Asn Asn Leu Gln Phe Gln Ile Arg Tyr Gly Leu Ser Gly
                565                 570                 575
Lys Glu Ile Gln Trp Lys Thr His Glu Val Phe Asp Ala Lys Ser Lys
                580                 585                 590
Ser Ala Ser Leu Leu Val Ser Asp Leu Cys Ala Val Tyr Val Val Gln
            595                 600                 605
Val Arg Cys Arg Arg Leu Asp Gly Leu Gly Tyr Trp Ser Asn Trp Ser
    610                 615                 620
Ser Pro Ala Tyr Thr Leu Val Met Asp Val Lys Val Pro Met Arg Gly
625                 630                 635                 640
Pro Glu Phe Trp Arg Lys Met Asp Gly Asp Val Thr Lys Lys Glu Arg
                645                 650                 655
Asn Val Thr Leu Leu Trp Lys Pro Leu Thr Lys Asn Asp Ser Leu Cys
                660                 665                 670
Ser Val Arg Arg Tyr Val Val Lys His Arg Thr Ala His Asn Gly Thr
            675                 680                 685
Trp Ser Glu Asp Val Gly Asn Arg Thr Asn Leu Thr Phe Leu Trp Thr
    690                 695                 700
Glu Pro Ala His Thr Val Thr Val Leu Ala Val Asn Ser Leu Gly Ala
705                 710                 715                 720
Ser Leu Val Asn Phe Asn Leu Thr Phe Ser Trp Pro Met Ser Lys Val
                725                 730                 735
Ser Ala Val Glu Ser Leu Ser Ala Tyr Pro Leu Ser Ser Ser Cys Val
                740                 745                 750
Ile Leu Ser Trp Thr Leu Ser Pro Asp Asp Tyr Ser Leu Leu Tyr Leu
            755                 760                 765
Val Ile Glu Trp Lys Ile Leu Asn Glu Asp Asp Gly Met Lys Trp Leu
    770                 775                 780
```

```
Arg Ile Pro Ser Asn Val Lys Lys Phe Tyr Ile His Asp Asn Phe Ile
785                 790                 795                 800

Pro Ile Glu Lys Tyr Gln Phe Ser Leu Tyr Pro Val Phe Met Glu Gly
                805                 810                 815

Val Gly Lys Pro Lys Ile Ile Asn Gly Phe Thr Lys Asp Ala Ile Asp
                820                 825                 830

Lys Gln Gln Asn Asp Ala Gly Leu Tyr Val Ile Val Pro Ile Ile Ile
                835                 840                 845

Ser Ser Cys Val Leu Leu Leu Gly Thr Leu Leu Ile Ser His Gln Arg
850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Arg Thr Asp Thr Leu
                885                 890
```

<210> SEQ ID NO 85
<211> LENGTH: 1165
<212> TYPE: PRT
<213> ORGANISM: Homo sapiens

<400> SEQUENCE: 85

```
Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
                20                  25                  30

Phe Lys Leu Ser Cys Met Pro Pro Asn Ser Thr Tyr Asp Tyr Phe Leu
                35                  40                  45

Leu Pro Ala Gly Leu Ser Lys Asn Thr Ser Asn Ser Asn Gly His Tyr
            50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
                100                 105                 110

Ser Thr Val Asn Ser Leu Val Phe Gln Gln Ile Asp Ala Asn Trp Asn
            115                 120                 125

Ile Gln Cys Trp Leu Lys Gly Asp Leu Lys Leu Phe Ile Cys Tyr Val
130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
                180                 185                 190

Cys Cys Glu Cys Leu Val Pro Val Pro Thr Ala Lys Leu Asn Asp Thr
            195                 200                 205

Leu Leu Met Cys Leu Lys Ile Thr Ser Gly Gly Val Ile Phe Gln Ser
210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
```

-continued

```
              260                 265                 270
Tyr Ser Glu Asn Ser Thr Thr Val Ile Arg Glu Ala Asp Lys Ile Val
            275                 280                 285
Ser Ala Thr Ser Leu Leu Val Asp Ser Ile Leu Pro Gly Ser Ser Tyr
            290                 295                 300
Glu Val Gln Val Arg Gly Lys Arg Leu Asp Gly Pro Gly Ile Trp Ser
305                 310                 315                 320
Asp Trp Ser Thr Pro Arg Val Phe Thr Thr Gln Asp Val Ile Tyr Phe
                325                 330                 335
Pro Pro Lys Ile Leu Thr Ser Val Gly Ser Asn Val Ser Phe His Cys
            340                 345                 350
Ile Tyr Lys Lys Glu Asn Lys Ile Val Pro Ser Lys Glu Ile Val Trp
            355                 360                 365
Trp Met Asn Leu Ala Glu Lys Ile Pro Gln Ser Gln Tyr Asp Val Val
            370                 375                 380
Ser Asp His Val Ser Lys Val Thr Phe Phe Asn Leu Asn Glu Thr Lys
385                 390                 395                 400
Pro Arg Gly Lys Phe Thr Tyr Asp Ala Val Tyr Cys Cys Asn Glu His
                405                 410                 415
Glu Cys His His Arg Tyr Ala Glu Leu Tyr Val Ile Asp Val Asn Ile
                420                 425                 430
Asn Ile Ser Cys Glu Thr Asp Gly Tyr Leu Thr Lys Met Thr Cys Arg
            435                 440                 445
Trp Ser Thr Ser Thr Ile Gln Ser Leu Ala Glu Ser Thr Leu Gln Leu
            450                 455                 460
Arg Tyr His Arg Ser Ser Leu Tyr Cys Ser Asp Ile Pro Ser Ile His
465                 470                 475                 480
Pro Ile Ser Glu Pro Lys Asp Cys Tyr Leu Gln Ser Asp Gly Phe Tyr
                485                 490                 495
Glu Cys Ile Phe Gln Pro Ile Phe Leu Leu Ser Gly Tyr Thr Met Trp
                500                 505                 510
Ile Arg Ile Asn His Ser Leu Gly Ser Leu Asp Ser Pro Pro Thr Cys
            515                 520                 525
Val Leu Pro Asp Ser Val Val Lys Pro Leu Pro Pro Ser Ser Val Lys
            530                 535                 540
Ala Glu Ile Thr Ile Asn Ile Gly Leu Leu Lys Ile Ser Trp Glu Lys
545                 550                 555                 560
Pro Val Phe Pro Glu Asn Asn Leu Gln Phe Gln Ile Arg Tyr Gly Leu
                565                 570                 575
Ser Gly Lys Glu Val Gln Trp Lys Met Tyr Glu Val Tyr Asp Ala Lys
            580                 585                 590
Ser Lys Ser Val Ser Leu Pro Val Pro Asp Leu Cys Ala Val Tyr Ala
            595                 600                 605
Val Gln Val Arg Cys Lys Arg Leu Asp Gly Leu Gly Tyr Trp Ser Asn
            610                 615                 620
Trp Ser Asn Pro Ala Tyr Thr Val Val Met Asp Ile Lys Val Pro Met
625                 630                 635                 640
Arg Gly Pro Glu Phe Trp Arg Ile Ile Asn Gly Asp Thr Met Lys Lys
                645                 650                 655
Glu Lys Asn Val Thr Leu Leu Trp Lys Pro Leu Met Lys Asn Asp Ser
            660                 665                 670
Leu Cys Ser Val Gln Arg Tyr Val Ile Asn His His Thr Ser Cys Asn
            675                 680                 685
```

-continued

```
Gly Thr Trp Ser Glu Asp Val Gly Asn His Thr Lys Phe Thr Phe Leu
    690             695                 700

Trp Thr Glu Gln Ala His Thr Val Thr Val Leu Ala Ile Asn Ser Ile
705             710             715                 720

Gly Ala Ser Val Ala Asn Phe Asn Leu Thr Phe Ser Trp Pro Met Ser
                725             730                 735

Lys Val Asn Ile Val Gln Ser Leu Ser Ala Tyr Pro Leu Asn Ser Ser
            740             745             750

Cys Val Ile Val Ser Trp Ile Leu Ser Pro Ser Asp Tyr Lys Leu Met
            755             760             765

Tyr Phe Ile Ile Glu Trp Lys Asn Leu Asn Glu Asp Gly Glu Ile Lys
770             775             780

Trp Leu Arg Ile Ser Ser Val Lys Lys Tyr Ile His Asp His
785             790             795             800

Phe Ile Pro Ile Glu Lys Tyr Gln Phe Ser Leu Tyr Pro Ile Phe Met
                805             810             815

Glu Gly Val Gly Lys Pro Lys Ile Ile Asn Ser Phe Thr Gln Asp Asp
            820             825             830

Ile Glu Lys His Gln Ser Asp Ala Gly Leu Tyr Val Ile Val Pro Val
            835             840             845

Ile Ile Ser Ser Ser Ile Leu Leu Leu Gly Thr Leu Leu Ile Ser His
850             855             860

Gln Arg Met Lys Lys Leu Phe Trp Glu Asp Val Pro Asn Pro Lys Asn
865             870             875             880

Cys Ser Trp Ala Gln Gly Leu Asn Phe Gln Lys Pro Glu Thr Phe Glu
                885             890             895

His Leu Phe Ile Lys His Thr Ala Ser Val Thr Cys Gly Pro Leu Leu
            900             905             910

Leu Glu Pro Glu Thr Ile Ser Glu Asp Ile Ser Val Asp Thr Ser Trp
            915             920             925

Lys Asn Lys Asp Glu Met Met Pro Thr Thr Val Val Ser Leu Leu Ser
930             935             940

Thr Thr Asp Leu Glu Lys Gly Ser Val Cys Ile Ser Asp Gln Phe Asn
945             950             955             960

Ser Val Asn Phe Ser Glu Ala Glu Gly Thr Glu Val Thr Tyr Glu Ala
                965             970             975

Glu Ser Gln Arg Gln Pro Phe Val Lys Tyr Ala Thr Leu Ile Ser Asn
            980             985             990

Ser Lys Pro Ser Glu Thr Gly Glu Glu Gln Gly Leu Ile Asn Ser Ser
            995             1000            1005

Val Thr Lys Cys Phe Ser Ser Lys Asn Ser Pro Leu Lys Asp Ser
    1010            1015               1020

Phe Ser Asn Ser Ser Trp Glu Ile Glu Ala Gln Ala Phe Phe Ile
    1025            1030              1035

Leu Ser Asp Gln His Pro Asn Ile Ile Ser Pro His Leu Thr Phe
    1040            1045              1050

Ser Glu Gly Leu Asp Glu Leu Leu Lys Leu Glu Gly Asn Phe Pro
    1055            1060              1065

Glu Glu Asn Asn Asp Lys Lys Ser Ile Tyr Tyr Leu Gly Val Thr
    1070            1075              1080

Ser Ile Lys Lys Arg Glu Ser Gly Val Leu Leu Thr Asp Lys Ser
    1085            1090              1095
```

```
Arg Val Ser Cys Pro Phe Pro Ala Pro Cys Leu Phe Thr Asp Ile
    1100                1105                1110

Arg Val Leu Gln Asp Ser Cys Ser His Phe Val Glu Asn Asn Ile
    1115                1120                1125

Asn Leu Gly Thr Ser Ser Lys Lys Thr Phe Ala Ser Tyr Met Pro
    1130                1135                1140

Gln Phe Gln Thr Cys Ser Thr Gln Thr His Lys Ile Met Glu Asn
    1145                1150                1155

Lys Met Cys Asp Leu Thr Val
    1160                1165

<210> SEQ ID NO 86
<211> LENGTH: 1110
<212> TYPE: PRT
<213> ORGANISM: Mus musculus
<220> FEATURE:
<221> NAME/KEY: MISC_FEATURE
<222> LOCATION: (29)..(29)
<223> OTHER INFORMATION: X can be any amino acid

<400> SEQUENCE: 86

Gly Leu Arg Ser Ala Ser Tyr Gln Pro Leu Lys Arg Phe Ser Arg Phe
1               5                   10                  15

Gln Ala Leu Ser Pro Cys Arg Ile Ser Thr Ser Leu Xaa Leu Val Pro
            20                  25                  30

Asn Ser Ala Arg Gly Cys Phe Gly Asn Glu Gln Gly Gln Asn Cys Ser
        35                  40                  45

Ala Leu Thr Asp Asn Thr Glu Gly Lys Thr Leu Ala Ser Val Val Lys
    50                  55                  60

Ala Ser Val Phe Arg Gln Leu Gly Val Asn Trp Asp Ile Glu Cys Trp
65                  70                  75                  80

Met Lys Gly Asp Leu Thr Leu Phe Ile Cys His Met Glu Pro Leu Pro
                85                  90                  95

Lys Asn Pro Phe Lys Asn Tyr Asp Ser Lys Val His Leu Leu Tyr Asp
            100                 105                 110

Leu Pro Glu Val Ile Asp Ser Pro Leu Pro Pro Leu Lys Asp Ser
        115                 120                 125

Phe Gln Thr Val Gln Cys Asn Cys Ser Leu Arg Gly Cys Glu Cys His
    130                 135                 140

Val Pro Val Pro Arg Ala Lys Leu Asn Tyr Ala Leu Leu Met Tyr Leu
145                 150                 155                 160

Glu Ile Thr Ser Ala Gly Val Ser Phe Gln Ser Pro Leu Met Ser Leu
                165                 170                 175

Gln Pro Met Leu Val Val Lys Pro Asp Pro Pro Leu Gly Leu His Met
            180                 185                 190

Glu Val Thr Asp Asp Gly Asn Leu Lys Ile Ser Trp Asp Ser Gln Thr
        195                 200                 205

Met Ala Pro Phe Pro Leu Gln Tyr Gln Val Lys Tyr Leu Glu Asn Ser
    210                 215                 220

Thr Ile Val Arg Glu Ala Ala Glu Ile Val Ser Ala Thr Ser Leu Leu
225                 230                 235                 240

Val Asp Ser Val Leu Pro Gly Ser Ser Tyr Glu Val Gln Val Arg Ser
                245                 250                 255

Lys Arg Leu Asp Gly Ser Gly Val Trp Ser Asp Trp Ser Ser Pro Gln
            260                 265                 270

Val Phe Thr Thr Gln Asp Val Val Tyr Phe Pro Pro Lys Ile Leu Thr
```

```
            275                 280                 285
Ser Val Gly Ser Asn Ala Ser Phe His Cys Ile Tyr Lys Asn Glu Asn
        290                 295                 300
Gln Ile Ile Ser Ser Lys Gln Ile Val Trp Trp Arg Asn Leu Ala Glu
305                 310                 315                 320
Lys Ile Pro Glu Ile Gln Tyr Ser Ile Val Ser Asp Arg Val Ser Lys
                325                 330                 335
Val Thr Phe Ser Asn Leu Lys Ala Thr Arg Pro Arg Gly Lys Phe Thr
            340                 345                 350
Tyr Asp Ala Val Tyr Cys Cys Asn Glu Gln Ala Cys His His Arg Tyr
                355                 360                 365
Ala Glu Leu Tyr Val Ile Asp Val Asn Ile Asn Ile Ser Cys Glu Thr
            370                 375                 380
Asp Gly Tyr Leu Thr Lys Met Thr Cys Arg Trp Ser Pro Ser Thr Ile
385                 390                 395                 400
Gln Ser Leu Val Gly Ser Thr Val Gln Leu Arg Tyr His Arg Arg Ser
                405                 410                 415
Leu Tyr Cys Pro Asp Ser Pro Ser Ile His Pro Thr Ser Glu Pro Lys
            420                 425                 430
Asn Cys Val Leu Gln Arg Asp Gly Phe Tyr Glu Cys Val Phe Gln Pro
            435                 440                 445
Ile Phe Leu Leu Ser Gly Tyr Thr Met Trp Ile Arg Ile Asn His Ser
            450                 455                 460
Leu Gly Ser Leu Asp Ser Pro Thr Cys Val Leu Pro Asp Ser Val
465                 470                 475                 480
Val Lys Pro Leu Pro Pro Ser Asn Val Lys Ala Glu Ile Thr Val Asn
                485                 490                 495
Thr Gly Leu Leu Lys Val Ser Trp Glu Lys Pro Val Phe Pro Glu Asn
            500                 505                 510
Asn Leu Gln Phe Gln Ile Arg Tyr Gly Leu Ser Gly Lys Glu Ile Gln
            515                 520                 525
Trp Lys Thr His Glu Val Phe Asp Ala Lys Ser Lys Ser Ala Ser Leu
            530                 535                 540
Leu Val Ser Asp Leu Cys Ala Val Tyr Val Val Gln Val Arg Cys Arg
545                 550                 555                 560
Arg Leu Asp Gly Leu Gly Tyr Trp Ser Asn Trp Ser Ser Pro Ala Tyr
                565                 570                 575
Thr Leu Val Met Asp Val Lys Val Pro Met Arg Gly Pro Glu Phe Trp
            580                 585                 590
Arg Lys Met Asp Gly Asp Val Thr Lys Lys Glu Arg Asn Val Thr Leu
            595                 600                 605
Leu Trp Lys Pro Leu Thr Lys Asn Asp Ser Leu Cys Ser Val Arg Arg
            610                 615                 620
Tyr Val Val Lys His Arg Thr Ala His Asn Gly Thr Trp Ser Glu Asp
625                 630                 635                 640
Val Gly Asn Arg Thr Asn Leu Thr Phe Leu Trp Thr Glu Pro Ala His
                645                 650                 655
Thr Val Thr Val Leu Ala Val Asn Ser Leu Gly Ala Ser Leu Val Asn
            660                 665                 670
Phe Asn Leu Thr Phe Ser Trp Pro Met Ser Lys Val Ser Ala Val Glu
            675                 680                 685
Ser Leu Ser Ala Tyr Pro Leu Ser Ser Ser Cys Val Ile Leu Ser Trp
            690                 695                 700
```

```
Thr Leu Ser Pro Asp Asp Tyr Ser Leu Leu Tyr Leu Val Ile Glu Trp
705                 710                 715                 720

Lys Ile Leu Asn Glu Asp Asp Gly Met Lys Trp Leu Arg Ile Pro Ser
            725                 730                 735

Asn Val Lys Lys Phe Tyr Ile His Asp Asn Phe Ile Pro Ile Glu Lys
            740                 745                 750

Tyr Gln Phe Ser Leu Tyr Pro Val Phe Met Glu Gly Val Gly Lys Pro
                755                 760                 765

Lys Ile Ile Asn Gly Phe Thr Lys Asp Ala Ile Asp Lys Gln Gln Asn
        770                 775                 780

Asp Ala Gly Leu Tyr Val Ile Val Pro Ile Ile Ile Ser Ser Cys Val
785                 790                 795                 800

Leu Leu Leu Gly Thr Leu Leu Ile Ser His Gln Arg Met Lys Lys Leu
                805                 810                 815

Phe Trp Asp Asp Val Pro Asn Pro Lys Asn Cys Ser Trp Ala Gln Gly
            820                 825                 830

Leu Asn Phe Gln Lys Pro Glu Thr Phe Glu Gln Leu Phe Thr Lys His
            835                 840                 845

Ala Glu Ser Val Ile Phe Gly Pro Leu Leu Leu Glu Pro Glu Pro Ile
850                 855                 860

Ser Glu Glu Ile Ser Val Asp Thr Ala Trp Lys Asn Lys Asp Glu Met
865                 870                 875                 880

Val Pro Ala Ala Met Val Ser Leu Leu Leu Thr Thr Pro Asp Pro Glu
                885                 890                 895

Ser Ser Ser Ile Cys Ile Ser Asp Gln Cys Asn Ser Ala Asn Phe Ser
                900                 905                 910

Gly Ser Gln Ser Thr Gln Val Thr Cys Glu Asp Glu Cys Gln Arg Gln
            915                 920                 925

Pro Ser Val Lys Tyr Ala Thr Leu Val Ser Asn Asp Lys Leu Val Glu
    930                 935                 940

Thr Asp Glu Glu Gln Gly Phe Ile His Ser Pro Val Ser Asn Cys Ile
945                 950                 955                 960

Ser Ser Asn His Ser Pro Leu Arg Gln Ser Phe Ser Ser Ser Ser Trp
                965                 970                 975

Glu Thr Glu Ala Gln Thr Phe Phe Leu Leu Ser Asp Gln Gln Pro Thr
            980                 985                 990

Met Ile Ser Pro Gln Leu Ser Phe  Ser Gly Leu Asp Glu  Leu Leu Glu
        995                 1000                1005

Leu Glu  Gly Ser Phe Pro Glu  Glu Asn His Arg Glu  Lys Ser Val
    1010                1015                1020

Cys Tyr  Leu Gly Val Thr Ser  Val Asn Arg Arg Glu  Ser Gly Val
    1025                1030                1035

Leu Leu  Thr Gly Glu Ala Gly  Ile Leu Cys Thr Phe  Pro Ala Gln
    1040                1045                1050

Cys Leu  Phe Ser Asp Ile Arg  Ile Leu Gln Glu Arg  Cys Ser His
    1055                1060                1065

Phe Val  Glu Asn Asn Leu Ser  Leu Gly Thr Ser Gly  Glu Asn Phe
    1070                1075                1080

Val Pro  Tyr Met Pro Gln Phe  Gln Thr Cys Ser Thr  His Ser His
    1085                1090                1095

Lys Ile  Met Glu Asn Lys Met  Cys Asp Leu Thr Val
    1100                1105                1110
```

-continued

```
<210> SEQ ID NO 87
<211> LENGTH: 840
<212> TYPE: PRT
<213> ORGANISM: Mus musculus
<220> FEATURE:
<221> NAME/KEY: MISC_FEATURE
<222> LOCATION: (29)..(29)
<223> OTHER INFORMATION: X can be any amino acid

<400> SEQUENCE: 87

Gly Leu Arg Ser Ala Ser Tyr Gln Pro Leu Lys Arg Phe Ser Arg Phe
1               5                   10                  15

Gln Ala Leu Ser Pro Cys Arg Ile Ser Thr Ser Leu Xaa Leu Val Pro
            20                  25                  30

Asn Ser Ala Arg Gly Cys Phe Gly Asn Glu Gln Gly Gln Asn Cys Ser
        35                  40                  45

Ala Leu Thr Asp Asn Thr Glu Gly Lys Thr Leu Ala Ser Val Val Lys
    50                  55                  60

Ala Ser Val Phe Arg Gln Leu Gly Val Asn Trp Asp Ile Glu Cys Trp
65                  70                  75                  80

Met Lys Gly Asp Leu Thr Leu Phe Ile Cys His Met Glu Pro Leu Pro
                85                  90                  95

Lys Asn Pro Phe Lys Asn Tyr Asp Ser Lys Val His Leu Leu Tyr Asp
            100                 105                 110

Leu Pro Glu Val Ile Asp Asp Ser Pro Leu Pro Leu Lys Asp Ser
        115                 120                 125

Phe Gln Thr Val Gln Cys Asn Cys Ser Leu Arg Gly Cys Glu Cys His
    130                 135                 140

Val Pro Val Pro Arg Ala Lys Leu Asn Tyr Ala Leu Leu Met Tyr Leu
145                 150                 155                 160

Glu Ile Thr Ser Ala Gly Val Ser Phe Gln Ser Pro Leu Met Ser Leu
                165                 170                 175

Gln Pro Met Leu Val Val Lys Pro Asp Pro Pro Leu Gly Leu His Met
            180                 185                 190

Glu Val Thr Asp Asp Gly Asn Leu Lys Ile Ser Trp Asp Ser Gln Thr
        195                 200                 205

Met Ala Pro Phe Pro Leu Gln Tyr Gln Val Lys Tyr Leu Glu Asn Ser
    210                 215                 220

Thr Ile Val Arg Glu Ala Ala Glu Ile Val Ser Ala Thr Ser Leu Leu
225                 230                 235                 240

Val Asp Ser Val Leu Pro Gly Ser Ser Tyr Glu Val Gln Val Arg Ser
                245                 250                 255

Lys Arg Leu Asp Gly Ser Gly Val Trp Ser Asp Trp Ser Ser Pro Gln
            260                 265                 270

Val Phe Thr Thr Gln Asp Val Val Tyr Phe Pro Pro Lys Ile Leu Thr
        275                 280                 285

Ser Val Gly Ser Asn Ala Ser Phe His Cys Ile Tyr Lys Asn Glu Asn
    290                 295                 300

Gln Ile Ile Ser Ser Lys Gln Ile Val Trp Trp Arg Asn Leu Ala Glu
305                 310                 315                 320

Lys Ile Pro Glu Ile Gln Tyr Ser Ile Val Ser Asp Arg Val Ser Lys
                325                 330                 335

Val Thr Phe Ser Asn Leu Lys Ala Thr Arg Pro Arg Gly Lys Phe Thr
            340                 345                 350

Tyr Asp Ala Val Tyr Cys Cys Asn Glu Gln Ala Cys His His Arg Tyr
```

```
                355                 360                 365
Ala Glu Leu Tyr Val Ile Asp Val Asn Ile Asn Ile Ser Cys Glu Thr
    370                 375                 380

Asp Gly Tyr Leu Thr Lys Met Thr Cys Arg Trp Ser Pro Ser Thr Ile
385                 390                 395                 400

Gln Ser Leu Val Gly Ser Thr Val Gln Leu Arg Tyr His Arg Arg Ser
                405                 410                 415

Leu Tyr Cys Pro Asp Ser Pro Ser Ile His Pro Thr Ser Glu Pro Lys
            420                 425                 430

Asn Cys Val Leu Gln Arg Asp Gly Phe Tyr Glu Cys Val Phe Gln Pro
        435                 440                 445

Ile Phe Leu Leu Ser Gly Tyr Thr Met Trp Ile Arg Ile Asn His Ser
    450                 455                 460

Leu Gly Ser Leu Asp Ser Pro Pro Thr Cys Val Leu Pro Asp Ser Val
465                 470                 475                 480

Val Lys Pro Leu Pro Pro Ser Asn Val Lys Ala Glu Ile Thr Val Asn
                485                 490                 495

Thr Gly Leu Leu Lys Val Ser Trp Glu Lys Pro Val Phe Pro Glu Asn
            500                 505                 510

Asn Leu Gln Phe Gln Ile Arg Tyr Gly Leu Ser Gly Lys Glu Ile Gln
        515                 520                 525

Trp Lys Thr His Glu Val Phe Asp Ala Lys Ser Lys Ser Ala Ser Leu
    530                 535                 540

Leu Val Ser Asp Leu Cys Ala Val Tyr Val Gln Val Arg Cys Arg
545                 550                 555                 560

Arg Leu Asp Gly Leu Gly Tyr Trp Ser Asn Trp Ser Ser Pro Ala Tyr
                565                 570                 575

Thr Leu Val Met Asp Val Lys Val Pro Met Arg Gly Pro Glu Phe Trp
            580                 585                 590

Arg Lys Met Asp Gly Asp Val Thr Lys Lys Glu Arg Asn Val Thr Leu
        595                 600                 605

Leu Trp Lys Pro Leu Thr Lys Asn Asp Ser Leu Cys Ser Val Arg Arg
    610                 615                 620

Tyr Val Val Lys His Arg Thr Ala His Asn Gly Thr Trp Ser Glu Asp
625                 630                 635                 640

Val Gly Asn Arg Thr Asn Leu Thr Phe Leu Trp Thr Glu Pro Ala His
                645                 650                 655

Thr Val Thr Val Leu Ala Val Asn Ser Leu Gly Ala Ser Leu Val Asn
            660                 665                 670

Phe Asn Leu Thr Phe Ser Trp Pro Met Ser Lys Val Ser Ala Val Glu
        675                 680                 685

Ser Leu Ser Ala Tyr Pro Leu Ser Ser Cys Val Ile Leu Ser Trp
    690                 695                 700

Thr Leu Ser Pro Asp Asp Tyr Ser Leu Leu Tyr Leu Val Ile Glu Trp
705                 710                 715                 720

Lys Ile Leu Asn Glu Asp Asp Gly Met Lys Trp Leu Arg Ile Pro Ser
                725                 730                 735

Asn Val Lys Lys Phe Tyr Ile His Asp Asn Phe Ile Pro Ile Glu Lys
            740                 745                 750

Tyr Gln Phe Ser Leu Tyr Pro Val Phe Met Glu Gly Val Gly Lys Pro
        755                 760                 765

Lys Ile Ile Asn Gly Phe Thr Lys Asp Ala Ile Asp Lys Gln Gln Asn
    770                 775                 780
```

```
Asp Ala Gly Leu Tyr Val Ile Val Pro Ile Ile Ser Ser Cys Val
785                 790                 795                 800

Leu Leu Leu Gly Thr Leu Leu Ile Ser His Gln Arg Met Lys Lys Leu
                805                 810                 815

Phe Trp Asp Asp Val Pro Asn Pro Lys Asn Cys Ser Trp Ala Gln Gly
                820                 825                 830

Leu Asn Phe Gln Lys Val Thr Val
                835                 840

<210> SEQ ID NO 88
<211> LENGTH: 848
<212> TYPE: PRT
<213> ORGANISM: Mus musculus
<220> FEATURE:
<221> NAME/KEY: MISC_FEATURE
<222> LOCATION: (29)..(29)
<223> OTHER INFORMATION: X can be any amino acid

<400> SEQUENCE: 88

Gly Leu Arg Ser Ala Ser Tyr Gln Pro Leu Lys Arg Phe Ser Arg Phe
1               5                   10                  15

Gln Ala Leu Ser Pro Cys Arg Ile Ser Thr Ser Leu Xaa Leu Val Pro
                20                  25                  30

Asn Ser Ala Arg Gly Cys Phe Gly Asn Glu Gln Gly Gln Asn Cys Ser
            35                  40                  45

Ala Leu Thr Asp Asn Thr Glu Gly Lys Thr Leu Ala Ser Val Val Lys
50                  55                  60

Ala Ser Val Phe Arg Gln Leu Gly Val Asn Trp Asp Ile Glu Cys Trp
65                  70                  75                  80

Met Lys Gly Asp Leu Thr Leu Phe Ile Cys His Met Glu Pro Leu Pro
                85                  90                  95

Lys Asn Pro Phe Lys Asn Tyr Asp Ser Lys Val His Leu Leu Tyr Asp
            100                 105                 110

Leu Pro Glu Val Ile Asp Asp Ser Pro Leu Pro Pro Leu Lys Asp Ser
        115                 120                 125

Phe Gln Thr Val Gln Cys Asn Cys Ser Leu Arg Gly Cys Glu Cys His
    130                 135                 140

Val Pro Val Pro Arg Ala Lys Leu Asn Tyr Ala Leu Leu Met Tyr Leu
145                 150                 155                 160

Glu Ile Thr Ser Ala Gly Val Ser Phe Gln Ser Pro Leu Met Ser Leu
                165                 170                 175

Gln Pro Met Leu Val Val Lys Pro Asp Pro Pro Leu Gly Leu His Met
            180                 185                 190

Glu Val Thr Asp Asp Gly Asn Leu Lys Ile Ser Trp Asp Ser Gln Thr
        195                 200                 205

Met Ala Pro Phe Pro Leu Gln Tyr Gln Val Lys Tyr Leu Glu Asn Ser
    210                 215                 220

Thr Ile Val Arg Glu Ala Ala Glu Ile Val Ser Ala Thr Ser Leu Leu
225                 230                 235                 240

Val Asp Ser Val Leu Pro Gly Ser Ser Tyr Glu Val Gln Val Arg Ser
                245                 250                 255

Lys Arg Leu Asp Gly Ser Gly Val Trp Ser Asp Trp Ser Ser Pro Gln
            260                 265                 270

Val Phe Thr Thr Gln Asp Val Val Tyr Phe Pro Pro Lys Ile Leu Thr
        275                 280                 285
```

-continued

```
Ser Val Gly Ser Asn Ala Ser Phe His Cys Ile Tyr Lys Asn Glu Asn
    290                 295                 300
Gln Ile Ile Ser Ser Lys Gln Ile Val Trp Trp Arg Asn Leu Ala Glu
305                 310                 315                 320
Lys Ile Pro Glu Ile Gln Tyr Ser Ile Val Ser Asp Arg Val Ser Lys
                325                 330                 335
Val Thr Phe Ser Asn Leu Lys Ala Thr Arg Pro Arg Gly Lys Phe Thr
            340                 345                 350
Tyr Asp Ala Val Tyr Cys Cys Asn Glu Gln Ala Cys His His Arg Tyr
        355                 360                 365
Ala Glu Leu Tyr Val Ile Asp Val Asn Ile Asn Ile Ser Cys Glu Thr
    370                 375                 380
Asp Gly Tyr Leu Thr Lys Met Thr Cys Arg Trp Ser Pro Ser Thr Ile
385                 390                 395                 400
Gln Ser Leu Val Gly Ser Thr Val Gln Leu Arg Tyr His Arg Arg Ser
                405                 410                 415
Leu Tyr Cys Pro Asp Ser Pro Ser Ile His Pro Thr Ser Glu Pro Lys
            420                 425                 430
Asn Cys Val Leu Gln Arg Asp Gly Phe Tyr Glu Cys Val Phe Gln Pro
        435                 440                 445
Ile Phe Leu Leu Ser Gly Tyr Thr Met Trp Ile Arg Ile Asn His Ser
    450                 455                 460
Leu Gly Ser Leu Asp Ser Pro Pro Thr Cys Val Leu Pro Asp Ser Val
465                 470                 475                 480
Val Lys Pro Leu Pro Pro Ser Asn Val Lys Ala Glu Ile Thr Val Asn
                485                 490                 495
Thr Gly Leu Leu Lys Val Ser Trp Glu Lys Pro Val Phe Pro Glu Asn
            500                 505                 510
Asn Leu Gln Phe Gln Ile Arg Tyr Gly Leu Ser Gly Lys Glu Ile Gln
        515                 520                 525
Trp Lys Thr His Glu Val Phe Asp Ala Lys Ser Lys Ser Ala Ser Leu
    530                 535                 540
Leu Val Ser Asp Leu Cys Ala Val Tyr Val Val Gln Val Arg Cys Arg
545                 550                 555                 560
Arg Leu Asp Gly Leu Gly Tyr Trp Ser Asn Trp Ser Ser Pro Ala Tyr
                565                 570                 575
Thr Leu Val Met Asp Val Lys Val Pro Met Arg Gly Pro Glu Phe Trp
            580                 585                 590
Arg Lys Met Asp Gly Asp Val Thr Lys Lys Glu Arg Asn Val Thr Leu
        595                 600                 605
Leu Trp Lys Pro Leu Thr Lys Asn Asp Ser Leu Cys Ser Val Arg Arg
    610                 615                 620
Tyr Val Val Lys His Arg Thr Ala His Asn Gly Thr Trp Ser Glu Asp
625                 630                 635                 640
Val Gly Asn Arg Thr Asn Leu Thr Phe Leu Trp Thr Glu Pro Ala His
                645                 650                 655
Thr Val Thr Val Leu Ala Val Asn Ser Leu Gly Ala Ser Leu Val Asn
            660                 665                 670
Phe Asn Leu Thr Phe Ser Trp Pro Met Ser Lys Val Ser Ala Val Glu
        675                 680                 685
Ser Leu Ser Ala Tyr Pro Leu Ser Ser Ser Cys Val Ile Leu Ser Trp
    690                 695                 700
Thr Leu Ser Pro Asp Asp Tyr Ser Leu Leu Tyr Leu Val Ile Glu Trp
```

```
                    705                 710                 715                 720

Lys Ile Leu Asn Glu Asp Asp Gly Met Lys Trp Leu Arg Ile Pro Ser
                    725                 730                 735

Asn Val Lys Lys Phe Tyr Ile His Asp Asn Phe Ile Pro Ile Glu Lys
                740                 745                 750

Tyr Gln Phe Ser Leu Tyr Pro Val Phe Met Glu Gly Val Gly Lys Pro
            755                 760                 765

Lys Ile Ile Asn Gly Phe Thr Lys Asp Ala Ile Asp Lys Gln Gln Asn
        770                 775                 780

Asp Ala Gly Leu Tyr Val Ile Val Pro Ile Ile Ser Ser Cys Val
785                 790                 795                 800

Leu Leu Leu Gly Thr Leu Leu Ile Ser His Gln Arg Met Lys Lys Leu
                805                 810                 815

Phe Trp Asp Asp Val Pro Asn Pro Lys Asn Cys Ser Trp Ala Gln Gly
            820                 825                 830

Leu Asn Phe Gln Lys Asp Ile Ser Leu His Glu Val Phe Ile Phe Arg
        835                 840                 845

<210> SEQ ID NO 89
<211> LENGTH: 314
<212> TYPE: PRT
<213> ORGANISM: Mus musculus
<220> FEATURE:
<221> NAME/KEY: MISC_FEATURE
<222> LOCATION: (79)..(79)
<223> OTHER INFORMATION: X can be any amino acid

<400> SEQUENCE: 89

Leu Arg Asp Leu Val Ser Gly Phe Glu Glu Ile Asn Lys Ile Lys Glu
1               5                   10                  15

Asn Phe Ser Arg Ala Gly Leu Leu Ala Glu Leu Arg Pro Thr Ala Phe
                20                  25                  30

Tyr Ile Ser Thr Leu Ser Leu Phe Pro Ser Ala Leu Ala Leu Asp Trp
            35                  40                  45

Ala Val Pro Gly Leu Val Leu Leu Phe Pro Gly Gly Asn Val Glu Leu
        50                  55                  60

His Glu Phe Trp Tyr Lys His Cys Gly Leu Cys Ala Asn Ile Xaa Cys
65                  70                  75                  80

Phe Leu Gln Pro Leu Thr Lys Asn Asp Ser Leu Cys Ser Val Arg Arg
                85                  90                  95

Tyr Val Val Lys His Arg Thr Ala His Asn Gly Thr Trp Ser Glu Asp
            100                 105                 110

Val Gly Asn Arg Thr Asn Leu Thr Phe Leu Trp Thr Glu Pro Ala His
        115                 120                 125

Thr Val Thr Val Leu Ala Val Asn Ser Leu Gly Ala Ser Leu Val Asn
130                 135                 140

Phe Asn Leu Thr Phe Ser Trp Pro Met Ser Lys Val Ser Ala Val Glu
145                 150                 155                 160

Ser Leu Ser Ala Tyr Pro Leu Ser Ser Cys Val Ile Leu Ser Trp
                165                 170                 175

Thr Leu Ser Pro Asp Asp Tyr Ser Leu Leu Tyr Leu Val Ile Glu Trp
            180                 185                 190

Lys Ile Leu Asn Glu Asp Asp Gly Met Lys Trp Leu Arg Ile Pro Ser
        195                 200                 205

Asn Val Lys Lys Phe Tyr Ile His Asp Asn Phe Ile Pro Ile Glu Lys
    210                 215                 220
```

```
Tyr Gln Phe Ser Leu Tyr Pro Val Phe Met Glu Gly Val Gly Lys Pro
225                 230                 235                 240

Lys Ile Ile Asn Gly Phe Thr Lys Asp Ala Ile Asp Lys Gln Gln Asn
            245                 250                 255

Asp Ala Gly Leu Tyr Val Ile Val Pro Ile Ile Ile Ser Ser Cys Val
        260                 265                 270

Leu Leu Leu Gly Thr Leu Leu Ile Ser His Gln Arg Met Lys Lys Leu
            275                 280                 285

Phe Trp Asp Asp Val Pro Asn Pro Lys Asn Cys Ser Trp Ala Gln Gly
    290                 295                 300

Leu Asn Phe Gln Lys Arg Thr Asp Thr Leu
305                 310
```

<210> SEQ ID NO 90
<211> LENGTH: 321
<212> TYPE: PRT
<213> ORGANISM: Mus musculus
<220> FEATURE:
<221> NAME/KEY: MISC_FEATURE
<222> LOCATION: (14)..(14)
<223> OTHER INFORMATION: X can be any amino acid
<220> FEATURE:
<221> NAME/KEY: MISC_FEATURE
<222> LOCATION: (19)..(19)
<223> OTHER INFORMATION: X can be any amino acid
<220> FEATURE:
<221> NAME/KEY: MISC_FEATURE
<222> LOCATION: (25)..(25)
<223> OTHER INFORMATION: X can be any amino acid
<220> FEATURE:
<221> NAME/KEY: MISC_FEATURE
<222> LOCATION: (58)..(58)
<223> OTHER INFORMATION: X can be any amino acid
<220> FEATURE:
<221> NAME/KEY: MISC_FEATURE
<222> LOCATION: (67)..(67)
<223> OTHER INFORMATION: X can be any amino acid
<220> FEATURE:
<221> NAME/KEY: MISC_FEATURE
<222> LOCATION: (68)..(68)
<223> OTHER INFORMATION: X can be any amino acid
<220> FEATURE:
<221> NAME/KEY: MISC_FEATURE
<222> LOCATION: (84)..(84)
<223> OTHER INFORMATION: X can be any amino acid
<220> FEATURE:
<221> NAME/KEY: MISC_FEATURE
<222> LOCATION: (86)..(86)
<223> OTHER INFORMATION: X can be any amino acid

<400> SEQUENCE: 90

```
Leu Arg Asp Leu Val Ser Gly Phe Glu Glu Ile Asn Lys Xaa Ile Lys
1               5                   10                  15

Glu Asn Xaa Phe Ser Arg Ala Gly Xaa Leu Leu Ala Glu Leu Arg Pro
            20                  25                  30

Thr Ala Phe Tyr Ile Ser Thr Leu Ser Leu Phe Pro Ser Ala Leu Ala
            35                  40                  45

Leu Asp Trp Ala Val Pro Gly Leu Val Xaa Leu Leu Phe Pro Gly Gly
        50                  55                  60

Asn Val Xaa Xaa Glu Leu His Glu Phe Trp Tyr Lys His Cys Gly Leu
65                  70                  75                  80

Cys Ala Asn Xaa Ile Xaa Cys Phe Leu Gln Pro Leu Thr Lys Asn Asp
                85                  90                  95

Ser Leu Cys Ser Val Arg Arg Tyr Val Val Lys His Arg Thr Ala His
            100                 105                 110
```

```
Asn Gly Thr Trp Ser Glu Asp Val Gly Asn Arg Thr Asn Leu Thr Phe
            115                 120                 125

Leu Trp Thr Glu Pro Ala His Thr Val Thr Val Leu Ala Val Asn Ser
130                 135                 140

Leu Gly Ala Ser Leu Val Asn Phe Asn Leu Thr Phe Ser Trp Pro Met
145                 150                 155                 160

Ser Lys Val Ser Ala Val Glu Ser Leu Ser Ala Tyr Pro Leu Ser Ser
            165                 170                 175

Ser Cys Val Ile Leu Ser Trp Thr Leu Ser Pro Asp Asp Tyr Ser Leu
            180                 185                 190

Leu Tyr Leu Val Ile Glu Trp Lys Ile Leu Asn Glu Asp Asp Gly Met
            195                 200                 205

Lys Trp Leu Arg Ile Pro Ser Asn Val Lys Lys Phe Tyr Ile His Asp
210                 215                 220

Asn Phe Ile Pro Ile Glu Lys Tyr Gln Phe Ser Leu Tyr Pro Val Phe
225                 230                 235                 240

Met Glu Gly Val Gly Lys Pro Lys Ile Ile Asn Gly Phe Thr Lys Asp
            245                 250                 255

Ala Ile Asp Lys Gln Gln Asn Asp Ala Gly Leu Tyr Val Ile Val Pro
            260                 265                 270

Ile Ile Ile Ser Ser Cys Val Leu Leu Leu Gly Thr Leu Leu Ile Ser
            275                 280                 285

His Gln Arg Met Lys Lys Leu Phe Trp Asp Asp Val Pro Asn Pro Lys
            290                 295                 300

Asn Cys Ser Trp Ala Gln Gly Leu Asn Phe Gln Lys Arg Thr Asp Thr
305                 310                 315                 320

Leu

<210> SEQ ID NO 91
<211> LENGTH: 320
<212> TYPE: PRT
<213> ORGANISM: Mus musculus
<220> FEATURE:
<221> NAME/KEY: MISC_FEATURE
<222> LOCATION: (79)..(79)
<223> OTHER INFORMATION: X can be any amino acid

<400> SEQUENCE: 91

Leu Arg Asp Leu Val Ser Gly Phe Glu Glu Ile Asn Lys Ile Lys Glu
1               5                   10                  15

Asn Phe Ser Arg Ala Gly Leu Leu Ala Glu Leu Arg Pro Thr Ala Phe
                20                  25                  30

Tyr Ile Ser Thr Leu Ser Leu Phe Pro Ser Ala Leu Ala Leu Asp Trp
            35                  40                  45

Ala Val Pro Gly Leu Val Leu Leu Phe Pro Gly Gly Asn Val Glu Leu
    50                  55                  60

His Glu Phe Trp Tyr Lys His Cys Gly Leu Cys Ala Asn Ile Xaa Cys
65                  70                  75                  80

Phe Leu Gln Pro Leu Thr Lys Asn Asp Ser Leu Cys Ser Val Arg Arg
                85                  90                  95

Tyr Val Val Lys His Arg Thr Ala His Asn Gly Thr Trp Ser Glu Asp
            100                 105                 110

Val Gly Asn Arg Thr Asn Leu Thr Phe Leu Trp Thr Glu Pro Ala His
            115                 120                 125

Thr Val Thr Val Leu Ala Val Asn Ser Leu Gly Ala Ser Leu Val Asn
```

-continued

```
                130                 135                 140
Phe Asn Leu Thr Phe Ser Trp Pro Met Ser Lys Val Ser Ala Val Glu
145                 150                 155                 160

Ser Leu Ser Ala Tyr Pro Leu Ser Ser Ser Cys Val Ile Leu Ser Trp
                165                 170                 175

Thr Leu Ser Pro Asp Asp Tyr Ser Leu Leu Tyr Leu Val Ile Glu Trp
                180                 185                 190

Lys Ile Leu Asn Glu Asp Asp Gly Met Lys Trp Leu Arg Ile Pro Ser
                195                 200                 205

Asn Val Lys Lys Phe Tyr Ile His Asp Asn Phe Ile Pro Ile Glu Lys
210                 215                 220

Tyr Gln Phe Ser Leu Tyr Pro Val Phe Met Glu Gly Val Gly Lys Pro
225                 230                 235                 240

Lys Ile Ile Asn Gly Phe Thr Lys Asp Ala Ile Asp Lys Gln Gln Asn
                245                 250                 255

Asp Ala Gly Leu Tyr Val Ile Val Pro Ile Ile Ser Ser Cys Val
                260                 265                 270

Leu Leu Leu Gly Thr Leu Leu Ile Ser His Gln Arg Met Lys Lys Leu
                275                 280                 285

Phe Trp Asp Asp Val Pro Asn Pro Lys Asn Cys Ser Trp Ala Gln Gly
290                 295                 300

Leu Asn Phe Gln Lys Asp Ile Ser Leu His Glu Val Phe Ile Phe Arg
305                 310                 315                 320
```

<210> SEQ ID NO 92
<211> LENGTH: 327
<212> TYPE: PRT
<213> ORGANISM: Mus musculus
<220> FEATURE:
<221> NAME/KEY: MISC_FEATURE
<222> LOCATION: (14)..(14)
<223> OTHER INFORMATION: X can be any amino acid
<220> FEATURE:
<221> NAME/KEY: MISC_FEATURE
<222> LOCATION: (19)..(19)
<223> OTHER INFORMATION: X can be any amino acid
<220> FEATURE:
<221> NAME/KEY: MISC_FEATURE
<222> LOCATION: (25)..(25)
<223> OTHER INFORMATION: X can be any amino acid
<220> FEATURE:
<221> NAME/KEY: MISC_FEATURE
<222> LOCATION: (58)..(58)
<223> OTHER INFORMATION: X can be any amino acid
<220> FEATURE:
<221> NAME/KEY: MISC_FEATURE
<222> LOCATION: (67)..(67)
<223> OTHER INFORMATION: X can be any amino acid
<220> FEATURE:
<221> NAME/KEY: MISC_FEATURE
<222> LOCATION: (68)..(68)
<223> OTHER INFORMATION: X can be any amino acid
<220> FEATURE:
<221> NAME/KEY: MISC_FEATURE
<222> LOCATION: (84)..(84)
<223> OTHER INFORMATION: X can be any amino acid
<220> FEATURE:
<221> NAME/KEY: MISC_FEATURE
<222> LOCATION: (86)..(86)
<223> OTHER INFORMATION: X can be any amino acid

<400> SEQUENCE: 92

```
Leu Arg Asp Leu Val Ser Gly Phe Glu Glu Ile Asn Lys Xaa Ile Lys
1               5                   10                  15

Glu Asn Xaa Phe Ser Arg Ala Gly Xaa Leu Leu Ala Glu Leu Arg Pro
```

```
                 20                  25                  30

Thr Ala Phe Tyr Ile Ser Thr Leu Ser Leu Phe Pro Ser Ala Leu Ala
             35                  40                  45

Leu Asp Trp Ala Val Pro Gly Leu Val Xaa Leu Leu Phe Pro Gly Gly
 50                  55                  60

Asn Val Xaa Xaa Glu Leu His Glu Phe Trp Tyr Lys His Cys Gly Leu
 65                  70                  75                  80

Cys Ala Asn Xaa Ile Xaa Cys Phe Leu Gln Pro Leu Thr Lys Asn Asp
                 85                  90                  95

Ser Leu Cys Ser Val Arg Arg Tyr Val Val Lys His Arg Thr Ala His
             100                 105                 110

Asn Gly Thr Trp Ser Glu Asp Val Gly Asn Arg Thr Asn Leu Thr Phe
         115                 120                 125

Leu Trp Thr Glu Pro Ala His Thr Val Thr Val Leu Ala Val Asn Ser
130                 135                 140

Leu Gly Ala Ser Leu Val Asn Phe Asn Leu Thr Phe Ser Trp Pro Met
145                 150                 155                 160

Ser Lys Val Ser Ala Val Glu Ser Leu Ser Ala Tyr Pro Leu Ser Ser
                165                 170                 175

Ser Cys Val Ile Leu Ser Trp Thr Leu Ser Pro Asp Asp Tyr Ser Leu
            180                 185                 190

Leu Tyr Leu Val Ile Glu Trp Lys Ile Leu Asn Glu Asp Asp Gly Met
        195                 200                 205

Lys Trp Leu Arg Ile Pro Ser Asn Val Lys Phe Tyr Ile His Asp
210                 215                 220

Asn Phe Ile Pro Ile Glu Lys Tyr Gln Phe Ser Leu Tyr Pro Val Phe
225                 230                 235                 240

Met Glu Gly Val Gly Lys Pro Lys Ile Ile Asn Gly Phe Thr Lys Asp
                245                 250                 255

Ala Ile Asp Lys Gln Gln Asn Asp Ala Gly Leu Tyr Val Ile Val Pro
            260                 265                 270

Ile Ile Ile Ser Ser Cys Val Leu Leu Leu Gly Thr Leu Leu Ile Ser
        275                 280                 285

His Gln Arg Met Lys Lys Leu Phe Trp Asp Asp Val Pro Asn Pro Lys
290                 295                 300

Asn Cys Ser Trp Ala Gln Gly Leu Asn Phe Gln Lys Asp Ile Ser Leu
305                 310                 315                 320

His Glu Val Phe Ile Phe Arg
                325

<210> SEQ ID NO 93
<211> LENGTH: 894
<212> TYPE: PRT
<213> ORGANISM: Mus musculus

<400> SEQUENCE: 93

Met Met Cys Gln Lys Phe Tyr Val Val Leu Leu His Trp Glu Phe Leu
1               5                   10                  15

Tyr Val Ile Ala Ala Leu Asn Leu Ala Tyr Pro Ile Ser Pro Trp Lys
                20                  25                  30

Phe Lys Leu Phe Cys Gly Pro Pro Asn Thr Thr Asp Asp Ser Phe Leu
            35                  40                  45

Ser Pro Ala Gly Ala Pro Asn Asn Ala Ser Ala Leu Lys Gly Ala Ser
        50                  55                  60
```

-continued

```
Glu Ala Ile Val Glu Ala Lys Phe Asn Ser Ser Gly Ile Tyr Val Pro
 65                  70                  75                  80

Glu Leu Ser Lys Thr Val Phe His Cys Cys Phe Gly Asn Glu Gln Gly
                 85                  90                  95

Gln Asn Cys Ser Ala Leu Thr Asp Asn Thr Glu Gly Lys Thr Leu Ala
            100                 105                 110

Ser Val Val Lys Ala Ser Val Phe Arg Gln Leu Gly Val Asn Trp Asp
                115                 120                 125

Ile Glu Cys Trp Met Lys Gly Asp Leu Thr Leu Phe Ile Cys His Met
130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Asp Ser Pro Leu Pro Pro
                165                 170                 175

Leu Lys Asp Ser Phe Gln Thr Val Gln Cys Asn Cys Ser Leu Arg Gly
                180                 185                 190

Cys Glu Cys His Val Pro Val Pro Arg Ala Lys Leu Asn Tyr Ala Leu
            195                 200                 205

Leu Met Tyr Leu Glu Ile Thr Ser Ala Gly Val Ser Phe Gln Ser Pro
210                 215                 220

Leu Met Ser Leu Gln Pro Met Leu Val Val Lys Pro Asp Pro Pro Leu
225                 230                 235                 240

Gly Leu His Met Glu Val Thr Asp Asp Gly Asn Leu Lys Ile Ser Trp
                245                 250                 255

Asp Ser Gln Thr Met Ala Pro Phe Pro Leu Gln Tyr Gln Val Lys Tyr
            260                 265                 270

Leu Glu Asn Ser Thr Ile Val Arg Glu Ala Ala Glu Ile Val Ser Ala
            275                 280                 285

Thr Ser Leu Leu Val Asp Ser Val Leu Pro Gly Ser Ser Tyr Glu Val
290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro
                325                 330                 335

Lys Ile Leu Thr Ser Val Gly Ser Asn Ala Ser Phe His Cys Ile Tyr
            340                 345                 350

Lys Asn Glu Asn Gln Ile Ile Ser Ser Lys Gln Ile Val Trp Trp Arg
            355                 360                 365

Asn Leu Ala Glu Lys Ile Pro Glu Ile Gln Tyr Ser Ile Val Ser Asp
370                 375                 380

Arg Val Ser Lys Val Thr Phe Ser Asn Leu Lys Ala Thr Arg Pro Arg
385                 390                 395                 400

Gly Lys Phe Thr Tyr Asp Ala Val Tyr Cys Cys Asn Glu Gln Ala Cys
                405                 410                 415

His His Arg Tyr Ala Glu Leu Tyr Val Ile Asp Val Asn Ile Asn Ile
            420                 425                 430

Ser Cys Glu Thr Asp Gly Tyr Leu Thr Lys Met Thr Cys Arg Trp Ser
            435                 440                 445

Pro Ser Thr Ile Gln Ser Leu Val Gly Ser Thr Val Gln Leu Arg Tyr
            450                 455                 460

His Arg Arg Ser Leu Tyr Cys Pro Asp Ser Pro Ser Ile His Pro Thr
465                 470                 475                 480

Ser Glu Pro Lys Asn Cys Val Leu Gln Arg Asp Gly Phe Tyr Glu Cys
```

-continued

```
                485                 490                 495
Val Phe Gln Pro Ile Phe Leu Leu Ser Gly Tyr Thr Met Trp Ile Arg
            500                 505                 510
Ile Asn His Ser Leu Gly Ser Leu Asp Ser Pro Thr Cys Val Leu
            515                 520                 525
Pro Asp Ser Val Val Lys Pro Leu Pro Pro Ser Asn Val Lys Ala Glu
            530                 535                 540
Ile Thr Val Asn Thr Gly Leu Leu Lys Val Ser Trp Glu Lys Pro Val
545                 550                 555                 560
Phe Pro Glu Asn Asn Leu Gln Phe Gln Ile Arg Tyr Gly Leu Ser Gly
                565                 570                 575
Lys Glu Ile Gln Trp Lys Thr His Glu Val Phe Asp Ala Lys Ser Lys
            580                 585                 590
Ser Ala Ser Leu Leu Val Ser Asp Leu Cys Ala Val Tyr Val Val Gln
            595                 600                 605
Val Arg Cys Arg Arg Leu Asp Gly Leu Gly Tyr Trp Ser Asn Trp Ser
            610                 615                 620
Ser Pro Ala Tyr Thr Leu Val Met Asp Val Lys Val Pro Met Arg Gly
625                 630                 635                 640
Pro Glu Phe Trp Arg Lys Met Asp Gly Asp Val Thr Lys Lys Glu Arg
                645                 650                 655
Asn Val Thr Leu Leu Trp Lys Pro Leu Thr Lys Asn Asp Ser Leu Cys
            660                 665                 670
Ser Val Arg Arg Tyr Val Val Lys His Arg Thr Ala His Asn Gly Thr
            675                 680                 685
Trp Ser Glu Asp Val Gly Asn Arg Thr Asn Leu Thr Phe Leu Trp Thr
690                 695                 700
Glu Pro Ala His Thr Val Thr Val Leu Ala Val Asn Ser Leu Gly Ala
705                 710                 715                 720
Ser Leu Val Asn Phe Asn Leu Thr Phe Ser Trp Pro Met Ser Lys Val
                725                 730                 735
Ser Ala Val Glu Ser Leu Ser Ala Tyr Pro Leu Ser Ser Ser Cys Val
            740                 745                 750
Ile Leu Ser Trp Thr Leu Ser Pro Asp Asp Tyr Ser Leu Leu Tyr Leu
            755                 760                 765
Val Ile Glu Trp Lys Ile Leu Asn Glu Asp Asp Gly Met Lys Trp Leu
            770                 775                 780
Arg Ile Pro Ser Asn Val Lys Lys Phe Tyr Ile His Asp Asn Phe Ile
785                 790                 795                 800
Pro Ile Glu Lys Tyr Gln Phe Ser Leu Tyr Pro Val Phe Met Glu Gly
                805                 810                 815
Val Gly Lys Pro Lys Ile Ile Asn Gly Phe Thr Lys Asp Ala Ile Asp
            820                 825                 830
Lys Gln Gln Asn Asp Ala Gly Leu Tyr Val Ile Val Pro Ile Ile Ile
            835                 840                 845
Ser Ser Cys Val Leu Leu Leu Gly Thr Leu Leu Ile Ser His Gln Arg
            850                 855                 860
Met Lys Lys Leu Phe Trp Asp Asp Val Pro Asn Pro Lys Asn Cys Ser
865                 870                 875                 880
Trp Ala Gln Gly Leu Asn Phe Gln Lys Arg Thr Asp Thr Leu
                885                 890
```

<210> SEQ ID NO 94

<211> LENGTH: 1162
<212> TYPE: PRT
<213> ORGANISM: Mus musculus

<400> SEQUENCE: 94

```
Met Met Cys Gln Lys Phe Tyr Val Val Leu Leu His Trp Glu Phe Leu
1               5                   10                  15

Tyr Val Ile Ala Ala Leu Asn Leu Ala Tyr Pro Ile Ser Pro Trp Lys
            20                  25                  30

Phe Lys Leu Phe Cys Gly Pro Pro Asn Thr Thr Asp Asp Ser Phe Leu
        35                  40                  45

Ser Pro Ala Gly Ala Pro Asn Asn Ala Ser Ala Leu Lys Gly Ala Ser
    50                  55                  60

Glu Ala Ile Val Glu Ala Lys Phe Asn Ser Ser Gly Ile Tyr Val Pro
65                  70                  75                  80

Glu Leu Ser Lys Thr Val Phe His Cys Cys Phe Gly Asn Glu Gln Gly
                85                  90                  95

Gln Asn Cys Ser Ala Leu Thr Asp Asn Thr Glu Gly Lys Thr Leu Ala
            100                 105                 110

Ser Val Val Lys Ala Ser Val Phe Arg Gln Leu Gly Val Asn Trp Asp
        115                 120                 125

Ile Glu Cys Trp Met Lys Gly Asp Leu Thr Leu Phe Ile Cys His Met
130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Asp Ser Pro Leu Pro Pro
                165                 170                 175

Leu Lys Asp Ser Phe Gln Thr Val Gln Cys Asn Cys Ser Leu Arg Gly
            180                 185                 190

Cys Glu Cys His Val Pro Val Pro Arg Ala Lys Leu Asn Tyr Ala Leu
        195                 200                 205

Leu Met Tyr Leu Glu Ile Thr Ser Ala Gly Val Ser Phe Gln Ser Pro
210                 215                 220

Leu Met Ser Leu Gln Pro Met Leu Val Val Lys Pro Asp Pro Pro Leu
225                 230                 235                 240

Gly Leu His Met Glu Val Thr Asp Asp Gly Asn Leu Lys Ile Ser Trp
                245                 250                 255

Asp Ser Gln Thr Met Ala Pro Phe Pro Leu Gln Tyr Gln Val Lys Tyr
            260                 265                 270

Leu Glu Asn Ser Thr Ile Val Arg Glu Ala Ala Glu Ile Val Ser Ala
        275                 280                 285

Thr Ser Leu Leu Val Asp Ser Val Leu Pro Gly Ser Ser Tyr Glu Val
290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro
                325                 330                 335

Lys Ile Leu Thr Ser Val Gly Ser Asn Ala Ser Phe His Cys Ile Tyr
            340                 345                 350

Lys Asn Glu Asn Gln Ile Ile Ser Ser Lys Gln Ile Val Trp Trp Arg
        355                 360                 365

Asn Leu Ala Glu Lys Ile Pro Glu Ile Gln Tyr Ser Ile Val Ser Asp
370                 375                 380

Arg Val Ser Lys Val Thr Phe Ser Asn Leu Lys Ala Thr Arg Pro Arg
```

-continued

```
            385                 390                 395                 400
Gly Lys Phe Thr Tyr Asp Ala Val Tyr Cys Cys Asn Glu Gln Ala Cys
                405                 410                 415

His His Arg Tyr Ala Glu Leu Tyr Val Ile Asp Val Asn Ile Asn Ile
                420                 425                 430

Ser Cys Glu Thr Asp Gly Tyr Leu Thr Lys Met Thr Cys Arg Trp Ser
                435                 440                 445

Pro Ser Thr Ile Gln Ser Leu Val Gly Ser Thr Val Gln Leu Arg Tyr
                450                 455                 460

His Arg Arg Ser Leu Tyr Cys Pro Asp Ser Pro Ser Ile His Pro Thr
465                 470                 475                 480

Ser Glu Pro Lys Asn Cys Val Leu Gln Arg Asp Gly Phe Tyr Glu Cys
                485                 490                 495

Val Phe Gln Pro Ile Phe Leu Leu Ser Gly Tyr Thr Met Trp Ile Arg
                500                 505                 510

Ile Asn His Ser Leu Gly Ser Leu Asp Ser Pro Pro Thr Cys Val Leu
                515                 520                 525

Pro Asp Ser Val Val Lys Pro Leu Pro Pro Ser Asn Val Lys Ala Glu
530                 535                 540

Ile Thr Val Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Ser Gly
                565                 570                 575

Lys Glu Ile Gln Trp Lys Thr His Glu Val Phe Asp Ala Lys Ser Lys
                580                 585                 590

Ser Ala Ser Leu Leu Val Ser Asp Leu Cys Ala Val Tyr Val Val Gln
                595                 600                 605

Val Arg Cys Arg Arg Leu Asp Gly Leu Gly Tyr Trp Ser Asn Trp Ser
                610                 615                 620

Ser Pro Ala Tyr Thr Leu Val Met Asp Val Lys Val Pro Met Arg Gly
625                 630                 635                 640

Pro Glu Phe Trp Arg Lys Met Asp Gly Asp Val Thr Lys Lys Glu Arg
                645                 650                 655

Asn Val Thr Leu Leu Trp Lys Pro Leu Thr Lys Asn Asp Ser Leu Cys
                660                 665                 670

Ser Val Arg Arg Tyr Val Val Lys His Arg Thr Ala His Asn Gly Thr
                675                 680                 685

Trp Ser Glu Asp Val Gly Asn Arg Thr Asn Leu Thr Phe Leu Trp Thr
                690                 695                 700

Glu Pro Ala His Thr Val Thr Val Leu Ala Val Asn Ser Leu Gly Ala
705                 710                 715                 720

Ser Leu Val Asn Phe Asn Leu Thr Phe Ser Trp Pro Met Ser Lys Val
                725                 730                 735

Ser Ala Val Glu Ser Leu Ser Ala Tyr Pro Leu Ser Ser Ser Cys Val
                740                 745                 750

Ile Leu Ser Trp Thr Leu Ser Pro Asp Asp Tyr Ser Leu Leu Tyr Leu
                755                 760                 765

Val Ile Glu Trp Lys Ile Leu Asn Glu Asp Asp Gly Met Lys Trp Leu
                770                 775                 780

Arg Ile Pro Ser Asn Val Lys Lys Phe Tyr Ile His Asp Asn Phe Ile
785                 790                 795                 800

Pro Ile Glu Lys Tyr Gln Phe Ser Leu Tyr Pro Val Phe Met Glu Gly
                805                 810                 815
```

Val Gly Lys Pro Lys Ile Ile Asn Gly Phe Thr Lys Asp Ala Ile Asp
            820                 825                 830

Lys Gln Gln Asn Asp Ala Gly Leu Tyr Val Ile Val Pro Ile Ile Ile
            835                 840                 845

Ser Ser Cys Val Leu Leu Gly Thr Leu Leu Ile Ser His Gln Arg
            850                 855                 860

Met Lys Lys Leu Phe Trp Asp Val Pro Asn Pro Lys Asn Cys Ser
865                 870                 875                 880

Trp Ala Gln Gly Leu Asn Phe Gln Lys Pro Glu Thr Phe Glu Gln Leu
                885                 890                 895

Phe Thr Lys His Ala Glu Ser Val Ile Phe Gly Pro Leu Leu Leu Glu
            900                 905                 910

Pro Glu Pro Ile Ser Glu Glu Ile Ser Val Asp Thr Ala Trp Lys Asn
            915                 920                 925

Lys Asp Glu Met Val Pro Ala Ala Met Val Ser Leu Leu Leu Thr Thr
            930                 935                 940

Pro Asp Pro Glu Ser Ser Ser Ile Cys Ile Ser Asp Gln Cys Asn Ser
945                 950                 955                 960

Ala Asn Phe Ser Gly Ser Gln Ser Thr Gln Val Thr Cys Glu Asp Glu
                965                 970                 975

Cys Gln Arg Gln Pro Ser Val Lys Tyr Ala Thr Leu Val Ser Asn Asp
            980                 985                 990

Lys Leu Val Glu Thr Asp Glu Glu Gln Gly Phe Ile His Ser Pro Val
            995                 1000                1005

Ser Asn Cys Ile Ser Ser Asn His Ser Pro Leu Arg Gln Ser Phe
            1010                1015                1020

Ser Ser Ser Ser Trp Glu Thr Glu Ala Gln Thr Phe Phe Leu Leu
            1025                1030                1035

Ser Asp Gln Gln Pro Thr Met Ile Ser Pro Gln Leu Ser Phe Ser
            1040                1045                1050

Gly Leu Asp Glu Leu Leu Glu Leu Glu Gly Ser Phe Pro Glu Glu
            1055                1060                1065

Asn His Arg Glu Lys Ser Val Cys Tyr Leu Gly Val Thr Ser Val
            1070                1075                1080

Asn Arg Arg Glu Ser Gly Val Leu Leu Thr Gly Glu Ala Gly Ile
            1085                1090                1095

Leu Cys Thr Phe Pro Ala Gln Cys Leu Phe Ser Asp Ile Arg Ile
            1100                1105                1110

Leu Gln Glu Arg Cys Ser His Phe Val Glu Asn Asn Leu Ser Leu
            1115                1120                1125

Gly Thr Ser Gly Glu Asn Phe Val Pro Tyr Met Pro Gln Phe Gln
            1130                1135                1140

Thr Cys Ser Thr His Ser His Lys Ile Met Glu Asn Lys Met Cys
            1145                1150                1155

Asp Leu Thr Val
    1160

<210> SEQ ID NO 95
<211> LENGTH: 892
<212> TYPE: PRT
<213> ORGANISM: Mus musculus

<400> SEQUENCE: 95

Met Met Cys Gln Lys Phe Tyr Val Val Leu Leu His Trp Glu Phe Leu

-continued

```
1               5                  10                 15
Tyr Val Ile Ala Ala Leu Asn Leu Ala Tyr Pro Ile Ser Pro Trp Lys
             20                 25                 30

Phe Lys Leu Phe Cys Gly Pro Pro Asn Thr Thr Asp Asp Ser Phe Leu
             35                 40                 45

Ser Pro Ala Gly Ala Pro Asn Asn Ala Ser Ala Leu Lys Gly Ala Ser
 50                 55                 60

Glu Ala Ile Val Glu Ala Lys Phe Asn Ser Ser Gly Ile Tyr Val Pro
 65                 70                 75                 80

Glu Leu Ser Lys Thr Val Phe His Cys Cys Phe Gly Asn Glu Gln Gly
                 85                 90                 95

Gln Asn Cys Ser Ala Leu Thr Asp Asn Thr Glu Gly Lys Thr Leu Ala
                100                105                110

Ser Val Val Lys Ala Ser Val Phe Arg Gln Leu Gly Val Asn Trp Asp
                115                120                125

Ile Glu Cys Trp Met Lys Gly Asp Leu Thr Leu Phe Ile Cys His Met
        130                135                140

Glu Pro Leu Pro Lys Asn Pro Phe Lys Asn Tyr Asp Ser Lys Val His
145                150                155                160

Leu Leu Tyr Asp Leu Pro Glu Val Ile Asp Ser Pro Leu Pro Pro
                165                170                175

Leu Lys Asp Ser Phe Gln Thr Val Gln Cys Asn Cys Ser Leu Arg Gly
                180                185                190

Cys Glu Cys His Val Pro Val Pro Arg Ala Lys Leu Asn Tyr Ala Leu
                195                200                205

Leu Met Tyr Leu Glu Ile Thr Ser Ala Gly Val Ser Phe Gln Ser Pro
        210                215                220

Leu Met Ser Leu Gln Pro Met Leu Val Val Lys Pro Asp Pro Pro Leu
225                230                235                240

Gly Leu His Met Glu Val Thr Asp Asp Gly Asn Leu Lys Ile Ser Trp
                245                250                255

Asp Ser Gln Thr Met Ala Pro Phe Pro Leu Gln Tyr Gln Val Lys Tyr
                260                265                270

Leu Glu Asn Ser Thr Ile Val Arg Glu Ala Ala Glu Ile Val Ser Ala
        275                280                285

Thr Ser Leu Leu Val Asp Ser Val Leu Pro Gly Ser Ser Tyr Glu Val
290                295                300

Gln Val Arg Ser Lys Arg Leu Asp Gly Ser Gly Val Trp Ser Asp Trp
305                310                315                320

Ser Ser Pro Gln Val Phe Thr Thr Gln Asp Val Val Tyr Phe Pro Pro
                325                330                335

Lys Ile Leu Thr Ser Val Gly Ser Asn Ala Ser Phe His Cys Ile Tyr
                340                345                350

Lys Asn Glu Asn Gln Ile Ile Ser Ser Lys Gln Ile Val Trp Trp Arg
                355                360                365

Asn Leu Ala Glu Lys Ile Pro Glu Ile Gln Tyr Ser Ile Val Ser Asp
        370                375                380

Arg Val Ser Lys Val Thr Phe Ser Asn Leu Lys Ala Thr Arg Pro Arg
385                390                395                400

Gly Lys Phe Thr Tyr Asp Ala Val Tyr Cys Cys Asn Glu Gln Ala Cys
                405                410                415

His His Arg Tyr Ala Glu Leu Tyr Val Ile Asp Val Asn Ile Asn Ile
        420                425                430
```

-continued

```
Ser Cys Glu Thr Asp Gly Tyr Leu Thr Lys Met Thr Cys Arg Trp Ser
            435                 440                 445

Pro Ser Thr Ile Gln Ser Leu Val Gly Ser Thr Val Gln Leu Arg Tyr
    450                 455                 460

His Arg Arg Ser Leu Tyr Cys Pro Asp Ser Pro Ser Ile His Pro Thr
465                 470                 475                 480

Ser Glu Pro Lys Asn Cys Val Leu Gln Arg Asp Gly Phe Tyr Glu Cys
                485                 490                 495

Val Phe Gln Pro Ile Phe Leu Leu Ser Gly Tyr Thr Met Trp Ile Arg
                500                 505                 510

Ile Asn His Ser Leu Gly Ser Leu Asp Ser Pro Thr Cys Val Leu
            515                 520                 525

Pro Asp Ser Val Val Lys Pro Leu Pro Ser Asn Val Lys Ala Glu
    530                 535                 540

Ile Thr Val Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Ser Gly
                565                 570                 575

Lys Glu Ile Gln Trp Lys Thr His Glu Val Phe Asp Ala Lys Ser Lys
                580                 585                 590

Ser Ala Ser Leu Leu Val Ser Asp Leu Cys Ala Val Tyr Val Val Gln
            595                 600                 605

Val Arg Cys Arg Arg Leu Asp Gly Leu Gly Tyr Trp Ser Asn Trp Ser
    610                 615                 620

Ser Pro Ala Tyr Thr Leu Val Met Asp Val Lys Val Pro Met Arg Gly
625                 630                 635                 640

Pro Glu Phe Trp Arg Lys Met Asp Gly Asp Val Thr Lys Lys Glu Arg
                645                 650                 655

Asn Val Thr Leu Leu Trp Lys Pro Leu Thr Lys Asn Asp Ser Leu Cys
                660                 665                 670

Ser Val Arg Arg Tyr Val Val Lys His Arg Thr Ala His Asn Gly Thr
            675                 680                 685

Trp Ser Glu Asp Val Gly Asn Arg Thr Asn Leu Thr Phe Leu Trp Thr
    690                 695                 700

Glu Pro Ala His Thr Val Thr Val Leu Ala Val Asn Ser Leu Gly Ala
705                 710                 715                 720

Ser Leu Val Asn Phe Asn Leu Thr Phe Ser Trp Pro Met Ser Lys Val
                725                 730                 735

Ser Ala Val Glu Ser Leu Ser Ala Tyr Pro Leu Ser Ser Ser Cys Val
            740                 745                 750

Ile Leu Ser Trp Thr Leu Ser Pro Asp Asp Tyr Ser Leu Leu Tyr Leu
            755                 760                 765

Val Ile Glu Trp Lys Ile Leu Asn Glu Asp Gly Met Lys Trp Leu
    770                 775                 780

Arg Ile Pro Ser Asn Val Lys Lys Phe Tyr Ile His Asp Asn Phe Ile
785                 790                 795                 800

Pro Ile Glu Lys Tyr Gln Phe Ser Leu Tyr Pro Val Phe Met Glu Gly
                805                 810                 815

Val Gly Lys Pro Lys Ile Ile Asn Gly Phe Thr Lys Asp Ala Ile Asp
                820                 825                 830

Lys Gln Gln Asn Asp Ala Gly Leu Tyr Val Ile Val Pro Ile Ile Ile
            835                 840                 845
```

```
Ser Ser Cys Val Leu Leu Gly Thr Leu Ile Ser His Gln Arg
    850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Val Thr Val
                885                 890

<210> SEQ ID NO 96
<211> LENGTH: 231
<212> TYPE: PRT
<213> ORGANISM: Mus musculus

<400> SEQUENCE: 96

Pro Leu Thr Lys Asn Asp Ser Leu Cys Ser Val Arg Arg Tyr Val Val
1               5                   10                  15

Lys His Arg Thr Ala His Asn Gly Thr Trp Ser Glu Asp Val Gly Asn
                20                  25                  30

Arg Thr Asn Leu Thr Phe Leu Trp Thr Glu Pro Ala His Thr Val Thr
            35                  40                  45

Val Leu Ala Val Asn Ser Leu Gly Ala Ser Leu Val Asn Phe Asn Leu
    50                  55                  60

Thr Phe Ser Trp Pro Met Ser Lys Val Ser Ala Val Glu Ser Leu Ser
65                  70                  75                  80

Ala Tyr Pro Leu Ser Ser Cys Val Ile Leu Ser Trp Thr Leu Ser
                85                  90                  95

Pro Asp Asp Tyr Ser Leu Leu Tyr Leu Val Ile Glu Trp Lys Ile Leu
                100                 105                 110

Asn Glu Asp Asp Gly Met Lys Trp Leu Arg Ile Pro Ser Asn Val Lys
            115                 120                 125

Lys Phe Tyr Ile His Asp Asn Phe Ile Pro Ile Glu Lys Tyr Gln Phe
130                 135                 140

Ser Leu Tyr Pro Val Phe Met Glu Gly Val Gly Lys Pro Lys Ile Ile
145                 150                 155                 160

Asn Gly Phe Thr Lys Asp Ala Ile Asp Lys Gln Gln Asn Asp Ala Gly
                165                 170                 175

Leu Tyr Val Ile Val Pro Ile Ile Ile Ser Ser Cys Val Leu Leu Leu
            180                 185                 190

Gly Thr Leu Leu Ile Ser His Gln Arg Met Lys Lys Leu Phe Trp Asp
        195                 200                 205

Asp Val Pro Asn Pro Lys Asn Cys Ser Trp Ala Gln Gly Leu Asn Phe
    210                 215                 220

Gln Lys Arg Thr Asp Thr Leu
225                 230

<210> SEQ ID NO 97
<211> LENGTH: 499
<212> TYPE: PRT
<213> ORGANISM: Mus musculus

<400> SEQUENCE: 97

Pro Leu Thr Lys Asn Asp Ser Leu Cys Ser Val Arg Arg Tyr Val Val
1               5                   10                  15

Lys His Arg Thr Ala His Asn Gly Thr Trp Ser Glu Asp Val Gly Asn
                20                  25                  30

Arg Thr Asn Leu Thr Phe Leu Trp Thr Glu Pro Ala His Thr Val Thr
            35                  40                  45
```

Val Leu Ala Val Asn Ser Leu Gly Ala Ser Leu Val Asn Phe Asn Leu
 50                  55                  60

Thr Phe Ser Trp Pro Met Ser Lys Val Ser Ala Val Glu Ser Leu Ser
 65                  70                  75                  80

Ala Tyr Pro Leu Ser Ser Cys Val Ile Leu Ser Trp Thr Leu Ser
                 85                  90                  95

Pro Asp Asp Tyr Ser Leu Leu Tyr Leu Val Ile Glu Trp Lys Ile Leu
                100                 105                 110

Asn Glu Asp Asp Gly Met Lys Trp Leu Arg Ile Pro Ser Asn Val Lys
            115                 120                 125

Lys Phe Tyr Ile His Asp Asn Phe Ile Pro Ile Glu Lys Tyr Gln Phe
130                 135                 140

Ser Leu Tyr Pro Val Phe Met Glu Gly Val Gly Lys Pro Lys Ile Ile
145                 150                 155                 160

Asn Gly Phe Thr Lys Asp Ala Ile Asp Lys Gln Gln Asn Asp Ala Gly
                165                 170                 175

Leu Tyr Val Ile Val Pro Ile Ile Ser Ser Cys Val Leu Leu Leu
                180                 185                 190

Gly Thr Leu Leu Ile Ser His Gln Arg Met Lys Lys Leu Phe Trp Asp
            195                 200                 205

Asp Val Pro Asn Pro Lys Asn Cys Ser Trp Ala Gln Gly Leu Asn Phe
210                 215                 220

Gln Lys Pro Glu Thr Phe Glu Gln Leu Phe Thr Lys His Ala Glu Ser
225                 230                 235                 240

Val Ile Phe Gly Pro Leu Leu Leu Glu Pro Glu Pro Ile Ser Glu Glu
                245                 250                 255

Ile Ser Val Asp Thr Ala Trp Lys Asn Lys Asp Glu Met Val Pro Ala
            260                 265                 270

Ala Met Val Ser Leu Leu Leu Thr Thr Pro Asp Pro Glu Ser Ser Ser
            275                 280                 285

Ile Cys Ile Ser Asp Gln Cys Asn Ser Ala Asn Phe Ser Gly Ser Gln
290                 295                 300

Ser Thr Gln Val Thr Cys Glu Asp Glu Cys Gln Arg Gln Pro Ser Val
305                 310                 315                 320

Lys Tyr Ala Thr Leu Val Ser Asn Asp Lys Leu Val Glu Thr Asp Glu
                325                 330                 335

Glu Gln Gly Phe Ile His Ser Pro Val Ser Asn Cys Ile Ser Ser Asn
            340                 345                 350

His Ser Pro Leu Arg Gln Ser Phe Ser Ser Ser Trp Glu Thr Glu
355                 360                 365

Ala Gln Thr Phe Phe Leu Leu Ser Asp Gln Pro Thr Met Ile Ser
    370                 375                 380

Pro Gln Leu Ser Phe Ser Gly Leu Asp Glu Leu Leu Glu Leu Glu Gly
385                 390                 395                 400

Ser Phe Pro Glu Glu Asn His Arg Glu Lys Ser Val Cys Tyr Leu Gly
                405                 410                 415

Val Thr Ser Val Asn Arg Arg Glu Ser Gly Val Leu Leu Thr Gly Glu
            420                 425                 430

Ala Gly Ile Leu Cys Thr Phe Pro Ala Gln Cys Leu Phe Ser Asp Ile
            435                 440                 445

Arg Ile Leu Gln Glu Arg Cys Ser His Phe Val Glu Asn Asn Leu Ser
450                 455                 460

Leu Gly Thr Ser Gly Glu Asn Phe Val Pro Tyr Met Pro Gln Phe Gln

```
465                 470                 475                 480
Thr Cys Ser Thr His Ser His Lys Ile Met Glu Asn Lys Met Cys Asp
                485                 490                 495
Leu Thr Val

<210> SEQ ID NO 98
<211> LENGTH: 229
<212> TYPE: PRT
<213> ORGANISM: Mus musculus

<400> SEQUENCE: 98

Pro Leu Thr Lys Asn Asp Ser Leu Cys Ser Val Arg Arg Tyr Val Val
1               5                   10                  15

Lys His Arg Thr Ala His Asn Gly Thr Trp Ser Glu Asp Val Gly Asn
                20                  25                  30

Arg Thr Asn Leu Thr Phe Leu Trp Thr Glu Pro Ala His Thr Val Thr
            35                  40                  45

Val Leu Ala Val Asn Ser Leu Gly Ala Ser Leu Val Asn Phe Asn Leu
    50                  55                  60

Thr Phe Ser Trp Pro Met Ser Lys Val Ser Ala Val Glu Ser Leu Ser
65                  70                  75                  80

Ala Tyr Pro Leu Ser Ser Cys Val Ile Leu Ser Trp Thr Leu Ser
                85                  90                  95

Pro Asp Asp Tyr Ser Leu Leu Tyr Leu Val Ile Glu Trp Lys Ile Leu
                100                 105                 110

Asn Glu Asp Asp Gly Met Lys Trp Leu Arg Ile Pro Ser Asn Val Lys
            115                 120                 125

Lys Phe Tyr Ile His Asp Asn Phe Ile Pro Ile Glu Lys Tyr Gln Phe
    130                 135                 140

Ser Leu Tyr Pro Val Phe Met Glu Gly Val Gly Lys Pro Lys Ile Ile
145                 150                 155                 160

Asn Gly Phe Thr Lys Asp Ala Ile Asp Lys Gln Asn Asp Ala Gly
                165                 170                 175

Leu Tyr Val Ile Val Pro Ile Ile Ile Ser Ser Cys Val Leu Leu Leu
                180                 185                 190

Gly Thr Leu Leu Ile Ser His Gln Arg Met Lys Lys Leu Phe Trp Asp
            195                 200                 205

Asp Val Pro Asn Pro Lys Asn Cys Ser Trp Ala Gln Gly Leu Asn Phe
    210                 215                 220

Gln Lys Val Thr Val
225

<210> SEQ ID NO 99
<211> LENGTH: 237
<212> TYPE: PRT
<213> ORGANISM: Mus musculus

<400> SEQUENCE: 99

Pro Leu Thr Lys Asn Asp Ser Leu Cys Ser Val Arg Arg Tyr Val Val
1               5                   10                  15

Lys His Arg Thr Ala His Asn Gly Thr Trp Ser Glu Asp Val Gly Asn
                20                  25                  30

Arg Thr Asn Leu Thr Phe Leu Trp Thr Glu Pro Ala His Thr Val Thr
            35                  40                  45

Val Leu Ala Val Asn Ser Leu Gly Ala Ser Leu Val Asn Phe Asn Leu
    50                  55                  60
```

```
Thr Phe Ser Trp Pro Met Ser Lys Val Ser Ala Val Glu Ser Leu Ser
 65                  70                  75                  80

Ala Tyr Pro Leu Ser Ser Ser Cys Val Ile Leu Ser Trp Thr Leu Ser
                 85                  90                  95

Pro Asp Asp Tyr Ser Leu Leu Tyr Leu Val Ile Glu Trp Lys Ile Leu
            100                 105                 110

Asn Glu Asp Asp Gly Met Lys Trp Leu Arg Ile Pro Ser Asn Val Lys
        115                 120                 125

Lys Phe Tyr Ile His Asp Asn Phe Ile Pro Ile Glu Lys Tyr Gln Phe
130                 135                 140

Ser Leu Tyr Pro Val Phe Met Glu Gly Val Gly Lys Pro Lys Ile Ile
145                 150                 155                 160

Asn Gly Phe Thr Lys Asp Ala Ile Asp Lys Gln Gln Asn Asp Ala Gly
                165                 170                 175

Leu Tyr Val Ile Val Pro Ile Ile Ile Ser Ser Cys Val Leu Leu Leu
            180                 185                 190

Gly Thr Leu Leu Ile Ser His Gln Arg Met Lys Lys Leu Phe Trp Asp
        195                 200                 205

Asp Val Pro Asn Pro Lys Asn Cys Ser Trp Ala Gln Gly Leu Asn Phe
    210                 215                 220

Gln Lys Asp Ile Ser Leu His Glu Val Phe Ile Phe Arg
225                 230                 235

<210> SEQ ID NO 100
<211> LENGTH: 162
<212> TYPE: PRT
<213> ORGANISM: Mus musculus

<400> SEQUENCE: 100

Met Ser Lys Val Ser Ala Val Glu Ser Leu Ser Ala Tyr Pro Leu Ser
 1               5                  10                  15

Ser Ser Cys Val Ile Leu Ser Trp Thr Leu Ser Pro Asp Asp Tyr Ser
                20                  25                  30

Leu Leu Tyr Leu Val Ile Glu Trp Lys Ile Leu Asn Glu Asp Asp Gly
            35                  40                  45

Met Lys Trp Leu Arg Ile Pro Ser Asn Val Lys Lys Phe Tyr Ile His
        50                  55                  60

Asp Asn Phe Ile Pro Ile Glu Lys Tyr Gln Phe Ser Leu Tyr Pro Val
 65                  70                  75                  80

Phe Met Glu Gly Val Gly Lys Pro Lys Ile Ile Asn Gly Phe Thr Lys
                 85                  90                  95

Asp Ala Ile Asp Lys Gln Gln Asn Asp Ala Gly Leu Tyr Val Ile Val
            100                 105                 110

Pro Ile Ile Ile Ser Ser Cys Val Leu Leu Leu Gly Thr Leu Leu Ile
        115                 120                 125

Ser His Gln Arg Met Lys Lys Leu Phe Trp Asp Asp Val Pro Asn Pro
130                 135                 140

Lys Asn Cys Ser Trp Ala Gln Gly Leu Asn Phe Gln Lys Arg Thr Asp
145                 150                 155                 160

Thr Leu

<210> SEQ ID NO 101
<211> LENGTH: 430
<212> TYPE: PRT
<213> ORGANISM: Mus musculus
```

<400> SEQUENCE: 101

```
Met Ser Lys Val Ser Ala Val Glu Ser Leu Ser Ala Tyr Pro Leu Ser
1               5                   10                  15
Ser Ser Cys Val Ile Leu Ser Trp Thr Leu Ser Pro Asp Asp Tyr Ser
            20                  25                  30
Leu Leu Tyr Leu Val Ile Glu Trp Lys Ile Leu Asn Glu Asp Asp Gly
        35                  40                  45
Met Lys Trp Leu Arg Ile Pro Ser Asn Val Lys Lys Phe Tyr Ile His
    50                  55                  60
Asp Asn Phe Ile Pro Ile Glu Lys Tyr Gln Phe Ser Leu Tyr Pro Val
65                  70                  75                  80
Phe Met Glu Gly Val Gly Lys Pro Lys Ile Ile Asn Gly Phe Thr Lys
                85                  90                  95
Asp Ala Ile Asp Lys Gln Gln Asn Asp Ala Gly Leu Tyr Val Ile Val
            100                 105                 110
Pro Ile Ile Ile Ser Ser Cys Val Leu Leu Leu Gly Thr Leu Leu Ile
        115                 120                 125
Ser His Gln Arg Met Lys Lys Leu Phe Trp Asp Asp Val Pro Asn Pro
    130                 135                 140
Lys Asn Cys Ser Trp Ala Gln Gly Leu Asn Phe Gln Lys Pro Glu Thr
145                 150                 155                 160
Phe Glu Gln Leu Phe Thr Lys His Ala Glu Ser Val Ile Phe Gly Pro
                165                 170                 175
Leu Leu Leu Glu Pro Glu Pro Ile Ser Glu Glu Ile Ser Val Asp Thr
            180                 185                 190
Ala Trp Lys Asn Lys Asp Glu Met Val Pro Ala Ala Met Val Ser Leu
        195                 200                 205
Leu Leu Thr Thr Pro Asp Pro Glu Ser Ser Ile Cys Ile Ser Asp
    210                 215                 220
Gln Cys Asn Ser Ala Asn Phe Ser Gly Ser Gln Ser Thr Gln Val Thr
225                 230                 235                 240
Cys Glu Asp Glu Cys Gln Arg Gln Pro Ser Val Lys Tyr Ala Thr Leu
                245                 250                 255
Val Ser Asn Asp Lys Leu Val Leu Thr Asp Glu Glu Gln Gly Phe Ile
            260                 265                 270
His Ser Pro Val Ser Asn Cys Ile Ser Ser Asn His Ser Pro Leu Arg
        275                 280                 285
Gln Ser Phe Ser Ser Ser Trp Glu Thr Glu Ala Gln Thr Phe Phe
    290                 295                 300
Leu Leu Ser Asp Gln Gln Pro Thr Met Ile Ser Pro Gln Leu Ser Phe
305                 310                 315                 320
Ser Gly Leu Asp Glu Leu Leu Glu Leu Glu Gly Ser Phe Pro Glu Glu
                325                 330                 335
Asn His Arg Glu Lys Ser Val Cys Tyr Leu Gly Val Thr Ser Val Asn
            340                 345                 350
Arg Arg Glu Ser Gly Val Leu Leu Thr Gly Glu Ala Gly Ile Leu Cys
        355                 360                 365
Thr Phe Pro Ala Gln Cys Leu Phe Ser Asp Ile Arg Ile Leu Gln Glu
    370                 375                 380
Arg Cys Ser His Phe Val Glu Asn Asn Leu Ser Leu Gly Thr Ser Gly
385                 390                 395                 400
Glu Asn Phe Val Pro Tyr Met Pro Gln Phe Gln Thr Cys Ser Thr His
```

```
                405                 410                 415
Ser His Lys Ile Met Glu Asn Lys Met Cys Asp Leu Thr Val
        420                 425                 430

<210> SEQ ID NO 102
<211> LENGTH: 160
<212> TYPE: PRT
<213> ORGANISM: Mus musculus

<400> SEQUENCE: 102

Met Ser Lys Val Ser Ala Val Glu Ser Leu Ser Ala Tyr Pro Leu Ser
1               5                   10                  15

Ser Ser Cys Val Ile Leu Ser Trp Thr Leu Ser Pro Asp Asp Tyr Ser
            20                  25                  30

Leu Leu Tyr Leu Val Ile Glu Trp Lys Ile Leu Asn Glu Asp Asp Gly
        35                  40                  45

Met Lys Trp Leu Arg Ile Pro Ser Asn Val Lys Lys Phe Tyr Ile His
    50                  55                  60

Asp Asn Phe Ile Pro Ile Glu Lys Tyr Gln Phe Ser Leu Tyr Pro Val
65                  70                  75                  80

Phe Met Glu Gly Val Gly Lys Pro Lys Ile Ile Asn Gly Phe Thr Lys
                85                  90                  95

Asp Ala Ile Asp Lys Gln Gln Asn Asp Ala Gly Leu Tyr Val Ile Val
            100                 105                 110

Pro Ile Ile Ile Ser Ser Cys Val Leu Leu Leu Gly Thr Leu Leu Ile
        115                 120                 125

Ser His Gln Arg Met Lys Lys Leu Phe Trp Asp Asp Val Pro Asn Pro
    130                 135                 140

Lys Asn Cys Ser Trp Ala Gln Gly Leu Asn Phe Gln Lys Val Thr Val
145                 150                 155                 160

<210> SEQ ID NO 103
<211> LENGTH: 168
<212> TYPE: PRT
<213> ORGANISM: Mus musculus

<400> SEQUENCE: 103

Met Ser Lys Val Ser Ala Val Glu Ser Leu Ser Ala Tyr Pro Leu Ser
1               5                   10                  15

Ser Ser Cys Val Ile Leu Ser Trp Thr Leu Ser Pro Asp Asp Tyr Ser
            20                  25                  30

Leu Leu Tyr Leu Val Ile Glu Trp Lys Ile Leu Asn Glu Asp Asp Gly
        35                  40                  45

Met Lys Trp Leu Arg Ile Pro Ser Asn Val Lys Lys Phe Tyr Ile His
    50                  55                  60

Asp Asn Phe Ile Pro Ile Glu Lys Tyr Gln Phe Ser Leu Tyr Pro Val
65                  70                  75                  80

Phe Met Glu Gly Val Gly Lys Pro Lys Ile Ile Asn Gly Phe Thr Lys
                85                  90                  95

Asp Ala Ile Asp Lys Gln Gln Asn Asp Ala Gly Leu Tyr Val Ile Val
            100                 105                 110

Pro Ile Ile Ile Ser Ser Cys Val Leu Leu Leu Gly Thr Leu Leu Ile
        115                 120                 125

Ser His Gln Arg Met Lys Lys Leu Phe Trp Asp Asp Val Pro Asn Pro
    130                 135                 140

Lys Asn Cys Ser Trp Ala Gln Gly Leu Asn Phe Gln Lys Asp Ile Ser
```

```
                145                 150                 155                 160

Leu His Glu Val Phe Ile Phe Arg
                165

<210> SEQ ID NO 104
<211> LENGTH: 142
<212> TYPE: PRT
<213> ORGANISM: Mus musculus

<400> SEQUENCE: 104

Pro Leu Thr Lys Asn Asp Ser Leu Cys Ser Val Arg Arg Tyr Val Val
1               5                   10                  15

Lys His Arg Thr Ala His Asn Gly Thr Trp Ser Glu Asp Val Gly Asn
            20                  25                  30

Arg Thr Asn Leu Thr Phe Leu Trp Thr Glu Pro Ala His Thr Val Thr
        35                  40                  45

Val Leu Ala Val Asn Ser Leu Gly Ala Ser Leu Val Asn Phe Asn Leu
    50                  55                  60

Thr Phe Ser Trp Pro Met Ser Lys Val Ser Ala Val Glu Ser Leu Ser
65                  70                  75                  80

Ala Tyr Pro Leu Ser Ser Ser Cys Val Ile Leu Ser Trp Thr Leu Ser
                85                  90                  95

Pro Asp Asp Tyr Ser Leu Leu Tyr Leu Val Ile Glu Trp Lys Ile Leu
            100                 105                 110

Asn Glu Asp Asp Gly Met Lys Trp Leu Arg Ile Pro Ser Asn Val Lys
        115                 120                 125

Lys Phe Tyr Ile His Gly Met Cys Thr Val Leu Phe Met Asp
    130                 135                 140

<210> SEQ ID NO 105
<211> LENGTH: 142
<212> TYPE: PRT
<213> ORGANISM: Mus musculus

<400> SEQUENCE: 105

Pro Leu Thr Lys Asn Asp Ser Leu Cys Ser Val Arg Arg Tyr Val Val
1               5                   10                  15

Lys His Arg Thr Ala His Asn Gly Thr Trp Ser Glu Asp Val Gly Asn
            20                  25                  30

Arg Thr Asn Leu Thr Phe Leu Trp Thr Glu Pro Ala His Thr Val Thr
        35                  40                  45

Val Leu Ala Val Asn Ser Leu Gly Ala Ser Leu Val Asn Phe Asn Leu
    50                  55                  60

Thr Phe Ser Trp Pro Met Ser Lys Val Ser Ala Val Glu Ser Leu Ser
65                  70                  75                  80

Ala Tyr Pro Leu Ser Ser Ser Cys Val Ile Leu Ser Trp Thr Leu Ser
                85                  90                  95

Pro Asp Asp Tyr Ser Leu Leu Tyr Leu Val Ile Glu Trp Lys Ile Leu
            100                 105                 110

Asn Glu Asp Asp Gly Met Lys Trp Leu Arg Ile Pro Ser Asn Val Lys
        115                 120                 125

Lys Phe Tyr Ile His Gly Met Cys Thr Val Leu Phe Met Asp
    130                 135                 140

<210> SEQ ID NO 106
<211> LENGTH: 142
<212> TYPE: PRT
```

<213> ORGANISM: Mus musculus

<400> SEQUENCE: 106

Pro Leu Thr Lys Asn Asp Ser Leu Cys Ser Val Arg Arg Tyr Val Val
1               5                   10                  15

Lys His Arg Thr Ala His Asn Gly Thr Trp Ser Glu Asp Val Gly Asn
            20                  25                  30

Arg Thr Asn Leu Thr Phe Leu Trp Thr Glu Pro Ala His Thr Val Thr
        35                  40                  45

Val Leu Ala Val Asn Ser Leu Gly Ala Ser Leu Val Asn Phe Asn Leu
    50                  55                  60

Thr Phe Ser Trp Pro Met Ser Lys Val Ser Ala Val Glu Ser Leu Ser
65                  70                  75                  80

Ala Tyr Pro Leu Ser Ser Ser Cys Val Ile Leu Ser Trp Thr Leu Ser
                85                  90                  95

Pro Asp Asp Tyr Ser Leu Leu Tyr Leu Val Ile Glu Trp Lys Ile Leu
            100                 105                 110

Asn Glu Asp Asp Gly Met Lys Trp Leu Arg Ile Pro Ser Asn Val Lys
        115                 120                 125

Lys Phe Tyr Ile His Gly Met Cys Thr Val Leu Phe Met Asp
    130                 135                 140

<210> SEQ ID NO 107
<211> LENGTH: 142
<212> TYPE: PRT
<213> ORGANISM: Mus musculus

<400> SEQUENCE: 107

Pro Leu Thr Lys Asn Asp Ser Leu Cys Ser Val Arg Arg Tyr Val Val
1               5                   10                  15

Lys His Arg Thr Ala His Asn Gly Thr Trp Ser Glu Asp Val Gly Asn
            20                  25                  30

Arg Thr Asn Leu Thr Phe Leu Trp Thr Glu Pro Ala His Thr Val Thr
        35                  40                  45

Val Leu Ala Val Asn Ser Leu Gly Ala Ser Leu Val Asn Phe Asn Leu
    50                  55                  60

Thr Phe Ser Trp Pro Met Ser Lys Val Ser Ala Val Glu Ser Leu Ser
65                  70                  75                  80

Ala Tyr Pro Leu Ser Ser Ser Cys Val Ile Leu Ser Trp Thr Leu Ser
                85                  90                  95

Pro Asp Asp Tyr Ser Leu Leu Tyr Leu Val Ile Glu Trp Lys Ile Leu
            100                 105                 110

Asn Glu Asp Asp Gly Met Lys Trp Leu Arg Ile Pro Ser Asn Val Lys
        115                 120                 125

Lys Phe Tyr Ile His Gly Met Cys Thr Val Leu Phe Met Asp
    130                 135                 140

<210> SEQ ID NO 108
<211> LENGTH: 73
<212> TYPE: PRT
<213> ORGANISM: Mus musculus

<400> SEQUENCE: 108

Met Ser Lys Val Ser Ala Val Glu Ser Leu Ser Ala Tyr Pro Leu Ser
1               5                   10                  15

Ser Ser Cys Val Ile Leu Ser Trp Thr Leu Ser Pro Asp Asp Tyr Ser
            20                  25                  30

Leu Leu Tyr Leu Val Ile Glu Trp Lys Ile Leu Asn Glu Asp Asp Gly
            35                  40                  45

Met Lys Trp Leu Arg Ile Pro Ser Asn Val Lys Lys Phe Tyr Ile His
 50                  55                  60

Gly Met Cys Thr Val Leu Phe Met Asp
 65                  70

<210> SEQ ID NO 109
<211> LENGTH: 889
<212> TYPE: PRT
<213> ORGANISM: Mus musculus

<400> SEQUENCE: 109

Met Met Cys Gln Lys Phe Tyr Val Val Leu Leu His Trp Glu Phe Leu
 1               5                  10                  15

Tyr Val Ile Ala Ala Leu Asn Leu Ala Tyr Pro Ile Ser Pro Trp Lys
                20                  25                  30

Phe Lys Leu Phe Cys Gly Pro Pro Asn Thr Thr Asp Asp Ser Phe Leu
            35                  40                  45

Ser Pro Ala Gly Ala Pro Asn Asn Ala Ser Ala Leu Lys Gly Ala Ser
 50                  55                  60

Glu Ala Ile Val Glu Ala Lys Phe Asn Ser Ser Gly Ile Tyr Val Pro
 65                  70                  75                  80

Glu Leu Ser Lys Thr Val Phe His Cys Cys Phe Gly Asn Glu Gln Gly
                85                  90                  95

Gln Asn Cys Ser Ala Leu Thr Asp Asn Thr Glu Gly Lys Thr Leu Ala
            100                 105                 110

Ser Val Val Lys Ala Ser Val Phe Arg Gln Leu Gly Val Asn Trp Asp
        115                 120                 125

Ile Glu Cys Trp Met Lys Gly Asp Leu Thr Leu Phe Ile Cys His Met
130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Asp Ser Pro Leu Pro Pro
                165                 170                 175

Leu Lys Asp Ser Phe Gln Thr Val Gln Cys Asn Cys Ser Leu Arg Gly
            180                 185                 190

Cys Glu Cys His Val Pro Val Pro Arg Ala Lys Leu Asn Tyr Ala Leu
        195                 200                 205

Leu Met Tyr Leu Glu Ile Thr Ser Ala Gly Val Ser Phe Gln Ser Pro
210                 215                 220

Leu Met Ser Leu Gln Pro Met Leu Val Val Lys Pro Asp Pro Pro Leu
225                 230                 235                 240

Gly Leu His Met Glu Val Thr Asp Asp Gly Asn Leu Lys Ile Ser Trp
                245                 250                 255

Asp Ser Gln Thr Met Ala Pro Phe Pro Leu Gln Tyr Gln Val Lys Tyr
            260                 265                 270

Leu Glu Asn Ser Thr Ile Val Arg Glu Ala Ala Glu Ile Val Ser Ala
        275                 280                 285

Thr Ser Leu Leu Val Asp Ser Val Leu Pro Gly Ser Ser Tyr Glu Val
    290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro

-continued

```
                325                 330                 335
Lys Ile Leu Thr Ser Val Gly Ser Asn Ala Ser Phe His Cys Ile Tyr
            340                 345                 350
Lys Asn Glu Asn Gln Ile Ile Ser Ser Lys Gln Ile Val Trp Trp Arg
        355                 360                 365
Asn Leu Ala Glu Lys Ile Pro Glu Ile Gln Tyr Ser Ile Val Ser Asp
    370                 375                 380
Arg Val Ser Lys Val Thr Phe Ser Asn Leu Lys Ala Thr Arg Pro Arg
385                 390                 395                 400
Gly Lys Phe Thr Tyr Asp Ala Val Tyr Cys Cys Asn Glu Gln Ala Cys
            405                 410                 415
His His Arg Tyr Ala Glu Leu Tyr Val Ile Asp Val Asn Ile Asn Ile
        420                 425                 430
Ser Cys Glu Thr Asp Gly Tyr Leu Thr Lys Met Thr Cys Arg Trp Ser
    435                 440                 445
Pro Ser Thr Ile Gln Ser Leu Val Gly Ser Thr Val Gln Leu Arg Tyr
            450                 455                 460
His Arg Arg Ser Leu Tyr Cys Pro Asp Ser Pro Ser Ile His Pro Thr
465                 470                 475                 480
Ser Glu Pro Lys Asn Cys Val Leu Gln Arg Asp Gly Phe Tyr Glu Cys
            485                 490                 495
Val Phe Gln Pro Ile Phe Leu Leu Ser Gly Tyr Thr Met Trp Ile Arg
        500                 505                 510
Ile Asn His Ser Leu Gly Ser Leu Asp Ser Pro Thr Cys Val Leu
    515                 520                 525
Pro Asp Ser Val Val Lys Pro Leu Pro Pro Ser Asn Val Lys Ala Glu
530                 535                 540
Ile Thr Val Asn Thr Gly Leu Leu Lys Val Ser Trp Glu Lys Pro Val
545                 550                 555                 560
Phe Pro Glu Asn Asn Leu Gln Phe Gln Ile Arg Tyr Gly Leu Ser Gly
            565                 570                 575
Lys Glu Ile Gln Trp Lys Thr His Glu Val Phe Asp Ala Lys Ser Lys
        580                 585                 590
Ser Ala Ser Leu Leu Val Ser Asp Leu Cys Ala Val Tyr Val Val Gln
    595                 600                 605
Val Arg Cys Arg Arg Leu Asp Gly Leu Gly Tyr Trp Ser Asn Trp Ser
610                 615                 620
Ser Pro Ala Tyr Thr Leu Val Met Asp Val Lys Val Pro Met Arg Gly
625                 630                 635                 640
Pro Glu Phe Trp Arg Lys Met Asp Gly Asp Val Thr Lys Lys Glu Arg
            645                 650                 655
Asn Val Thr Leu Leu Trp Lys Pro Leu Thr Lys Asn Asp Ser Leu Cys
        660                 665                 670
Ser Val Arg Arg Tyr Val Val Lys His Arg Thr Ala His Asn Gly Thr
    675                 680                 685
Trp Ser Glu Asp Val Gly Asn Arg Thr Asn Leu Thr Phe Leu Trp Thr
690                 695                 700
Glu Pro Ala His Thr Val Thr Val Leu Ala Val Asn Ser Leu Gly Ala
705                 710                 715                 720
Ser Leu Val Asn Phe Asn Leu Thr Phe Ser Trp Pro Met Ser Lys Val
            725                 730                 735
Ser Ala Val Glu Ser Leu Ser Ala Tyr Pro Leu Ser Ser Ser Cys Val
        740                 745                 750
```

Ile Leu Ser Trp Thr Leu Ser Pro Asp Asp Tyr Ser Leu Leu Tyr Leu
            755                 760                 765

Val Ile Glu Trp Lys Ile Leu Asn Glu Asp Asp Gly Met Lys Trp Leu
        770                 775                 780

Arg Ile Pro Ser Asn Val Lys Lys Phe Tyr Ile His Asp Asn Phe Ile
785                 790                 795                 800

Pro Ile Glu Lys Tyr Gln Phe Ser Leu Tyr Pro Val Phe Met Glu Gly
                805                 810                 815

Val Gly Lys Pro Lys Ile Ile Asn Gly Phe Thr Lys Asp Ala Ile Asp
            820                 825                 830

Lys Gln Gln Asn Asp Ala Gly Leu Tyr Val Ile Val Pro Ile Ile Ile
        835                 840                 845

Ser Ser Cys Val Leu Leu Leu Gly Thr Leu Leu Ile Ser His Gln Arg
    850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys
                885

<210> SEQ ID NO 110
<211> LENGTH: 867
<212> TYPE: PRT
<213> ORGANISM: Mus musculus

<400> SEQUENCE: 110

Asn Leu Ala Tyr Pro Ile Ser Pro Trp Lys Phe Lys Leu Phe Cys Gly
1               5                   10                  15

Pro Pro Asn Thr Thr Asp Asp Ser Phe Leu Ser Pro Ala Gly Ala Pro
            20                  25                  30

Asn Asn Ala Ser Ala Leu Lys Gly Ala Ser Glu Ala Ile Val Glu Ala
        35                  40                  45

Lys Phe Asn Ser Ser Gly Ile Tyr Val Pro Glu Leu Ser Lys Thr Val
    50                  55                  60

Phe His Cys Cys Phe Gly Asn Glu Gln Gly Gln Asn Cys Ser Ala Leu
65                  70                  75                  80

Thr Asp Asn Thr Glu Gly Lys Thr Leu Ala Ser Val Val Lys Ala Ser
                85                  90                  95

Val Phe Arg Gln Leu Gly Val Asn Trp Asp Ile Glu Cys Trp Met Lys
            100                 105                 110

Gly Asp Leu Thr Leu Phe Ile Cys His Met Glu Pro Leu Pro Lys Asn
        115                 120                 125

Pro Phe Lys Asn Tyr Asp Ser Lys Val His Leu Leu Tyr Asp Leu Pro
    130                 135                 140

Glu Val Ile Asp Asp Ser Pro Leu Pro Pro Leu Lys Asp Ser Phe Gln
145                 150                 155                 160

Thr Val Gln Cys Asn Cys Ser Leu Arg Gly Cys Glu Cys His Val Pro
                165                 170                 175

Val Pro Arg Ala Lys Leu Asn Tyr Ala Leu Leu Met Tyr Leu Glu Ile
            180                 185                 190

Thr Ser Ala Gly Val Ser Phe Gln Ser Pro Leu Met Ser Leu Gln Pro
        195                 200                 205

Met Leu Val Val Lys Pro Asp Pro Pro Leu Gly Leu His Met Glu Val
    210                 215                 220

Thr Asp Asp Gly Asn Leu Lys Ile Ser Trp Asp Ser Gln Thr Met Ala

```
                      -continued
225              230             235             240

Pro Phe Pro Leu Gln Tyr Gln Val Lys Tyr Leu Glu Asn Ser Thr Ile
                245                 250                 255

Val Arg Glu Ala Ala Glu Ile Val Ser Ala Thr Ser Leu Leu Val Asp
                260                 265                 270

Ser Val Leu Pro Gly Ser Ser Tyr Glu Val Gln Val Arg Ser Lys Arg
                275                 280                 285

Leu Asp Gly Ser Gly Val Trp Ser Asp Trp Ser Ser Pro Gln Val Phe
            290                 295                 300

Thr Thr Gln Asp Val Val Tyr Phe Pro Pro Lys Ile Leu Thr Ser Val
305                 310                 315                 320

Gly Ser Asn Ala Ser Phe His Cys Ile Tyr Lys Asn Glu Asn Gln Ile
                325                 330                 335

Ile Ser Ser Lys Gln Ile Val Trp Trp Arg Asn Leu Ala Glu Lys Ile
                340                 345                 350

Pro Glu Ile Gln Tyr Ser Ile Val Ser Asp Arg Val Ser Lys Val Thr
                355                 360                 365

Phe Ser Asn Leu Lys Ala Thr Arg Pro Arg Gly Lys Phe Thr Tyr Asp
370                 375                 380

Ala Val Tyr Cys Cys Asn Glu Gln Ala Cys His His Arg Tyr Ala Glu
385                 390                 395                 400

Leu Tyr Val Ile Asp Val Asn Ile Asn Ile Ser Cys Glu Thr Asp Gly
                405                 410                 415

Tyr Leu Thr Lys Met Thr Cys Arg Trp Ser Pro Ser Thr Ile Gln Ser
                420                 425                 430

Leu Val Gly Ser Thr Val Gln Leu Arg Tyr His Arg Arg Ser Leu Tyr
                435                 440                 445

Cys Pro Asp Ser Pro Ser Ile His Pro Thr Ser Glu Pro Lys Asn Cys
            450                 455                 460

Val Leu Gln Arg Asp Gly Phe Tyr Glu Cys Val Phe Gln Pro Ile Phe
465                 470                 475                 480

Leu Leu Ser Gly Tyr Thr Met Trp Ile Arg Ile Asn His Ser Leu Gly
                485                 490                 495

Ser Leu Asp Ser Pro Pro Thr Cys Val Leu Pro Asp Ser Val Val Lys
            500                 505                 510

Pro Leu Pro Pro Ser Asn Val Lys Ala Glu Ile Thr Val Asn Thr Gly
            515                 520                 525

Leu Leu Lys Val Ser Trp Glu Lys Pro Val Phe Pro Glu Asn Asn Leu
            530                 535                 540

Gln Phe Gln Ile Arg Tyr Gly Leu Ser Gly Lys Glu Ile Gln Trp Lys
545                 550                 555                 560

Thr His Glu Val Phe Asp Ala Lys Ser Lys Ser Ala Ser Leu Leu Val
                565                 570                 575

Ser Asp Leu Cys Ala Val Tyr Val Val Gln Val Arg Cys Arg Arg Leu
            580                 585                 590

Asp Gly Leu Gly Tyr Trp Ser Asn Trp Ser Ser Pro Ala Tyr Thr Leu
            595                 600                 605

Val Met Asp Val Lys Val Pro Met Arg Gly Pro Glu Phe Trp Arg Lys
            610                 615                 620

Met Asp Gly Asp Val Thr Lys Lys Glu Arg Asn Val Thr Leu Leu Trp
625                 630                 635                 640

Lys Pro Leu Thr Lys Asn Asp Ser Leu Cys Ser Val Arg Arg Tyr Val
                645                 650                 655
```

```
Val Lys His Arg Thr Ala His Asn Gly Thr Trp Ser Glu Asp Val Gly
            660                 665                 670

Asn Arg Thr Asn Leu Thr Phe Leu Trp Thr Glu Pro Ala His Thr Val
            675                 680                 685

Thr Val Leu Ala Val Asn Ser Leu Gly Ala Ser Leu Val Asn Phe Asn
            690                 695                 700

Leu Thr Phe Ser Trp Pro Met Ser Lys Val Ser Ala Val Glu Ser Leu
705                 710                 715                 720

Ser Ala Tyr Pro Leu Ser Ser Cys Val Ile Leu Ser Trp Thr Leu
                725                 730                 735

Ser Pro Asp Asp Tyr Ser Leu Leu Tyr Leu Val Ile Glu Trp Lys Ile
            740                 745                 750

Leu Asn Glu Asp Asp Gly Met Lys Trp Leu Arg Ile Pro Ser Asn Val
            755                 760                 765

Lys Lys Phe Tyr Ile His Asp Asn Phe Ile Pro Ile Glu Lys Tyr Gln
            770                 775                 780

Phe Ser Leu Tyr Pro Val Phe Met Glu Gly Val Gly Lys Pro Lys Ile
785                 790                 795                 800

Ile Asn Gly Phe Thr Lys Asp Ala Ile Asp Lys Gln Gln Asn Asp Ala
                805                 810                 815

Gly Leu Tyr Val Ile Val Pro Ile Ile Ser Ser Cys Val Leu Leu
            820                 825                 830

Leu Gly Thr Leu Leu Ile Ser His Gln Arg Met Lys Lys Leu Phe Trp
            835                 840                 845

Asp Asp Val Pro Asn Pro Lys Asn Cys Ser Trp Ala Gln Gly Leu Asn
            850                 855                 860

Phe Gln Lys
865

<210> SEQ ID NO 111
<211> LENGTH: 862
<212> TYPE: PRT
<213> ORGANISM: Mus musculus

<400> SEQUENCE: 111

Ile Ser Pro Trp Lys Phe Lys Leu Phe Cys Gly Pro Pro Asn Thr Thr
1               5                   10                  15

Asp Asp Ser Phe Leu Ser Pro Ala Gly Ala Pro Asn Asn Ala Ser Ala
            20                  25                  30

Leu Lys Gly Ala Ser Glu Ala Ile Val Glu Ala Lys Phe Asn Ser Ser
            35                  40                  45

Gly Ile Tyr Val Pro Glu Leu Ser Lys Thr Val Phe His Cys Cys Phe
        50                  55                  60

Gly Asn Glu Gln Gly Gln Asn Cys Ser Ala Leu Thr Asp Asn Thr Glu
65              70                  75                  80

Gly Lys Thr Leu Ala Ser Val Val Lys Ala Ser Val Phe Arg Gln Leu
                85                  90                  95

Gly Val Asn Trp Asp Ile Glu Cys Trp Met Lys Gly Asp Leu Thr Leu
            100                 105                 110

Phe Ile Cys His Met Glu Pro Leu Pro Lys Asn Pro Phe Lys Asn Tyr
            115                 120                 125

Asp Ser Lys Val His Leu Leu Tyr Asp Leu Pro Glu Val Ile Asp Asp
            130                 135                 140

Ser Pro Leu Pro Pro Leu Lys Asp Ser Phe Gln Thr Val Gln Cys Asn
```

-continued

```
            145                 150                 155                 160
Cys Ser Leu Arg Gly Cys Glu Cys His Val Pro Val Pro Arg Ala Lys
                165                 170                 175
Leu Asn Tyr Ala Leu Leu Met Tyr Leu Glu Ile Thr Ser Ala Gly Val
                180                 185                 190
Ser Phe Gln Ser Pro Leu Met Ser Leu Gln Pro Met Leu Val Val Lys
                195                 200                 205
Pro Asp Pro Leu Gly Leu His Met Glu Val Thr Asp Asp Gly Asn
                210                 215                 220
Leu Lys Ile Ser Trp Asp Ser Gln Thr Met Ala Pro Phe Pro Leu Gln
225                 230                 235                 240
Tyr Gln Val Lys Tyr Leu Glu Asn Ser Thr Ile Val Arg Glu Ala Ala
                245                 250                 255
Glu Ile Val Ser Ala Thr Ser Leu Leu Val Asp Ser Val Leu Pro Gly
                260                 265                 270
Ser Ser Tyr Glu Val Gln Val Arg Ser Lys Arg Leu Asp Gly Ser Gly
                275                 280                 285
Val Trp Ser Asp Trp Ser Ser Pro Gln Val Phe Thr Thr Gln Asp Val
                290                 295                 300
Val Tyr Phe Pro Pro Lys Ile Leu Thr Ser Val Gly Ser Asn Ala Ser
305                 310                 315                 320
Phe His Cys Ile Tyr Lys Asn Glu Asn Gln Ile Ile Ser Ser Lys Gln
                325                 330                 335
Ile Val Trp Trp Arg Asn Leu Ala Glu Lys Ile Pro Glu Ile Gln Tyr
                340                 345                 350
Ser Ile Val Ser Asp Arg Val Ser Lys Val Thr Phe Ser Asn Leu Lys
                355                 360                 365
Ala Thr Arg Pro Arg Gly Lys Phe Thr Tyr Asp Ala Val Tyr Cys Cys
                370                 375                 380
Asn Glu Gln Ala Cys His His Arg Tyr Ala Glu Leu Tyr Val Ile Asp
385                 390                 395                 400
Val Asn Ile Asn Ile Ser Cys Glu Thr Asp Gly Tyr Leu Thr Lys Met
                405                 410                 415
Thr Cys Arg Trp Ser Pro Ser Thr Ile Gln Ser Leu Val Gly Ser Thr
                420                 425                 430
Val Gln Leu Arg Tyr His Arg Arg Ser Leu Tyr Cys Pro Asp Ser Pro
                435                 440                 445
Ser Ile His Pro Thr Ser Glu Pro Lys Asn Cys Val Leu Gln Arg Asp
                450                 455                 460
Gly Phe Tyr Glu Cys Val Phe Gln Pro Ile Phe Leu Leu Ser Gly Tyr
465                 470                 475                 480
Thr Met Trp Ile Arg Ile Asn His Ser Leu Gly Ser Leu Asp Ser Pro
                485                 490                 495
Pro Thr Cys Val Leu Pro Asp Ser Val Val Lys Pro Leu Pro Pro Ser
                500                 505                 510
Asn Val Lys Ala Glu Ile Thr Val Asn Thr Gly Leu Leu Lys Val Ser
                515                 520                 525
Trp Glu Lys Pro Val Phe Pro Glu Asn Asn Leu Gln Phe Gln Ile Arg
                530                 535                 540
Tyr Gly Leu Ser Gly Lys Glu Ile Gln Trp Lys Thr His Glu Val Phe
545                 550                 555                 560
Asp Ala Lys Ser Lys Ser Ala Ser Leu Leu Val Ser Asp Leu Cys Ala
                565                 570                 575
```

```
Val Tyr Val Val Gln Val Arg Cys Arg Arg Leu Asp Gly Leu Gly Tyr
            580                 585                 590

Trp Ser Asn Trp Ser Ser Pro Ala Tyr Thr Leu Val Met Asp Val Lys
        595                 600                 605

Val Pro Met Arg Gly Pro Glu Phe Trp Arg Lys Met Asp Gly Asp Val
    610                 615                 620

Thr Lys Lys Glu Arg Asn Val Thr Leu Leu Trp Lys Pro Leu Thr Lys
625                 630                 635                 640

Asn Asp Ser Leu Cys Ser Val Arg Arg Tyr Val Val Lys His Arg Thr
                645                 650                 655

Ala His Asn Gly Thr Trp Ser Glu Asp Val Gly Asn Arg Thr Asn Leu
            660                 665                 670

Thr Phe Leu Trp Thr Glu Pro Ala His Thr Val Thr Val Leu Ala Val
        675                 680                 685

Asn Ser Leu Gly Ala Ser Leu Val Asn Phe Asn Leu Thr Phe Ser Trp
    690                 695                 700

Pro Met Ser Lys Val Ser Ala Val Glu Ser Leu Ser Ala Tyr Pro Leu
705                 710                 715                 720

Ser Ser Ser Cys Val Ile Leu Ser Trp Thr Leu Ser Pro Asp Asp Tyr
                725                 730                 735

Ser Leu Leu Tyr Leu Val Ile Glu Trp Lys Ile Leu Asn Glu Asp Asp
            740                 745                 750

Gly Met Lys Trp Leu Arg Ile Pro Ser Asn Val Lys Lys Phe Tyr Ile
        755                 760                 765

His Asp Asn Phe Ile Pro Ile Glu Lys Tyr Gln Phe Ser Leu Tyr Pro
    770                 775                 780

Val Phe Met Glu Gly Val Gly Lys Pro Lys Ile Ile Asn Gly Phe Thr
785                 790                 795                 800

Lys Asp Ala Ile Asp Lys Gln Gln Asn Asp Ala Gly Leu Tyr Val Ile
                805                 810                 815

Val Pro Ile Ile Ile Ser Ser Cys Val Leu Leu Leu Gly Thr Leu Leu
            820                 825                 830

Ile Ser His Gln Arg Met Lys Lys Leu Phe Trp Asp Asp Val Pro Asn
        835                 840                 845

Pro Lys Asn Cys Ser Trp Ala Gln Gly Leu Asn Phe Gln Lys
    850                 855                 860

<210> SEQ ID NO 112
<211> LENGTH: 757
<212> TYPE: PRT
<213> ORGANISM: Mus musculus

<400> SEQUENCE: 112

Met Lys Gly Asp Leu Thr Leu Phe Ile Cys His Met Glu Pro Leu Pro
1               5                   10                  15

Lys Asn Pro Phe Lys Asn Tyr Asp Ser Lys Val His Leu Leu Tyr Asp
            20                  25                  30

Leu Pro Glu Val Ile Asp Asp Ser Pro Leu Pro Pro Leu Lys Asp Ser
        35                  40                  45

Phe Gln Thr Val Gln Cys Asn Cys Ser Leu Arg Gly Cys Glu Cys His
    50                  55                  60

Val Pro Val Pro Arg Ala Lys Leu Asn Tyr Ala Leu Leu Met Tyr Leu
65                  70                  75                  80

Glu Ile Thr Ser Ala Gly Val Ser Phe Gln Ser Pro Leu Met Ser Leu
```

```
                    85                  90                  95
Gln Pro Met Leu Val Val Lys Pro Asp Pro Leu Gly Leu His Met
                100                 105                 110

Glu Val Thr Asp Asp Gly Asn Leu Lys Ile Ser Trp Asp Ser Gln Thr
            115                 120                 125

Met Ala Pro Phe Pro Leu Gln Tyr Gln Val Lys Tyr Leu Glu Asn Ser
    130                 135                 140

Thr Ile Val Arg Glu Ala Ala Glu Ile Val Ser Ala Thr Ser Leu Leu
145                 150                 155                 160

Val Asp Ser Val Leu Pro Gly Ser Ser Tyr Glu Val Gln Val Arg Ser
                165                 170                 175

Lys Arg Leu Asp Gly Ser Gly Val Trp Ser Asp Trp Ser Ser Pro Gln
            180                 185                 190

Val Phe Thr Thr Gln Asp Val Val Tyr Phe Pro Pro Lys Ile Leu Thr
        195                 200                 205

Ser Val Gly Ser Asn Ala Ser Phe His Cys Ile Tyr Lys Asn Glu Asn
    210                 215                 220

Gln Ile Ile Ser Ser Lys Gln Ile Val Trp Trp Arg Asn Leu Ala Glu
225                 230                 235                 240

Lys Ile Pro Glu Ile Gln Tyr Ser Ile Val Ser Asp Arg Val Ser Lys
                245                 250                 255

Val Thr Phe Ser Asn Leu Lys Ala Thr Arg Pro Arg Gly Lys Phe Thr
            260                 265                 270

Tyr Asp Ala Val Tyr Cys Cys Asn Glu Gln Ala Cys His His Arg Tyr
        275                 280                 285

Ala Glu Leu Tyr Val Ile Asp Val Asn Ile Asn Ile Ser Cys Glu Thr
    290                 295                 300

Asp Gly Tyr Leu Thr Lys Met Thr Cys Arg Trp Ser Pro Ser Thr Ile
305                 310                 315                 320

Gln Ser Leu Val Gly Ser Thr Val Gln Leu Arg Tyr His Arg Arg Ser
                325                 330                 335

Leu Tyr Cys Pro Asp Ser Pro Ser Ile His Pro Thr Ser Glu Pro Lys
            340                 345                 350

Asn Cys Val Leu Gln Arg Asp Gly Phe Tyr Glu Cys Val Phe Gln Pro
        355                 360                 365

Ile Phe Leu Leu Ser Gly Tyr Thr Met Trp Ile Arg Ile Asn His Ser
    370                 375                 380

Leu Gly Ser Leu Asp Ser Pro Pro Thr Cys Val Leu Pro Asp Ser Val
385                 390                 395                 400

Val Lys Pro Leu Pro Pro Ser Asn Val Lys Ala Glu Ile Thr Val Asn
                405                 410                 415

Thr Gly Leu Leu Lys Val Ser Trp Glu Lys Pro Val Phe Pro Glu Asn
            420                 425                 430

Asn Leu Gln Phe Gln Ile Arg Tyr Gly Leu Ser Gly Lys Glu Ile Gln
        435                 440                 445

Trp Lys Thr His Glu Val Phe Asp Ala Lys Ser Lys Ser Ala Ser Leu
    450                 455                 460

Leu Val Ser Asp Leu Cys Ala Val Tyr Val Val Gln Val Arg Cys Arg
465                 470                 475                 480

Arg Leu Asp Gly Leu Gly Tyr Trp Ser Asn Trp Ser Ser Pro Ala Tyr
                485                 490                 495

Thr Leu Val Met Asp Val Lys Val Pro Met Arg Gly Pro Glu Phe Trp
            500                 505                 510
```

Arg Lys Met Asp Gly Asp Val Thr Lys Lys Glu Arg Asn Val Thr Leu
                515                 520                 525
Leu Trp Lys Pro Leu Thr Lys Asn Asp Ser Leu Cys Ser Val Arg Arg
            530                 535                 540
Tyr Val Val Lys His Arg Thr Ala His Asn Gly Thr Trp Ser Glu Asp
545                 550                 555                 560
Val Gly Asn Arg Thr Asn Leu Thr Phe Leu Trp Thr Glu Pro Ala His
                565                 570                 575
Thr Val Thr Val Leu Ala Val Asn Ser Leu Gly Ala Ser Leu Val Asn
            580                 585                 590
Phe Asn Leu Thr Phe Ser Trp Pro Met Ser Lys Val Ser Ala Val Glu
        595                 600                 605
Ser Leu Ser Ala Tyr Pro Leu Ser Ser Ser Cys Val Ile Leu Ser Trp
    610                 615                 620
Thr Leu Ser Pro Asp Asp Tyr Ser Leu Leu Tyr Leu Val Ile Glu Trp
625                 630                 635                 640
Lys Ile Leu Asn Glu Asp Asp Gly Met Lys Trp Leu Arg Ile Pro Ser
                645                 650                 655
Asn Val Lys Lys Phe Tyr Ile His Asp Asn Phe Ile Pro Ile Glu Lys
            660                 665                 670
Tyr Gln Phe Ser Leu Tyr Pro Val Phe Met Glu Gly Val Gly Lys Pro
        675                 680                 685
Lys Ile Ile Asn Gly Phe Thr Lys Asp Ala Ile Asp Lys Gln Gln Asn
    690                 695                 700
Asp Ala Gly Leu Tyr Val Ile Val Pro Ile Ile Ile Ser Ser Cys Val
705                 710                 715                 720
Leu Leu Leu Gly Thr Leu Leu Ile Ser His Gln Arg Met Lys Lys Leu
                725                 730                 735
Phe Trp Asp Asp Val Pro Asn Pro Lys Asn Cys Ser Trp Ala Gln Gly
            740                 745                 750
Leu Asn Phe Gln Lys
        755

<210> SEQ ID NO 113
<211> LENGTH: 157
<212> TYPE: PRT
<213> ORGANISM: Mus musculus

<400> SEQUENCE: 113

Met Ser Lys Val Ser Ala Val Glu Ser Leu Ser Ala Tyr Pro Leu Ser
1               5                   10                  15
Ser Ser Cys Val Ile Leu Ser Trp Thr Leu Ser Pro Asp Asp Tyr Ser
            20                  25                  30
Leu Leu Tyr Leu Val Ile Glu Trp Lys Ile Leu Asn Glu Asp Asp Gly
        35                  40                  45
Met Lys Trp Leu Arg Ile Pro Ser Asn Val Lys Lys Phe Tyr Ile His
    50                  55                  60
Asp Asn Phe Ile Pro Ile Glu Lys Tyr Gln Phe Ser Leu Tyr Pro Val
65                  70                  75                  80
Phe Met Glu Gly Val Gly Lys Pro Lys Ile Ile Asn Gly Phe Thr Lys
                85                  90                  95
Asp Ala Ile Asp Lys Gln Gln Asn Asp Ala Gly Leu Tyr Val Ile Val
            100                 105                 110
Pro Ile Ile Ile Ser Ser Cys Val Leu Leu Leu Gly Thr Leu Leu Ile

```
                115                 120                 125
Ser His Gln Arg Met Lys Lys Leu Phe Trp Asp Asp Val Pro Asn Pro
    130                 135                 140

Lys Asn Cys Ser Trp Ala Gln Gly Leu Asn Phe Gln Lys
145                 150                 155

<210> SEQ ID NO 114
<211> LENGTH: 796
<212> TYPE: PRT
<213> ORGANISM: Mus musculus

<400> SEQUENCE: 114

Met Met Cys Gln Lys Phe Tyr Val Val Leu Leu His Trp Glu Phe Leu
1               5                   10                  15

Tyr Val Ile Ala Ala Leu Asn Leu Ala Tyr Pro Ile Ser Pro Trp Lys
                20                  25                  30

Phe Lys Leu Phe Cys Gly Pro Pro Asn Thr Thr Asp Asp Ser Phe Leu
            35                  40                  45

Ser Pro Ala Gly Ala Pro Asn Asn Ala Ser Ala Leu Lys Gly Ala Ser
        50                  55                  60

Glu Ala Ile Val Glu Ala Lys Phe Asn Ser Ser Gly Ile Tyr Val Pro
65                  70                  75                  80

Glu Leu Ser Lys Thr Val Phe His Cys Cys Phe Gly Asn Glu Gln Gly
                85                  90                  95

Gln Asn Cys Ser Ala Leu Thr Asp Asn Thr Glu Gly Lys Thr Leu Ala
            100                 105                 110

Ser Val Val Lys Ala Ser Val Phe Arg Gln Leu Gly Val Asn Trp Asp
        115                 120                 125

Ile Glu Cys Trp Met Lys Gly Asp Leu Thr Leu Phe Ile Cys His Met
    130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Asp Ser Pro Leu Pro Pro
                165                 170                 175

Leu Lys Asp Ser Phe Gln Thr Val Gln Cys Asn Cys Ser Leu Arg Gly
            180                 185                 190

Cys Glu Cys His Val Pro Val Pro Arg Ala Lys Leu Asn Tyr Ala Leu
        195                 200                 205

Leu Met Tyr Leu Glu Ile Thr Ser Ala Gly Val Ser Phe Gln Ser Pro
    210                 215                 220

Leu Met Ser Leu Gln Pro Met Leu Val Val Lys Pro Asp Pro Pro Leu
225                 230                 235                 240

Gly Leu His Met Glu Val Thr Asp Asp Gly Asn Leu Lys Ile Ser Trp
                245                 250                 255

Asp Ser Gln Thr Met Ala Pro Phe Pro Leu Gln Tyr Gln Val Lys Tyr
            260                 265                 270

Leu Glu Asn Ser Thr Ile Val Arg Glu Ala Ala Glu Ile Val Ser Ala
        275                 280                 285

Thr Ser Leu Leu Val Asp Ser Val Leu Pro Gly Ser Ser Tyr Glu Val
    290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro
                325                 330                 335
```

-continued

```
Lys Ile Leu Thr Ser Val Gly Ser Asn Ala Ser Phe His Cys Ile Tyr
            340                 345                 350
Lys Asn Glu Asn Gln Ile Ile Ser Ser Lys Gln Ile Val Trp Trp Arg
            355                 360                 365
Asn Leu Ala Glu Lys Ile Pro Glu Ile Gln Tyr Ser Ile Val Ser Asp
            370                 375                 380
Arg Val Ser Lys Val Thr Phe Ser Asn Leu Lys Ala Thr Arg Pro Arg
385                 390                 395                 400
Gly Lys Phe Thr Tyr Asp Ala Val Tyr Cys Cys Asn Glu Gln Ala Cys
            405                 410                 415
His His Arg Tyr Ala Glu Leu Tyr Val Ile Asp Val Asn Ile Asn Ile
            420                 425                 430
Ser Cys Glu Thr Asp Gly Tyr Leu Thr Lys Met Thr Cys Arg Trp Ser
            435                 440                 445
Pro Ser Thr Ile Gln Ser Leu Val Gly Ser Thr Val Gln Leu Arg Tyr
            450                 455                 460
His Arg Arg Ser Leu Tyr Cys Pro Asp Ser Pro Ser Ile His Pro Thr
465                 470                 475                 480
Ser Glu Pro Lys Asn Cys Val Leu Gln Arg Asp Gly Phe Tyr Glu Cys
            485                 490                 495
Val Phe Gln Pro Ile Phe Leu Leu Ser Gly Tyr Thr Met Trp Ile Arg
            500                 505                 510
Ile Asn His Ser Leu Gly Ser Leu Asp Ser Pro Pro Thr Cys Val Leu
            515                 520                 525
Pro Asp Ser Val Val Lys Pro Leu Pro Pro Ser Asn Val Lys Ala Glu
            530                 535                 540
Ile Thr Val Asn Thr Gly Leu Leu Lys Val Ser Trp Glu Lys Pro Val
545                 550                 555                 560
Phe Pro Glu Asn Asn Leu Gln Phe Gln Ile Arg Tyr Gly Leu Ser Gly
            565                 570                 575
Lys Glu Ile Gln Trp Lys Thr His Glu Val Phe Asp Ala Lys Ser Lys
            580                 585                 590
Ser Ala Ser Leu Leu Val Ser Asp Leu Cys Ala Val Tyr Val Val Gln
            595                 600                 605
Val Arg Cys Arg Arg Leu Asp Gly Leu Gly Tyr Trp Ser Asn Trp Ser
            610                 615                 620
Ser Pro Ala Tyr Thr Leu Val Met Asp Val Lys Val Pro Met Arg Gly
625                 630                 635                 640
Pro Glu Phe Trp Arg Lys Met Asp Gly Asp Val Thr Lys Lys Glu Arg
            645                 650                 655
Asn Val Thr Leu Leu Trp Lys Pro Leu Thr Lys Asn Asp Ser Leu Cys
            660                 665                 670
Ser Val Arg Arg Tyr Val Val Lys His Arg Thr Ala His Asn Gly Thr
            675                 680                 685
Trp Ser Glu Asp Val Gly Asn Arg Thr Asn Leu Thr Phe Leu Trp Thr
690                 695                 700
Glu Pro Ala His Thr Val Thr Val Leu Ala Val Asn Ser Leu Gly Ala
705                 710                 715                 720
Ser Leu Val Asn Phe Asn Leu Thr Phe Ser Trp Pro Met Ser Lys Val
            725                 730                 735
Ser Ala Val Glu Ser Leu Ser Ala Tyr Pro Leu Ser Ser Ser Cys Val
            740                 745                 750
Ile Leu Ser Trp Thr Leu Ser Pro Asp Asp Tyr Ser Leu Leu Tyr Leu
```

-continued

```
                755                 760                 765
Val Ile Glu Trp Lys Ile Leu Asn Glu Asp Asp Gly Met Lys Trp Leu
770                 775                 780

Arg Ile Pro Ser Asn Val Lys Lys Phe Tyr Ile His
785                 790                 795

<210> SEQ ID NO 115
<211> LENGTH: 774
<212> TYPE: PRT
<213> ORGANISM: Mus musculus

<400> SEQUENCE: 115

Asn Leu Ala Tyr Pro Ile Ser Pro Trp Lys Phe Lys Leu Phe Cys Gly
1               5                   10                  15

Pro Pro Asn Thr Thr Asp Asp Ser Phe Leu Ser Pro Ala Gly Ala Pro
                20                  25                  30

Asn Asn Ala Ser Ala Leu Lys Gly Ala Ser Glu Ala Ile Val Glu Ala
            35                  40                  45

Lys Phe Asn Ser Ser Gly Ile Tyr Val Pro Glu Leu Ser Lys Thr Val
50                  55                  60

Phe His Cys Cys Phe Gly Asn Glu Gln Gly Gln Asn Cys Ser Ala Leu
65                  70                  75                  80

Thr Asp Asn Thr Glu Gly Lys Thr Leu Ala Ser Val Val Lys Ala Ser
                85                  90                  95

Val Phe Arg Gln Leu Gly Val Asn Trp Asp Ile Glu Cys Trp Met Lys
                100                 105                 110

Gly Asp Leu Thr Leu Phe Ile Cys His Met Glu Pro Leu Pro Lys Asn
            115                 120                 125

Pro Phe Lys Asn Tyr Asp Ser Lys Val His Leu Leu Tyr Asp Leu Pro
130                 135                 140

Glu Val Ile Asp Asp Ser Pro Leu Pro Pro Leu Lys Asp Ser Phe Gln
145                 150                 155                 160

Thr Val Gln Cys Asn Cys Ser Leu Arg Gly Cys Glu Cys His Val Pro
                165                 170                 175

Val Pro Arg Ala Lys Leu Asn Tyr Ala Leu Leu Met Tyr Leu Glu Ile
                180                 185                 190

Thr Ser Ala Gly Val Ser Phe Gln Ser Pro Leu Met Ser Leu Gln Pro
            195                 200                 205

Met Leu Val Val Lys Pro Asp Pro Pro Leu Gly Leu His Met Glu Val
210                 215                 220

Thr Asp Asp Gly Asn Leu Lys Ile Ser Trp Asp Ser Gln Thr Met Ala
225                 230                 235                 240

Pro Phe Pro Leu Gln Tyr Gln Val Lys Tyr Leu Glu Asn Ser Thr Ile
                245                 250                 255

Val Arg Glu Ala Ala Glu Ile Val Ser Ala Thr Ser Leu Leu Val Asp
                260                 265                 270

Ser Val Leu Pro Gly Ser Ser Tyr Glu Val Gln Val Arg Ser Lys Arg
            275                 280                 285

Leu Asp Gly Ser Gly Val Trp Ser Asp Trp Ser Ser Pro Gln Val Phe
290                 295                 300

Thr Thr Gln Asp Val Val Tyr Phe Pro Pro Lys Ile Leu Thr Ser Val
305                 310                 315                 320

Gly Ser Asn Ala Ser Phe His Cys Ile Tyr Lys Asn Glu Asn Gln Ile
                325                 330                 335
```

-continued

```
Ile Ser Ser Lys Gln Ile Val Trp Trp Arg Asn Leu Ala Glu Lys Ile
            340                 345                 350

Pro Glu Ile Gln Tyr Ser Ile Val Ser Asp Arg Val Ser Lys Val Thr
        355                 360                 365

Phe Ser Asn Leu Lys Ala Thr Arg Pro Arg Gly Lys Phe Thr Tyr Asp
    370                 375                 380

Ala Val Tyr Cys Cys Asn Glu Gln Ala Cys His His Arg Tyr Ala Glu
385                 390                 395                 400

Leu Tyr Val Ile Asp Val Asn Ile Asn Ile Ser Cys Glu Thr Asp Gly
                405                 410                 415

Tyr Leu Thr Lys Met Thr Cys Arg Trp Ser Pro Ser Thr Ile Gln Ser
            420                 425                 430

Leu Val Gly Ser Thr Val Gln Leu Arg Tyr His Arg Arg Ser Leu Tyr
        435                 440                 445

Cys Pro Asp Ser Pro Ser Ile His Pro Thr Ser Glu Pro Lys Asn Cys
    450                 455                 460

Val Leu Gln Arg Asp Gly Phe Tyr Glu Cys Val Phe Gln Pro Ile Phe
465                 470                 475                 480

Leu Leu Ser Gly Tyr Thr Met Trp Ile Arg Ile Asn His Ser Leu Gly
                485                 490                 495

Ser Leu Asp Ser Pro Pro Thr Cys Val Leu Pro Asp Ser Val Val Lys
            500                 505                 510

Pro Leu Pro Pro Ser Asn Val Lys Ala Glu Ile Thr Val Asn Thr Gly
        515                 520                 525

Leu Leu Lys Val Ser Trp Glu Lys Pro Val Phe Pro Glu Asn Asn Leu
    530                 535                 540

Gln Phe Gln Ile Arg Tyr Gly Leu Ser Gly Lys Glu Ile Gln Trp Lys
545                 550                 555                 560

Thr His Glu Val Phe Asp Ala Lys Ser Lys Ser Ala Ser Leu Leu Val
                565                 570                 575

Ser Asp Leu Cys Ala Val Tyr Val Val Gln Val Arg Cys Arg Arg Leu
            580                 585                 590

Asp Gly Leu Gly Tyr Trp Ser Asn Trp Ser Ser Pro Ala Tyr Thr Leu
        595                 600                 605

Val Met Asp Val Lys Val Pro Met Arg Gly Pro Glu Phe Trp Arg Lys
    610                 615                 620

Met Asp Gly Asp Val Thr Lys Lys Glu Arg Asn Val Thr Leu Leu Trp
625                 630                 635                 640

Lys Pro Leu Thr Lys Asn Asp Ser Leu Cys Ser Val Arg Arg Tyr Val
                645                 650                 655

Val Lys His Arg Thr Ala His Asn Gly Thr Trp Ser Glu Asp Val Gly
            660                 665                 670

Asn Arg Thr Asn Leu Thr Phe Leu Trp Thr Glu Pro Ala His Thr Val
        675                 680                 685

Thr Val Leu Ala Val Asn Ser Leu Gly Ala Ser Leu Val Asn Phe Asn
    690                 695                 700

Leu Thr Phe Ser Trp Pro Met Ser Lys Val Ser Ala Val Glu Ser Leu
705                 710                 715                 720

Ser Ala Tyr Pro Leu Ser Ser Cys Val Ile Leu Ser Trp Thr Leu
                725                 730                 735

Ser Pro Asp Asp Tyr Ser Leu Leu Tyr Leu Val Ile Glu Trp Lys Ile
            740                 745                 750

Leu Asn Glu Asp Asp Gly Met Lys Trp Leu Arg Ile Pro Ser Asn Val
```

Lys Lys Phe Tyr Ile His
    770

<210> SEQ ID NO 116
<211> LENGTH: 769
<212> TYPE: PRT
<213> ORGANISM: Mus musculus

<400> SEQUENCE: 116

Ile Ser Pro Trp Lys Phe Lys Leu Phe Cys Gly Pro Pro Asn Thr Thr
1               5                   10                  15

Asp Asp Ser Phe Leu Ser Pro Ala Gly Ala Pro Asn Ala Ser Ala
            20                  25                  30

Leu Lys Gly Ala Ser Glu Ala Ile Val Glu Ala Lys Phe Asn Ser Ser
        35                  40                  45

Gly Ile Tyr Val Pro Glu Leu Ser Lys Thr Val Phe His Cys Cys Phe
    50                  55                  60

Gly Asn Glu Gln Gly Gln Asn Cys Ser Ala Leu Thr Asp Asn Thr Glu
65                  70                  75                  80

Gly Lys Thr Leu Ala Ser Val Val Lys Ala Ser Val Phe Arg Gln Leu
                85                  90                  95

Gly Val Asn Trp Asp Ile Glu Cys Trp Met Lys Gly Asp Leu Thr Leu
            100                 105                 110

Phe Ile Cys His Met Glu Pro Leu Pro Lys Asn Pro Phe Lys Asn Tyr
        115                 120                 125

Asp Ser Lys Val His Leu Leu Tyr Asp Leu Pro Glu Val Ile Asp Asp
    130                 135                 140

Ser Pro Leu Pro Pro Leu Lys Asp Ser Phe Gln Thr Val Gln Cys Asn
145                 150                 155                 160

Cys Ser Leu Arg Gly Cys Glu Cys His Val Pro Val Pro Arg Ala Lys
                165                 170                 175

Leu Asn Tyr Ala Leu Leu Met Tyr Leu Glu Ile Thr Ser Ala Gly Val
            180                 185                 190

Ser Phe Gln Ser Pro Leu Met Ser Leu Gln Pro Met Leu Val Val Lys
        195                 200                 205

Pro Asp Pro Pro Leu Gly Leu His Met Glu Val Thr Asp Asp Gly Asn
    210                 215                 220

Leu Lys Ile Ser Trp Asp Ser Gln Thr Met Ala Pro Phe Pro Leu Gln
225                 230                 235                 240

Tyr Gln Val Lys Tyr Leu Glu Asn Ser Thr Ile Val Arg Glu Ala Ala
                245                 250                 255

Glu Ile Val Ser Ala Thr Ser Leu Leu Val Asp Ser Val Leu Pro Gly
            260                 265                 270

Ser Ser Tyr Glu Val Gln Val Arg Ser Lys Arg Leu Asp Gly Ser Gly
        275                 280                 285

Val Trp Ser Asp Trp Ser Ser Pro Gln Val Phe Thr Thr Gln Asp Val
    290                 295                 300

Val Tyr Phe Pro Pro Lys Ile Leu Thr Ser Val Gly Ser Asn Ala Ser
305                 310                 315                 320

Phe His Cys Ile Tyr Lys Asn Glu Asn Gln Ile Ile Ser Ser Lys Gln
                325                 330                 335

Ile Val Trp Trp Arg Asn Leu Ala Glu Lys Ile Pro Glu Ile Gln Tyr
            340                 345                 350

-continued

```
Ser Ile Val Ser Asp Arg Val Ser Lys Val Thr Phe Ser Asn Leu Lys
        355                 360                 365

Ala Thr Arg Pro Arg Gly Lys Phe Thr Tyr Asp Ala Val Tyr Cys Cys
        370                 375                 380

Asn Glu Gln Ala Cys His His Arg Tyr Ala Glu Leu Tyr Val Ile Asp
385                 390                 395                 400

Val Asn Ile Asn Ile Ser Cys Glu Thr Asp Gly Tyr Leu Thr Lys Met
                405                 410                 415

Thr Cys Arg Trp Ser Pro Ser Thr Ile Gln Ser Leu Val Gly Ser Thr
                420                 425                 430

Val Gln Leu Arg Tyr His Arg Arg Ser Leu Tyr Cys Pro Asp Ser Pro
        435                 440                 445

Ser Ile His Pro Thr Ser Glu Pro Lys Asn Cys Val Leu Gln Arg Asp
        450                 455                 460

Gly Phe Tyr Glu Cys Val Phe Gln Pro Ile Phe Leu Leu Ser Gly Tyr
465                 470                 475                 480

Thr Met Trp Ile Arg Ile Asn His Ser Leu Gly Ser Leu Asp Ser Pro
                485                 490                 495

Pro Thr Cys Val Leu Pro Asp Ser Val Val Lys Pro Leu Pro Pro Ser
            500                 505                 510

Asn Val Lys Ala Glu Ile Thr Val Asn Thr Gly Leu Leu Lys Val Ser
        515                 520                 525

Trp Glu Lys Pro Val Phe Pro Glu Asn Asn Leu Gln Phe Gln Ile Arg
        530                 535                 540

Tyr Gly Leu Ser Gly Lys Glu Ile Gln Trp Lys Thr His Glu Val Phe
545                 550                 555                 560

Asp Ala Lys Ser Lys Ser Ala Ser Leu Leu Val Ser Asp Leu Cys Ala
                565                 570                 575

Val Tyr Val Val Gln Val Arg Cys Arg Arg Leu Asp Gly Leu Gly Tyr
                580                 585                 590

Trp Ser Asn Trp Ser Ser Pro Ala Tyr Thr Leu Val Met Asp Val Lys
        595                 600                 605

Val Pro Met Arg Gly Pro Glu Phe Trp Arg Lys Met Asp Gly Asp Val
        610                 615                 620

Thr Lys Lys Glu Arg Asn Val Thr Leu Leu Trp Lys Pro Leu Thr Lys
625                 630                 635                 640

Asn Asp Ser Leu Cys Ser Val Arg Arg Tyr Val Val Lys His Arg Thr
                645                 650                 655

Ala His Asn Gly Thr Trp Ser Glu Asp Val Gly Asn Arg Thr Asn Leu
                660                 665                 670

Thr Phe Leu Trp Thr Glu Pro Ala His Thr Val Thr Val Leu Ala Val
        675                 680                 685

Asn Ser Leu Gly Ala Ser Leu Val Asn Phe Asn Leu Thr Phe Ser Trp
        690                 695                 700

Pro Met Ser Lys Val Ser Ala Val Glu Ser Leu Ser Ala Tyr Pro Leu
705                 710                 715                 720

Ser Ser Ser Cys Val Ile Leu Ser Trp Thr Leu Ser Pro Asp Asp Tyr
                725                 730                 735

Ser Leu Leu Tyr Leu Val Ile Glu Trp Lys Ile Leu Asn Glu Asp Asp
        740                 745                 750

Gly Met Lys Trp Leu Arg Ile Pro Ser Asn Val Lys Lys Phe Tyr Ile
        755                 760                 765

His
```

<210> SEQ ID NO 117
<211> LENGTH: 771
<212> TYPE: PRT
<213> ORGANISM: Mus musculus

<400> SEQUENCE: 117

Asp Pro Ile Ser Pro Trp Lys Phe Lys Leu Phe Cys Gly Pro Pro Asn
1               5                   10                  15

Thr Thr Asp Asp Ser Phe Leu Ser Pro Ala Gly Ala Pro Asn Asn Ala
            20                  25                  30

Ser Ala Leu Lys Gly Ala Ser Glu Ala Ile Val Glu Ala Lys Phe Asn
        35                  40                  45

Ser Ser Gly Ile Tyr Val Pro Glu Leu Ser Lys Thr Val Phe His Cys
    50                  55                  60

Cys Phe Gly Asn Glu Gln Gly Gln Asn Cys Ser Ala Leu Thr Asp Asn
65                  70                  75                  80

Thr Glu Gly Lys Thr Leu Ala Ser Val Val Lys Ala Ser Val Phe Arg
                85                  90                  95

Gln Leu Gly Val Asn Trp Asp Ile Glu Cys Trp Met Lys Gly Asp Leu
            100                 105                 110

Thr Leu Phe Ile Cys His Met Glu Pro Leu Pro Lys Asn Pro Phe Lys
        115                 120                 125

Asn Tyr Asp Ser Lys Val His Leu Leu Tyr Asp Leu Pro Glu Val Ile
    130                 135                 140

Asp Asp Ser Pro Leu Pro Leu Lys Asp Ser Phe Gln Thr Val Gln
145                 150                 155                 160

Cys Asn Cys Ser Leu Arg Gly Cys Glu Cys His Val Pro Val Pro Arg
                165                 170                 175

Ala Lys Leu Asn Tyr Ala Leu Leu Met Tyr Leu Glu Ile Thr Ser Ala
            180                 185                 190

Gly Val Ser Phe Gln Ser Pro Leu Met Ser Leu Gln Pro Met Leu Val
        195                 200                 205

Val Lys Pro Asp Pro Pro Leu Gly Leu His Met Glu Val Thr Asp Asp
    210                 215                 220

Gly Asn Leu Lys Ile Ser Trp Asp Ser Gln Thr Met Ala Pro Phe Pro
225                 230                 235                 240

Leu Gln Tyr Gln Val Lys Tyr Leu Glu Asn Ser Thr Ile Val Arg Glu
                245                 250                 255

Ala Ala Glu Ile Val Ser Ala Thr Ser Leu Leu Val Asp Ser Val Leu
            260                 265                 270

Pro Gly Ser Ser Tyr Glu Val Gln Val Arg Ser Lys Arg Leu Asp Gly
        275                 280                 285

Ser Gly Val Trp Ser Asp Trp Ser Ser Pro Gln Val Phe Thr Thr Gln
    290                 295                 300

Asp Val Val Tyr Phe Pro Pro Lys Ile Leu Thr Ser Val Gly Ser Asn
305                 310                 315                 320

Ala Ser Phe His Cys Ile Tyr Lys Asn Glu Asn Gln Ile Ile Ser Ser
                325                 330                 335

Lys Gln Ile Val Trp Trp Arg Asn Leu Ala Glu Lys Ile Pro Glu Ile
            340                 345                 350

Gln Tyr Ser Ile Val Ser Asp Arg Val Ser Lys Val Thr Phe Ser Asn
        355                 360                 365

Leu Lys Ala Thr Arg Pro Arg Gly Lys Phe Thr Tyr Asp Ala Val Tyr

```
            370                 375                 380
Cys Cys Asn Glu Gln Ala Cys His His Arg Tyr Ala Glu Leu Tyr Val
385                 390                 395                 400

Ile Asp Val Asn Ile Asn Ile Ser Cys Glu Thr Asp Gly Tyr Leu Thr
                405                 410                 415

Lys Met Thr Cys Arg Trp Ser Pro Ser Thr Ile Gln Ser Leu Val Gly
                420                 425                 430

Ser Thr Val Gln Leu Arg Tyr His Arg Arg Ser Leu Tyr Cys Pro Asp
                435                 440                 445

Ser Pro Ser Ile His Pro Thr Ser Glu Pro Lys Asn Cys Val Leu Gln
450                 455                 460

Arg Asp Gly Phe Tyr Glu Cys Val Phe Gln Pro Ile Phe Leu Leu Ser
465                 470                 475                 480

Gly Tyr Thr Met Trp Ile Arg Ile Asn His Ser Leu Gly Ser Leu Asp
                485                 490                 495

Ser Pro Pro Thr Cys Val Leu Pro Asp Ser Val Val Lys Pro Leu Pro
                500                 505                 510

Pro Ser Asn Val Lys Ala Glu Ile Thr Val Asn Thr Gly Leu Leu Lys
                515                 520                 525

Val Ser Trp Glu Lys Pro Val Phe Pro Glu Asn Asn Leu Gln Phe Gln
530                 535                 540

Ile Arg Tyr Gly Leu Ser Gly Lys Glu Ile Gln Trp Lys Thr His Glu
545                 550                 555                 560

Val Phe Asp Ala Lys Ser Lys Ser Ala Ser Leu Leu Val Ser Asp Leu
                565                 570                 575

Cys Ala Val Tyr Val Val Gln Val Arg Cys Arg Arg Leu Asp Gly Leu
                580                 585                 590

Gly Tyr Trp Ser Asn Trp Ser Ser Pro Ala Tyr Thr Leu Val Met Asp
                595                 600                 605

Val Lys Val Pro Met Arg Gly Pro Glu Phe Trp Arg Lys Met Asp Gly
                610                 615                 620

Asp Val Thr Lys Lys Glu Arg Asn Val Thr Leu Leu Trp Lys Pro Leu
625                 630                 635                 640

Thr Lys Asn Asp Ser Leu Cys Ser Val Arg Arg Tyr Val Val Lys His
                645                 650                 655

Arg Thr Ala His Asn Gly Thr Trp Ser Glu Asp Val Gly Asn Arg Thr
                660                 665                 670

Asn Leu Thr Phe Leu Trp Thr Glu Pro Ala His Thr Val Thr Val Leu
                675                 680                 685

Ala Val Asn Ser Leu Gly Ala Ser Leu Val Asn Phe Asn Leu Thr Phe
                690                 695                 700

Ser Trp Pro Met Ser Lys Val Ser Ala Val Glu Ser Leu Ser Ala Tyr
705                 710                 715                 720

Pro Leu Ser Ser Ser Cys Val Ile Leu Ser Trp Thr Leu Ser Pro Asp
                725                 730                 735

Asp Tyr Ser Leu Leu Tyr Leu Val Ile Glu Trp Lys Ile Leu Asn Glu
                740                 745                 750

Asp Asp Gly Met Lys Trp Leu Arg Ile Pro Ser Asn Val Lys Lys Phe
                755                 760                 765

Tyr Ile His
        770

<210> SEQ ID NO 118
```

<211> LENGTH: 684
<212> TYPE: PRT
<213> ORGANISM: Mus musculus

<400> SEQUENCE: 118

```
Ser Val Val Lys Ala Ser Val Phe Arg Gln Leu Gly Val Asn Trp Asp
1               5                   10                  15

Ile Glu Cys Trp Met Lys Gly Asp Leu Thr Leu Phe Ile Cys His Met
            20                  25                  30

Glu Pro Leu Pro Lys Asn Pro Phe Lys Asn Tyr Asp Ser Lys Val His
        35                  40                  45

Leu Leu Tyr Asp Leu Pro Glu Val Ile Asp Ser Pro Leu Pro Pro
    50                  55                  60

Leu Lys Asp Ser Phe Gln Thr Val Gln Cys Asn Cys Ser Leu Arg Gly
65                  70                  75                  80

Cys Glu Cys His Val Pro Val Pro Arg Ala Lys Leu Asn Tyr Ala Leu
                85                  90                  95

Leu Met Tyr Leu Glu Ile Thr Ser Ala Gly Val Ser Phe Gln Ser Pro
            100                 105                 110

Leu Met Ser Leu Gln Pro Met Leu Val Val Lys Pro Asp Pro Pro Leu
        115                 120                 125

Gly Leu His Met Glu Val Thr Asp Asp Gly Asn Leu Lys Ile Ser Trp
    130                 135                 140

Asp Ser Gln Thr Met Ala Pro Phe Pro Leu Gln Tyr Gln Val Lys Tyr
145                 150                 155                 160

Leu Glu Asn Ser Thr Ile Val Arg Glu Ala Ala Glu Ile Val Ser Ala
                165                 170                 175

Thr Ser Leu Leu Val Asp Ser Val Leu Pro Gly Ser Ser Tyr Glu Val
            180                 185                 190

Gln Val Arg Ser Lys Arg Leu Asp Gly Ser Gly Val Trp Ser Asp Trp
        195                 200                 205

Ser Ser Pro Gln Val Phe Thr Thr Gln Asp Val Val Tyr Phe Pro Pro
    210                 215                 220

Lys Ile Leu Thr Ser Val Gly Ser Asn Ala Ser Phe His Cys Ile Tyr
225                 230                 235                 240

Lys Asn Glu Asn Gln Ile Ile Ser Ser Lys Gln Ile Val Trp Trp Arg
                245                 250                 255

Asn Leu Ala Glu Lys Ile Pro Glu Ile Gln Tyr Ser Ile Val Ser Asp
            260                 265                 270

Arg Val Ser Lys Val Thr Phe Ser Asn Leu Lys Ala Thr Arg Pro Arg
        275                 280                 285

Gly Lys Phe Thr Tyr Asp Ala Val Tyr Cys Cys Asn Glu Gln Ala Cys
    290                 295                 300

His His Arg Tyr Ala Glu Leu Tyr Val Ile Asp Val Asn Ile Asn Ile
305                 310                 315                 320

Ser Cys Glu Thr Asp Gly Tyr Leu Thr Lys Met Thr Cys Arg Trp Ser
                325                 330                 335

Pro Ser Thr Ile Gln Ser Leu Val Gly Ser Thr Val Gln Leu Arg Tyr
            340                 345                 350

His Arg Arg Ser Leu Tyr Cys Pro Asp Ser Pro Ser Ile His Pro Thr
        355                 360                 365

Ser Glu Pro Lys Asn Cys Val Leu Gln Arg Asp Gly Phe Tyr Glu Cys
    370                 375                 380

Val Phe Gln Pro Ile Phe Leu Leu Ser Gly Tyr Thr Met Trp Ile Arg
```

```
                385                 390                 395                 400
Ile Asn His Ser Leu Gly Ser Leu Asp Ser Pro Pro Thr Cys Val Leu
                405                 410                 415

Pro Asp Ser Val Val Lys Pro Leu Pro Pro Ser Asn Val Lys Ala Glu
                420                 425                 430

Ile Thr Val Asn Thr Gly Leu Leu Lys Val Ser Trp Glu Lys Pro Val
                435                 440                 445

Phe Pro Glu Asn Asn Leu Gln Phe Gln Ile Arg Tyr Gly Leu Ser Gly
                450                 455                 460

Lys Glu Ile Gln Trp Lys Thr His Glu Val Phe Asp Ala Lys Ser Lys
465                 470                 475                 480

Ser Ala Ser Leu Leu Val Ser Asp Leu Cys Ala Val Tyr Val Val Gln
                485                 490                 495

Val Arg Cys Arg Arg Leu Asp Gly Leu Gly Tyr Trp Ser Asn Trp Ser
                500                 505                 510

Ser Pro Ala Tyr Thr Leu Val Met Asp Val Lys Val Pro Met Arg Gly
                515                 520                 525

Pro Glu Phe Trp Arg Lys Met Asp Gly Asp Val Thr Lys Lys Glu Arg
                530                 535                 540

Asn Val Thr Leu Leu Trp Lys Pro Leu Thr Lys Asn Asp Ser Leu Cys
545                 550                 555                 560

Ser Val Arg Arg Tyr Val Val Lys His Arg Thr Ala His Asn Gly Thr
                565                 570                 575

Trp Ser Glu Asp Val Gly Asn Arg Thr Asn Leu Thr Phe Leu Trp Thr
                580                 585                 590

Glu Pro Ala His Thr Val Thr Val Leu Ala Val Asn Ser Leu Gly Ala
                595                 600                 605

Ser Leu Val Asn Phe Asn Leu Thr Phe Ser Trp Pro Met Ser Lys Val
                610                 615                 620

Ser Ala Val Glu Ser Leu Ser Ala Tyr Pro Leu Ser Ser Ser Cys Val
625                 630                 635                 640

Ile Leu Ser Trp Thr Leu Ser Pro Asp Asp Tyr Ser Leu Leu Tyr Leu
                645                 650                 655

Val Ile Glu Trp Lys Ile Leu Asn Glu Asp Asp Gly Met Lys Trp Leu
                660                 665                 670

Arg Ile Pro Ser Asn Val Lys Lys Phe Tyr Ile His
                675                 680

<210> SEQ ID NO 119
<211> LENGTH: 64
<212> TYPE: PRT
<213> ORGANISM: Mus musculus

<400> SEQUENCE: 119

Met Ser Lys Val Ser Ala Val Glu Ser Leu Ser Ala Tyr Pro Leu Ser
1               5                   10                  15

Ser Ser Cys Val Ile Leu Ser Trp Thr Leu Ser Pro Asp Asp Tyr Ser
                20                  25                  30

Leu Leu Tyr Leu Val Ile Glu Trp Lys Ile Leu Asn Glu Asp Asp Gly
                35                  40                  45

Met Lys Trp Leu Arg Ile Pro Ser Asn Val Lys Lys Phe Tyr Ile His
        50                  55                  60

<210> SEQ ID NO 120
<211> LENGTH: 9
```

<212> TYPE: PRT
<213> ORGANISM: Mus musculus

<400> SEQUENCE: 120

Gly Met Cys Thr Val Leu Phe Met Asp
1               5

<210> SEQ ID NO 121
<211> LENGTH: 227
<212> TYPE: PRT
<213> ORGANISM: Mus musculus

<400> SEQUENCE: 121

Asp Arg Trp Gly Ser Tyr Ala Glu Leu Tyr Val Ile Asp Val Asn Ile
1               5                   10                  15

Asn Ile Ser Cys Glu Thr Asp Gly Tyr Leu Thr Lys Met Thr Cys Arg
            20                  25                  30

Trp Ser Pro Ser Thr Ile Gln Ser Leu Val Gly Ser Thr Val Gln Leu
        35                  40                  45

Arg Tyr His Arg Arg Ser Leu Tyr Cys Pro Asp Ser Pro Ser Ile His
    50                  55                  60

Pro Thr Ser Glu Pro Lys Asn Cys Val Leu Gln Arg Asp Gly Phe Tyr
65                  70                  75                  80

Glu Cys Val Phe Gln Pro Ile Phe Leu Leu Ser Gly Tyr Thr Met Trp
                85                  90                  95

Ile Arg Ile Asn His Ser Leu Gly Ser Leu Asp Ser Pro Pro Thr Cys
            100                 105                 110

Val Leu Pro Asp Ser Val Val Lys Pro Leu Pro Pro Ser Asn Val Lys
        115                 120                 125

Ala Glu Ile Thr Val Asn Thr Gly Leu Leu Lys Val Ser Trp Glu Lys
    130                 135                 140

Pro Val Phe Pro Glu Asn Asn Leu Gln Phe Gln Ile Arg Tyr Gly Leu
145                 150                 155                 160

Ser Gly Lys Glu Ile Gln Trp Lys Thr His Glu Val Phe Asp Ala Lys
                165                 170                 175

Ser Lys Ser Ala Ser Leu Leu Val Ser Asp Leu Cys Ala Val Tyr Val
            180                 185                 190

Val Gln Val Arg Cys Arg Arg Leu Asp Gly Leu Gly Tyr Trp Ser Asn
        195                 200                 205

Trp Ser Ser Pro Ala Tyr Thr Leu Val Met Asp Val Lys Val Pro Met
    210                 215                 220

Arg Gly Pro
225

<210> SEQ ID NO 122
<211> LENGTH: 227
<212> TYPE: PRT
<213> ORGANISM: Mus musculus

<400> SEQUENCE: 122

Asp Arg Trp Gly Ser Tyr Ala Glu Leu Tyr Val Ile Asp Val Asn Ile
1               5                   10                  15

Asn Ile Ser Cys Glu Thr Asp Gly Tyr Leu Thr Lys Met Thr Cys Arg
            20                  25                  30

Trp Ser Pro Ser Thr Ile Gln Ser Leu Val Gly Ser Thr Val Gln Leu
        35                  40                  45

Arg Tyr His Arg Arg Ser Leu Tyr Cys Pro Asp Ser Pro Ser Ile His

-continued

```
                50                  55                  60
Pro Thr Ser Glu Pro Lys Asn Cys Val Leu Gln Arg Asp Gly Phe Tyr
 65                  70                  75                  80

Glu Cys Val Phe Gln Pro Ile Phe Leu Leu Ser Gly Tyr Thr Met Trp
                 85                  90                  95

Ile Arg Ile Asn His Ser Leu Gly Ser Leu Asp Ser Pro Pro Thr Cys
             100                 105                 110

Val Leu Pro Asp Ser Val Val Lys Pro Leu Pro Pro Ser Asn Val Lys
         115                 120                 125

Ala Glu Ile Thr Val Asn Thr Gly Leu Leu Lys Val Ser Trp Glu Lys
 130                 135                 140

Pro Val Phe Pro Glu Asn Asn Leu Gln Phe Gln Ile Arg Tyr Gly Leu
145                 150                 155                 160

Ser Gly Lys Glu Ile Gln Trp Lys Thr His Glu Val Phe Asp Ala Lys
                165                 170                 175

Ser Lys Ser Ala Ser Leu Leu Val Ser Asp Leu Cys Ala Val Tyr Val
            180                 185                 190

Val Gln Val Arg Cys Arg Arg Leu Asp Gly Leu Gly Tyr Trp Ser Asn
        195                 200                 205

Trp Ser Ser Pro Ala Tyr Thr Leu Val Met Asp Val Lys Val Pro Met
    210                 215                 220

Arg Gly Pro
225

<210> SEQ ID NO 123
<211> LENGTH: 529
<212> TYPE: PRT
<213> ORGANISM: Mus musculus

<400> SEQUENCE: 123

Asp Arg Trp Gly Ser Ser Val Phe Arg Gln Leu Gly Val Asn Trp Asp
  1               5                  10                  15

Ile Glu Cys Trp Met Lys Gly Asp Leu Thr Leu Phe Ile Cys His Met
                 20                  25                  30

Glu Pro Leu Pro Lys Asn Pro Phe Lys Asn Tyr Asp Ser Lys Val His
             35                  40                  45

Leu Leu Tyr Asp Leu Pro Glu Val Ile Asp Asp Ser Pro Leu Pro Pro
         50                  55                  60

Leu Lys Asp Ser Phe Gln Thr Val Gln Cys Asn Cys Ser Leu Arg Gly
 65                  70                  75                  80

Cys Glu Cys His Val Pro Val Pro Arg Ala Lys Leu Asn Tyr Ala Leu
                 85                  90                  95

Leu Met Tyr Leu Glu Ile Thr Ser Ala Gly Val Ser Phe Gln Ser Pro
            100                 105                 110

Leu Met Ser Leu Gln Pro Met Leu Val Val Lys Pro Asp Pro Pro Leu
        115                 120                 125

Gly Leu His Met Glu Val Thr Asp Asp Gly Asn Leu Lys Ile Ser Trp
    130                 135                 140

Asp Ser Gln Thr Met Ala Pro Phe Pro Leu Gln Tyr Gln Val Lys Tyr
145                 150                 155                 160

Leu Glu Asn Ser Thr Ile Val Arg Glu Ala Ala Glu Ile Val Ser Ala
                165                 170                 175

Thr Ser Leu Leu Val Asp Ser Val Leu Pro Gly Ser Ser Tyr Glu Val
            180                 185                 190
```

-continued

```
Gln Val Arg Ser Lys Arg Leu Asp Gly Ser Gly Val Trp Ser Asp Trp
            195                 200                 205

Ser Ser Pro Gln Val Phe Thr Thr Gln Asp Val Val Tyr Phe Pro Pro
    210                 215                 220

Lys Ile Leu Thr Ser Val Gly Ser Asn Ala Ser Phe His Cys Ile Tyr
225                 230                 235                 240

Lys Asn Glu Asn Gln Ile Ile Ser Ser Lys Gln Ile Val Trp Trp Arg
                    245                 250                 255

Asn Leu Ala Glu Lys Ile Pro Glu Ile Gln Tyr Ser Ile Val Ser Asp
                260                 265                 270

Arg Val Ser Lys Val Thr Phe Ser Asn Leu Lys Ala Thr Arg Pro Arg
            275                 280                 285

Gly Lys Phe Thr Tyr Asp Ala Val Tyr Cys Cys Asn Glu Gln Ala Cys
        290                 295                 300

His His Arg Tyr Ala Glu Leu Tyr Val Ile Asp Val Asn Ile Asn Ile
305                 310                 315                 320

Ser Cys Glu Thr Asp Gly Tyr Leu Thr Lys Met Thr Cys Arg Trp Ser
                    325                 330                 335

Pro Ser Thr Ile Gln Ser Leu Val Gly Ser Thr Val Gln Leu Arg Tyr
                340                 345                 350

His Arg Arg Ser Leu Tyr Cys Pro Asp Ser Pro Ser Ile His Pro Thr
            355                 360                 365

Ser Glu Pro Lys Asn Cys Val Leu Gln Arg Asp Gly Phe Tyr Glu Cys
        370                 375                 380

Val Phe Gln Pro Ile Phe Leu Leu Ser Gly Tyr Thr Met Trp Ile Arg
385                 390                 395                 400

Ile Asn His Ser Leu Gly Ser Leu Asp Ser Pro Pro Thr Cys Val Leu
                    405                 410                 415

Pro Asp Ser Val Val Lys Pro Leu Pro Pro Ser Asn Val Lys Ala Glu
                420                 425                 430

Ile Thr Val Asn Thr Gly Leu Leu Lys Val Ser Trp Glu Lys Pro Val
            435                 440                 445

Phe Pro Glu Asn Asn Leu Gln Phe Gln Ile Arg Tyr Gly Leu Ser Gly
        450                 455                 460

Lys Glu Ile Gln Trp Lys Thr His Glu Val Phe Asp Ala Lys Ser Lys
465                 470                 475                 480

Ser Ala Ser Leu Leu Val Ser Asp Leu Cys Ala Val Tyr Val Val Gln
                    485                 490                 495

Val Arg Cys Arg Arg Leu Asp Gly Leu Gly Tyr Trp Ser Asn Trp Ser
                500                 505                 510

Ser Pro Ala Tyr Thr Leu Val Met Asp Val Lys Val Pro Met Arg Gly
            515                 520                 525

Pro

<210> SEQ ID NO 124
<211> LENGTH: 529
<212> TYPE: PRT
<213> ORGANISM: Mus musculus

<400> SEQUENCE: 124

Asp Arg Trp Gly Ser Ser Val Phe Arg Gln Leu Gly Val Asn Trp Asp
1               5                   10                  15

Ile Glu Cys Trp Met Lys Gly Asp Leu Thr Leu Phe Ile Cys His Met
            20                  25                  30
```

-continued

```
Glu Pro Leu Pro Lys Asn Pro Phe Lys Asn Tyr Asp Ser Lys Val His
         35                  40                  45
Leu Leu Tyr Asp Leu Pro Glu Val Ile Asp Asp Ser Pro Leu Pro Pro
 50                  55                  60
Leu Lys Asp Ser Phe Gln Thr Val Gln Cys Asn Cys Ser Leu Arg Gly
 65                  70                  75                  80
Cys Glu Cys His Val Pro Val Pro Arg Ala Lys Leu Asn Tyr Ala Leu
                 85                  90                  95
Leu Met Tyr Leu Glu Ile Thr Ser Ala Gly Val Ser Phe Gln Ser Pro
             100                 105                 110
Leu Met Ser Leu Gln Pro Met Leu Val Val Lys Pro Asp Pro Pro Leu
             115                 120                 125
Gly Leu His Met Glu Val Thr Asp Asp Gly Asn Leu Lys Ile Ser Trp
 130                 135                 140
Asp Ser Gln Thr Met Ala Pro Phe Pro Leu Gln Tyr Gln Val Lys Tyr
 145                 150                 155                 160
Leu Glu Asn Ser Thr Ile Val Arg Glu Ala Ala Glu Ile Val Ser Ala
                 165                 170                 175
Thr Ser Leu Leu Val Asp Ser Val Leu Pro Gly Ser Ser Tyr Glu Val
             180                 185                 190
Gln Val Arg Ser Lys Arg Leu Asp Gly Ser Gly Val Trp Ser Asp Trp
             195                 200                 205
Ser Ser Pro Gln Val Phe Thr Thr Gln Asp Val Val Tyr Phe Pro Pro
 210                 215                 220
Lys Ile Leu Thr Ser Val Gly Ser Asn Ala Ser Phe His Cys Ile Tyr
 225                 230                 235                 240
Lys Asn Glu Asn Gln Ile Ile Ser Ser Lys Gln Ile Val Trp Trp Arg
                 245                 250                 255
Asn Leu Ala Glu Lys Ile Pro Glu Ile Gln Tyr Ser Ile Val Ser Asp
             260                 265                 270
Arg Val Ser Lys Val Thr Phe Ser Asn Leu Lys Ala Thr Arg Pro Arg
             275                 280                 285
Gly Lys Phe Thr Tyr Asp Ala Val Tyr Cys Cys Asn Glu Gln Ala Cys
 290                 295                 300
His His Arg Tyr Ala Glu Leu Tyr Val Ile Asp Val Asn Ile Asn Ile
 305                 310                 315                 320
Ser Cys Glu Thr Asp Gly Tyr Leu Thr Lys Met Thr Cys Arg Trp Ser
                 325                 330                 335
Pro Ser Thr Ile Gln Ser Leu Val Gly Ser Thr Val Gln Leu Arg Tyr
             340                 345                 350
His Arg Arg Ser Leu Tyr Cys Pro Asp Ser Pro Ser Ile His Pro Thr
             355                 360                 365
Ser Glu Pro Lys Asn Cys Val Leu Gln Arg Asp Gly Phe Tyr Glu Cys
 370                 375                 380
Val Phe Gln Pro Ile Phe Leu Leu Ser Gly Tyr Thr Met Trp Ile Arg
 385                 390                 395                 400
Ile Asn His Ser Leu Gly Ser Leu Asp Ser Pro Thr Cys Val Leu
                 405                 410                 415
Pro Asp Ser Val Val Lys Pro Leu Pro Pro Ser Asn Val Lys Ala Glu
             420                 425                 430
Ile Thr Val Asn Thr Gly Leu Leu Lys Val Ser Trp Glu Lys Pro Val
             435                 440                 445
Phe Pro Glu Asn Asn Leu Gln Phe Gln Ile Arg Tyr Gly Leu Ser Gly
```

-continued

```
              450                 455                 460
Lys Glu Ile Gln Trp Lys Thr His Glu Val Phe Asp Ala Lys Ser Lys
465                 470                 475                 480

Ser Ala Ser Leu Leu Val Ser Asp Leu Cys Ala Val Tyr Val Val Gln
                485                 490                 495

Val Arg Cys Arg Arg Leu Asp Gly Leu Gly Tyr Trp Ser Asn Trp Ser
                500                 505                 510

Ser Pro Ala Tyr Thr Leu Val Met Asp Val Lys Val Pro Met Arg Gly
            515                 520                 525

Pro

<210> SEQ ID NO 125
<211> LENGTH: 214
<212> TYPE: PRT
<213> ORGANISM: Mus musculus

<400> SEQUENCE: 125

Asp Arg Trp Gly Ser Leu Gly Val Asn Trp Asp Ile Glu Cys Trp Met
1               5                   10                  15

Lys Gly Asp Leu Thr Leu Phe Ile Cys His Met Glu Pro Leu Pro Lys
                20                  25                  30

Asn Pro Phe Lys Asn Tyr Asp Ser Lys Val His Leu Leu Tyr Asp Leu
            35                  40                  45

Pro Glu Val Ile Asp Asp Ser Pro Leu Pro Leu Lys Asp Ser Phe
    50                  55                  60

Gln Thr Val Gln Cys Asn Cys Ser Leu Arg Gly Cys Glu Cys His Val
65                  70                  75                  80

Pro Val Pro Arg Ala Lys Leu Asn Tyr Ala Leu Leu Met Tyr Leu Glu
                85                  90                  95

Ile Thr Ser Ala Gly Val Ser Phe Gln Ser Pro Leu Met Ser Leu Gln
                100                 105                 110

Pro Met Leu Val Val Lys Pro Asp Pro Pro Leu Gly Leu His Met Glu
            115                 120                 125

Val Thr Asp Asp Gly Asn Leu Lys Ile Ser Trp Asp Ser Gln Thr Met
130                 135                 140

Ala Pro Phe Pro Leu Gln Tyr Gln Val Lys Tyr Leu Glu Asn Ser Thr
145                 150                 155                 160

Ile Val Arg Glu Ala Ala Glu Ile Val Ser Ala Thr Ser Leu Leu Val
                165                 170                 175

Asp Ser Val Leu Pro Gly Ser Ser Tyr Glu Val Gln Val Arg Ser Lys
            180                 185                 190

Arg Leu Asp Gly Ser Gly Val Trp Ser Asp Trp Ser Ser Pro Gln Val
        195                 200                 205

Phe Thr Thr Gln Asp Val
    210

<210> SEQ ID NO 126
<211> LENGTH: 214
<212> TYPE: PRT
<213> ORGANISM: Mus musculus

<400> SEQUENCE: 126

Asp Arg Trp Gly Ser Leu Gly Val Asn Trp Asp Ile Glu Cys Trp Met
1               5                   10                  15

Lys Gly Asp Leu Thr Leu Phe Ile Cys His Met Glu Pro Leu Pro Lys
                20                  25                  30
```

-continued

```
Asn Pro Phe Lys Asn Tyr Asp Ser Lys Val His Leu Leu Tyr Asp Leu
        35                  40                  45
Pro Glu Val Ile Asp Asp Ser Pro Leu Pro Pro Leu Lys Asp Ser Phe
    50                  55                  60
Gln Thr Val Gln Cys Asn Cys Ser Leu Arg Gly Cys Glu Cys His Val
65                  70                  75                  80
Pro Val Pro Arg Ala Lys Leu Asn Tyr Ala Leu Leu Met Tyr Leu Glu
            85                  90                  95
Ile Thr Ser Ala Gly Val Ser Phe Gln Ser Pro Leu Met Ser Leu Gln
            100                 105                 110
Pro Met Leu Val Val Lys Pro Asp Pro Pro Leu Gly Leu His Met Glu
        115                 120                 125
Val Thr Asp Asp Gly Asn Leu Lys Ile Ser Trp Asp Ser Gln Thr Met
        130                 135                 140
Ala Pro Phe Pro Leu Gln Tyr Gln Val Lys Tyr Leu Glu Asn Ser Thr
145                 150                 155                 160
Ile Val Arg Glu Ala Ala Glu Ile Val Ser Ala Thr Ser Leu Leu Val
            165                 170                 175
Asp Ser Val Leu Pro Gly Ser Ser Tyr Glu Val Gln Val Arg Ser Lys
            180                 185                 190
Arg Leu Asp Gly Ser Gly Val Trp Ser Asp Trp Ser Ser Pro Gln Val
        195                 200                 205
Phe Thr Thr Gln Asp Val
        210
```

DB, THE RECEPTOR FOR LEPTIN, NUCLEIC ACIDS ENCODING THE RECEPTOR, AND USES THEREOF

This invention was made with government support under DK41096-07 awarded by the NIH. Accordingly, the United States Government has certain rights in the invention.

PRIORITY CLAIM

The present application claims the benefit of priority pursuant to 35 U.S.C. §120 to application Ser. No. 08/599,974, filed Feb. 14, 1996, now pending, and to application Ser. No. 08/586,594, filed Jan. 16, 1996, now pending, each of which is incorporated herein by reference in its entirety.

FIELD OF THE INVENTION

The present invention relates to identification of a receptor for a satiety factor, which is involved in body weight homeostasis. Mutations in this receptor are associated with obese phenotypes. In particular, the present invention relates to identification and characterization of the receptor for leptin, including a naturally occurring soluble form of the receptor that is expected to modulate leptin activity, in particular to agonize leptin activity. The invention further relates to the nucleic acids encoding the receptor, and to methods for using the receptor, e.g., to identify leptin analogs, therapeutically, or diagnostically.

BACKGROUND OF THE INVENTION

Obesity, defined as an excess of body fat relative to lean body mass, is associated with important psychological and medical morbidities, the latter including hypertension, elevated blood lipids, and Type II or non-insulin-dependent diabetes melitis (NIDDM). There are 6-10 million individuals with NIDDM in the U.S., including 18% of the population of 65 years of age [Harris et al., *Int. J. Obes.*, 11:275-283 (1987)]. Approximately 45% of males and 70% of females with NIDDM are obese, and their diabetes is substantially improved or eliminated by weight reduction [Harris, *Diabetes Care*, 14(3):639-648 (1991)]. As described below, both obesity and NIDDM are strongly heritable.

The assimilation, storage, and utilization of nutrient energy constitute a complex homeostatic system central to survival of metazoa. Among land-dwelling mammals, storage in adipose tissue of large quantities of metabolic fuel as triglycerides is crucial for surviving periods of food deprivation. The need to maintain a fixed level of energy stores without continual alterations in the size and shape of the organism requires the achievement of a balance between energy intake and expenditure.

An individual's level of adiposity is, to a large extent, genetically determined. Examination of the concordance rates of body weight and adiposity amongst mono- and dizygous twins or adoptees and their biological parents have suggested that the heritability of obesity (0.4-0.8) exceeds that of many other traits commonly thought to have a substantial genetic component, such as schizophrenia, alcoholism, and atherosclerosis [Stunkard et al., *N. Engl. J. Med.*, 322:1483-1487 (1990)]. Familial similarities in rates of energy expenditure have also been reported [Bogardus et al., *Diabetes*, 35:1-5 (1986)]. Genetic analysis in geographically delimited populations has suggested that a relatively small number of genes may account for the 30-50% of variance in body composition [Moll et al., *Am. J. Hum. Genet.*, 49:1243-1255 (1991)].

Rodent models of obesity include seven apparently single-gene mutations. The most intensively studied mouse obesity mutations are the ob (obese) and db (diabetes) genes. When present on the same genetic strain background, ob and db result in indistinguishable metabolic and behavioral phenotypes, suggesting that these genes may function in the same physiologic pathway [Coleman et al., *Diabetologia*, 14:141-148 (1978)]. Mice homozygous for either mutation are hyperphagic and hypometabolic, leading to an obese phenotype that is notable at one month of age. The weight of these animals tends to stabilize at 60-70 g (compared with 30-35 g in control mice). ob and db animals manifest a myriad of other hormonal and metabolic changes that had made it difficult to identify the primary defect attributable to the mutation [Bray et al., *Am. J. Clin. Nutr.*, 50:891-902 (1989)]. As noted below, identification of the OB gene led to an understanding of one molecular element.

Each of the rodent obesity models is accompanied by alterations in carbohydrate metabolism resembling those in Type II diabetes in man. In some cases, the severity of the diabetes depends in part on the background mouse strain [Leiter, *Endocrinology*, 124:912-922 (1989)]. For both ob and db, congenic C57BL/Ks mice develop a severe diabetes with ultimate β cell necrosis and islet atrophy, resulting in a relative insulinopenia. Conversely, congenic C57BL/6J ob and db mice develop a transient insulin-resistant diabetes that is eventually compensated by β cell hypertrophy, resembling human Type II diabetes.

The phenotype of ob and db mice resembles human obesity in ways other than the development of diabetes—the mutant mice eat more and expend less energy than do lean controls (as do obese humans). This phenotype is also quite similar to that seen in animals with lesions of the ventromedial hypothalamus, which suggests that both mutations may interfere with the ability to properly integrate or respond to nutritional information within the central nervous system. Support for this hypothesis comes from the results of parabiosis experiments [Coleman, *Diabetologia*, 9:294-298 (1973)] that suggest ob mice are deficient in a circulating satiety factor and that db mice are resistant to the effects of the ob factor (possibly due to an ob receptor defect). These experiments have led to the conclusion that obesity in these mutant mice may result from different defects in an afferent loop and/or integrative center of the postulated feedback mechanism that controls body composition.

Using molecular and classical genetic markers, the ob and db genes have been mapped to proximal chromosome 6 and midchromosome 4, respectively [Bahary et al., *Proc. Nat. Acad. Sci. USA*, 87:8642-8646 (1990); Friedman et al., *Genomics*, 11:1054-1062 (1991)]. In both cases, the mutations map to regions of the mouse genome that are syntenic with human, suggesting that, if there are human homologs of ob and db, they are likely to map, respectively, to human chromosomes 7q and 1p. Defects in the db gene may result in obesity in other mammalian species: in genetic crosses between Zucker fa/fa rats and Brown Norway +/+ rats, the fa mutation (rat chromosome 5) is flanked by the same loci that flank db in mouse [Truett et al., *Proc. Natl. Acad. Sci. USA*, 88:7806-7809 (1991)].

A major advance in understanding the molecular basis for obesity occurred with the cloning of the ob gene. The mouse obesity (ob) gene encodes an adipose tissue-derived signaling factor for body weight homeostasis [Zhang et al., *Nature*, 372:425 (1994); U.S. patent application Ser. No. 08/292,345 filed Aug. 17, 1994; U.S. patent application Ser. No. 08/483,211, filed Jun. 7, 1995; International Patent Publication No. WO 96/05309, published Feb. 22, 1996, each of which is hereby incorporated by reference in its entirety]. Several recent studies have shown that recombinant OB protein (leptin) purified from *Escherichia coli* can correct the obesity related phenotypes in ob/ob mice when exogenously administered [Campfield et al., *Science,* 269:546 (1995); Pellymounter et al., *Science,* 269:540, (1995); Halaas et al., *Science,* 269:543 (1995); Stephens et al., *Nature,* 377:530 (1995)]. Weight-reducing effects of recombinant leptin were also observed in normal mice and mice with diet-induced obesity. Although the target tissues that mediate the effects of leptin have not yet been defined, the instant inventors have predicted the brain as a target of leptin activity. Indeed, the work of Campfield et al. (supra) and Stephens et al. (supra) demonstrates that leptin introduced into the lateral or third brain ventricle is effective at low doses, arguing for a direct central affect of the leptin molecule.

Recent studies have suggested that obese humans and rodents (other than ob/ob mice) are not defective in their ability to produce leptin mRNA or protein and generally produce higher levels than lean individuals [Maffei et al., *Nature Med.,* 1:1155 (1995); Considine et al., *J. Clin. Invest.,* 95:2986 (1995); Lonnqvist et al., *Nature Med.,* 1:950 (1995); Hamilton et al., *Nature Med.,* 1:953 (1995)]. These data suggest that resistance to normal or elevated levels of leptin may be important factors in human obesity. However, a recent report of identification of a leptin receptor did not identify any mutations in the ob allele [Tartaglia et al., *Cell,* 83:1263-1271 (1995)].

Accordingly, there is a need in the art to identify a receptor for leptin.

There is a further need to characterize mutations in the leptin receptor, particularly as they may be associated with obesity.

There is a still further need to identify and characterize functions of the leptin receptor, or variants thereof.

These and other needs in the art are addressed by the present invention.

The citation of any reference herein should not be construed as an admission that such a reference is available as prior art to the application.

SUMMARY OF THE INVENTION

The present invention is directed to a leptin receptor (OB-R) polypeptide, nucleic acids encoding such polypeptide, non-coding nucleic acids flanking the coding sequences of the gene, oligonucleotides that hybridize to such nucleic acids, antibodies to the polypeptide, and diagnostic, therapeutic, and cosmetic compositions and methods utilizing the polypeptide, nucleic acids, or antibodies, or combinations thereof.

Thus, in a first aspect of the invention, the leptin receptor (also termed herein OB receptor or OB-R) is characterized by specific binding to leptin under physiological conditions; expression at high levels in cells of the hypothalamus, and expression at lower levels in adipose tissue, testes, heart, and brain; and having sequence similarity to gp130 cytokine receptors. In another embodiment, the leptin receptor is encoded by a nucleic acid which is identifiable with a polymerase chain reaction (PCR) probe selected from group consisting of a probe for clone 7 (forward primer SEQ ID NO:42 and reverse primer SEQ ID NO:43), a probe for clone 11 (forward primer SEQ ID NO:44 and reverse primer SEQ ID NO:45), and both clone 7 and clone 11. In a specific embodiments, leptin receptor is encoded by a nucleic acid which is identifiable with a PCR probe selected from the group consisting of a probe for clone 42 (forward primer SEQ ID NO:26 and reverse primer SEQ ID NO:46); a probe for clone 46 (forward primer SEQ ID NO:47 and reverse primer SEQ ID NO:48); a probe for clone 58 (forward primer SEQ ID NO:49 and reverse primer SEQ ID NO:50); a probe for clone S14 (forward primer SEQ ID NO:51 and reverse primer SEQ ID NO:52); and a probe for clone S3 (forward primer SEQ ID NO:53 and reverse primer SEQ ID NO:54).

In specific Examples, infra, the leptin receptor is selected from the group consisting of OB-Ra (SEQ ID NO:2), OB-Rb (SEQ ID NO:4), OB-Rc (SEQ ID NO:6), OB-Rd (SEQ ID NO:8), and OB-Re (SEQ ID NO:10), or allelic variants thereof. Alternatively, the leptin receptor may have a sequence selected from the group consisting of:

N-terminal corresponding to OB-Ra through $Lys^{889}$ and C-terminal corresponding to a C-terminal selected from the group consisting of OB-Rb, OB-Rc, and OB-Rd after $Lys^{889}$;

N-terminal corresponding to OB-Rb or OB-Rc through $Lys^{889}$, and C-terminal corresponding to OB-Ra or OB-Rd after $Lys^{889}$;

N-terminal corresponding to OB-Rd through $Lys^{889}$, and C-terminal corresponding to OB-Ra, OB-Rb, or OB-Rc;

N-terminal corresponding to OB-R from $Pro^{664}$ to $Lys^{889}$, and C-terminal corresponding to OB-Ra, OB-Rb, OB-Rc, and OB-Rd; and N-terminal corresponding to OB-R from $Met^{773}$ to $Lys^{889}$, and C-terminal corresponding to OB-Ra, OB-Rb, OB-Rc, and OB-Rd; and N-terminal selected from the group consisting of OB-Ra, OB-Rb, OB-Rd, and OB-R from $Pro^{664}$ to $His^{796}$, and OB-Re from $His^{796}$;

N-terminal selected from the group consisting of OB-Ra, OB-Rb, OB-Rd, and OB-R from $Met^{733}$ to $His^{796}$, and OB-Re from $His^{796}$, or allelic variants thereof.

In another embodiment, leptin receptor may have an N-terminal sequence is selected from the group consisting of
 amino acid residues 1-889;
 amino acid residues 23-889;
 amino acid residues 28-889;
 amino acid residues 133-889;
 amino acid residues 733-889;
 amino acid residues 1-796;
 amino acid residues 23-796;
 amino acid residues 28-796;
 amino acid residues 133-796; and
 amino acid residues 733-796; and and a C-terminal sequence is selected from the group consisting of SEQ ID NO:11; SEQ ID NO:12; SEQ ID NO:13; SEQ ID NO:14; and SEQ ID NO:15, wherein the numbering is based on the amino acid sequence of the full length transcribed murine leptin receptor, including the signal peptide, or allelic variants thereof.

In a specific embodiment, the leptin receptor is a soluble receptor. Such a soluble receptor may be selected from the group consisting of OB-Re; an N-terminal sequence which selected from the group consisting of OB-Ra, OB-Rb, OB-Rd, and OB-R from $Pro^{664}$ to $His^{796}$, and a C-terminal sequence which is OB-Re from $His^{796}$; and OB-R from $Met^{733}$ to $His^{796}$, and a C-terminal sequence which is OB-Re from $His^{796}$; an N-terminal sequence which is selected from the group consisting of
 amino acid residues 1-796;
 amino acid residues 23-796;
 amino acid residues 28-796;
 amino acid residues 133-796; and
 amino acid residues 733-796; and a C-terminal sequence which is SEQ ID NO:15; wherein the numbering is based on the amino acid sequence of the full length transcribed murine leptin receptor, including the signal peptide, or allelic variants thereof. In a specific embodiment, soluble OB-R is produced in a recombinant baculovirus expression system.

The foregoing embodiments include those in which the N-terminus or C-terminus, or both, include non-naturally occurring amino acid residues, such as heterogeneous signal peptides or signal peptide cleavage site residues. For example, in specific embodiments, the present invention provides the following soluble forms of OB-R:

```
Asp-Pro-Ile28 → Phe-Tyr-Ile-His796-
Gly-Met-Cys-Thr-Val-Leu-Phe-Met-
Asp805 (SEQ ID NO: 15);

Asp-Arg-Trp-Gly-Ser-Tyr420
(SEQ ID NO: 77) → Pro641;

Asp-Arg-Trp-Gly-Ser-Ser118
(SEQ ID NO: 78) → Pro641;

Asp-Arg-Trp-Gly-Ser-Leu123
(SEQ ID NO: 79) → Val331.
```

The present invention further contemplates various mutations and substitutions. For example, highly divergent amino acid residues from one species (e.g., mouse) can be substituted for the corresponding residue in another species (e.g., human) to yield a biologically or functionally active leptin receptor, or fragment thereof. Alternatively, certain structural or putative structural residues may be substituted with residues that increase or decrease that structural propensity. In a specific embodiment, infra, cysteine residues or cystine pairs may be substituted with serine (or another comparable amino acid residue, such as threonine, methionine, alanine, etc.) to delete disulfide bonds. In a specific embodiment, infra, one or more of Cys 188 and 193, 471 and 602, 471 and 526, and 602 and 611 are mutated to Ser, thus yielding a protein that does not form disulfides. Such substitutions may avoid formation of incorrect disulfide crosslinks during expression in a genetically engineered system, and are also preferred for crystallization.

Alternatively, the leptin receptor comprises a transmembrane domain, and is an integral membrane protein. In this embodiment, the leptin receptor may further comprise a JAK binding motif selected from "Box 1," "Box 2," and "Box 1" and "Box 2", which motif is downstream of the transmembrane domain.

In one specific embodiment, the leptin receptor is a human leptin receptor. In another specific embodiment, exemplified infra, the leptin receptor is a murine leptin receptor. In a further specific embodiment, the leptin receptor is a human leptin receptor comprising a divergent amino acid substitution from the corresponding position of the murine leptin receptor. In another embodiment, the leptin receptor is a human leptin receptor comprising conservative amino acid substitutions. In a specific embodiment, conservative amino acid substitutions from murine leptin receptor are made in human leptin receptor. In yet another embodiment, conservative amino acid substitutions that enhance secondary structure, e.g., α-helical propensity, are made.

The present invention further provides an antigenic fragment of the leptin receptor. In a specific embodiment, the antigenic fragment is selected from the group consisting of SEQ ID NO:32, SEQ ID NO:33, and SEQ ID NO:34.

The invention further relates to a derivative of the soluble form of the leptin receptor attached to a chemical moiety. Preferably, the chemical moiety is a water-soluble polymer. More preferably, the water soluble polymer is polyethylene glycol.

In another aspect, the invention provides an isolated nucleic acid encoding the leptin receptor, particularly as set forth above. In specific examples, infra, the invention provides cDNA encoding various splice forms of murine leptin receptor. In particular, the present invention provides nucleic acids having sequences corresponding or complementary to SEQ ID NO:1, 3, 5, 7, or 9.

More particularly, the invention provides an isolated DNA molecule encoding on expression a leptin receptor polypeptide selected from the group consisting of:

a polypeptide coding sequence of a DNA molecule of SEQ ID NO:1, 3, 5, 7, or 9;

a DNA molecule complementary to the DNA molecule defined in (a);

a DNA molecule which hybridizes to the DNA molecule of (a) or (b), or a hybridizable fragment thereof;

a DNA molecule which is identifiable with a polymerase chain reaction (PCR) probe selected from group consisting of a probe for clone 7 (forward primer SEQ ID NO:42 and reverse primer SEQ ID NO:43), a probe for clone 11 (forward primer SEQ ID NO:44 and reverse primer SEQ ID NO:45), and both clone 7 and clone 11; and a DNA molecule that codes on expression for the polypeptide encoded by any of the foregoing DNA molecules.

Preferably the DNA molecule is human. In specific Examples, infra, the DNA molecule is murine. In specific embodiments, the DNA molecule codes on expression for a polypeptide selected from the group consisting of a leptin receptor selected from the group consisting of OB-Ra, OB-Rb, OB-Rc, OB-Rd, and OB-Re, or allelic variants thereof; a leptin receptor selected from the group consisting of:

N-terminal corresponding to OB-Ra through $Lys^{889}$ and C-terminal corresponding to a C-terminal selected from the group consisting of OB-Rb, OB-Rc, and OB-Rd after $Lys^{889}$;

N-terminal corresponding to OB-Rb or OB-Rc through $Lys^{889}$, and C-terminal corresponding to OB-Ra or OB-Rd after $Lys^{889}$;

N-terminal corresponding to OB-Rd through $Lys^{889}$, and C-terminal corresponding to OB-Ra, OB-Rb, or OB-Rc;

N-terminal corresponding to OB-R from $Pro^{664}$ to $Lys^{889}$, and C-terminal corresponding to OB-Ra, OB-Rb, OB-Rc, and OB-Rd; and N-terminal corresponding to OB-R from $Met^{733}$ to $Lys^{889}$, and C-terminal corresponding to OB-Ra, OB-Rb, OB-Rc, and OB-Rd; and N-terminal selected from the group consisting of OB-Ra, OB-Rb, OB-Rd, and OB-R from $Pro^{664}$ to $His^{796}$, and OB-Re from $His^{796}$;

N-terminal selected from the group consisting of OB-Ra, OB-Rb, OB-Rd, and OB-R from $Met^{733}$ to $His^{796}$, and OB-Re from $His^{796}$, or allelic variants thereof;

a leptin receptor wherein the N-terminal sequence is selected from the group consisting of amino acid residues 1-889;

amino acid residues 23-889;

amino acid residues 28-889;

amino acid residues 133-889;

amino acid residues 733-889;

amino acid residues 1-796;

amino acid residues 23-796;

amino acid residues 28-796;

amino acid residues 133-796; and
amino acid residues 733-796;

and the C-terminal sequence is selected from the group consisting of SEQ ID NO:11; SEQ ID NO:12; SEQ ID NO:13; SEQ ID NO:14; and SEQ ID NO:15 (after His796), wherein the numbering is based on the amino acid sequence of the full length transcribed murine leptin receptor, including the signal peptide, or allelic variants thereof.

In a further embodiment, the present invention provides an isolated nucleic acid, in particular a DNA molecule, encoding on expression a soluble leptin receptor in which the N-terminus or C-terminus, or both, include non-naturally occurring amino acid residues, such as heterogeneous signal peptides or signal peptide cleavage site residues. For example, in specific embodiments, the present invention provides DNA encoding the following soluble forms of OB-R:

Asp-Pro-Ile28 → Phe-Tyr- (SEQ ID NO: 15)
Ile-His796-Gly-Met-Cys-
Thr-Val-Leu-Phe-Met-
Asp805;

Asp-Arg-Trp-Gly-Ser-    (SEQ ID NO: 77) → Pro641;
Tyr420

Asp-Arg-Trp-Gly-Ser-    (SEQ ID NO: 78) → Pro641;
Ser118

Asp-Arg-Trp-Gly-Ser-    (SEQ ID NO: 79) → Val331.
Leu123

The present invention further contemplates DNA encoding leptin receptor having the various mutations and substitutions discussed above. For example, cysteine residues or cystine pairs may be substituted with serine (or threonine, methionine, or alanine) to delete disulfide bonds. In a specific embodiment, infra, the present invention provides DNA molecules encoding soluble OB-R in which one or more of Cys 188 and 193, 471 and 602, 471 and 526, and 602 and 611 are mutated to Ser, thus yielding a protein that does not form disulfides.

The invention further contemplates, as a corollary to the coding nucleic acids described above, an oligonucleotide hybridizable under stringent conditions to the nucleic acid molecule, in particular, DNA molecule, encoding leptin receptor. In specific embodiments, exemplified infra, the oligonucleotide is selected from the group consisting of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, and SEQ ID NO:54. The oligonucleotide may be labeled.

In addition to the coding DNA, the present invention provides vectors comprising such DNA. A vector of the invention may be a cloning vector, or it may be an expression vector, which comprises the DNA encoding leptin receptor operatively associated with an expression control sequence. Naturally, the invention extends to an unicellular host transformed or transfected with a DNA molecule, cloning vector, or expression vector of the invention. Such a unicellular host may be selected from the group consisting of bacteria, yeast, mammalian cells, plant cells, and insect cells, in tissue culture. In specific embodiments, the host may be selected from the group consisting of *E. coli, Pseudomonas, Bacillus, Streptomyces, Saccharomyces, Pichia, Candida, Hansenula, Torulopsis*, CHO, R1.1, B-W, LM, COS 1, COS 7, BSC1, BSC40, BMT10, and Sf9 cells.

The invention further relates to a recombinant method for preparing a leptin receptor polypeptide comprising culturing a host cell comprising an expression vector of the invention under conditions that provide for expression of the leptin receptor polypeptide; and recovering the expressed polypeptide.

The invention further provides an antisense nucleic acid that hybridizes with an mRNA encoding leptin receptor, and a ribozyme which cleaves an mRNA encoding a leptin receptor.

In another embodiment, the invention provides a transgenic vector comprising a DNA molecule encoding leptin receptor, or an expression vector of the invention.

In another aspect, the invention provides an antibody specific for a leptin receptor. The antibody may be a monoclonal or polyclonal antibody. Such antibodies include antibodies generated to antigenic fragments of the leptin receptor, including synthetic polypeptide fragments of about 10 to 30 amino acid residues. In a specific embodiment, the antibody may be labeled with a detectable label. Naturally, the invention extends to an immortal cell line that produces a monoclonal antibody.

In a specific embodiment, the invention provides a method for preparing an antibody specific for a leptin receptor, comprising: immunizing a host animal with the leptin receptor or an immunogenic fragment thereof admixed with an adjuvant; and obtaining antibody from the immunized host animal. In another specific embodiment, exemplified infra, the method for preparing an antibody specific for a leptin receptor comprises conjugating a peptide having a sequence selected from the group consisting of SEQ ID NO:32, SEQ ID NO:33, and SEQ ID NO:34 to a carrier protein; immunizing a host animal with the peptide-carrier protein conjugate of step (a) admixed with an adjuvant; and obtaining antibody from the immunized host animal.

In conjunction with the antibodies of the invention, the invention provides a method for measuring the presence of a leptin receptor in a sample, comprising contacting a sample suspected of containing a leptin receptor with an antibody that specifically binds to the leptin receptor under conditions which allow for the formation of reaction complexes comprising the antibody and the leptin receptor; and detecting the formation of reaction complexes comprising the antibody and leptin receptor in the sample, wherein detection of the formation of reaction complexes indicates the presence of leptin receptor in the sample. In a specific embodiment, the antibody is bound to a solid phase support. As a corollary to the method of measuring the presence of leptin receptor in a sample, the invention provides an in vitro method for evaluating the level of leptin receptor in a biological sample comprising detecting the formation of reaction complexes in a biological sample as described; and evaluating the amount of reaction complexes formed, which amount of reaction complexes corresponds to the level of leptin receptor in the biological sample. The invention further relates to an in vitro method for detecting or diagnosing the presence of a disease associated with elevated or decreased levels of leptin receptor in a subject comprising evaluating the level of leptin receptor in a biological sample from a subject as described; and comparing the level detected in step (a) to a level of leptin receptor present in normal subjects or in the subject at an earlier time, wherein an increase in the level of leptin receptor as compared to normal levels indicates a disease associated with elevated levels of leptin receptor, and decreased level of leptin receptor as compared to normal levels indicates a disease associated with decreased levels of leptin receptor.

The present invention also provides a pharmaceutical composition comprising a soluble leptin receptor, and a pharmaceutically acceptable carrier. Alternatively, a pharmaceutical composition of the invention may comprise a transgenic vector, e.g., a viral vector or naked DNA, for administration to a subject for gene therapy. Preferably, such a vector is targeted to the brain, more preferably the hypothalamus. The invention further provides a method for treating obesity in a subject comprising administering a therapeutically effective amount of the pharmaceutical composition of the invention. The method of treatment may further comprise administering a treatment for diabetes, high blood pressure, and high cholesterol.

In another embodiment, the invention provides a body appearance improving cosmetic composition for reducing the body weight of an individual comprising a soluble leptin receptor, and an acceptable carrier. The invention further provides a method for improving the body appearance of an individual comprising administering the cosmetic composition of the invention.

Accordingly, it is a principal object of the present invention to provide modulators of body weight as defined herein in purified form, that exhibit certain characteristics and activities associated with control and variation of adiposity and fat content of mammals.

It is a further object of the present invention to provide methods for the detection and measurement of the modulators of weight control as set forth herein, as a means of the effective diagnosis and monitoring of pathological conditions wherein the variation in level of such modulators is or may be a characterizing feature.

It is a still further object of the present invention to provide a method and associated assay system for the screening of substances, such as drugs, agents and the like, that are potentially effective to either mimic or inhibit the activity of leptin binding to its receptor, e.g., agonists and antagonists of the modulators of the invention in mammals.

It is a still further object of the present invention to provide a method for the treatment of mammals to control body weight and fat content in mammals, and/or to treat certain of the pathological conditions of which abnormal depression or elevation of body weight is a characterizing feature.

It is a still further object of the present invention to prepare genetic constructs for use in genetic therapeutic protocols and/or pharmaceutical compositions for comparable therapeutic methods, which comprise or are based upon one or more of the modulators, binding partners, or agents that may control their production, or that may mimic or antagonize their activities.

Other objects and advantages will become apparent to those skilled in the art from a review of the ensuing description which proceeds with reference to the following illustrative drawings.

DETAILED DESCRIPTION OF THE INVENTION

Figure 1:
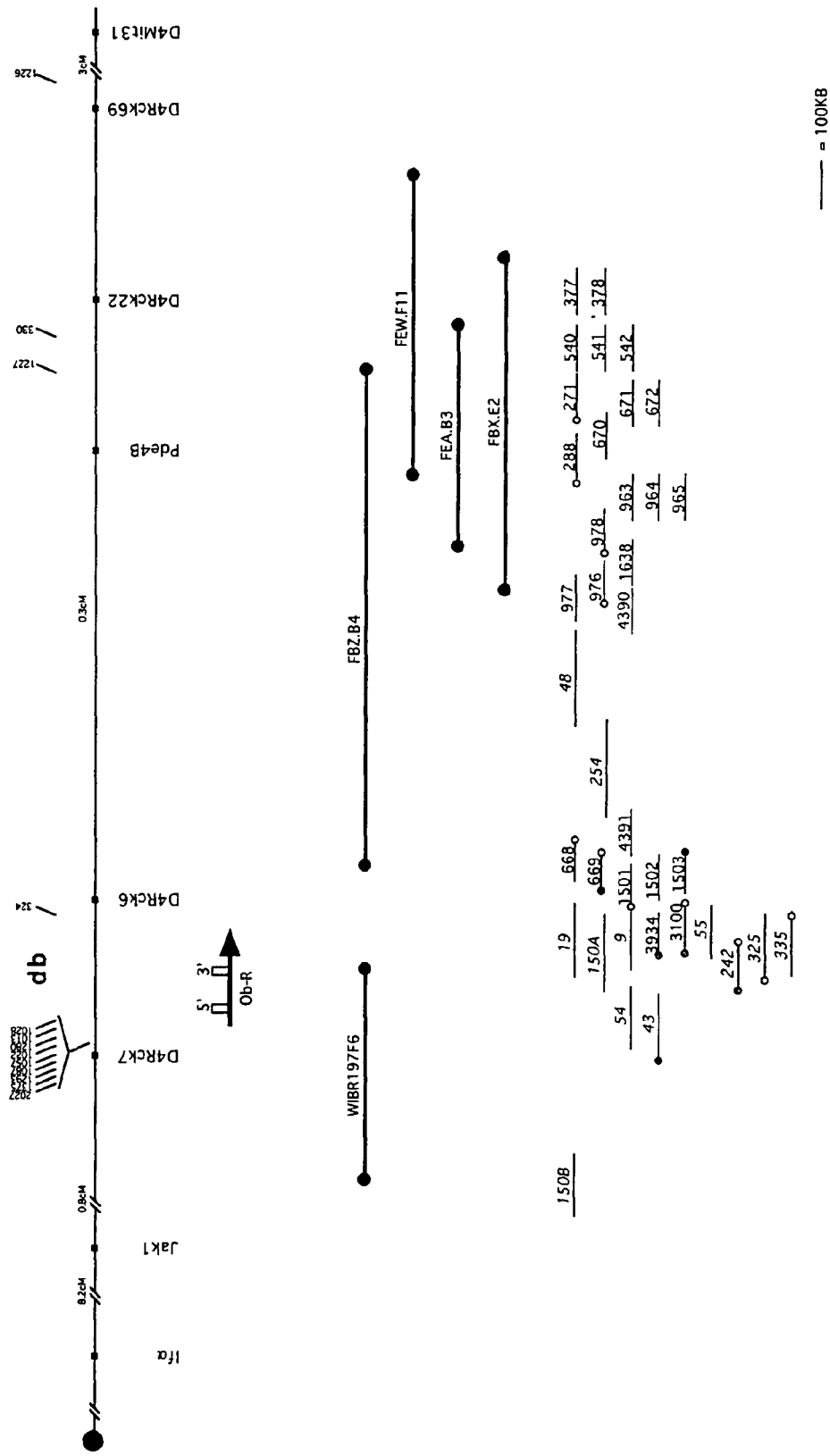
FIG. 1. Localization of the leptin receptor to the region of the db gene. The db mutation was segregated in two crosses totaling 750 meioses. A genetic map was compiled by genotyping the progeny of these crosses with the markers indicated in the map. Key recombinant animals are noted on the map as numbers above the line. A chromosome walk was initiated with the microdissection clone D4Rck22. The walk spanned 2.7 megabases and was composed of YACs (bold lines), BACs (italics) and P1 bacteriophage (numbers). Genotyping of the recombinant animals with two SSLP markers, D4Rck6 and D4Rck7 from the ends of these genomic clones, localized the db gene to the approximately 300 Kb interval between the recombination events in animals 324 and 1028. This interval was spanned by BACs 242 and 43. Southern blots and PCR revealed that the 5' ends of the leptin receptor mapped to BAC 150A and the 3' end to BAC 19, indicating the gene is transcribed toward the telomeres.

The present invention relates to the elucidation and discovery of a protein, termed herein OB receptor (OB-R) or leptin receptor, nucleic acids encoding the protein, including the OB-R gene (also termed herein DB—it should be noted that where all capitals are used it refers to the natural protein or gene; all lower case refers to a mutant protein or gene; italics indicates a gene or nucleic acid molecule; and normal type indicates a protein or polypeptide), including degenerate variations thereof, e.g., that incorporate optimal codons for expression in a particular expression system, which protein demonstrates the ability to participate in the control of mammalian body weight. In particular, the protein demonstrates the ability to bind leptin. In a specific embodiment, the protein mediates signal transduction upon binding to leptin.

The OB receptor of the invention may contain three important structural domains: an extracellular (or extracytoplasmic) domain, a transmembrane domain, and a cytoplasmic domain. The extracellular domain is postulated to bind leptin, leptin-protein complexes (such as leptin bound to a soluble leptin receptor), and may possibly bind other proteins or ligands. Indeed, as shown herein, the extracytoplasmic domain binds leptin with very high affinity, and includes two leptin-binding sites. In a specific embodiment, a receptor of the invention comprises only an extracellular domain, i.e., it is a soluble receptor. The transmembrane domain comprises a stretch of highly non-polar amino acid residues that localize to the hydrophobic region of the cell membrane. In this respect, the term transmembrane domain has its ordinary meaning in molecular and cellular biology. Finally, the cytoplasmic domain of an OB receptor of the invention may contain none, one, or two JAK-binding consensus sequences, termed "Box 1" and "Box 2". A receptor having "Box 1" and "Box 2" is believed competent for signal transduction via the JAK-Stat pathway upon bind ligand, e.g., leptin.

Furthermore, the protein has been identified as having numerous splice-forms. In one aspect, the splice variations lead to divergence of the C-terminal sequences. Thus, the protein can be found in a secreted form postulated to agonize leptin activity; it can be found as an integral membrane receptor that may facilitate leptin transfer across the blood-brain barrier, but that lacks domains involved in signal transduction; and it can be found as a integral membrane receptor containing domains involved in signal transduction. In another aspect, splice variations lead to divergence of the N-terminal polypeptide sequence.

The nucleic acids in object represent the coding sequences corresponding to the animal, specifically murine and human OB-R polypeptide, which, by mediating (or failing to mediate) signal transduction on binding leptin, is postulated to play a critical role in the regulation of body weight and adiposity. Data presented herein indicate that one splice variant of the polypeptide product of a nucleic acid of the invention may be secreted by the cells that express it, or it may be expressed as an integral membrane protein. In either event, the polypeptide functions as a leptin receptor by binding to leptin. Additional experimental data suggest that the naturally occurring splice-from of the OB-R polypeptide is very effective in treating obesity in mice carrying a mutation of the ob gene.

In addition, the Examples herein demonstrate that mRNA encoding the OB-R polypeptide, alternatively termed herein "leptin receptor," is expressed in hypothalamus, testes, and adipocytes. Data also demonstrate expression of the protein in the choroid plexus.

In a further aspect, the OB-R polypeptide from one species is closely related (homologous) to the OB-R in another species. In particular, the human OB-R polypeptide is highly homologous to murine OB-R polypeptide. This observation is consistent with the data showing that human leptin is active in mice: for the hormone to be active interspecies, one would expect a high degree of similarity or homology between the receptors from different species as well.

In its primary aspect, the present invention is directed to the identification of materials that function as modulators of mammalian body weight. In particular, the invention concerns the isolation, purification, and sequencing of certain nucleic acids that correspond to the OB-R gene (alternatively referred to herein and in the literature as DB) or its coding region in both mice and humans, as well as the corresponding polypeptides expressed by these nucleic acids. The invention thus comprises the discovery of nucleic acids having the nucleotide sequences set forth in SEQ ID NOS:1, 3, 5, 7, and 9 and to degenerate variants, alleles and fragments thereof, all possessing the activity of modulating body weight and adiposity. The correspondence of the present nucleic acids to the OB-R gene portends their significant impact on conditions such as obesity as well as other maladies and dysfunctions where abnormalities in body weight are a contributory factor. The invention extends to the proteins expressed by the nucleic acids of the invention, and particularly to those proteins set forth in SEQ ID NOS:2, 4, 6, 8, and 10, as well as to conserved variants and active fragments.

Of particular interest according to the invention are different splice variants of OB-R, e.g., as represented by OB-Ra, OB-Rb, OB-Rc, OB-Rd, and OB-Re. The present invention anticipates other OB-R splice variants as well.

Thus, in specific embodiments, the term OB-R refers to splice variants as follows (amino acid numbering correspond to the numbering applied to murine OB-R [Tartaglia et al., Cell, 83:1263 (1995)], which has been adopted herein):

N-terminal corresponding to OB-Ra through $Lys^{889}$ and C-terminal corresponding to a C-terminal selected from the group consisting of OB-Rb, OB-Rc, and OB-Rd after $Lys^{889}$;

N-terminal corresponding to OB-Rb or OB-Rc through $Lys^{889}$, and C-terminal corresponding to OB-Ra or OB-Rd after $Lys^{889}$;

N-terminal corresponding to OB-Rd through $Lys^{889}$, and C-terminal corresponding to OB-Ra, OB-Rb, or OB-Rc;

N-terminal corresponding to OB-R from $Pro^{664}$ to $Lys^{889}$, and C-terminal corresponding to OB-Ra, OB-Rb, OB-Rc, and OB-Rd;

N-terminal corresponding to OB-R from $Met^{733}$ to $Lys^{889}$, and C-terminal corresponding to OB-Ra, OB-Rb, OB-Rc, and OB-Rd;

N-terminal selected from the group consisting of OB-Ra, OB-Rb, OB-Rd, and OB-R from $Pro^{664}$, to $His^{796}$, and OB-Re from $His^{796}$; and N-terminal corresponding to OB-R from $Met^{733}$ to $His^{796}$, and OB-Re from $His^{796}$.

Various forms of the OB-R, which may act as agonists (e.g., the naturally occurring secreted form of the OB-R) or antagonists (e.g., a truncated form of OB-R that only binds leptin), may be prepared in pharmaceutical compositions, with a suitable carrier and at a strength effective for administration by various means to a patient experiencing abnormal fluctuations in body weight or adiposity, either alone or as part of an adverse medical condition such as cancer or AIDS, for the treatment thereof. A variety of administrative techniques may be utilized, among them oral administration, nasal and other forms of transmucosal administration, parenteral techniques such as subcutaneous, intravenous and intraperitoneal injections, catheterizations and the like. Appropriate quantities of the soluble OB-R molecules may vary and in particular should be based upon the recommendations and prescription of a qualified physician or veterinarian.

In accordance with the above, an assay system for screening potential drugs effective to mimic or antagonize the activity of leptin may be prepared. The prospective drug may be contacted with a soluble form of the OB-R, or alternatively may be used with cells that express a receptor form of OB-R, to determine whether it binds to, or activates (or antagonizes) OB-R. For example, in an expression assay system, the culture may be examined to observe any changes in the activity of the cells, due either to the addition of the prospective drug alone, or due to the effect of added quantities of the known weight modulator leptin.

As stated earlier, the molecular cloning of the OB-R gene described herein has led to the identification of a class of materials that function on the molecular level to modulate mammalian body weight. The discovery of the modulators of the invention has important implications for the diagnosis and treatment of nutritional disorders including, but not limited to, obesity, weight loss associated with cancer and the treatment of diseases associated with obesity such as hypertension, heart disease, and Type II diabetes. In addition, there are potential agricultural uses for the gene product in cases where one might wish to modulate the body weight of animals. The discussion that follows with specific reference to the OB-R gene bears general applicability to the class of modulators that comprise a part of the present invention, and is therefore to be accorded such latitude and scope of interpretation.

In a particular embodiment, the functional activity of the OB-R polypeptide can be evaluated transgenically. The OB-R gene can be used in complementation studies employing transgenic mice. Transgenic vectors, including viral vectors, or cosmid clones (or phage clones) corresponding to the wild type locus of candidate gene, can be constructed using the isolated OB-R gene. Cosmids may be introduced into transgenic mice using published procedures [Jaenisch, Science, 240:1468-1474 (1988)]. The constructs are introduced into fertilized eggs derived from an intercross between F1 progeny of a C57BL/6J db/db X DBA intercross. Genotype at the db loci in cosmid transgenic animals can be determined by typing animals with tightly linked RFLPs or microsatellites which flank the mutation and which are polymorphic between the progenitor strains. Complementation will be demonstrated when a particular construct renders a genetically obese F2 animal (as scored by RFLP analysis) lean and non-diabetic. Under these circumstances, final proof of complementation will require that the db/db animal carrying the transgene be mated to the db/db ovarian transplants. In this cross, all N2 animals which do not carry the transgene will be obese and insulin resistant/diabetic, while those that do carry the transgene will be lean and have normal glucose and insulin concentrations in plasma. In a genetic sense, the transgene acts as a suppressor mutation.

Alternatively, OB-R genes can be tested by examining their phenotypic effects when expressed in antisense orientation in wild-type animals. In this approach, expression of the wild-type allele is suppressed, which leads to a mutant phenotype. RNA•RNA duplex formation (antisense-sense) prevents normal handling of mRNA, resulting in partial or complete elimination of wild-type gene effect. This technique has been used to inhibit TK synthesis in tissue culture and to produce phenotypes of the Kruppel mutation in Drosophila, and the Shiverer mutation in mice [Izant et al., Cell, 36:1007-1015 (1984); Green et al., Annu. Rev. Biochem., 55:569-597 (1986); Katsuki et al., Science, 241:593-595 (1988)]. An important advantage of this approach is that only a small portion of the gene need be expressed for effective inhibition of expression of the entire cognate mRNA. The antisense transgene will be placed under control of its own promoter or another promoter expressed in the correct cell type, and placed upstream of the SV40 poly A site. This transgene can be used to make transgenic mice. Transgenic mice can also be mated ovarian transplants to test whether ob heterozygotes are more sensitive to the effects of the antisense construct.

In the long term, the OB-R gene product (the OB-R polypeptide or protein) is useful for identifying small molecule agonists and antagonists that affect its activity.

Various terms used throughout this specification shall have the definitions set out herein, for example, below.

The term "body weight modulator", "modulator", "modulators", and any variants not specifically listed, may be used herein interchangeably, and as used throughout the present application and claims refers in one instance to both nucleotides and to proteinaceous material, the latter including both single or multiple proteins. More specifically, the aforementioned terms extend to the nucleotides and to the DNA having the sequences described herein and presented in SEQ ID NOS:1, 3, 5, 7, and 9. Likewise, the proteins having the amino acid sequence data described herein and presented in SEQ ID NOS:2, 4, 6, 8, and 10 are likewise contemplated, as are the profile of activities set forth with respect to all materials both herein and in the claims.

Specific binding to leptin means that leptin is a ligand for OB-R, as that term is used to describe ligand-receptor binding. Generally, such binding will have an affinity represented by an association constant of greater than $1 \times 10^7 M^{-1}$, preferably greater than $1 \times 10^8 M^{-1}$, and more preferably greater than $1 \times 10^9 M^{-1}$. However, the exact association constant may vary.

Homology with gp130 refers to conservation of residues, particularly cysteine residues, motifs, and other important residues. The term "gp130" is used herein to refer generally to the class I cytokine receptor family, particularly interleukin-6 (IL-6) receptor, granulocyte colony-stimulating factor (G-CSF) receptor, ciliary neurotrophic factor (CNTF) receptor, and leukemia inhibitory factor (LIF) receptor.

Additionally, nucleotides displaying substantially equivalent or altered activity are likewise contemplated, including substantially similar analogs and allelic variations. Likewise, proteins displaying substantially equivalent or altered activity, including proteins modified deliberately, as for example, by site-directed mutagenesis, or accidentally through mutations in hosts that produce the modulators are likewise contemplated.

The term "allelic variants" refers to the corresponding gene in different individuals that may have point mutations. For example, the various ob mutation represent allelic variants of OB-R.

The term "homologues" or "homologs", in all of its grammatical forms, specifically includes the corresponding gene or protein from another species. In a specific embodiment, a homolog of murine OB-R is human OB-R. The term can also include genes or proteins mutated or altered, e.g., by substitution of variant amino acid residues from one species in the polypeptide of another, so as to correspond to an analogous gene or protein as if from another species. As is well known in the art, homologous genes can readily be identified by sequence similarity, hybridization with probes specific for the gene in another species, detection by PCR analysis using primers for a different species, or mapping to a syntenic location of the chromosome, to mention but a few such methods. Protein homology can be detected by antibody cross reactivity, similar protease digestion profile, comparable molecular weight and isoelectric points, and similar secondary or tertiary structure, to mention some of the well known tests for homologous proteins.

The term "substantially similar" as used herein with respect to nucleic acid or amino acid sequences means at least 50% sequence similarity, preferably at least 60% sequence similarity, more preferably at least 70% sequence similarity, even more preferably at least 80% sequence similarity, and most preferably at least 90% sequence similarity.

The term "gene" as used herein refers to a nucleic acid, such as DNA, which codes on expression for a protein. Unless stated otherwise, gene may include mRNA, cDNA, or genomic DNA.

A composition comprising "A" (where "A" is a single protein, DNA molecule, vector, recombinant host cell, etc.) is substantially free of "B" (where "B" comprises one or more contaminating proteins, DNA molecules, vectors, etc., but excluding racemic forms of A) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

A "BAC" is a bacterial artificial chromosome; "STS" refers to sequence tagged site; a "YAC" is a yeast artificial chromosome. Other terms have the standard meanings ordinarily intended in the art.

The OB-R Polypeptides

The terms "protein," which refers to the naturally occurring polypeptide, and "polypeptide" are used herein interchangeably with respect to the OB-R gene product and variants thereof. More particularly, OB-R refers to any of the splice forms of the OB-R (DB) gene product, such as but not limited to the product with two JAK binding boxes in the cytoplasmic domain; the product with only one JAK binding box in the cytoplasmic domain; the product with no boxes; and the secreted (soluble) product. The term OB-R also refers to various splice-forms with divergent N-terminal amino acid sequences.

The term OB-R specifically encompasses different splice forms of the polypeptide, including but not limited to the follows:

| Splice Form | Characteristics | Specific Embodiment |
|---|---|---|
| OB-Ra | Transmembrane protein with a "Box 1" but no "Box 2"; expected to bind leptin but does not directly mediate signal transduction via JAKs. Comprised of an extracellular domain, and a truncated cytoplasmic domain. N-terminus diverges from published OB-R sequence upstream of $Cys^{88}$. | SEQ ID NO: 2 |
| OB-Rb | Transmembrane protein expected to mediate leptin signalling in hypothalamus and other cells. contains a larger cytoplasmic domain containing both a "Box 1 and "Box 2" sites. N-terminal portion appears to be truncated, diverging from the published OB-R sequence upstream of $Pro^{664}$. | SEQ ID NO: 4 |
| OB-Rc | Corresponds to OB-Rb with a tripeptide residue C-terminal to $Lys^{889}$ rather than the longer sequence; no "Box 2" site. | SEQ ID NO: 6 |
| OB-Rd | Corresponds to published OB-R with a different eleven amino acid sequence C-terminal to $Lys^{889}$. | SEQ ID NO: 8 |
| OB-Re | Soluble/secreted receptor with a leptin-binding domain. Lacks a transmembrane or cytoplasmic domain, but comprises a large extracellular domain. Corresponds to published OB-R to $His^{796}$, where it diverges. | SEQ ID NO: 10 |

The term OB-R specifically contemplates splice variants that incorporate different elements from the above-noted variants, e.g., as described above.

More particularly, the present invention is directed to OB-R with the N-terminal signal sequence cleaved. In one embodiment, amino acid residues 1-22 are cleaved. In another embodiment, amino acid residues 1-27 are cleaved.

As noted above, in specific embodiments polypeptides of the invention include those having the amino acid sequences set forth herein e.g., SEQ ID NOS:2, 4, 6, 8, and 10. The term further includes polypeptides modified with conservative amino acid substitutions, as well as biologically active fragments, analogs, and derivatives thereof. In yet another embodiment, the term includes polypeptides in which one or more cysteine residues or cystine pairs are replaced with serine, or a similar polar or neutral amino acid residue such as, but not necessarily limited to, threonine, methionine, or alanine.

The term "biologically active," is used herein to refer to a specific effect of the polypeptide, including but not limited to specific binding, e.g., to leptin, an anti-OB-R antibody, or other recognition molecule; activation of signal transduction pathways on a molecular level; and/or induction (or inhibition by antagonists) of physiological effects mediated by the native leptin in vivo. OB-R polypeptides, including fragments, analogs, and derivatives, can be prepared synthetically, e.g., using the well known techniques of solid phase or solution phase peptide synthesis. Preferably, solid phase synthetic techniques are employed. Alternatively, OB-R polypeptides of the invention can be prepared using well known genetic engineering techniques, as described infra. In yet another embodiment, the soluble form of the OB-R polypeptide can be purified, e.g., by immunoaffinity purification, from a biological fluid, such as but not limited to plasma, serum, or urine, preferably human plasma, serum, or urine, and more preferably from a subject who overexpresses the polypeptide.

The structure of the OB-R polypeptide, preferably human OB-R polypeptide, can be analyzed by various methods known in the art. The protein sequence can be characterized by a hydrophilicity analysis [e.g., Hopp et al., *Proc. Natl. Acad. Sci. USA*, 78:3824 (1981)]. A hydrophilicity profile can be used to identify the hydrophobic and hydrophilic regions of the OB-R polypeptide, which may indicate regions buried in the interior of the folded polypeptide, the transmembrane domain, and regions accessible on the exterior of the polypeptide. In addition, secondary structural analysis [e.g., Chou et al, *Biochem.*, 13:222 (1974)] can also be done, to identify regions of OB-R polypeptide that assume specific secondary structures. Manipulation of the predicted or determined structure, including secondary structure prediction, can be accomplished using computer software programs available in the art.

By providing an abundant source of recombinant OB-R polypeptide, the present invention enables quantitative structural determination of the polypeptide. In particular, enough material is provided for nuclear magnetic resonance (NMR), infrared (IR), Raman, and ultraviolet (UV), especially circular dichroism (CD), spectroscopic analysis. In particular NMR provides very powerful structural analysis of molecules in solution, which more closely approximates their native environment [Marion et al., *Biochim. Biophys. Res. Comm.*, 113:967-974 (1983); Bar et al., *J. Magn. Reson.*, 65:355-360 (1985); Kimura et al., *Proc. Natl. Acad. Sci. USA*, 77:1681-1685 (1980)]. Other methods of structural analysis can also be employed. These include but are not limited to X-ray crystallography [Engstom, *Biochem. Exp. Biol.*, 11:7-13 (1974)]. In a preferred aspect, either soluble form or a membrane-binding form of OB-R is co-crystallized with leptin to provide structural information about both molecules. In a more preferred embodiment, OB-R or soluble OB-R lacking one or more cystine crosslinks is used to form crystals or co-crystals with leptin.

In yet a further embodiment, an analog of OB-R polypeptide can be tested to determine whether it cross-reacts with an antibody specific for native OB-R polypeptide, or specific fragments thereof. The degree of cross-reactivity provides information about structural homology or similarity of proteins, or about the accessibility of regions corresponding to portions of the polypeptide that were used to generate fragment-specific antibodies.

Fragments of the OB-R Polypeptide

In a particular embodiment, the present invention contemplates that naturally occurring fragments, or truncated forms, of the OB-R polypeptide may be important. As noted above, a large number of splice forms of OB-R have been found. Thus, the present invention encompasses a naturally occurring soluble form of the OB-R, as well as integral membrane forms that have 0, 1, or 2 JAK box consensus sites. In addition to the naturally occurring splice isoforms of the polypeptide, the present invention further envisions recombinantly modified isoforms, e.g, by deletion of one or more of the cytoplasmic domain; the cytoplasmic consensus domain from the transmembrane domain to lysine-889; the box 1 or box two, or both regions; they cytoplasmic domain C-terminal of lysine-889; the transmembrane domain; the ligand binding domain; the extracytoplasmic domain; or portions thereof.

The present invention specifically contemplates soluble truncated forms of OB-R lacking a transmembrane domain and a cytoplasmic domain. In a specific embodiment, the OB-R fragment is OB-Re. In a still further embodiments, an OB-R fragment of the invention corresponds to the N-terminal portion of OB-Re that binds leptin, e.g., OB-R from about Leu123 to about Val331; the C-terminal portion of OB-Re that binds leptin, e.g., OB-R from about Tyr420 to about Pro641; the a protein having the N and C-terminal portion of OB-Re that binds leptin with very high affinity, e.g., OB-R from about Ser118 or Leu123 to about Pro641.

OB-R Polypeptide Chimeras

One or more of the splice-forms of the cytoplasmic domain can be used in a chimeric construct with another ligand-binding domain to artificially signal leptin binding [e.g., Capon et al., U.S. Pat. No. 5,359,046, issued Oct. 25, 1994; Sanchez et al., *J. Exp. Med.*, 178:1049 (1993); Burkhardt et al., *Mol. Cell. Biol.*, 14:1095; International Patent Publications WO 96/23814, WO 96/23881, and WO 96/24671; Kotenko et al., *J. Biol. Chem.* 271:17174 (1996)]. In another embodiment, the extracytoplasmic (leptin-binding) domain can be joined to a different cytoplasmic signal transduction domain, or alternatively to a glycosyl-phosphalidylinositol linker domain to provide for activation of cells via gp130.

Analogs of the OB-R Polypeptide

The present invention specifically contemplates preparation of analogs of the OB-R polypeptide, which are characterized by being capable of a biological activity of OB-R polypeptide, e.g., of binding to leptin or to an anti-OB-R antibody. In one embodiment, the analog agonizes OB-R activity. Preferably, an OB-R agonist is more effective than the native protein. For example, an OB-R agonist analog may bind to leptin with higher affinity, thus amplifying the signal. Such an analog may be particularly desirable for gene therapy, where increased signal transduction efficiency can compensate for any deficiency in the level of receptor expression. In another embodiment, the analog antagonizes OB-R activity. For example, an OB-R analog that binds to leptin, and inhibits leptin binding to signal-transduction competent OB-R, can competitively inhibit binding of native OB to the receptor, thus decreasing leptin activity in vivo. Such an OB-R antagonist analog is preferably a soluble form of the OB-R.

In one embodiment, an analog of OB-R polypeptide is the OB-R polypeptide modified by substitution of amino acids at positions on the polypeptide that are not essential for structure or function. For example, since it is expected that human OB-R polypeptide is biologically active in mouse, substitution of divergent amino acid residues in the human sequence as compared to the murine amino acid sequence will likely yield useful analogs of OB-R polypeptide. For example, the following residues in the human OB-R [numbering for human OB-R amino acids employs the numbering convention adopted in Tartaglia et al., *Cell*, 83:1263 (1995)] could be substituted with a divergent murine residue found at that position, or with a non-conservative amino acid substitution, such as one or more of: Phe for $Ser^{36}$; Asp for $Tyr^{44}$; Ser for $Leu^{49}$; Pro for $Ser^{54}$; Leu for $Ser^{60}$; Ala for $His^{63}$; Ala for $Thr^{66}$; Ala for $Pro^{70}$; Ile for $Thr^{77}$; Tyr for $His^{78}$; Pro for $Ser^{80}$; Gly for $Arg^{92}$; Gly for $Asp^{96}$; Thr for $Ala^{103}$ or $Ile^{106}$; Ser for $Leu^{118}$; Gly for $Asp^{124}$; Thr for $Lys^{138}$; Pro for $Ser^{146}$; Asp for $Val^{164}$; Leu for $Gln^{177}$; Asp for $Gly^{179}$; Gly for $Glu^{192}$; deletion for $Cys^{193}$; His for $Leu^{197}$; Ser for $Ile^{221}$; Leu for $Asn^{273}$; Leu for $Ser^{273}$; deletion for $Thr^{278}$; Ala for $Asp^{285}$; Glu for $Lys^{286}$; Ser for $Gly^{310}$; Arg for $Met^{370}$; Ile for $Ser^{379}$; Ser for $Phe^{394}$; Ala for $Glu^{417}$; Gly for $Glu^{459}$; Ser for $Ile^{476}$; Thr for $Ile^{476}$; Thr for $Ile^{551}$; His for $Tyr^{586}$; Lys for $Ile^{648}$; Ala for $Ser^{686}$; His for $Cys^{687}$; Thr for $Ile^{759}$; Ile for $Asn^{776}$; Asp for $Gly^{781}$; Gly for $Glu^{782}$; Gly for $Ser^{827}$; Ala for $Asp^{832}$; Arg for $Pro^{892}$; Thr for $Glu^{893}$; Asp for $Thr^{894}$; or Leu for $Glu^{896}$.

Also contemplated by the present invention are analogs comprising conservative amino acid substitutions. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. In some instances, one polar amino acid may be substituted with another to preserve local hydrophilicity; more likely, a substitution that conserves charge, or at least does not introduce the opposite charge, is required. Such alterations will not be expected to affect apparent molecular weight as determined by polyacrylamide gel electrophoresis, or isoelectric point.

In still another embodiment, amino acid residues can be substituted with residues to form analogs of OB-R polypeptide that demonstrate enhanced propensity for forming, or which form more stable, secondary structures. For example, α-helix structure would be preferred if Glu, Ala, Leu, His, Trp are introduced as substitutes for amino acid residues found in the native OB polypeptide. Preferably, conservative amino acid substitutions are employed, e.g., substituting aspartic acid with glutamic acid(s) (Glu); substituting isoleucine(s) with leucine; substituting glycine or valine, or any divergent amino acid (i.e., an amino acid that is not conserved between OB-R from different species), with alanine (e.g., serine at position 273 of the human OB-R polypeptide with alanine); substituting arginine or lysine with histidine; and substituting tyrosine and/or phenylalanine with tryptophan. Increasing the degree, or more importantly, the stability of α-helix structure may yield an OB-R analog with greater activity, increased binding affinity, or longer half-life. Also contemplated are truncated OB-R polypeptide analogs that incorporate structure-forming, e.g., helix-forming, amino acid residues to compensate for the greater propensity of polypeptide fragments to lack stable structure.

In another embodiment, an analog of the OB-R polypeptide, preferably the human OB-R polypeptide, is a truncated form of the polypeptide. For example, it has already been demonstrated that the transmembrane domain is not essential, since a naturally occurring isoform of the polypeptide is encoded by cDNA that expresses a soluble protein. Similarly, it may be possible to delete some or all of the divergent amino acid residues in human OB-R (as compared to the murine OB-R). In addition, the invention contemplates providing an OB-R analog having the minimum amino acid sequence necessary for a biological activity. This can be readily determined, e.g., by testing the activity of fragments of OB-R for the ability to bind to OB-R-specific antibodies, inhibit the activity of the native leptin (by competitive binding), or agonize the activity of native leptin.

The present invention specifically contemplates providing a soluble splice-form of the OB-R that is believed to agonize leptin activity. In particular, it is believed that OB-Rd (as referred to herein) binds leptin, and facilitates leptin binding to OB-Rb (which is believed to be competent for signal transduction). Thus, in this embodiment, OB-R appears to behave analogously to other receptor systems [Kishimoto et al., *Cell*, 76:253 (1994); Davis et al., *Science*, 260:1805 (1993); Davis et al., *Science*, 259:1736 (1993)].

It will be appreciated by one of ordinary skill in the art that the foregoing fragment sizes are approximate, and that additional amino acids e.g. from one to about five, can be included or deleted from each or both ends, or from the interior of the polypeptide or fragments thereof, of the recited truncated analogs.

Analogs, such as fragments, may be produced, for example, by digestion of the OB-R, e.g., with trypsin, chymotrypsin, pepsin, papain, thrombolytic proteases, carboxypeptidase A, proteinase-K, etc. Other analogs, such as muteins, can be produced by standard site-directed mutagenesis of weight modulator peptide coding sequences.

Screening for Leptin Analogs

Various screening techniques are known in the art for screening for analogs of polypeptides. Various libraries of chemicals are available. Accordingly, the present invention contemplates screening such libraries, e.g., libraries of synthetic compounds generated over years of research, libraries of natural compounds, and combinatorial libraries, as described in greater detail, infra, for analogs of leptin. The invention contemplates screening such libraries for compounds that bind to OB-R, either in soluble or transmembrane forms. Preferably, such molecules agonize or antagonize signal transduction by OB-R. Thus, the present invention contemplates screens for small molecule ligands or ligand analogs and mimics, as well as screens for natural ligands that bind to and agonize or antagonize activate OB receptor in vivo.

Knowledge of the primary sequence of the receptor, and the similarity of that sequence with proteins of known function, can provide an initial clue as to the agonists or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott et al., *Science*, 249:386-390 (1990); Cwirla et al., *Proc. Natl. Acad. Sci. USA*, 87:6378-6382 (1990); Devlin et al., *Science*, 249: 404-406 (1990)], very large libraries can be constructed ($10^6$-$10^8$ chemical entities). A second approach uses primarily chemical methods, of which the Geysen method [Geysen et al., *Molecular Immunology*, 23:709-715 (1986); Geysen et al., *J. Immunologic Method*, 102:259-274 (1987)] and the recent method of Fodor et al., *Science*, 251:767-773 (1991) are examples. Other references [Furka et al. 14th International Congress of Biochemistry, Volume 5, Abstract FR:013 (1988); Furka, *Int. J. Peptide Protein Res.*, 37:487-493 (1991); Houghton (U.S. Pat. No. 4,631,211, issued December 1986); and Rutter et al. (U.S. Pat. No. 5,010,175, issued Apr. 23, 1991)] describe methods to produce a mixture of peptides that can be tested as agonists or antagonists.

In another aspect, synthetic libraries [Needels et al., *Proc. Natl. Acad. Sci. USA*, 90:10700-10704 (1993); Lam et al., International Patent Publication No. WO 92/00252; Kocis et al., International Patent Publication No. WO 94/28028, each of which is incorporated herein by reference in its entirety], and the like can be used to screen for OB receptor ligands according to the present invention.

In particular, assays for binding of soluble ligand to cells that express recombinant forms of the OB receptor ligand binding domain can be performed. The soluble ligands can be provided readily as recombinant or synthetic leptin polypeptide.

The screening can be performed with recombinant cells that express the OB receptor, or alternatively, using purified receptor protein, e.g., produced recombinantly, as described above. For example, the ability of labeled, soluble, or solubilized OB receptor, that includes the ligand-binding portion of the molecule, to bind ligand can be used to screen libraries, as described in the foregoing references.

Derivatives of OB Polypeptides

Generally, a soluble form of the present polypeptide may be derivatized by the attachment of one or more chemical moieties to the polypeptide moiety. The chemically modified derivatives may be further formulated for intraarterial, intraperitoneal, intramuscular, subcutaneous, intravenous, oral, nasal, rectal, buccal, sublingual, pulmonary, topical, transdermal, or other routes of administration. Chemical modification of biologically active proteins has been found to provide additional advantages under certain circumstances, such as increasing the stability and circulation time of the therapeutic protein and decreasing immunogenicity [see U.S. Pat. No. 4,179,337, Davis et al., issued Dec. 18, 1979; for a review, see Abuchowski et al., "Soluble Polymer-Enzyme Adducts", in *Enzymes as Drugs*, pp. 367-383, Holcenberg and Roberts, eds., Wiley-Interscience, New York, N.Y., (1981)]. A review article describing protein modification and fusion proteins is Francis, *Focus on Growth Factors*, 3:4-10 (1992).

Chemical Moieties For Derivatization

The chemical moieties suitable for derivatization may be selected from among various polymers, in particular water soluble polymers. The polymer selected is preferably water soluble so that the protein to which it is attached does not precipitate in an aqueous environment, such as a physiological environment. However, apolar polymers can also be used where a particular application benefits from their use, e.g., in a controlled release matrix in which accessibility of water is restricted. Preferably, for therapeutic use of the end-product preparation, the polymer will be pharmaceutically acceptable. One skilled in the art will be able to select the desired polymer based on such considerations as whether the polymer/protein conjugate will be used therapeutically, and if so, the desired dosage, circulation time, resistance to proteolysis, and other considerations. For the present proteins and peptides, these may be ascertained using the assays provided herein.

Polymer Molecules

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols and polyvinyl alcohol. Polyethylene glycol propionaldenhyde may provide advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Polymer/Protein Ratio

The number of polypeptide molecules attached to each polymer may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

Attachment of the Chemical Moiety to the Protein

The polyethylene glycol molecules (or other chemical moieties) should be attached to the protein with consideration of effects on functional or antigenic domains of the protein. There are a number of attachment methods available to those skilled in the art, e.g., EP 0 401 384 herein incorporated by reference (coupling PEG to G-CSF). See also Malik et al., *Exp. Hematol.*, 20:1028-1035 (1992) (reporting pegylation of GM-CSF using tresyl chloride). For example, polyethylene glycol may be covalently bound through amino acid residues via a reactive group, such as a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecule(s). Preferred for therapeutic purposes is attachment at an amino group, such as attachment at the N-terminus or lysine group. Attachment at residues important for receptor binding should be avoided if receptor binding is desired.

N-Terminally Chemically Modified Proteins

One may specifically desire N-terminally chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the $pK_a$ differences between the $\epsilon$-amino groups of the lysine residues and that of the $\alpha$-amino group of the N-terminal residue of the protein. By such selective derivatization attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

Nucleic Acids Associated With OB-R Polypeptide

As noted above, the present invention is directed to nucleic acids encoding OB-R polypeptides, as well as associated genomic non-coding sequences 5', 3', and intronic to the OB-R gene. Thus, in accordance with the present invention there may be employed conventional molecular biology, microbiology, and recombinant DNA techniques within the skill of the art. Such techniques are explained fully in the literature [see, e.g., Sambrook et al., *Molecular Cloning: A Laboratory Manual*, Second Edition, Cold Spring Harbor Laboratory Press, Cold Spring Harbor, N.Y. (1989); Glover ed., *DNA Cloning: A Practical Approach*, Volumes I and II, MRL Press, Ltd., Oxford, U.K. (1985); Gait ed., *Oligonucleotide Synthesis*, Oxford University Press (1984); Hames et al., eds., *Nucleic Acid Hybridization*, Springer-Verlag (1985); Hames et al., eds. *Transcription And Translation*, Oxford University Press (1984); Freshney ed., *Animal Cell Culture*, Oxford University Press (1986); *Immobilized Cells And Enzymes*, IRL Press (1986); Perbal, *A Practical Guide To Molecular Cloning*, Wiley, New York (1984)]. Of particular relevance to the present invention are strategies for isolating, cloning, sequencing, analyzing, and characterizing a gene or nucleic acid based on the well known polymerase chain reaction (PCR) techniques.

A "replicon" is any genetic element (e.g., plasmid, chromosome, virus) that functions as an autonomous unit of DNA replication in vivo, i.e., capable of replication under its own control.

A "vector" is a replicon, such as a plasmid, phage or cosmid, to which another DNA segment may be attached so as to bring about the replication of the attached segment.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

"Heterologous" DNA refers to DNA not naturally located in the cell, or in a chromosomal site of the cell. Preferably, the heterologous DNA includes a gene foreign to the cell.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single-stranded form, or a double-stranded helix. Double-stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single-stranded form of the nucleic acid molecule can anneal to the other nucleic acid molecule under the appropriate conditions of temperature and solution ionic strength (see Sambrook et al., 1989, supra). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., 1989, supra, 9.50-0.51). For hybridization with shorter nucleic acids, i.e., oligonucleotides, the position of mismatches becomes more important, and the length of the oligonucleotide determines its specificity (see Sambrook et al., 1989, supra, 11.7-11.8). Preferably a minimum length for a hybridizable nucleic acid is at least about 10 nucleotides; more preferably at least about 15 nucleotides; most preferably the length is at least about 20 nucleotides.

In a specific embodiment, the term "standard hybridization conditions" refers to a Tm of 55° C., using conditions as set forth above. In a preferred embodiment, the Tm is 60° C.; in a more preferred embodiment, the Tm is 60° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Isolation of OB-R Coding and Flanking Sequences

The nucleic acids contemplated by the present invention include nucleic acids that code on expression for peptides such as those set forth in SEQ ID NOS:2, 4, 6, 8, and 10. Accordingly, while specific DNA has been isolated and sequenced in relation to the OB-R gene, any animal cell potentially can serve as the nucleic acid source for the molecular cloning of a gene encoding the polypeptides of the invention. The DNA may be obtained by standard procedures known in the art from cloned DNA (e.g., a DNA "library"), by chemical synthesis, by cDNA cloning, or by the cloning of genomic DNA, or fragments thereof, purified from the desired cell [see, for example, Sambrook et al., 1989, supra; Glover, 1985, supra]. Clones derived from genomic DNA may contain regulatory and intronic DNA regions in addition to coding regions; clones derived from cDNA will not contain intron sequences. Whatever the source, the gene should be molecularly cloned into a suitable vector for propagation of the gene.

In the molecular cloning of the gene from genomic DNA, the genomic DNA can be amplified using primers selected from the cDNA sequences. Alternatively, DNA fragments are generated, some of which will encode the desired gene. The DNA may be cleaved at specific sites using various restriction enzymes. One may also use DNase in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired OB-R-gene may be accomplished in a number of ways. For example, if an amount of a portion of a OB-R-gene or its specific RNA, or a fragment thereof, is available and can be purified and labeled, the generated DNA fragments may be screened by nucleic acid hybridization to a labeled probe [Benton et al., Science, 196:180 (1977); Grunstein et al., Proc. Natl. Acad. Sci. USA, 72:3961 (1975)]. The present invention provides such nucleic acid probes, which can be conveniently prepared from the specific sequences disclosed herein, e.g., a hybridizable probe having a nucleotide sequence corresponding to at least a 10, preferably a 15, and more preferably at least a 20 nucleotide fragment of the sequences depicted in SEQ ID NOS:1, 3, 5, 7, and 9. Preferably, a fragment is selected that is highly unique to the nucleic acids of the invention. Those DNA fragments with substantial sequence similarity to the probe, e.g., a homologous DNA, will hybridize. As noted above, the greater the degree of sequence similarity, the more stringent the hybridization conditions that can be used. In one embodiment, low stringency hybridization conditions are used to identify a homologous leptin receptor nucleic acid. However, in a preferred aspect, and as demonstrated experimentally herein, a nucleic acid encoding a polypeptide of the invention will hybridize to a nucleic acid having a nucleotide sequence such as depicted in (SEQ ID NOS:1, 3, 5, 7, and 9), or a hybridizable fragment thereof, under moderately stringent conditions; more preferably, it will hybridize under high stringency conditions.

In another specific embodiment, the DNA of the invention can be identified using one of the PCR probes obtained by exon trapping and cDNA selection. For example, the primer pairs described in Example 3 can be used to will amplify a DNA of the invention.

Preferably, these primers will amplify DNA under moderately to high stringency conditions, e.g., using pre-hybridization at 65° using Rapid-hyb buffer (Amersham Life Sciences), followed by hybridization for 6 hours at 65°, followed by washing first with 2×SSC/0.1% SDS for 30 min at room temperature (RT), and a second wash at higher stringency with 0.3×SSC/0.1% SDS, RT, for 30 min. As will be appreciated by those of skill in the art, the stringency of the second wash is flexible and depends on the length of the probe and the degree of sequence similarity of each probe. For example, since human and mouse coding regions are about 78% homologous, the same hybridization conditions may be employed with a lower the stringency second wash (e.g., twice with 2×SSC/0.1% SDS, RT). If this results in no signal with no-background, hybridization can be attempted at a lower temperature (lower stringency), e.g., 42° C. If there is too much background, the stringency of the second wash can be increased, (e.g., 0.5 or 0.3×SSC, 0.1% SDS, RT). According to the invention, the above-noted PCR probes will define a nucleic acid molecule, e.g., DNA, encoding OB-R from human as well as murine DNA libraries under similar hybridization conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, leptin binding activity, or antigenic properties as known for the present OB-R. For example, antibodies of the instant invention can conveniently be used to screen for homologs of OB-R from other sources. Preferably, proteins from candidate genes are tested for leptin binding.

A gene encoding a polypeptide of the invention can also be identified by mRNA selection, i.e., by nucleic acid hybridization followed by in vitro translation. In this procedure, fragments are used to isolate complementary mRNAs by hybridization. Such DNA fragments may represent available, purified modulator DNA. Immunoprecipitation analysis or functional assays (e.g., leptin binding activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against a modulator peptide.

A radiolabeled modulator peptide cDNA can be synthesized using the selected mRNA (from the adsorbed polysomes) as a template. The radiolabeled mRNA or cDNA may then be used as a probe to identify homologous modulator peptide DNA fragments from among other genomic DNA fragments.

As mentioned above, a DNA sequence encoding weight modulator peptides as disclosed herein can be prepared synthetically rather than cloned. The DNA sequence can be designed with the appropriate codons for the OB-R amino acid sequences. In general, one will select preferred codons for the intended host if the sequence will be used for expression. The complete sequence may be assembled from overlapping oligonucleotides prepared by standard methods and assembled into a complete coding sequence [see, e.g., Edge, *Nature*, 292:756 (1981); Nambair et al., *Science*, 223:1299 (1984); Jay et al., *J. Biol. Chem.*, 259:6311 (1984)].

Synthetic DNA sequences allow convenient construction of genes that will express OB-R analogs, as described above. Alternatively, DNA encoding analogs can be made by site-directed mutagenesis of native OB-R genes or cDNAs, and analogs can be made directly using conventional polypeptide synthesis.

A general method for site-specific incorporation of unnatural amino acids into proteins is described in Noren et al, *Science*, 244:182-188 (1989). This method may be used to create analogs of the OB-R polypeptide with unnatural amino acids.

Due to the degeneracy of nucleotide coding sequences, other DNA sequences which encode substantially the same amino acid sequence as a OB-R gene may be used in the practice of the present invention. These include but are not limited to allelic genes, homologous genes from other species, and nucleotide sequences comprising all or portions of OB-R genes which are altered by the substitution of different codons that encode the same amino acid residue within the sequence, thus producing a silent change. Likewise, the OB-R derivatives of the invention include, but are not limited to, those containing, as a primary amino acid sequence, all or part of the amino acid sequence of a OB-R protein including altered sequences in which functionally equivalent amino acid residues are substituted for residues within the sequence resulting in a conservative amino acid substitution, as described above in connection with OB-R analogs.

Non-Coding Nucleic Acids

The present invention extends to the preparation of antisense nucleotides and ribozymes that may be used to interfere with the expression of the proteins at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [See Weintraub, *Sci. Am.*, 262:40-46 (1990); Marcus-Sekura, *Anal. Biochem.*, 172:289-295 (1988)]. In the cell, they hybridize to that mRNA, forming a double-stranded molecule. The cell does not translate an mRNA complexed in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into weight modulator peptide-producing cells. Antisense methods have been used to inhibit the expression of many genes in vitro [(Marcus-Sekura, 1988 supra; Hambor et al., *J. Exp. Med.*, 168:1237-1245 (1988)].

Ribozymes are RNA molecules possessing the ability to specifically cleave other single-stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it [Cech, *J. Am. Med. Assoc.*, 260:3030-3034 (1988)]. Because ribozymes are sequence-specific, only mRNAs with particular sequences are inactivated.

Investigators have identified two types of ribozymes, *Tetrahymena*-type and "hammerhead"-type. *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species, and eighteen base recognition sequences are preferable to shorter recognition sequences.

The DNA sequences described herein may thus be used to prepare antisense molecules against and ribozymes that cleave mRNAs for weight modulator proteins and their ligands, thus inhibiting expression of the OB-R gene, and leading to increased weight gain and adiposity.

In another embodiment, short oligonucleotides complementary to the coding and complementary strands of the OB-R nucleic acid, or to non-coding regions of the OB-R gene 5', 3', or internal (intronic) to the coding region are provided by the present invention. Such nucleic acids are useful as probes, either as directly labeled oligonucleotide probes, or as primers for the polymerase chain reaction, for evaluating the presence of mutations in the ob-r gene, or the level of expression of OB-R mRNA. Preferably, the non-coding nucleic acids of the invention are from the human OB-R gene.

In a specific embodiment, the non-coding nucleic acids provide for homologous recombination for integration of an amplifiable gene and/or other regulatory sequences in proximity to the OB-R gene, e.g., to provide for higher levels of expression of the OB-R polypeptide, or to overcome a mutation in the ob-r gene regulatory sequences that prevent proper levels of expression of the OB-R polypeptide [See International Patent Publication WO 91/06666, published May 16, 1991 by Skoultchi; International Patent Publication No. WO 91/09955, published Jul. 11, 1991 by Chappel; see also International Patent Publication No. WO 90/14092, published Nov. 29, 1990, by Kucherlapati and Campbell].

Production of OB-R Polypeptide: Expression and Synthesis

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is also used herein to refer to this sort of signal sequence. Translocation signal sequences can be found associated with a variety of proteins native to eukaryotes and prokaryotes, and are often functional in both types of organisms. According to the present invention, amino acid residues 1-27 of the murine and human OB-R polypeptides (see SEQ ID NOS:8, 10) comprise the signal peptide. In another embodiment, amino acid residues 1-22 comprise the signal peptide [Tartaglia et al., Cell, 83:1263 (1995)].

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted upstream (5') of and in reading frame with the gene.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal, and synthetic DNA sequences. Suitable vectors include derivatives of SV40 and known bacterial plasmids, e.g., E. coli plasmids col E1, pCR1, pBR322, pMB9, pUC or pUC plasmid derivatives, e.g., pGEX vectors, pET vectors, pma1-c, pFLAG, etc., and their derivatives, plasmids such as RP4; phage DNAs, e.g., the numerous derivatives of phage λ, such as NM989, and other phage DNA, e.g., M13 and filamentous single-stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the AOX 1 promoter of methylotrophic yeast, the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces; fungi such as yeasts (Saccharomyces, and methylotrophic yeast such as Pichia, Candida, Hansenula, and Torulopsis); and animal cells, such as CHO, R1.1, B-W and LM cells, African Green Monkey kidney cells (e.g., COS 1, COS 7, BSC1, BSC40, and BMT10), insect cells (e.g., Sf9), and human cells and plant cells in tissue culture. Particularly preferred is expression in baculovirus with an insect signal peptide replacing the OB-R signal peptide, for example, in vector pMelBac (Invitrogen; Catalog No. V1950-20).

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors, a person skilled in the art will be able to construct a variety of vector/expression control sequence/host combinations that will express the DNA sequences of this invention on fermentation or in large scale animal culture.

In a specific embodiment, an OB-R fusion protein can be expressed. An OB-R fusion protein comprises at least a functionally active portion of a non-OB-R protein joined via a peptide bond to at least a functionally active portion of an OB polypeptide. The non-OB-R sequences can be amino- or carboxy-terminal to the OB-R sequences. For example, in preparing "artificial" receptors, joining the OB-R encoding coding domain for the leptin binding (extracytoplasmic) portion at the 5' position will yield a protein that binds leptin and mediates some other action based on the non-OB-R protein's activity. Conversely, joining a different protein (such as a growth factor, cytokine, or hormone receptor binding coding domain) 5' to a OB-R cytoplasmic coding domain (containing "Box 1" and "Box 2") will allow for activation via OB-R upon binding a different ligand than leptin. In another embodiment, a chimeric construct may simply facilitate expression of OB-R. In a specific embodiment, infra, OB-Re and fragments thereof are expressed with an N-terminal melittin signal peptide.

In another aspect, the pGEX vector [Smith et al., Gene 67:31-40 (1988)] can be used. This vector fuses the schistosoma japonicum glutathionine S-transferase cDNA to the sequence of interest. Bacterial proteins are harvested and recombinant proteins can be quickly purified on a reduced glutathione affinity column. The GST carrier can subsequently be cleaved from fusion proteins by digestion with site-specific proteases. After cleavage, the carrier and uncleaved fusion protein can be removed by absorption on glutathione agarose. Difficulty with the system occasionally arises when the encoded protein is insoluble in aqueous solutions.

Expression of recombinant proteins in bacterial systems may result in incorrect folding of the expressed protein, requiring refolding. The recombinant protein can be refolded prior to or after cleavage to form a functionally active OB polypeptide. The OB polypeptide may be refolded by the steps of (i) incubating the protein in a denaturing buffer that contains a reducing agent, and then (ii) incubating the protein in a buffer that contains an oxidizing agent, and preferably also contains a protein stabilizing agent or a chaotropic agent, or both. Suitable redox (reducing/oxidizing) agent pairs include, but are not limited to, reduced glutathione/glutathione disulfide, cystine/cysteine, cystamine/cysteamine, and 2-mercaptoethanol/2-hydroxyethyldisulfide. In a particular aspect, the fusion protein can be solubilized in a denaturant, such as urea, prior to exchange into the reducing buffer. In preferred embodiment, the protein is also purified, e.g., by ion exchange or Ni-chelation chromatography, prior to exchange into the reducing buffer. Denaturing agents include but are not limited to urea and guanidine-HCl. The recombinant protein is then diluted about at least 10-fold, more preferably about 100-fold, into an oxidizing buffer that contains an oxidizing agent, such as but not limited to 0.1 M Tris-HCl, pH 8.0, 1 mM EDTA, 0.15 M NaCl, 0.3 M oxidized glutathione. The fusion protein is then incubated for about 1 to about 24 hours, preferably about 2 to about 16 hours, at room temperature in the oxidizing buffer. The oxidizing buffer may comprise a protein stabilizing agent, e.g., a sugar, an alcohol, or ammonium sulfate. The oxidizing buffer may further comprises a chaotropic agent at low concentration, to destabilize incorrect intermolecular interactions and thus promote proper folding. Suitable chaotropic agents include but are not limited to a detergent, a polyol, L-arginine, guanidine-HCl and polyethylene glycol (PEG). It is important to use a low enough concentration of the chaotropic agent to avoid denaturing the protein. The refolded protein can be concentrated by at least about 10-fold, more preferably by the amount it was diluted into the oxidizing buffer.

Alternatively, the invention contemplates periplasmic expression of a protein of the invention.

Bacterial fermentation processes can also result in a recombinant protein preparation that contains unacceptable levels of endotoxins. Therefore, the invention contemplates removal of such endotoxins, e.g., by using endotoxin-specific antibodies or other endotoxin binding molecules. The presence of endotoxins can be determined by standard techniques, such as by employing E-TOXATE Reagents (Sigma, St. Louis, Mo.), or with bioassays.

In addition to the specific example, the present inventors contemplate use of baculovirus, mammalian, and yeast expression systems to express the ob protein. For example, in baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen (195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)). In a specific embodiment, infra, the pMel Bac expression vector (Invitrogen) is employed.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR [see Kaufman, *Current Protocols in Molecular Biology*, 16.12 (1991)]). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker, Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors [see, Kaufman, 1991, supra] for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express OB polypeptide. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

It is further intended that body weight modulator polypeptides and analogs may be prepared from nucleotide sequences derived within the scope of the present invention.

In addition to recombinant expression of OB-R polypeptide, the present invention envisions and fully enables preparation of OB-R polypeptide, or fragments thereof, using the well known and highly developed techniques of solid phase peptide synthesis. The invention contemplates using both the popular Boc and Fmoc, as well as other protecting group strategies, for preparing ob polypeptide or fragments thereof. Various techniques for refolding and oxidizing the cysteine side chains to form a disulfide bond are also well-known in the art.

Antibodies to the OB-R Polypeptide

According to the invention, OB-R polypeptide produced recombinantly or by chemical synthesis, and fragments or other derivatives or analogs thereof, including fusion proteins, may be used as an immunogen to generate antibodies that recognize the OB-R polypeptide. Such antibodies include but are not limited to polyclonal, monoclonal, chimeric, single chain, Fab fragments, and an Fab expression library.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, F(ab')$_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds antigen.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response [Hood et al., in *Immunology*, p. 384, Second Ed., Benjamin/Cummings, Menlo Park, Calif. (1984)]. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Various procedures known in the art may be used for the production of polyclonal antibodies to OB-R polypeptide, or fragment, derivative or analog thereof. For the production of antibody, various host animals can be immunized by injection with the OB-R polypeptide, or a derivative (e.g., fragment or fusion protein) thereof, including but not limited to rabbits, mice, rats, sheep, goats, etc. In one embodiment, the OB-R polypeptide or fragment thereof can be conjugated to an immunogenic carrier, e.g., bovine serum albumin (BSA) or keyhole limpet hemocyanin (KLH). Specific OB-R antigenic fragments (SEQ ID NOS:32, 33, 34) are disclosed in Example 2, infra. In another embodiment, an antibody is generated to the C-terminal portion of the OB-Re form of OB-R, e.g., a polypeptide corresponding to about amino acid residues 420-641 of SEQ ID NO:10. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the OB-R polypeptide, or fragment, analog, or derivative thereof, any technique that provides for the production of antibody molecules by continuous cell lines in culture may be used. These include but are not limited to the hybridoma technique originally developed by Kohler et al., *Nature*, 256: 495-497 (1975), as well as the trioma technique, the human B-cell hybridoma technique [Kozbor et al., *Immunology Today*, 4:72 (1983)], and the EBV-hybridoma technique to produce human monoclonal antibodies [Cole et al., in *Monoclonal Antibodies and Cancer Therapy*, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus [see, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451, 570; 4,466,917; 4,472,500; 4,491,632; and 4,493,890].

In an additional embodiment of the invention, monoclonal antibodies can be produced in germ-free animals [International Patent Publication No. WO 89/12690, published 28 Dec. 1989]. According to the invention, human antibodies may be used and can be obtained by using human hybridomas [Cote et al., *Proc. Natl. Acad. Sci. USA*, 80:2026-2030 (1983)] or by transforming human B cells with EBV virus in vitro (Cole et al., 1985, supra). In fact, according to the invention, techniques developed for the production of "chimeric antibodies" [Morrison et al., *J. Bacteriol.*, 159-870 (1984); Neuberger et al., *Nature*, 312:604-608 (1984); Takeda et al., *Nature*, 314:452-454 (1985)] by splicing the genes from a mouse antibody molecule specific for an ob polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476, 786 and 5,132,405 to Huston; U.S. Pat. No. 4,946,778) can be adapted to produce OB-R polypeptide-specific single chain antibodies. An additional embodiment of the invention utilizes the techniques described for the construction of Fab expression libraries [Huse et al., *Science*, 246:1275-1281 (1989)] to allow rapid and easy identification of monoclonal Fab fragments with the desired specificity for an ob polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an OB polypeptide. one may assay generated hybridomas for a product which binds to an OB polypeptide fragment containing such epitope. For selection of an antibody specific to an OB polypeptide from a particular species of animal, one can select on the basis of positive binding with OB polypeptide expressed by or isolated from cells of that species of animal.

The foregoing antibodies can be used in methods known in the art relating to the localization and activity of the OB-R polypeptide, e.g., for Western blotting, imaging OB-R polypeptide in situ, measuring levels thereof in appropriate physiological samples, detecting expression of OB-R, etc.

In a specific embodiment, antibodies that agonize or antagonize the activity of OB-R polypeptide can be generated. Such antibodies can be tested using the assays described infra for identifying ligands.

In a particular aspect, antibodies are developed by immunizing rabbits with synthetic peptides predicted by the protein sequence or with recombinant proteins made using bacterial expression vectors. The choice of synthetic peptides is made after careful analysis of the predicted protein structure, as described above. In particular, peptide sequences between putative cleavage sites are chosen. Synthetic peptides are conjugated to a carrier such as KLH hemocyanin or BSA using carbodiimide and used in Freunds adjuvant to immunize rabbits. In order to prepare recombinant protein, the pGEX vector can be used to express the polypeptide [Smith et al., 1988, supra]. Alternatively, one can use only hydrophilic domains to generate the fusion protein. The expressed protein will be prepared in quantity and used to immunize rabbits in Freunds adjuvant.

In a specific embodiment, infra, peptides corresponding to amino acid residues 145-158, 465-484, 863-881, and 420-641 (from the murine OB-R polypeptide depicted in any one of SEQ ID NOS:8, 10) can be generated by solid phase peptide synthesis or by expression, optionally conjugated to a carrier such as KLH, and used to immunize rabbits, rats, goats, chickens, etc.

In another specific embodiment, recombinant OB-R polypeptide is used to immunize chickens, and the chicken anti-OB-R antibodies are recovered from egg yolk, e.g., by affinity purification on an OB-R-column. Preferably, chickens used in immunization are kept under specific pathogen free (SPF) conditions.

In yet another embodiment, recombinant OB-R polypeptide is used to immunize rabbits, and the polyclonal antibodies are immunopurified prior to further use. The purified antibodies are particularly useful for semi-quantitative assays, particularly for detecting the presence of the circulating (soluble) splice form(s) of OB-R polypeptide in serum or plasma.

Panels of monoclonal antibodies produced against modulator peptides can be screened for various properties; i.e., isotype, epitope, affinity, etc. Of particular interest are monoclonal antibodies that neutralize the activity of the modulator peptides. Such monoclonals can be readily identified in activity assays for the weight modulators. High affinity antibodies are also useful when immunoaffinity purification of native or recombinant polypeptide is desired.

Preferably, the anti-modulator antibody used in the diagnostic and therapeutic methods of this invention is an affinity-purified polyclonal antibody. More preferably, the antibody is a monoclonal antibody (mAb). In addition, it is preferable for the anti-modulator antibody molecules used herein be in the form of Fab, Fab', F(ab')$_2$ or F(v) portions of whole antibody molecules.

Diagnostics

The present invention also relates to a variety of diagnostic applications, including methods for detecting the presence of conditions and/or stimuli that impact upon abnormalities in body weight or adiposity, by reference to their ability to elicit the activities which are mediated by the present OB-R polypeptides. As mentioned earlier, the peptides can be used to produce antibodies to themselves by a variety of known techniques, and such antibodies could then be isolated and utilized as in tests for the presence of particular transcriptional activity in suspect target cells. Alternatively, the nucleic acids of the invention can be employed in diagnosis.

Antibody-Based Diagnostics

As suggested earlier, a diagnostic method useful in the present invention comprises examining a cellular sample or medium by means of an assay including an effective amount of an OB-R binding partner, such as an anti-modulator antibody or leptin, preferably an affinity-purified polyclonal antibody, and more preferably a mAb. In addition, it is preferable for the antibody molecules used herein be in the form of Fab, Fab', F(ab')$_2$ or F(v) portions or whole antibody molecules. As previously discussed, patients capable of benefiting from this method include those suffering from cancer, AIDS, obesity or other conditions where abnormal body weight is an element of the condition.

Also, antibodies including both polyclonal and monoclonal antibodies, may possess certain diagnostic applications and may for example, be utilized for the purpose of detecting and/or measuring conditions where abnormalities in body weight are or may be likely to develop.

The diagnostic methods can be used to detect OB-R in a biological sample from an individual. The biological sample can be a biological fluid, such as but not limited to, blood, serum, plasma, interstitial fluid, plural effusions, urine, cerebrospinal fluid, and the like. Preferably, soluble OB-R is detected in serum or urine, which are both readily obtained. Alternatively, OB-R can be detected from cellular sources, such as, but not limited to, brain tissue biopsies, adipocytes, testes, heart, and the like. For example, cells can be obtained from an individual by biopsy and lysed, e.g., by freeze-thaw cycling, or treatment with a mild cytolytic detergent such as, but not limited to, TRITON X-100® polyoxyethylene ester, digitonin, IGEPAL/NONIDET P (NP)-40® (octylphenoxy)-polyethoxyethanol, saponin, and the like, or combinations thereof (see, e.g., International Patent Publication WO 92/08981, published May 29, 1992). In yet another embodiment, samples containing both cells and body fluids can be used (see ibid.).

The presence of OB-R in cells or in a biological fluid can be ascertained by the usual immunological procedures applicable to such determinations. A number of useful procedures are known. Three such procedures which are especially useful utilize either the OB-R (particularly the secreted splice form) labeled with a detectable label, antibody Ab$_1$ labeled with a detectable label, or antibody Ab$_2$ labeled with a detectable label.

The procedures and their application are all familiar to those skilled in the art and accordingly may be utilized within the scope of the present invention. For example, a "competitive" procedure, is described in U.S. Pat. Nos. 3,654,090 and 3,850,752. A "sandwich" procedure, is described in U.S. Pat. Nos. RE 31,006 and 4,016,043. Still other procedures are known such as the "double antibody", or "DASP" procedure.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, and auramine. A particular detecting material is anti-rabbit antibody prepared in goats and conjugated with fluorescein through an isothiocyanate.

The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{99}$Tc, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, test kits suitable for use by a medical specialist may be prepared to determine the presence or absence of OB-R in suspected target cells or biological fluids. In accordance with the testing techniques discussed above, one class of such kits will contain at least the labeled OB-R polypeptide or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Nucleic Acid-Based Diagnostics

As demonstrated in the examples, infra, nucleic acids of the invention can be used to detect defects associated with defects in the OB-R polypeptide associated with an obese phenotypes. For example, nucleic acid probes (e.g., in Northern analysis or RT-PCR analysis) can be used to determine whether an obese phenotype is associated with lack of expression of OB-R mRNA, or expression of non-functional OB-R mRNA, e.g., as in db/db mice (where the deficiency results from lack of an effective leptin receptor), or where a mutation yields a non-transcribed mRNA. Moreover, the nucleic acid-based diagnostic techniques of the invention can be used in conjunction with antibody-based techniques to further develop a molecular understanding of obese or anorexic phenotypes.

Human cDNA clones may be sequenced. This facilitates the determination of the complete sequence of the human gene. DNA sequences from the introns of the human OB-R gene may thus be been obtained, and these can be used to prepare PCR primers to PCR amplify the coding sequence of the OB-R gene from human genomic DNA so as to identify mutations or allelic variants of the OB-R gene, all in accordance with protocols described in detail earlier herein.

The current hypothesis is that heterozygous mutations in the DB gene will be associated with mild/moderate obesity while homozygous mutations would be associated with severe obesity. This would allow the ascertainment of people at risk for the development of obesity and make possible the application of drug treatment and/or lifestyle changes before an increased body weight is fully developed.

Alternatively, the presence of microsatellites that segregate with mutant forms of human ob-r can be used for diagnosis. Various PCR primers, can be used in this respect.

The OB-R gene may also be useful diagnostically for measurements of its encoded RNA and protein in nutritional disorders. It will be of importance to know, in a particular nutritional disorder, whether OB-R RNA and/or its encoded protein is upregulated or downregulated. Thus, if an obese person has increased levels of OB-R, it would appear that the problem is downstream of OB-R, while if OB-R expression is reduced, it would appear that inappropriately low levels of OB-R may be cause of obesity (whether or not the defect is in the OB-R gene). Conversely, if a cancer or AIDS patient who lost weight had elevated levels of OB-R, it may be concluded that inappropriately high expression of OB-R is responsible for the weight loss.

The present invention is concerned with not only inappropriate levels of expression of OB-R, but also with expression of non-functional or dysfunctional splice forms. The nucleic acid diagnostics of the invention provide for determining whether the predominantly expressed form is dysfunctional, e.g., for signal transduction. As demonstrated in the Examples, infra, db mutant mice (C57BL/Ks db/db) express a longer OB-R mRNA (as determined by RT-PCR).

Therapeutics

The polypeptides, nucleic acids, and antibodies of the invention have significant therapeutic potential. Preferably, a therapeutically effective amount of such an agent (e.g., soluble form of the protein, or DNA for gene therapy, or an antisense nucleic acid for antagonizing leptin activity) is administered in a pharmaceutically acceptable carrier, diluent, or excipient.

The phrase "pharmaceutically acceptable" refers to molecular entities and compositions that are physiologically tolerable and do not typically produce an allergic or similarly untoward reaction, such as gastric upset, dizziness and the like, when administered to a human. In one embodiment, as used herein, the term "pharmaceutically acceptable" may mean approved by a regulatory agency of the federal or a state government or listed in the *U.S. Pharmacopeia* or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or solution saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa. (1990).

The phrase "therapeutically effective amount" is used herein to mean an amount sufficient to reduce by at least about 15%, preferably by at least 50%, more preferably by at least 90%, and most preferably prevent, a clinically significant deficit in the activity, function and response of the host. Alternatively, a therapeutically effective amount is sufficient to cause an improvement in a clinically significant condition in the host. Modulation of OB-R activity can be useful for reducing body weight (by increasing its activity) or increasing body weight (by decreasing its activity).

Administration of recombinant soluble OB-R polypeptide corresponding to OB-Re is expected to result in weight loss, in particular, a decrease in fat tissue. Soluble type OB-Re polypeptide can be prepared using standard bacterial and/or mammalian expression vectors, synthetically, or purified from plasma or serum, all as stated in detail earlier herein. Alternatively, increased expression of native soluble OB-R polypeptide may be induce by homologous recombination techniques, as described supra.

Reduction of leptin activity (by developing antagonists, inhibitors, use of neutralizing antibodies, or antisense molecules) should result in weight gain as might be desirable for the treatment of the weight loss associated with cancer, AIDS or anorexia nervosa. In one embodiment, a leptin-binding form of soluble OB-R that lacks portions necessary for signal transduction or enhancement can be employed.

Polypeptide-Based Therapeutic Treatment

In the simplest analysis, the OB-R gene is intimately associated with determination of body weight in animals, in particular, mice, rats, dogs, and man. The OB-R gene product, and, correspondingly, cognate molecules, appear to be part of a signaling pathway by which adipose tissue communicates with the brain and the other organs. It is believed that at least one splice form of the OB-R polypeptide (e.g., OB-Rb) is itself a signaling molecule, i.e., a receptor for the hormone leptin.

The soluble OB-R polypeptide, or functionally active fragment thereof, or an antagonist thereof, can be administered orally or parenterally, preferably parenterally. Because metabolic homeostasis is a continuous process, controlled release administration of soluble OB-R polypeptide (OB-Re) is preferred. For example, the polypeptide may be administered using intravenous infusion, an implantable osmotic pump, a transdermal patch, liposomes, or other modes of administration. In one embodiment, a pump may be used [Langer et al. eds., *Medical Applications of Controlled Release*, CRC Pres., Boca Raton, Fla. (1974); Sefton, *CRC Crit. Ref. Biomed. Eng.*, 14:201 (1987); Buchwald et al., *Surgery*, 88:507 (1980); Saudek et al., *N. Engl. J. Med.*, 321:574 (1989)]. In another embodiment, polymeric materials can be used [Langer, 1974, supra; Sefton, 1987, supra; Smolen et al., eds., *Controlled Drug Bioavailability, Drug Product Design and Performance*, Wiley, New York (1984); Ranger et al., *J. Macromol. Sci. Rev. Macromol. Chem.*, 23:61 (1983); see also Levy et al., *Science*, 228:190 (1985); During et al., *Ann. Neurol.*, 25:351 (1989); Howard et al., *J. Neurosurg.*, 71:105 (1989)]. In yet another embodiment, a controlled release system can be placed in proximity of the therapeutic target, i.e., the brain, thus requiring only a fraction of the systemic dose [see, e.g., Goodson, in *Medical Applications of Controlled Release*, vol. 2, pp. 115-138 (1984)]. Other controlled release systems are discussed in the review by Langer, *Science*, 249: 1527-1533 (1990). In another embodiment, the therapeutic compound can be delivered in a vesicle, in particular a liposome [see Langer, 1990 supra; Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid.].

In a further aspect, recombinant cells that have been transformed with the soluble splice form of the OB-R cDNA (e.g., OB-Re, which will be used herein to refer to a soluble OB-R agonist of leptin) and that express high levels of the polypeptide can be transplanted in a subject in need of enhancement of leptin activity. Preferably autologous cells transformed with OB-Re are transplanted to avoid rejection; alternatively, technology is available to shield non-autologous cells that produce soluble factors within a polymer matrix that prevents immune recognition and rejection.

The OB-Re polypeptide can be delivered by intravenous, intraarterial, intraperitoneal, intramuscular, or subcutaneous routes of administration. Alternatively, the OB-Re polypeptide, properly formulated, can be administered by nasal or oral administration. A constant supply of OB-Re can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

It can readily be appreciated by one of ordinary skill in the art that any soluble OB-R polypeptide, e.g., leptin antagonist, can also be administered as described above for OB-Re.

Pharmaceutical Compositions

In yet another aspect of the present invention, pharmaceutical compositions of the above are provided. Such pharmaceutical compositions may be for administration by injection, or for oral, pulmonary, nasal or other forms of administration. In general, comprehended by the invention are pharmaceutical compositions comprising effective amounts of protein or derivative products of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosal, benzyl alcohol) and bulking substances (e.g., lactose, mannitol); incorporation of the material into particulate preparations of polymeric compounds such as polylactic acid, polyglycolic acid, etc., or into liposomes. Hyaluronic acid or other anionic polymers may also be used. Such compositions may influence the physical state, stability, rate of in vivo release, and rate of in vivo clearance of the present proteins and derivatives [see, e.g., Martin, *Remington's Pharmaceutical Sciences*, 18th Ed. (1990, Mack Publishing Co., Easton, Pa. 18042) pages 1435-1712 which is herein incorporated by reference]. The compositions may be prepared in liquid form, or may be in dried powder, such as lyophilized form.

Oral Delivery

Contemplated for use herein are oral solid dosage forms, which are described generally in Martin, *Remington's Pharmaceutical Sciences*, 18th Ed. (1990 Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres [U.S. Pat. No. 4,925,673]). Liposomal encapsulation may be used and the liposomes may be derivatized with various polymers [e.g., U.S. Pat. No. 5,013,556]. A description of possible solid dosage forms for the therapeutic is given by Marshall, in *Modern Pharmaceutics*, Chapter 10, Banker and Rhodes ed., (1979), herein incorporated by reference. In general, the formulation will include the protein (or chemically modified protein), and inert ingredients which allow for protection against the stomach environment, and release of the biologically active material in the intestine.

Also specifically contemplated are oral dosage forms of the above derivatized proteins. Protein may be chemically modified so that oral delivery of the derivative is efficacious. Generally, the chemical modification contemplated is the attachment of at least one moiety to the protein (or peptide) molecule itself, where said moiety permits (a) inhibition of proteolysis; and (b) uptake into the blood stream from the stomach or intestine. Also desired is the increase in overall stability of the protein and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline [Abuchowski et al., 1981, supra; Newmark et al., *J. Appl. Biochem.*, 4:185-189 (1982)]. Other polymers that could be used are poly-1,3-dioxolane and poly-1,3,6-trioxocane. Preferred for pharmaceutical usage, as indicated above, are polyethylene glycol moieties.

For the protein (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic, e.g., powder; for liquid forms, a soft gelatin shell may be used. The shell material of cachets could be thick starch or other edible paper. For pills, lozenges, molded tablets, or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to: stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, and Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent.

Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the protein (or derivative) are for instance the fatty acids oleic acid, linoleic acid and linolenic acid.

Controlled release formulation may be desirable. The drug could be incorporated into an inert matrix which permits release by either diffusion or leaching mechanisms, e.g., chewing gums. Slowly degenerating matrices may also be incorporated into the formulation. Another form of a controlled release of this therapeutic is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film-coated tablet; the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Pulmonary Delivery

Also contemplated herein is pulmonary delivery of the present soluble protein (or derivatives thereof). The protein (or derivative) is delivered to the lungs of a mammal while inhaling and traverses across the lung epithelial lining to the blood-stream. Other reports of this include Adjei et al., *Pharmaceutical Research*, 7(6):565-569 (1990); Adjei et al., *International Journal of Pharmaceutics*, 63:135-144 (1990) (leuprolide acetate); Braquet et al., *Journal of Cardiovascular Pharmacology*, 13(suppl. 5):143-146 (1989) (endothelin-1); Hubbard et al., *Annals of Internal Medicine*, 3(3):206-212 (1989) (α1-antitrypsin); Smith et al., *J. Clin. Invest.*, 84:1145-1146 (1989) (α1-proteinase); Oswein et al., "Aerosolization of Proteins", *Proceedings of Symposium on Respiratory Drug Delivery II*, Keystone, Colo., (March 1990) (recombinant human growth hormone); Debs et al., *J. Immunol.*, 140:3482-3488 (1988) and Platz et al., U.S. Pat. No. 5,284,656 (granulocyte colony stimulating factor). Contemplated for use in the practice of this invention are a wide range of mechanical devices designed for pulmonary delivery of therapeutic products, including but not limited to nebulizers, metered-dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of protein (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified protein may also be prepared in different formulations depending on the type of chemical modification or the type of device employed.

Formulations suitable for use with a nebulizer, either jet or ultrasonic, will typically comprise protein (or derivative) dissolved in water at a concentration of about 0.1 to 25 mg of biologically active protein per ml of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the protein (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing protein (or derivative) and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 µm (or microns), most preferably 0.5 to 5 µm, for most effective delivery to the distal lung.

Nasal Delivery

Nasal delivery of the protein (or derivative) is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Methods of Treatment, Methods of Preparing a Medicament

In yet another aspect of the present invention, methods of treatment and manufacture of a medicament are provided. Conditions alleviated by or modulated by the administration of the present derivatives are those indicated above.

Dosages

For all of the above molecules, as further studies are conducted, information will emerge regarding appropriate dosage levels for treatment of various conditions in various patients, and the ordinary skilled worker, considering the therapeutic context, age and general health of the recipient, will be able to ascertain the proper dosage. Generally, for injection or infusion, dosage will be between 0.01 µg of biologically active protein/kg body weight, (calculating the mass of the protein alone, without chemical modification), and 10 mg/kg (based on the same). The dosing schedule may vary, depending on the circulation half-life of the protein or derivative used, whether the polypeptide is delivered by bolus dose or continuous infusion, and the formulation used.

Administration With Other Compounds

For therapy associated with obesity, one may administer the present soluble protein (or derivatives) in conjunction with one or more pharmaceutical compositions used for treating other clinical complications of obesity, such as those used for treatment of diabetes (e.g., insulin), high blood pressure, high cholesterol, and other adverse conditions incident to obesity. Also, other appetite suppressants may be co-administered, e.g., amphetamines. Administration may be simultaneous (for example, administration of a mixture of the present protein and insulin) or may be in seriatim.

Nucleic Acid-Based Therapeutic Treatment

An OB-R gene capable of mediating signal transduction, e.g., OB-Rb, could be introduced into human hypothalamus cells to develop gene therapy for obesity. Such therapy would be expected to decrease body weight. Conversely, introduction of antisense constructs into brain cells, particularly hypothalamus but also including choroid plexus, or other cells where OB-R is expressed, would reduce the levels of active OB-R polypeptide and would be predicted to increase body adiposity.

In one embodiment, a gene encoding an OB-R polypeptide is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, brain tissue can be specifically targeted. Examples of particular vectors include, but are not limited to, a defective herpes virus 1 (HSV1) vector [Kaplitt et al., *Molec. Cell. Neurosci.*, 2:320-330 (1991)], an attenuated adenovirus vector, such as the vector described by Stratford-Perricaudet et al., *J. Clin. Invest.*, 90:626-630 (1992), and a defective adeno-associated virus vector [Samulski et al., *J. Virol.*, 61:3096-3101 (1987); Samulski et al., *J. Virol.*, 63:3822-3828 (1989)].

In another embodiment, the gene can be introduced in a retroviral vector [e.g., Anderson et al., U.S. Pat. No. 5,399, 346; Mann et al., *Cell*, 33:153 (1983); Temin et al., U.S. Pat. No. 4,650,764; Temin et al., U.S. Pat. No. 4,980,289; Markowitz et al., *J. Virol.*, 62:1120 (1988); Temin et al., U.S. Pat. No. 5,124,263; International Patent Publication No. WO 95/07358, published Mar. 16, 1995, by Dougherty et al.; and Kuo et al., *Blood*, 82:845 (1993)].

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Feigner et al., *Proc. Natl. Acad. Sci. USA,* 84:7413-7417 (1987); see Mackey et al., *Proc. Natl. Acad. Sci. USA,* 85:8027-8031 (1988)]. The use of cationic lipids may promote encapsulation of negatively charged nucleic acids, and also promote fusion with negatively charged cell membranes [Felgner et al., *Science,* 337:387-388 (1989)]. The use of lipofection to introduce exogenous genes into specific organs in vivo has certain practical advantages. Molecular targeting of liposomes to specific cells represents one area of benefit. It is clear that directing transfection to particular cell types would be particularly advantageous in a tissue with cellular heterogeneity, such as the pancreas, liver, kidney, and brain. Lipids may be chemically coupled to other molecules for the purpose of targeting (see Mackey et al., 1988, supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.,* 267:963-967 (1992); Wu et al., *J. Biol. Chem.,* 263:14621-14624 (1988); Hartmut et al., Canadian Patent Application No. 2,012,311, filed Mar. 15, 1990)].

Agricultural Applications

The OB-R gene can also be isolated from domestic animals, and the corresponding OB-R polypeptide obtained thereby. It is expected that the probe derived from the murine OB-R gene hybridizes to corresponding homologous coding sequences from a large number of species of animals. As discussed for human therapies, recombinant proteins can also be prepared and administered to domestic animals. Administration of the soluble polypeptide can be implemented to produce leaner food animals, such as beef cattle, swine, poultry, sheep, etc. Preferably, an autologous OB polypeptide is administered, although the invention contemplates administration of non-autologous polypeptide as well. Since the soluble OB-R polypeptide consists of approximately 800 amino acid residues, it may be highly immunogenic. Thus, administration of autologous polypeptide is preferred.

Alternatively, the introduction of the cloned genes into transgenic domestic animals would allow one to potentially decrease body weight and adiposity by overexpressing an OB-R transgene. The simplest means of achieving this would be to target an OB-R transgene to brain using its own or another brain specific promoter.

Conversely, increases in body fat might be desirable in other circumstances such as for the development of Kobe beef or fatty liver to make foie gras. This could be accomplished by targeting an antisense OB-R transgene to brain, or by using gene knockout technology. Alternatively, where an increase in body weight at percentage of fat is desired, an inhibitor or antagonist of the OB-R polypeptide can be administered. Such inhibitors or antagonists include, but are not limited to, antibodies reactive with the polypeptide, and fragments of the polypeptide that bind but do not activate the OB receptor, i.e., antagonists of leptin.

Cosmetic Implications

The OB-R polypeptide has significant value for cosmetic use, in addition to the health benefits. In particular, since the OB-R polypeptides of the invention, including derivatives and agonist analogs thereof, are useful for modulation of the rate and quantity of fat cell deposition in an animal, they are useful for reducing unsightly fat tissue, e.g., fat deposits in the abdomen, hips, thighs, neck, and chin that do not necessarily amount to an obese condition, but which nevertheless detract from an individual's appearance. The fat reduction effect is thought to be accomplished, in part, by a reduction in appetite, i.e., a reduction in food intake, by an increase in basal metabolism, or both. Thus, the present soluble OB-Re polypeptide, or its derivatives or agonist analogs, is useful for administration to a subject to effect cosmetic changes in fat tissue deposits, whether by modulating fat deposition, reducing appetite, or both.

In addition, the present compositions and methods may be used in conjunction with various procedures, such as cosmetic surgeries designed to alter the overall appearance of a body (e.g., liposuction or laser surgeries designed to reduce body mass by aspirating or ablating fat tissue), exercise (especially running and weight training), low fat diet, hypnosis, biofeedback, as examples of the ways one may attempt to decrease the percentage of fat tissue and improve the appearance of the body.

Accordingly, the present invention relates to a method for effecting cosmetic fat tissue modulation in an individual comprising administering a fat modulating amount of a soluble OB-R polypeptide, or derivative or agonist analog thereof, to an individual who desires cosmetic fat tissue modulation to improve overall body appearance. In a particular aspect, the fat tissue modulation is a consequence of appetite suppression. Preferably, the fat tissue modulation is a reduction in fat tissue.

In a further embodiment, the invention relates to a method for effecting cosmetic fat tissue loss comprising combining a procedure for changing body appearance with administration of a fat modulating amount of a soluble OB-R polypeptide, or derivative or agonist analog thereof, to an individual who desires cosmetic fat tissue modulation to improve overall body appearance.

The invention may be better understood by reference to the following Examples, which are intended to be exemplary of the invention and not limiting thereof.

Example 1

Isolation of db cDNA Clones

Mutations in the mouse db gene result in severe obesity and diabetes in a syndrome that resembles morbid human obesity [Hummel et al., *Science,* 153:1127 (1966)]. Previous data suggested that the db gene encoded the receptor for the gene product of the ob locus, known as leptin [Coleman, *Diabetologia,* 14:141 (1978); Zhang et al., *Nature,* 372:425 (1994)]. Recently, a report that the leptin receptor was cloned from choroid plexus appeared; this clone was shown to map to the same region of chromosome 4 as db [Tartaglia et al., *Cell,* 83:1263 (1995)]. This receptor is a member of the family of receptors that associate with the JAK tyrosine kinases. However, mutations in this receptor were not identified in C57BL/6J db/db mice, suggesting that the mutation in these animals might be in a splice variant of this gene [Tartaglia et al., supra].

The present Example shows that the leptin receptor maps to the same 300 kB interval on mouse chromosome 4 as db. cDNA selection and exon trapping from this region identified several ESTs with sequences identical to the leptin receptor. Characterization of the corresponding cDNA clones isolated from a mouse brain cDNA library revealed that there are at least five alternatively spliced forms of the leptin receptor, each with differences at their amino and/or carboxy terminus. One of the splice variants is expressed at a high level in the hypothalamus and at a lower level in other tissues. This transcript is mutant in C57BL/Ks db/db mice. This mutation is the result of abnormal splicing leading to a 106 bp insertion into the 3' end of the RNA, which results in a truncated cytoplasmic region that deletes "Box 2", a protein site known to interact with JAK proteins [Murakami et al., *Proc. Natl. Acad. Sci. USA*, 88:11349 (1991); Fukunaga, et al., *EMBO*, 10:2855 (1991)]; it is likely to be defective in signal transduction [Bahary et al., *Proc. Natl. Acad. Sci. USA*, 87:8642 (1990); Modl et al., *Dytogenetics Cell Genetics*, 67:232 (1995)]. These data suggest that the weight reducing effects of leptin are mediated via interactions with a receptor in the hypothalamus, and perhaps other tissues.

Materials and Methods

Isolation of genomic clones. YAC clones were isolated by PCR screening and sized on a CHEF MAPPER (Bio-Rad) [Green et al., *Proc. Natl. Acad. Sci. USA*, 87:1213 (1996); Kasumi et al., *Mammalian Genome*, 4:391 (1993)]. YAC ends were recovered using vectorette PCR and plasmid end rescue [Riley et al., *Nucl. Acids Res.*, 18:2887 (1990); Hermanson et al., *Nucl. Acids Res.*, 19:4943 (1991)]. P1 clones were isolated by sending specific pairs of PCR primers to Genome Systems Inc. (St. Louis, Mo.) who provided single picks of individual mouse P1 clones [Sternsberg, *Trends Genet.*, 8:11 (1992)]. P1 ends were recovered using vectorette PCR [Hartl et al., *Bio Techniques*, 15:201 (1993)]. BACs were isolated as described [Shizuya, *Proc. Natl. Acad. Sci. USA*, 89:8794 (1992)]. Primer selection and PCR amplification were performed as described: initial denaturation at 94° C. for 3 min., 25 cycles of 94° for 1 min., 55° for 2 min. and 72° for 3 min [Zhang, 1994, supra.] The primers were:

```
D4Rck6f
5' ATCTTGGGTTCTCTGAAGAA 3';      (SEQ ID NO: 20)

D4Rck6r
5' GAGATTGTCAGTCACAGCCTC3';      (SEQ ID NO: 21)

D4Rck7f
5' ATCTGAATTGGAATCAAATACAC 3';   (SEQ ID NO: 22)

D4Rck 7r
5' AAATCTGTTATCCTTCTGAAAC 3'.    (SEQ ID NO: 23)
```

Isolation of db clones. cDNA selection was performed as described using mouse brain hypothalamic RNA as the starting material [Morgan et al., *Nucl. Acids Res.*, 20:5173 (1992). Library screening, exon trapping, and DNA sequencing were performed as described [Zhang et al., 1994, supra, (see Example 3)]. The C-terminal sequences of OB-Ra, OB-Re, OB-Rd and OB-Re were found in different cDNA clones. The C-terminal sequence of OB-Rb was not full length. The C-terminus sequence of this variant was initially completed by sequencing genomic DNA. The template was prepared using vectorette PCR of BAC 242 with primers from the cDNA[29] [Riley et al., *Nucl. Acids Res.*, 18:2887 (1990)]. The sequence was confirmed by sequencing RT-PCR products.

Identification of mutations in db. RT-PCR and sequencing were performed as described. Genomic sequences at the splice acceptor of OB-Rb were obtained by vectorette PCR of BAC 242 with the OB-Rb reverse primer. For RT-PCR of OB-Ra, OB-Rb, OB-Re and OB-Rd the forward primer was the same 5' ACACTGTTAATTTCACACCAGAG 3' (SEQ ID NO:24) (also labeled F1 in FIG. 3C). The reverse (r) primers were:

```
OB-Ra
5' AGTCATTCAAACCATTAGTTTAGG 3',  (SEQ ID NO: 25)

OB-Rb
5' TGGATAAACCCTTGCTCTTCA 3',     (SEQ ID NO: 26)

OB-Rc
5' TGAACACAACAACATAAAGCCC 3',    (SEQ ID NO: 27)

OB-Rd
5' AGGCTCCCTCAGGGCCAC 3'.        (SEQ ID NO: 28)

The intron primer for OB-Rb (labeled F2 in FIG.
3C) was
5' GTGACTGAATGAAGATGTAATATAC 3'. (SEQ ID NO: 29)
```

Tissue distribution of the alternatively spliced leptin receptor. RT-PCR was performed as described. The primer sequences for OB-Ra, OB-Rb, OB-Rc, and OB-Rd are shown above. The primers for OB-Re were:

```
f
5' TGTTATATCTGGTTATTGAATGG,      (SEQ ID NO: 30)

r
5' CATTAAATGATTTATTATCAGAATTGC 3'. (SEQ ID NO: 31)
```

Results and Discussion

A series of genetic crosses segregating db were established. These included 50 obese (db/db) progeny of a C57BL/Ks db/db× *Mus spretus* intercross and 350 obese (db/db) progeny of a C57BL/Ks db/db× *Mus castaneus* intercross. The assignment of genotype as the db locus was made as previously described [Bahary et al. *Proc. Nat. Acad. Sci. USA*, 37:8642 (1990).

Several microsatellite markers flanking db were used to type DNA from each animal. These included a distal marker, D4Mit31 and a proximal marker, 1fnα. A genetic map in the region of db was compiled using these and other loci (FIG. 1). The mouse homologous of two previously cloned human genes were found in the region of db: JAK1 and PDE4B. Both of these genes map to human chromosome 1p31 suggesting that the human db gene maps to this chromosomal region [Modl et al., *Cytogenetics Cell Genetics*, 69:232 (1995); Milatovich et al., *Somatic Cell Mol. Gen.*, 20:75 (1994)].

A microdissection clone, D4Rck22, was found to be distal to db and recombinant in three animals [Bahary et al., *Mammalian Genome*, 4:511-515 (1993)]. D6Rck 22 was used as the starting point of a chromosome walk using yeast artificial chromosomes (YACs,) bacterial artificial chromosomes (BACs) and P1 bacteriophage clones [Zhang et al., 1994, supra; Steinberg, *Trends Genet.*, 8:11 (1994); Shizuya, *Proc. Natl. Acad. Sci. USA*, 89:8794 (1992)]. A 2.7 mB contig was assembled by chromosome walking from this marker. Of note, an approximately 200 kB region was not identified in any available mouse YAC library (~12 genome equivalents screened). This gap in the contig was closed after chromosome walking with a series of BAC and P1 clones followed by the isolation of an additional YAC that extended an additional 500 kB proximal to this region. Recombinant animals were typed with genetic markers (both RFLPs and SSLPs) derived from the ends of the individual genomic clones. The db mutation was located between the distal recombination event in animals 324 and the proximal recombination events in animal 1028. Seven other proximal recombinations were noted with 50 kB, suggesting that this is a hot spot for recombination. The entire nonrecombinant interval corresponds to ~300 kB of DNA, and was spanned by two BACs, 43 and 242 (FIG. 1).

Candidate genes for db were isolated from BACs 43 and 242 using exon trapping and cDNA selection from mouse hypothalamus [Church et al, Nature Genetics, 6:98 (1994); Morgan et al, Nucl. Acids. Res., 20:5173 (1992)]. A mouse brain cDNA library was screened with putative gene fragments. Analysis of eight brain cDNA clones indicated that six independent products of cDNA selection and two cDNAs identified using trapped exons were present on overlapping transcripts. The nucleotide sequence of each cDNA clone predicted N-terminal sequences at least partially identical to the mouse leptin receptor (OB-R). The position of sequences from the 5' and 3' end of the OB-R RNA was determined by the STS content of each BAC and are shown on the physical map (FIG. 1). These data indicate that the gene spans ~100 kB and is transcribed toward the telomere.

Figure 2:
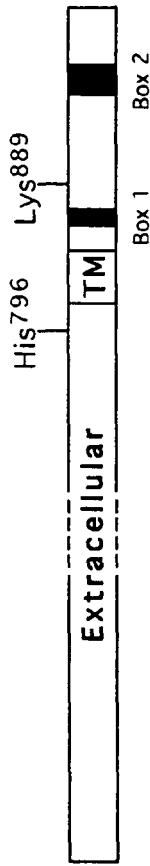
FIG. 2A-B. Several splice variants of the leptin receptor are present. (A) A schematic drawing of the leptin receptor, with putative motifs for JAK binding and signal transduction, "Box 1" and "Box 2" (shaded areas). "TM" indicates a putative transmembrane domain. A total of 8 cDNA clones were isolated from mouse brain. These cDNAs were found to correspond to five different splice variants of the leptin receptor. (B) Six of the clones had partly identical sequences upstream of lysine 889 of the leptin receptor (OB-Ra, OB-Rb, OB-Rc and OB-Rd), at which point the predicted proteins diverged. The predicted C-terminal amino acid sequences of these clones is shown (SEQ ID NOS:11-14, respectively). OB-Ra, b, c, and d all predict a Box 1 motif. OB-Rb also predicts a peptide sequence potentially homologous to Box 2 (underlined). Two independent cDNA clones were identical to the leptin receptor upstream of histidine 796, at which point the sequences diverged (OB-Re)(SEQ ID NO:15). The nucleotide sequence predicts a soluble receptor.
Figure 2:
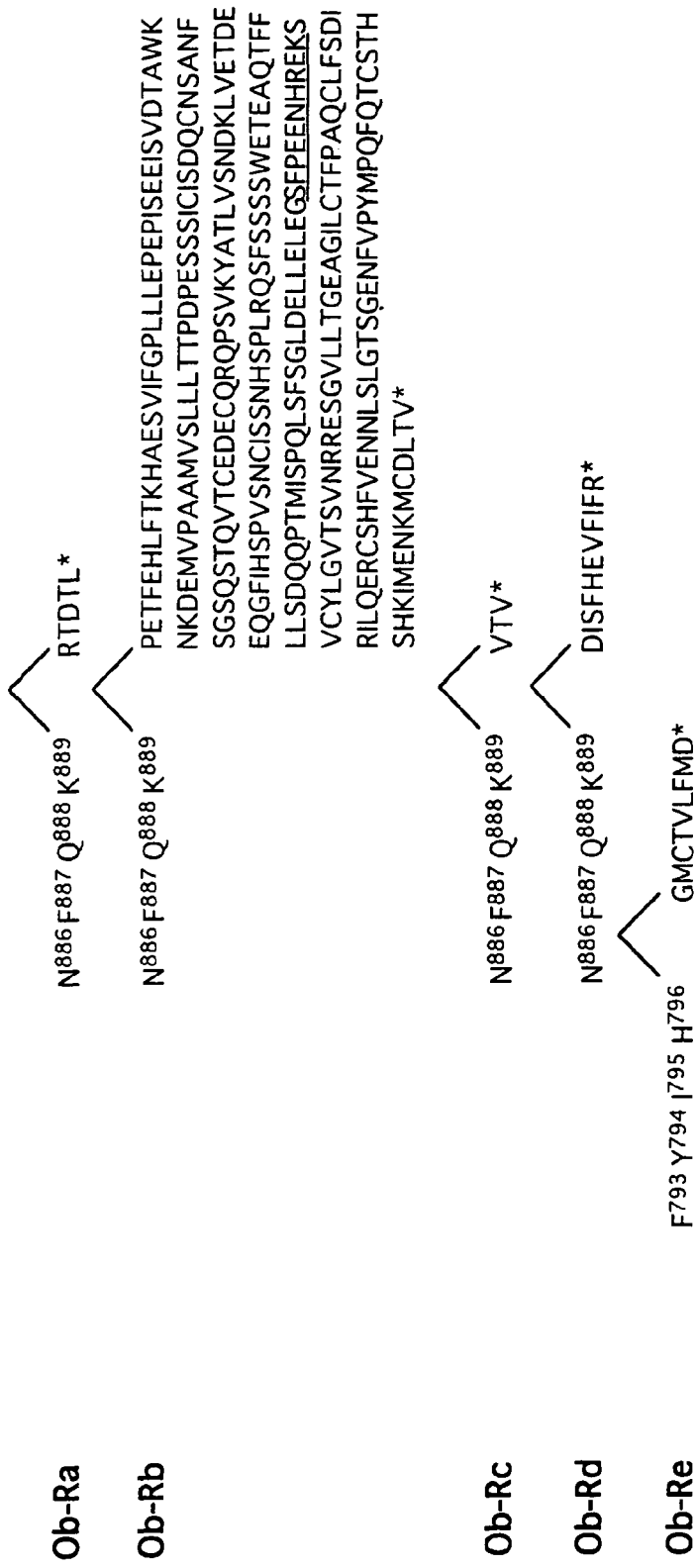

These cDNA clones diverge at the carboxy terminus. In four cases, the predicted sequences were at least partially identical up to lysine 889 of the leptin receptor, which includes the transmembrane domain. Beyond this point, the cDNAs predicts proteins with differences in the cytoplasmic domain designated OB-Ra (SEQ ID NO:11), OB-Rb (SEQ ID NO:12), OB-Rc (SEQ ID NO:13), and OB-Rd (SEQ ID NO:14) (FIG. 2B). OB-Re predicted a different amino acid sequence after $His^{796}$ (SEQ ID NO:15), which appears to encode a soluble receptor (FIG. 2B). Clones for OB-Ra, OB-Rb, and OB-Re diverged at its N-terminus. In all cases, the divergent sequence also mapped to the BAC contig. OB-Ra corresponds generally to mouse OB-R [Tartaglia et al., Cell, 83:1263 (1995)].

The C-terminus of OB-Rb was 78 percent identical to the human OB receptor, suggesting that it is the mouse homologue [Tartaglia et al., supra]. Leptin receptor is a member of the gp-130 family of receptors that interact with JAK protein kinase. The cytoplasmic domains of gp-130 receptors are generally required for binding JAKs and signal transduction [Kishimoto et al., Cell, 76:253 (1994)]. The OB-Rb cDNA sequence predicts a potential "box 2" sequence (underlined in FIG. 2B), a protein motif required for binding with JAK protein kinases [Kishimoto, supra]. "Box 2" is conserved among many members of this receptor family and is required for signal transduction of the GCSF and IL6 receptors [Murakami et al., Proc. Natl. Acad. Sci. USA, 88:11349 (1991); Fukunaga et al., EMBO J., 10:2855 (1991). None of the other transcripts predict a "Box 2" sequence. Of the eight cDNA clones characterized, OB-Ra was isolated three times and OB-Re two times. OB-Rb, OB-Rc, and OB-Rd were each isolated once. Additional splice variants are likely to be identified.

Figure 3:
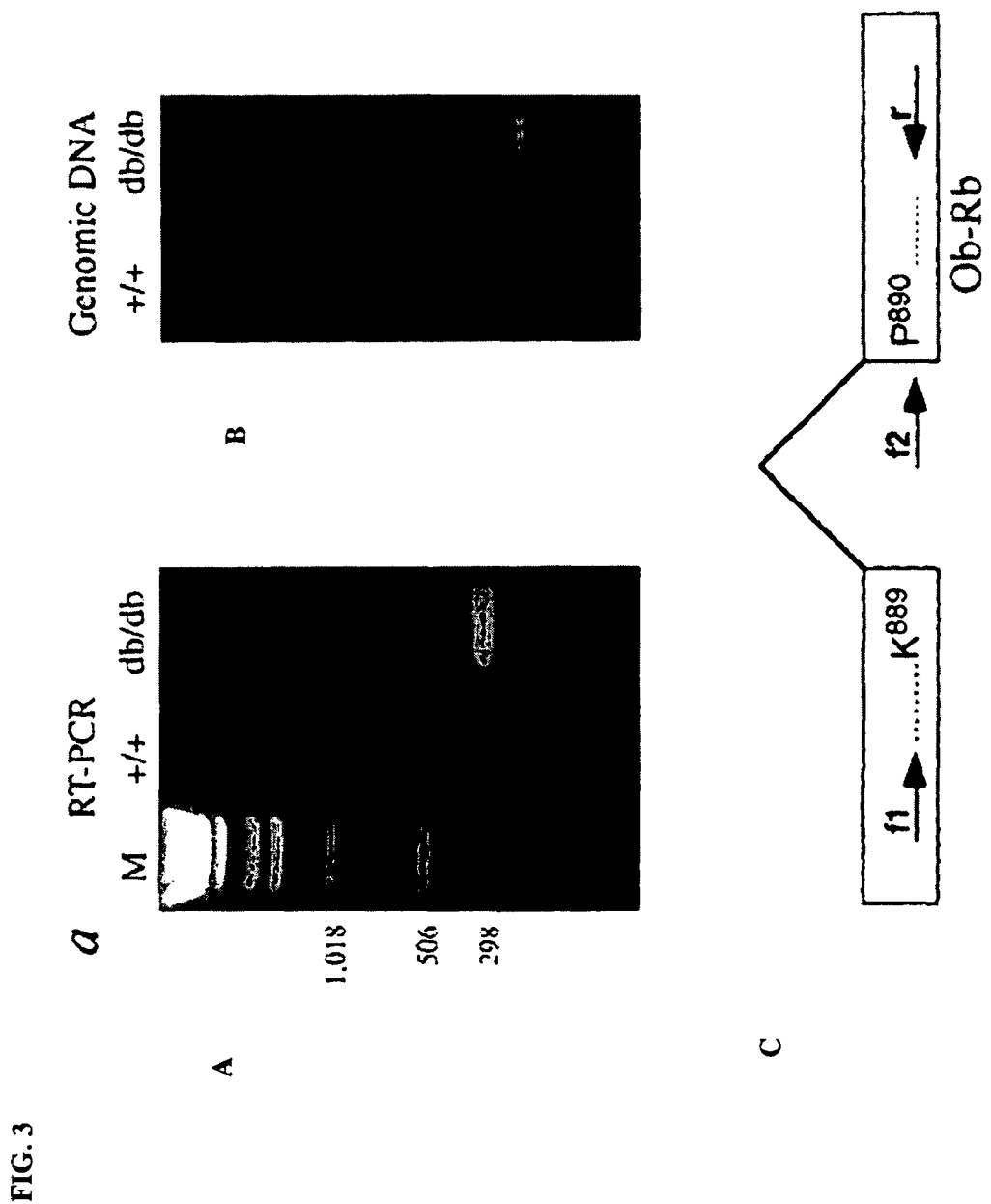
FIG. 3A-C. The db mutation results in abnormal RNA splicing and conversion of the splice variant OB-Rb to OB-Ra. (A) RT-PCR products from C57BL/Ks db/db and wild type mice were amplified using a primer pair specific for OB-Rb RNA (F1 and $R_3$). Electrophoresis revealed that the amplified fragment from these db mice was larger than from wild type animals. The PCR products of genomic DNA spanning the OB-Rb splice acceptor at $Pro^{890}$ were of identical size in C57 BL/Ks db/db mice and littermate controls. (B) Primers F2 and R were used to amplify the genomic DNA. The F2 primer was selected after using vectorette PCR and BAC 242 to obtain the sequence of genomic DNA upstream of the splice acceptor at $P^{890}$. (C) Localization of primers for RT-PCR and genomic PCR amplification.
Figure 4:
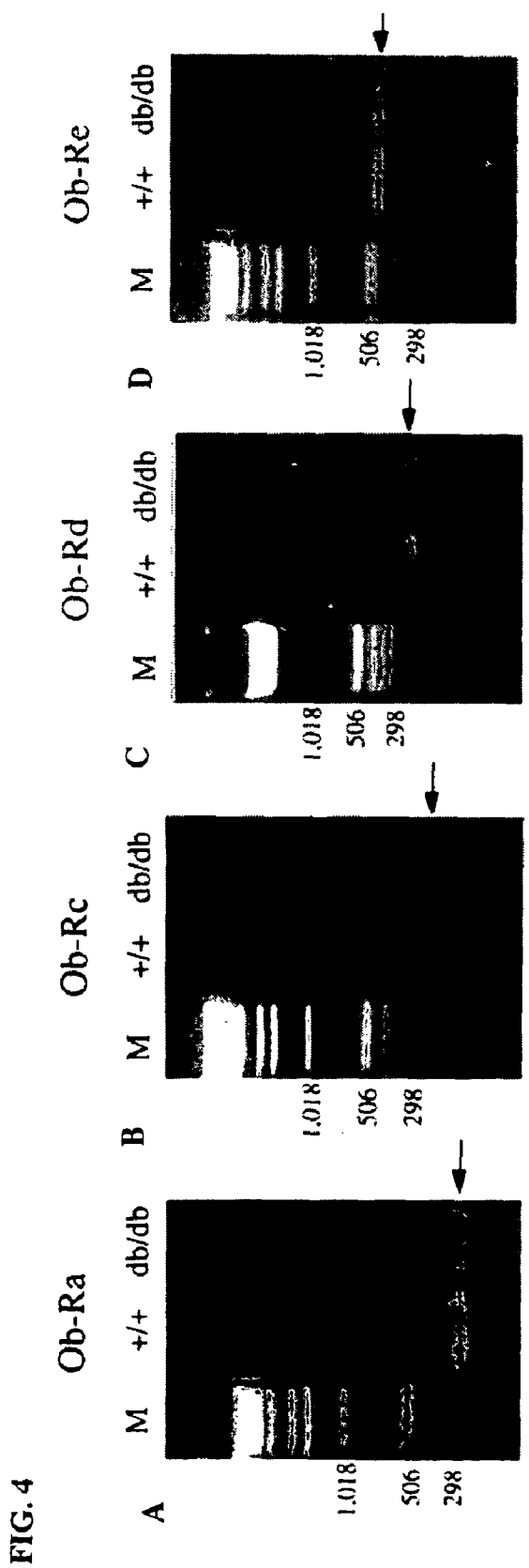
FIG. 4A-D. Hypothalamic RNA of wild type mice. The hypothalamic RT-PCR products for the C-terminal coding region of (A) OB-Ra, (B) OB-Re, (C) OB-Rd and (D) OB-Re were of normal size in db mice. The DNA sequence across the splice junction was normal in each of these RT-PCR products. This indicates that the splice donor at $Lys^{889}$ is wild type.

C57BL/Ks db/db mice have a longer fragment length of OB-Rb specific RT-PCR products (it should be noted that this PCR amplified 3' nucleic acids, and thus is specific for all splice variants having a cytoplasmic domain characteristics of OB-OB-Rb, but provides no data on the extracellular domain) from hypothalamic RNA than wild type littermates (FIG. 3A). However, PCR amplified genomic DNA spanning the splice acceptor at $Pro^{890}$ was of normal size in C57BL/Ks db/db compared to wild type (FIG. 3B). DNA sequencing of this fragment confirmed that the genomic sequences at the splice acceptor are wild type in db mice. In addition, both the size and nucleotide sequence of RT-PCR products corresponding to the other 3' ends were normal in the db mice, suggesting that the splice donor at $Lys^{889}$ is also normal (FIG. 4). These data suggested that the longer OB-Rb-specific fragment from C57BL/Ks db/db mice was the result of abnormal splicing.

Figure 5:
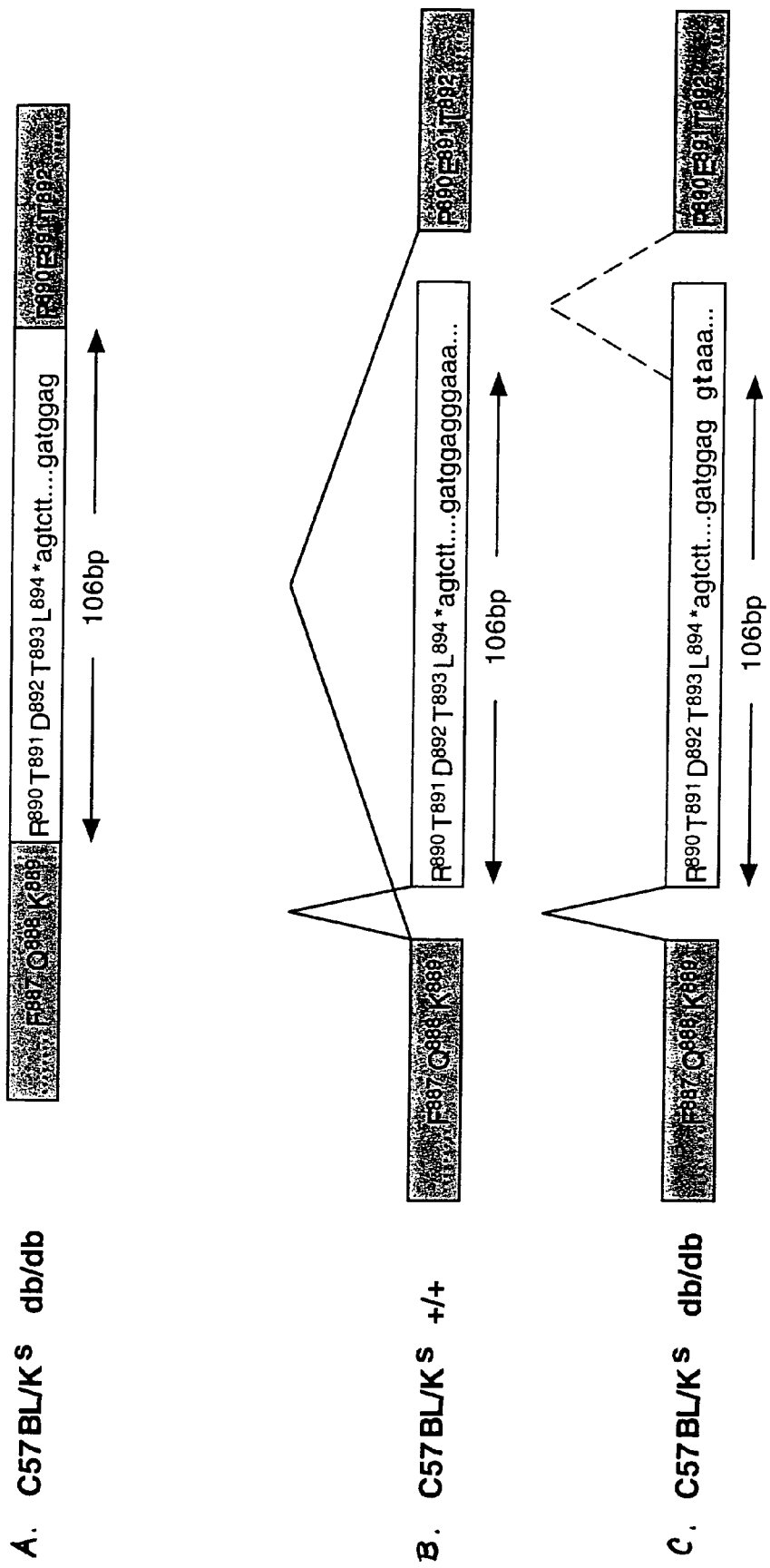
FIG. 5 A-C. Identification of splice mutations in db mice. (A) DNA sequencing identified a 106 bp insertion in the mutant OB-Rb RNA at the splice junction between $Lys^{889}$ and $Pro^{890}$ (SEQ ID NO:16). The sequence of the insertion was identical to the first 106 bp of the C-terminal exon of OB-RA. The insertion predicts a premature stop codon and changes the amino acid sequence of OB-Rb (SEQ ID NO:17) to OB-Ra. (B, C) The presumed genomic organization of the OB-Ra and OB-Rb 3' ends are shown. DNA sequencing of the OB-Ra exon from the C57 BL/$K^9$ db/db mice (SEQ ID NO:18) and littermate controls (SEQ ID NO:19) revealed a G to T mutation 106 base pairs after the splice acceptor at $R^{890}$. This mutation results in the appearance of a consensus splice donor site, AGGTAAA, which leads to the insertion of 106 bp of the C-terminal exon of OB-Ra into that of OB-Rb.

Sequencing of the RT-PCR products of OB-Rb from the mutant mice revealed a 106 bp insertion between the splice donor at $Lys^{889}$ and splice acceptor at $Pro^{890}$. The sequence of the inserted DNA was identical to the first 106 bp of the unique OB-Ra exon downstream of its splice acceptor at $Arg^{890}$ (FIG. 5A). Sequencing of genomic DNA and RT-PCR products from the 3' untranslated region of OB-Ra of C57BL/Ks db/db mice identified a g→t mutation 106 bp after the splice acceptor (compare FIG. 5B and 5C). This mutation results in the appearance of a consensus splice donor site, AGGTAAA (FIG. 5C) [Lodish et al., Mol. Cell. Biol., Scientific American Books: New York, pp. 1-1344 (1986)]. This mutant splice donor results in the splicing of 106 bp of the OB-Ra terminal exon into the splice acceptor at $Pro^{890}$ at OB-Rb RNA. The resulting mutant OB-Rb protein has a termination codon five amino acids after the splice and an identical amino acid sequence to OB-Ra. The mutant receptor is missing most of the cytoplasmic region including the potential "Box 2" motif. While RT-PCR demonstrated that the sizes of the other 3' ends were normal in $C57BL/K^9$ db/db mice, it is possible that this alternative exon is inserted into other transcripts as well.

Figure 6:
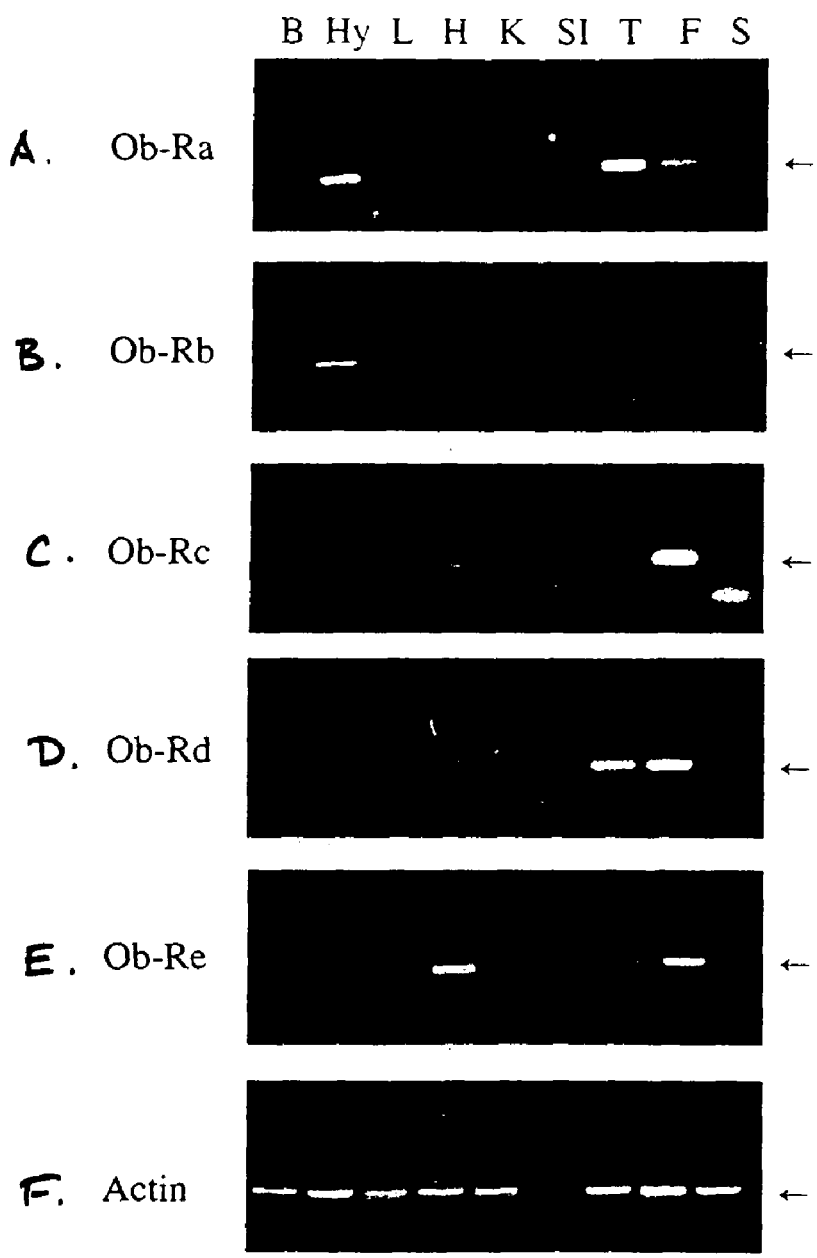
FIG. 6A-F. Tissue distribution of the alternatively spliced leptin receptor. RT-PCR was performed from the tissue sources indicated. In each case, one primer from a region of shared nucleotide sequence was used in combination with a primer specific for the alternatively spliced exon; actin mRNA served as a control. (B) Brain, (H) Hypothalamus, (L) Liver, (H) Heart, (K) Kidney, (S) Spleen, (T) Testis, (F) Adipose Tissue, (S) Spleen.

The OB-Rb leptin receptor is expressed at a high level in the hypothalamus relative to other tissues (FIG. 6). Lower level expression is seen in testes with an even lower level in adipose tissue. The other alternatively spliced mRNAs are expressed in several tissues including in some cases hypothalamus (FIG. 6). OB-Re, which encodes a putative soluble receptor, is highly expressed in adipose tissue and is expressed at a lower level in brain, heart, and testes (FIG. 6E).

The C57BL/Ks db/db mutation is coisogenic and results in the functional replacement of the cytoplasmic domain corresponding to OB-Rb by that of OB-Ra. These data, combined with the localization of the leptin receptor to precisely the same chromosomal region as db, strongly confirm that OB-Rb is allelic with db. The identification of mutations in the two other available alleles of db will provide additional information on the structure-function relationship of the protein. The fact that the C57BL/Ks db/db mutation is found in the unique C-terminus of OB-Rb explains why the sequence of OB-Ra was unchanged in C57BL/Ks db/db mice, and that binding of leptin to the choroid plexus was normal in these animals. Leptin binding in C57BL/Ks db/db mice is likely to be normal in all locations. Rather, the obese phenotype appears to result from the inability of the OB-Ra C-terminus to initiate signal transduction when expressed in place of the C-terminus of OB-Rb. Elucidation of the signal transduction pathway and identification of possible sites of JAK binding to the cytoplasmic region of this receptor are contemplated.

These results suggest that the weight reducing effects of leptin are at least partially mediated via interactions with the OB-Rb receptor having a C-terminal (cytoplasmic) domain characteristic of OB-Rb in the hypothalamus, a brain region known to play an important role in regulating body weight. This is supported by the increased potency of leptin when administered directly into the CSF and the affects of leptin on the electrical activity of hypothalamic neurons. Leptin may modulate the activity of NPY, GLP-1 and other peptides known to affect feeding behavior in the hypothalamus and brain [Stephens et al., supra; Tarton et al., Nature, 379:69 (1996)]. It may also have effects other tissues expressing the leptin receptor including fat. The receptor expressed in choroid plexus, possibly OB-Ra or a splice variant sharing a similar C-terminus, may act to transport the protein to the CSF, a mechanism similar to that proposed for transport of insulin by the insulin receptor [Bahary et al., 1990, supra; Partridge et al., Neurochem., 44:1771 (1985); Van Houten and Posner, Nature, 282:623 (1979); Wood and Park, Am. J. Physiol., 233:E331-E334 (1979)].

OB-Re, the putative soluble receptor is believed to bind to leptin in the circulation. It could function as a transport protein to agonize leptin activity [see, e.g., Davis et al., Science, 259:1736 (1993); Kishimoto et al., supra; Davis et al., Science, 260:1805 (1993)].

Example 2

Preparation of Antibodies to the OB Polypeptide

In addition to use of the recombinant protein to generate polyclonal antibodies, a set of three peptide sequences from the deduced full length murine OB-R sequence (i.e., SEQ ID NOS:2, 4, 6, 8, 10) were identified. The four internal peptide fragments are:

```
Peptide A (amino acid numbers        (SEQ ID NO: 32)
145-158):
Glu-Pro-Leu-Pro-Lys-Asn-Pro-Phe-Lys-Asn-Tyr-Asp-
Ser-Lys Peptide B (amino acid numbers        (SEQ ID NO: 33)
465-484):
His-Arg-Arg-Ser-Leu-Tyr-Cys-Pro-Asp-Ser-Pro-Ser-
Ile-His-Pro-Thr-Ser-Glu-Pro-Lys Peptide C (amino acid numbers        (SEQ ID NO: 34)
863-881):
Gln-Arg-Met-Lys-Lys-Leu-Phe-Trp-Asp-Asp-Val-Pro-
Asn-Pro-Lys-Asn-Cys-Ser-Trp
```

These peptides were prepared using standard solid phase peptide synthesis. The purified synthetic peptides are conjugated to KLH, and the peptide-KLH conjugates are used to immunize rabbits using standard techniques. Polyclonal antisera specific for each peptide is recovered from the rabbits.

Example 3

Preparation of PCR Probes From cDNA Selection and Exon Trapping clones

This Example describes the cDNA selection clones that were identified to correspond to OB-R. PCR primers from these clones were used as probes for OB-R cDNA and genomic clones, and are useful for identifying OB-R DNA, as well as characterizing different OB-R splice variants.

Five cDNA selection clones were found to be useful as probes: clones 7 (SEQ ID NO:35), 11 (SEQ ID NO:36), 42 (SEQ ID NO:37), 46 (SEQ ID NO:38), and 58 (SEQ ID NO:39). Two cDNA selection clones identified by hybridization with exon trapping clones were also found to be useful probes: clones S3 (SEQ ID NO:40) and S14 (SEQ ID NO:41).

PCR primers were prepared from each of the above-noted clones for use as probes in identifying OB-R DNA. Table 1 reports the forward and reverse primers for each of the clones, and notes which splice variants of OB-R, as well as the predicted coding region, each probe labels.

TABLE 1

PCR Primer Probes for OB-R DNA

| Source Clone (direction) | Sequence | SEQ ID NO: | Splice variant | Recognition region |
|---|---|---|---|---|
| 7 (forward) | CCGAGGGAATTGACAGCC | 42 | all | extracellular |
| 7 (reverse) | CTCACTGTGTAGTGTGAGGAGG | 43 | | |
| 11 (f) | TCCTGTGGACAGAACCAGC | 44 | all | extracellular |
| 11 (r) | TGACACAGCTGCTGCTCAG | 45 | | |
| 42 (f) | TGGATAAACCCTTGCTCTTCA | 26 | b | far 3' region |
| 42 (r) | GGTCTCAGAGCACCCAGGTA | 46 | | |
| 46 (f) | AGAGAGATCCCTGACCCTAGTT | 47 | d | 3' non-coding |
| 46 (r) | AACTTTCTGCCTTCTCATGTCA | 48 | | |
| 58 (f) | TTTCTCATCTAACAAGCAAGCA | 49 | b | far 5' |
| 58 (r) | ATCTGTTTCTTGCGCAGGAT | 50 | | |
| S14 (f) | CATTGTTTGGGGCTCCAG | 51 | d, e | extracellular |
| S14 (r) | AATCGTTCTGCAAATCCAGG | 52 | | |
| S3 (f) | TGAAGTCATAGATGATTCGCC | 53 | a, d, e | extracellular |
| S3 (r) | GTTCGTACCCGACGTCACTG | 54 | | |

As indicated in the table, probes from clones 7 and 11 have been useful in identifying all splice forms of OB-R identified to date. Probe 42 is useful to identify a splice variant with a cytoplasmic domain corresponding to OB-Rb, i.e., that is putatively signal transduction competent. Probes 46 and S14 are useful to identify splice variants having an N-terminal amino acid sequence corresponding to OB-Rd and OB-Re (which is identical to the N-terminal sequence of the published murine OB-R up to the C-terminal splice sites identified for these proteins; see FIG. 2B). Probe 58 is useful to identify an OB-R containing a unique 5' region found in the OB-Rb splice variant cDNA, which may be a non-coding region. S3 identifies nucleic acids encoding extracellular domains found in variants a, d, and e (corresponding to the published murine OB-R extracellular domain).

The hybridization conditions for screening mouse brain cDNA library were as follows: probes with a length of about 150-300 bp long were labeled with $^{32}$P-dCTP using hot-PCR. The filters were first pre-hybridized for at least one hour at 65° C. using RAPID-HYB buffer (Amersham LIFE SCIENCES). The labeled probe was added to a final concentration of $10^6$ cpm/ml of RAPID-HYB solution and the hybridization was done for at least 6 hours at 65° C. The filters were washed with 2×SSC/0.1% SDS, RT, for 30 min, followed by a more stringent wash with 0.3×SSC/0.1% SDS, RT, for ½ hour.

Thus, the probes described in this example are useful for identifying OB-R, as well as identifying unique splice variants. It is believed, for example, that a splice variant with an extracellular domain corresponding to OB-Ra, or OB-Rc/d/e may be joined with a cytoplasmic domain corresponding to OB-Rb.

Example 4

Leptin Receptor Mutations in 129 DB$^{3J}$/DB$^{3J}$ Mice and NIH Fa$^{cp}$/Fa$^{cp}$ Rats Mutations in the mouse db gene and its rat homologue fa, result in obesity and diabetes as part of a syndrome resembling morbid human obesity. To date, mutations in the leptin receptor (Lepr) have been reported in C57BL/Ks db/db mice and 13M fa/fa rats. This Example shows that NIH fa$^{cp}$/fa$^{cp}$ rats have a nonsense mutation at amino acid Tyr763 and that 129 db$^{3J}$/db$^{3J}$ mice have a 17 base pair deletion and frameshift that results in a truncated protein of 636 amino acids. These data confirm the fact that the db gene and Lepr are allelic. In addition, the phenotype of 129 db$^{3J}$/db$^{3J}$ mice, who have defects in all forms of Lept, and C57BL/6J db/db mice, which lack only Ob-Rb, are identical. These data suggest that the other alternatively spliced forms of leptin receptors (OB-Ra, c, d, e) are not likely to serve functions independent of OB-Rb.

The cloning of leptin and its receptor have led to the identification of a novel signal transduction pathway important in body weight regulation. The data in Example 1 indicate that the db gene encodes several alternatively spliced forms of the receptor for the ob gene product, leptin. Of these splice forms, only one, OB-Rb, contains a long cytoplasmic domain, which includes motifs implicated in signal transduction. OB-Rb is highly expressed in the hypothalamus and is abnormally spliced in C57BL/Ks db/db mice which results in the truncation of the OB-Rb isoform, and loss of its signal transducing capability [Example 1, supra; Ghitardi et al., *Proc. Natl. Acad. Sci, USA*, 93:632-635 (1996); Vaisse et al., *Nature Genetics*, 14:95-97 (1996)]. Recently a missense mutation, in fatty rats (which is allelic with db) was identified in the fatty (fa/fa) Zucker rat [Chua et al., *Diabetes* 45:1141-1143 (1996)]. This mutation presumably alters the binding of leptin at the cell surface [Chua et al., (1996) supra; Philips et al., *Nature Genetics* 13:18-19 (1996)].

Mutations in the mouse db locus and its rat homologue, fatty, have independently arisen many times [Truett et al., *Proc. Natl. Acad. Sci. USA* 88:7806-7809 (1991); Hummel et al., *Science* 153:1127-1128 (1966); Aubert et al., *Journal of Nutrition* 115:327-333, (1985); Koletsky, *Experimental & Molecular Pathology* 19:53-60 (1973); Leiter et al., *Diabetologia* 19:58-65 (1980)]. The molecular basis of the mutations in these other mutant strains could provide information on the structure-function relationship of leptin and Lepr. This Example shows the molecular basis of the mutations in the coding regions of Lepr from mutant 129 db$^{3J}$/db$^{3J}$ rats and NIH fa$^{cp}$/fa$^{cp}$ rats.

Materials and Methods

Sequence determination of mouse and rat Lepr (OB-R). Brain and hypothalamus RNA were isolated by a modified guanidine HCl method [Chirgwin et al., *Biochemistry* 18:5294-5299 (1979)]. Ten micrograms of total RNA was used as a template to synthesize cDNA with Mo-MuLV reverse transcriptase according to the manufacturer's recommendations [Lee et al., (1996) supra]. Lepr DNA fragments were amplified using cDNA or genomic DNA from mutant and wild type animals with Taq DNA polymerase and primers based on the murine or rat Lepr cDNA sequence. Samples were amplified with the primers 43 M137R 5'-CTCACTGT-GTAGTGTGAGGAGG-3' (SEQ ID NO:43) and A83'R 5'-CCTTGTGCCCAGGAACAATTC-3' (SEQ ID NO:55). Amplified fragments were purified from agarose gels and sequenced using an ABI DNA sequencer as described [Zhang et al., *Nature* 372:425432 (1994)]. Agarose gels were run as described [Zhang et al., (1994) supra].

PCR of cDNA and genomic DNA. Both cDNA and genomic DNA from the extracellular region of Lepr were PCR amplified. DNA was obtained from 129 db$^{3J}$/db$^{3J}$ and wild type mice. Primer sequences are as follows: for cDNA, the forward primer was 3JF1 5'GAGAATAACCTTCAAT-TCCAGATTC3' (SEQ ID NO:56), and the reverse primer was 3JR1 5'CCAAGCTTAAGGCCCTCTCATAGGAAC3' (SEQ ID NO:57); for genomic DNA, the forward primer was 3JF2 5'GACCTCTCTGCAGTCTATGTGGTCCA3' (SEQ ID NO:58), and the reverse primer was 3JR2 5'GAAAG-GTTTTCAGTCACGCTTGAAG3' (SEQ ID NO:59).

Results and Discussion

Figure 7:
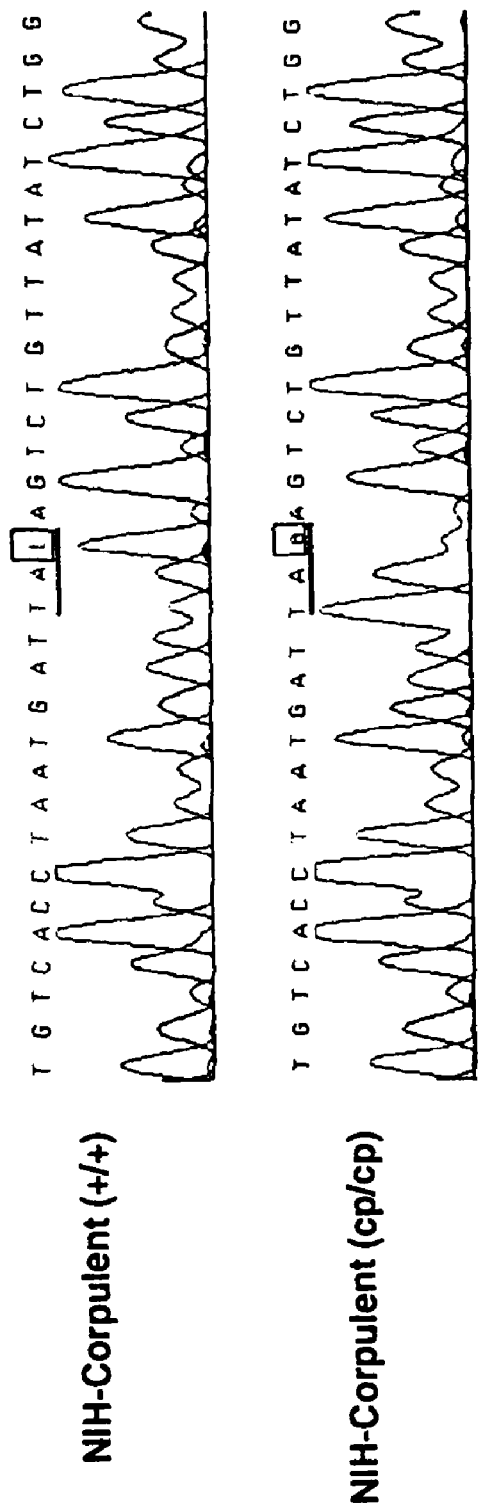
FIG. 7. The NIH-corpulent rat (cp/cp) mutation. A DNA sequence of Lepr from obese NIH fa$^{cp}$/fa$^{cp}$ and lean rats is shown. cDNA was synthesized from RNA isolated from the brain of obese cp/cp rats and lean littermates. The PCR products were gel purified and sequenced with above primers on an automated sequencer. The cp/cp rat has a base change of T→A at nucleotide 2289 resulting in a stop codon at Tyr763.

The obese NIH-corpulent rat (cp/cp) is an inbred genetic model of non-insulin-dependent diabetes characterized by progressively increasing obesity and hyperinsulinemia before the appearance of sustained hyperglycemia [Koletsky (1973) supra]. The cp mutation had previously been shown to be a fa allele (fa$^{cp}$/fa$^{cp}$) since crosses of rats carrying the fa mutation with rats carrying the cp mutation yielded obese progeny [Yen et al., *Heredity* 38 (1977)]. cDNA was prepared from the hypothalamus of lean and obese rats and the sequence of the complete coding region for Lepr was compared. A single base change of T to A at nucleotide 2289 was identified in the obese corpulent rat resulting in the conversion of Tyr763 to a stop codon (FIG. 7). To confirm this, specific primers closely flanking the mutation, corp-F and corp-R, were used to amplify genomic DNA from both lean and obese rats. Sequencing of genomic DNA confirmed the T to A change. This nonsense mutation results in termination of translation aminoterminal of the transmembrane domain. As a consequence, none of the Lepr isoforms in cp/cp rats contain a transmembrane domain, nor any of the motifs necessary for signal transduction.

Figure 8:
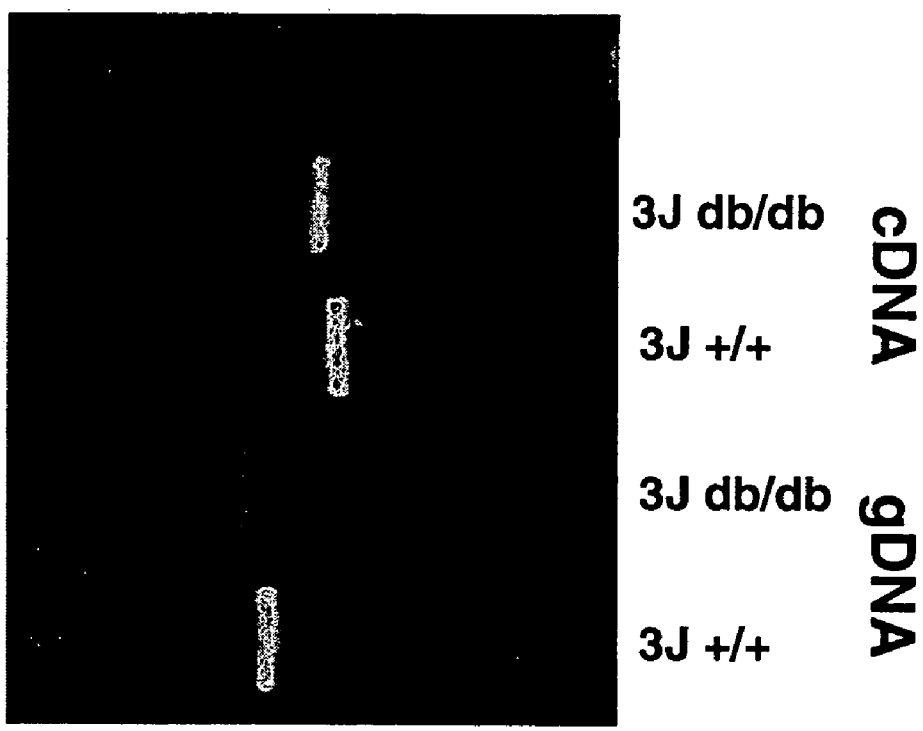
FIG. 8. PCR of Lepr from wild type and db$^{3J}$/db$^{3J}$ mice. Both cDNA and genomic DNA from the extracellular region of Lepr were PCR amplified using DNA from 129 db$^{3J}$/db$^{3J}$ and wild type mice. In both cases the PCR product was shorter in the mutant mice. All primers are from the Ob-R coding region except for 3JR2, which is intronic so that amplified product from genomic DNA can be resolved on agarose gel.
Figure 9:
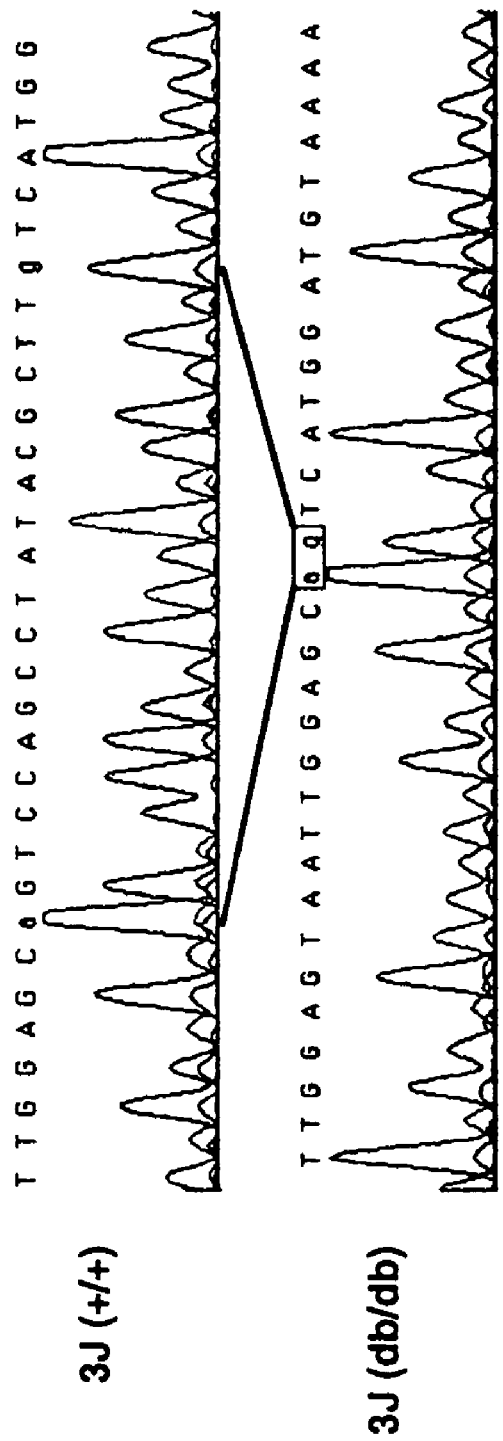
FIG. 9. The PCR product from db$^{3J}$/db$^{3J}$ mice was sequenced. A deletion of 17 bp was identified in this mutant. The same deletion was identified in both genomic DNA and cDNA.

The db$^{3J}$ mutation occurred spontaneously in the 129/J strain at Jackson Laboratory. The mutant animals present with severe obesity and hypoglycemia, rather than hyperglycemia, coupled with marked hyperinsulinemia and massively enlarged Islets of Langerhans [Leiter et al., (1980) supra]. To identify the db$^{3J}$ mutation, RNA was prepared from hypothalamus of db$^{3J}$ and wild type mice. Agarose gel electrophoresis revealed that an RT-PCR product from the amino terminus of the db$^{3J}$ receptor mice is smaller than that from 129+/+ mice. The PCR product of genomic DNA from this region of the receptor was also shorter in the mutant mice (FIG. 8). Sequencing of the PCR products identified a 17 nucleotide deletion beginning at base G$^{1874}$ (Ser625) in mutant mice, causing a reading frame shift (FIG. 9). In the db$^{3J}$/db$^{3J}$ mice, the translation of OB-R stops at the 11th amino acid after the deletion site. The result is the synthesis of a truncated protein without a transmembrane domain. Immunoblots confirm that the receptor protein band is absent in this mutant. Thus, this mutation leads to a truncated receptor affecting all the Lepr splice variants.

Figure 10:
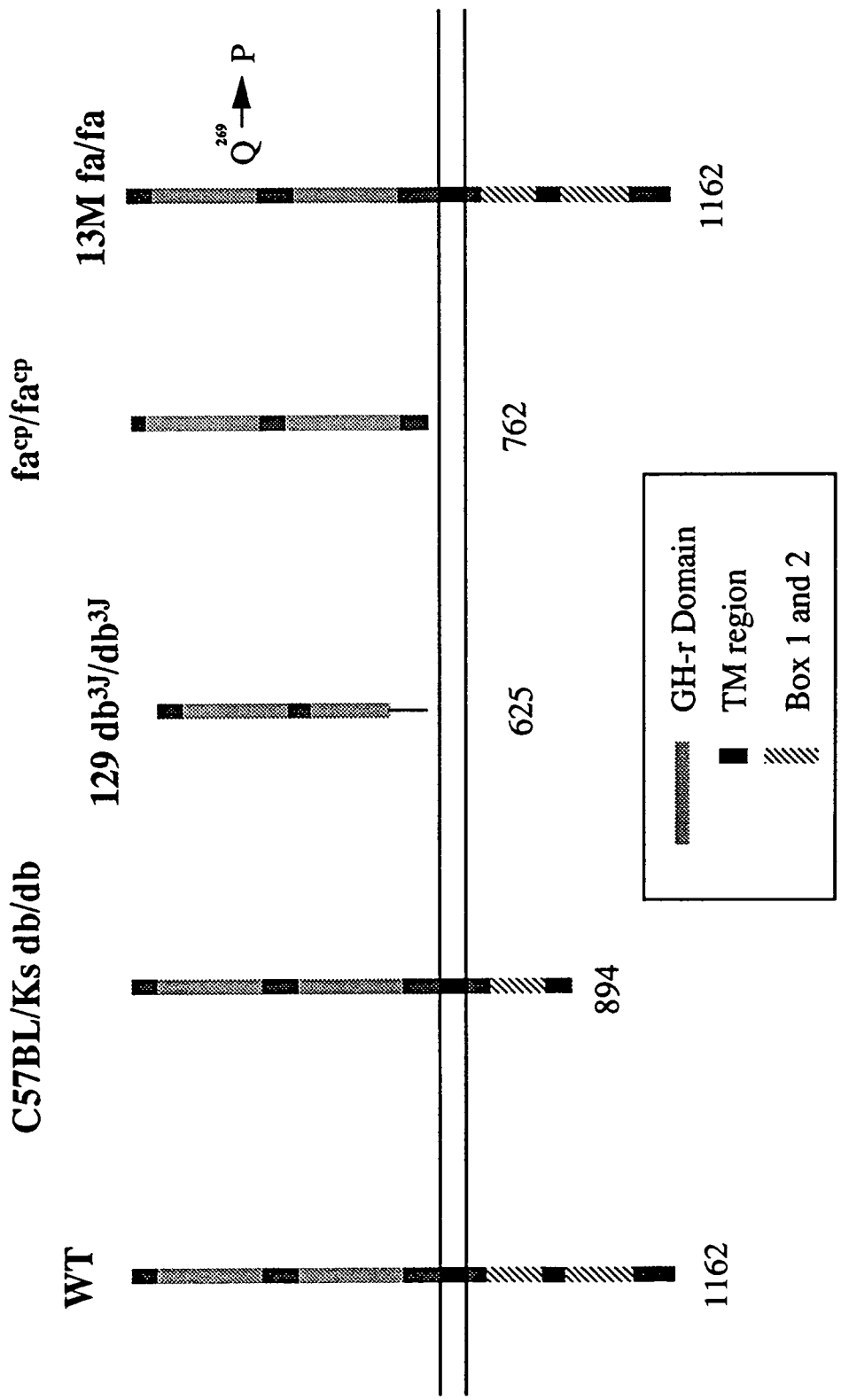
FIG. 10. Schematic of leptin receptor mutations. The predicted protein of each of the Lepr alleles is shown. Numbers at the end of each receptor represent the amino acid residue at the carboxy terminus. The short straight line at the end of the db$^{3J}$/db$^{3J}$ diagram denote the 11 additional residues following amino acid 625 that are caused by frameshift.

The nonsense mutation in Corpulent (cp/cp) rat and the frameshift db mutation in 129J (db/db) mice confirm that defects in the leptin receptor leads to abnormalities in the leptin-Lepr pathway and an obese phenotype. In addition, the phenotype of 129 db$^{3J}$/db$^{3J}$ mice, who have defects in all forms of Lepr, and C57BL/6J db/db mice, which lack only OB-Rb, are identical (FIG. 10). These data suggest that the other alternatively spliced forms of leptin receptors (OB-Ra, c, d, e) are not likely to serve functions independent of OB-Rb.

Example 5

Figure 11:
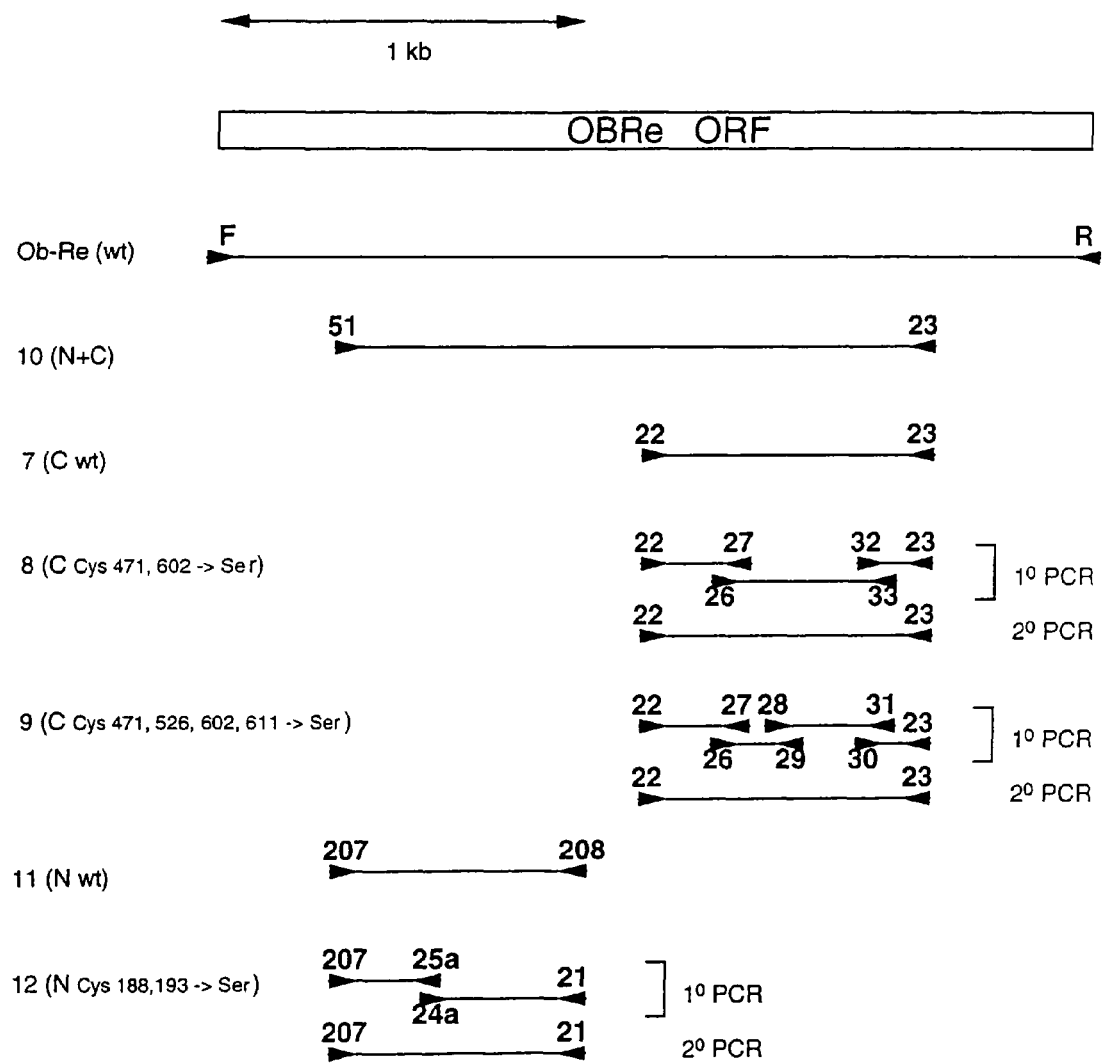
FIG. 11. PCR primers and strategies for amplification of OB-Re and OB-Re mutants. The arrows represent PCR primers (Table 2, infra), which are labelled with numbers; all 1° PCR reactions were performed with Ob-Re cDNA template; all 2° PCR reactions were performed using mixtures of equal amounts from the corresponding 1° PCR products as a template.

Expression of Mouse Soluble OB Receptor and OB Receptor Mutants Using Baculovirus System Generation of baculovirus transfer constructs. All constructs for expression of soluble OB receptor (OB-Re) and OB-Re mutants were generated on the basis of a baculovirus polyhedrin promoter-based transfer cloning vector called pMelBac (Invitrogen; Cat. no. V1950-20). This vector is designed to direct expression of recombinant proteins through the secretory pathway to the extracellular medium. The vector contains a signal sequence for honeybee melittin (HBM), that is highly expressed and efficiently secreted by SF9 cells, an insect cell line. The HBM signal sequence in pMel Bac replaces the endogenous signal sequence of the recombinant protein. PCR was used during the initial cloning step to generate inserts for ligation. OB-Re cDNA served as a PCR template (SEQ ID NO:10). Priming oligonucleotides for PCR were designed to amplify the required region of OB-Re cDNA, to introduce the desired point mutation(s) and stop codon, when necessary, as well as to generate restriction enzyme recognition sequences, that were needed for cloning into pMelBac vector (FIG. 11, Table 2).

TABLE 2

PCR Primers Sequences and Restriction Enzymes Used to Express OB-Re and Mutants.

| Construct | 1° PCR Primers | 2° PCR Primers | Restriction Enzymes used | Cloning vector |
| --- | --- | --- | --- | --- |
| Mouse Ob-Re full length ORF (Ob-R) | F: 5'-TAACCTGGCGGATCCGATCTCTCCCTGGAA-3'<br>R: 5'-ATTATCAGAATAAGCTTTCTACAGTGTCAT-3' | — | BamHI<br>Hind III | pMelBac B |
| Mouse Ob-Re C domain wild-type (7) | 22: 5'-CGCGGATCCTATGCTGAATTATACG-3'<br>23: 5'-CCCAAGCTTAAGGCCCTCTCATAGGAAC-3' | — | BamHI<br>Hind III | pMelBac A |
| Mouse Ob-Re C domain Cys 471, 602 -> Ser (8) | 22: 5'-CGCGGATCCTATGCTGAATTATACG-3'<br>27: 5'-ATCAGGAGAATACAGGCTGCGCCT-3'<br>26: 5'-CTGTATTCTCCTGATAGTCCATCT-3'<br>33: 5'-GACTGCAGAGAGGTCTGACACCAGCA<br>32: 5'-GACCTCTCTGCAGTCTATGTGGTCCA-3'<br>23: 5'-CCCAAGCTTAAGGCCCTCTCATAGGAAC-3' | 22-23 | BamHI<br>Hind III | pMelBac A |
| Mouse Ob-Re C domain Cys 471, 526, 602, 611 -> Ser (9) | 22: 5'-CGCGGATCCTATGCTGAATTATACG-3'<br>27: 5'-ATCAGGAGAATACAGGCTGCGCCT-3'<br>26: 5'-CTGTATTCTCCTGATAGTCCATCT-3'<br>29: 5'-AAGGACAGACGTTGGTGGCGAGTC-3'<br>28: 5'-CCAACGTCTGTCCTTCCTGACTCC-3'<br>31: 5'-GGAGCGAACCTGGACCACATAGACTGCAGAGAGGTCTGACACCAG-3'<br>30: 5'-TCTGCAGTCTATGTGGTCCAGGTTCGCTCCCGGCGGTTGGATGGA-3'<br>23: 5'-CCCAAGCTTAAGGCCCTCTCATAGGAAC-3' | 22-23 | BamHI<br>Hind III | pMelBac A |
| Mouse Ob-Re N + C domains wild-type (10) | 51: 5'-CTAGGATCCTCAGTTTTTCGCCAGCTAGGT-3'<br>23: 5'-CCCAAGCTTAAGGCCCTCTCATAGGAAC-3' | — | BamHI<br>Hind III | pMelBac A |
| Mouse Ob-Re N domain wild-type (11) | 207: 5'-GTTTTGGATCCGCTAGGTGTAAACTGGGACATAG-3'<br>208: 5'-GGTGGGGATCCTCAAACATCTTGTGTGGTAAAGAC-3' | — | BamHI | pMelBac B |
| Mouse Ob-Re | 207: 5'-GTTTTGGATCCGCTAGGTGTAAACTGGGACATAG-3' | 207-21 | BamHI | pMelBac B |

TABLE 2-continued

PCR Primers Sequences and Restriction Enzymes Used to Express OB-Re and Mutants.

| Construct | 1° PCR Primers | 2° PCR Primers | Restriction Enzymes used | Cloning vector |
|---|---|---|---|---|
| N domain | 25a: 5'-TTCAGATCCCCGAAGACTGGAGTTGCATTGGACAGTCTGA-3' | | Hind III | |
| Cys 188, 193 -> Ser (12) | | | | |
| | 24a: 5'-AACTCCAGTCTTCGGGGATCTGAATGTCATGTGCCGGTAC-3' | | | |
| | 21: 5'-CAGTAAGCTTCAAACATCTTGTGTGGTAAAGAC-3' | | | |

The choice between pMelBac A, B, or C cloning vectors was based on their open reading frames, which allow insertion of the recombinant gene in-frame with the melittin signal sequence for secretion of the recombinant protein. PCR products and cloning vectors were digested with the corresponding restriction enzymes (New England Biolabs) prior to ligation, which was carried overnight at 16° C. using T4 ligase (Gibco BRL). Ligation mixtures were transformed into DH5a cells, that were grown overnight on LB plates containing 50 μg/ml ampicillin. Clones were analyzed by PCR using the Recombinant Baculovirus PCR Primers from Invitrogen (Cat. N610-04) for the presence of the insert. Positive clones, identified by PCR, were sequenced with the Polyhedrin Forward (Cat. N598-02) and Baculovirus (+15) Reverse (Cat. N615-02) Sequencing Primers from Invitrogen to confirm that the recombinant gene was correctly oriented and fused to the melittin secretion signal.

Production of Recombinant Virus. SF9 insect cells were used for the production and amplification of recombinant virus. Grace's insect growth medium was obtained from Gibco BRL (Cat. 11605) and supplemented with 10% Fetal Bovine Serum (Gibco BRL, Cat. 26140), 1 μg/ml of gentamicin (Gibco BRL, Cat. 15710), and 625 ng/ml fungizone (Gibco BRL, Cat. 15295). Pluronic F-68 acid (Sigma, Cat. P-1300) was added to suspension cell cultures at 0.2% (w/v). Recombinant constructs were co-transfected with the linearized Bac-N-Blue DNA into SF9 cells using Bac-N-Blue Transfection Kit from Invitrogen (Cat. BK855-01) according to the manufacturer's specifications. Growth medium containing a mixture of recombinant and wild-type virus particles was collected 72 hrs and 120 hrs post transfection. Putative recombinant virus isolates were purified by infecting SF9 cells with dilutions of the transfection stock and isolating focal points of infection (plaques) from an agarose overlay (plaque assay). Recombinant viruses were identified by their ability to form blue plaques on X-gal due to the presence of lacZ gene in a pMelBac transfer vector. Putative recombinant plaques were amplified to low titer low scale P1 viral stocks by infecting approximately 2×106 SF9 cells and collecting growth medium 5-7 days post infection. The presence of a recombinant gene insert in a putative recombinant virus and the purity of recombinant plaque were confirmed by PCR analysis of virus DNA using Recombinant Baculovirus PCR Primers described above.

Expression of recombinant protein was confirmed by Western blot analysis of growth medium using rabbit polyclonal antibodies developed against peptides that were derived from OB-Re amino acid sequence (Example 2, supra). In addition, the OB-Re C-terminal portion (amino acids 420-641) was used to immunize rabbits. PCR and Western analyses-positive P1 viral stocks were further amplified into high-titer low-scale P2 stocks by infecting suspension culture of approximately $2 \times 10^8$ SF9 cells and collecting growth medium 5-7 days post infection. Virus titer of the P2 stocks was determined by performing plaque assay from serial dilutions of virus stocks and counting number of plaques. Viruses were further amplified into high titer high scale master stocks by infecting suspension cultures of SF9 cells with the P2 stocks of known virus titer at multiplicity of infection (MOI) equal 0.5 (0.5 infectious viral particles per one SF9 cell). The resulting master stocks were titered and used for the recombinant protein expression studies.

Expression of Recombinant Protein. Expression levels of the recombinant proteins were optimized by testing different cells lines, different MOI, and by optimizing time points of protein harvesting. Typically, all OB-R-derived recombinant proteins were expressed at significantly higher levels in High Five cells (Cat. B855-02, Invitrogen), compared to the expression levels in SF9 cells. EX-CELL 405 growth medium (JRH Biosciences, Cat. 14405-79P), supplemented with 3 μg/ml of gentamicin and 1.25 μg/ml fungizone, was used for the serum-free growth of High Five cells to facilitate purification of secreted recombinant proteins. Optimal MOI ranged from 5 to 10. Optimal protein collection time was usually around 72 hrs post infection.

For the large-scale expression of recombinant protein suspension culture of High Five cells was grown on a shaker at 27° C. at about 100-120 rpm to the density of approximately $2 \times 10^6$ cells/ml (log stage of growth). Cells were infected with a master recombinant virus stock at the optimal MOI and growth medium was collected at optimal time point. Cell debris were removed by centrifugation at 5,000 g for 10 minutes, and secreted proteins were precipitated by addition of ammonium sulfate. FPLC-based protocols are employed for further purification of the recombinant proteins.

Figure 12:
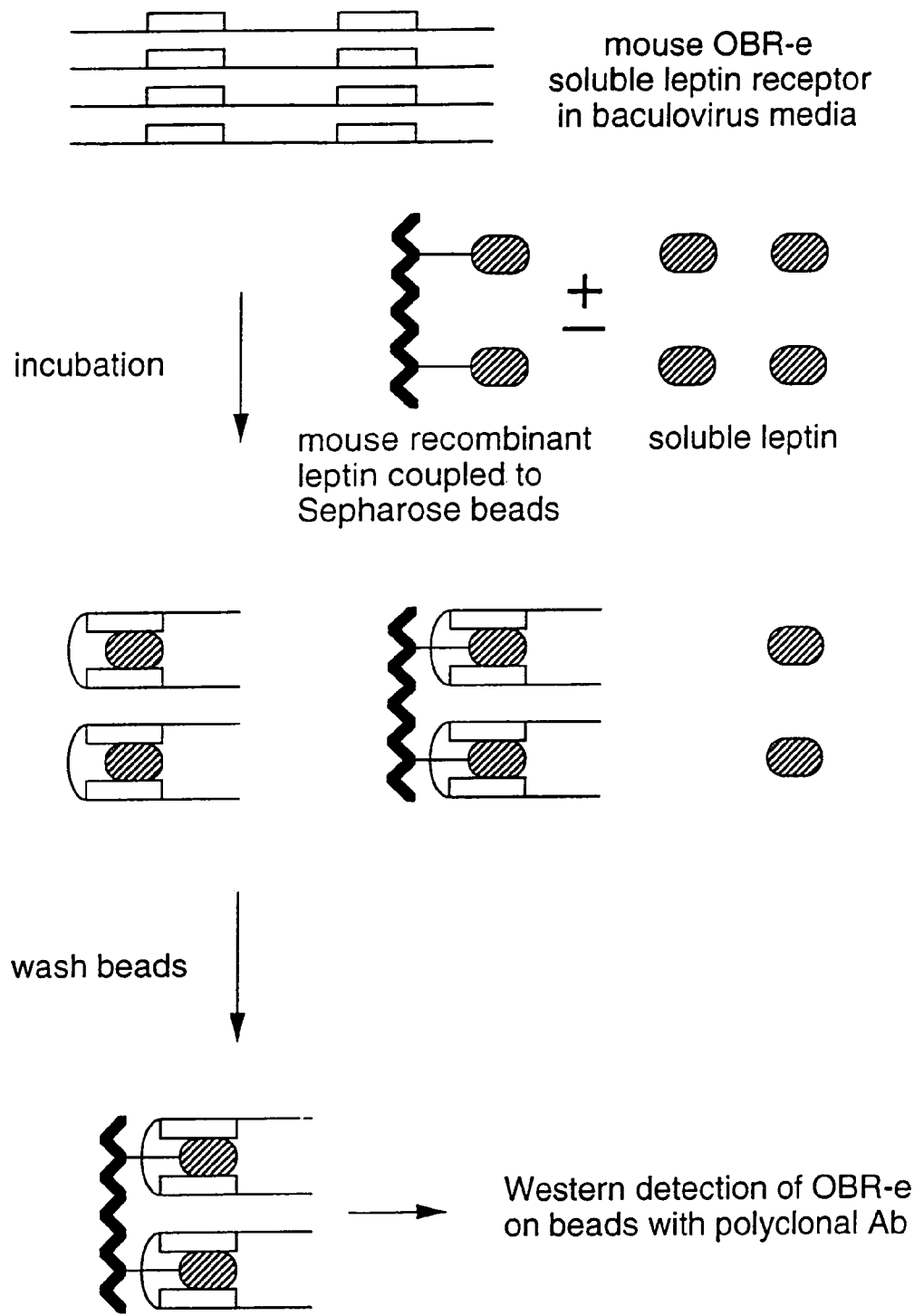
FIG. 12. Schematic of leptin-binding experiment. The schematic shows competitive inhibition of recombinant Ob-Re binding to leptin-SEPHAROSE with a free leptin.

Assay for Biological Activity (Leptin Binding). Biological activity of the recombinant OB-Re and OB-Re mutants was tested by their ability to bind leptin conjugated to SEPHAROSE beads. Growth medium, containing secreted recombinant protein was incubated overnight with leptin-SEPHAROSE beads. Beads were washed, boiled with SDS, and bound proteins were analyzed by Western blot. All recombinant proteins analyzed were able to bind leptin. Binding of the recombinant full-length OB-Re to leptin is very strong, as OB-Re could not be eluted from leptin-SEPHAROSE column at room temperature with strong chaotropic agents such as SDS, urea, or guanidinium hydrochloride. The specificity of the recombinant protein-leptin interaction was evaluated by competitive inhibition assay (FIG. 12). Medium containing recombinant proteins was pre-incubated with soluble leptin prior to incubation with leptin-Sepharose. The soluble leptin was found to inhibit binding of the recombinant OB-Re proteins to leptin-Sepharose beads in a concentration-dependent manner (Table 3).

TABLE 3

Current Expression Status of the Recombinant Ob-Re and Ob-Re Mutants Using Baculovirus System.

| Construct | Amino acids | Mutations | Antibody Reactivity | Binding to Leptin | Competition for Binding to Leptin |
|---|---|---|---|---|---|
| Mouse Ob-Re full length ORFHis796--(Ob-Re) | Asp-Pro-Ile 28 -> GMCTVLFM D805Stop | — | ~88 kDa protein 401 (+); 402 (+) 368 (+) | Binds leptin-SEPHA-ROSE beads with very high affinity | Free leptin competes for binding to leptin-SEPHAROSE beads |
| Mouse Ob-Re C domain wild-type (7) | Asp-Arg-Trp-Gly-Ser--Tyr 420 -> Pro 641 | — | ~27 kDa protein 402 (+) 368 (+) | Binds leptin-SEPHA-ROSE beads | Free leptin competes for binding to leptin-SEPHAROSE beads |
| Mouse Ob-Re C domain 2 mutated Cys (8) | Asp-Arg-Trp-Gly-Ser--Tyr 420 -> Pro 641 | Cys 471, 602 -> Ser | ~27 kDa protein is seeing (unconfirmed) | | |
| Mouse Ob-Re C domain 4 mutated Cys (9) | Asp-Arg-Trp-Gly-Ser--Tyr 420 -> Pro 641 | Cys 471, 526 -> Ser Cys 602, 611 -> Ser | | | |
| Mouse Ob-Re N + C domains wild-type (10) | Asp-Arg-Trp-Gly-Ser--Ser118 -> Pro 641 | — | ~63 kDa protein 401 (+); 402 (+) 368 (+) | Binds leptin-SEPHA-ROSE beads | Free leptin competes for binding to leptin-SEPHAROSE beads |
| Mouse Ob-Re N domain wild-type (11) | Asp-Arg-Trp-Gly-Ser--Leu123 -> Val331 | — | | | |
| Mouse Ob-Re N domain 2 mutated Cys (12) | Asp-Arg-Trp-Gly-Ser--Leu123 -> Val331 | Cys 188, 193 -> Ser | | | |

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Where nucleotide or amino acid sequence lengths are provided, or molecular weight values given, they are approximate.

Various publications are cited herein, the disclosures of which are incorporated by reference in their entireties. In particular, [Tartaglia et al., *Cell,* 83:1263-1271 (1995)] is incorporated herein by reference in its entirety.

---

What is claimed is:

1. A derivative of the leptin receptor (OB-R) polypeptide attached to a chemical moiety said derivative comprising:
    a linear polypeptide of a soluble leptin receptor selected form the group consisting of:
    an N-terminal sequence of OB-R from amino acid residues 1-796 wherein said OB-R is SEQ ID NO:93 and a C-terminal sequence which is selected from the group consisting of SEQ ID NO:15 and SEQ ID NO:120;
    an N-terminal sequence of OB-R from amino acid residues 23-796 wherein said OB-R is SEQ ID NO:93 and a C-terminal sequence which is selected from the group consisting of SEQ ID NO:15 and SEQ ID NO:120;
    an N-terminal sequence of OB-R from amino acid residues 28-796 wherein said OB-R is SEQ ID NO:93 and a C-terminal sequence which is selected from the group consisting of SEQ ID NO:15 and SEQ ID NO:120; and
    an N-terminal sequence of OB-R from amino acid residues 133-796 wherein said OB-R is SEQ ID NO:93 and a C-terminal sequence which is selected from the group consisting of SEQ ID NO:15 and SEQ ID NO:120.

2. The derivative of claim 1 wherein the chemical moiety is a water-soluble polymer.

3. The derivative of claim 2 wherein the water soluble polymer is polyethylene glycol.

4. A fragment of the leptin receptor (OB-R) polypeptide attached to a chemical moiety, wherein said fragment is capable of binding leptin, comprising a soluble leptin receptor fragment selected from the group consisting of:
    an OB-R from about Leu123 to about Val331, wherein said OB-R is SEQ ID NO: 93;
    an OB-R from about Tyr420 to about Pro641, wherein said OB-R is SEQ ID NO: 93;
    an OB-R from about Ser118 to about Pro641, wherein said OB-R is SEQ ID NO: 93;
    and an OB-R from about Leu123 to about Pro641, wherein said OB-R is SEQ ID NO: 93.

5. The fragment of claim 4 wherein the chemical moiety is a water-soluble polymer.

6. The fragment of claim 5 wherein the water soluble polymer is polyethylene glycol.

* * * * *